(12) United States Patent
Shair et al.

(10) Patent No.: US 9,321,713 B2
(45) Date of Patent: Apr. 26, 2016

(54) HYPERFORIN ANALOGS, METHODS OF SYNTHESIS, AND USES THEREOF

(75) Inventors: Matthew D. Shair, Lexington, MA (US); Brian A. Sparling, Watertown, MA (US); David Moebius, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/123,255

(22) PCT Filed: Jun. 1, 2012

(86) PCT No.: PCT/US2012/040379
§ 371 (c)(1),
(2), (4) Date: Jan. 29, 2014

(87) PCT Pub. No.: WO2012/167021
PCT Pub. Date: Dec. 6, 2012

(65) Prior Publication Data
US 2014/0135287 A1 May 15, 2014

Related U.S. Application Data

(60) Provisional application No. 61/493,250, filed on Jun. 3, 2011.

(51) Int. Cl.
| | | |
|---|---|---|
| A61K 31/122 | (2006.01) | |
| C07C 49/29 | (2006.01) | |
| C07C 49/753 | (2006.01) | |
| C07C 49/733 | (2006.01) | |
| C07C 49/743 | (2006.01) | |
| C07C 45/29 | (2006.01) | |
| C07D 493/08 | (2006.01) | |
| C07F 7/08 | (2006.01) | |
| C07F 7/18 | (2006.01) | |

(52) U.S. Cl.
CPC ............. *C07C 49/753* (2013.01); *C07C 45/29* (2013.01); *C07C 49/733* (2013.01); *C07C 49/743* (2013.01); *C07D 493/08* (2013.01); *C07F 7/0818* (2013.01); *C07F 7/0834* (2013.01); *C07F 7/1836* (2013.01)

(58) Field of Classification Search
CPC ....... A61K 31/122; C07C 49/12; C07C 49/29
USPC ........... 568/303, 368, 374; 514/675, 690, 691
See application file for complete search history.

(56) References Cited

U.S. PATENT DOCUMENTS

| 6,444,662 | B1 | 9/2002 | Chatterjee et al. | |
|---|---|---|---|---|
| 7,105,705 | B2 * | 9/2006 | Bombardelli et al. | 568/375 |
| 2005/0090693 | A1 | 4/2005 | Seeber et al. | |
| 2005/0165117 | A1 | 7/2005 | Bombardelli et al. | |
| 2005/0222274 | A1 | 10/2005 | Bombardelli et al. | |

FOREIGN PATENT DOCUMENTS

| JP | 2005-515979 A | 6/2005 |
|---|---|---|
| WO | WO 99/64388 A1 | 12/1999 |
| WO | WO 00/54760 A2 | 9/2000 |
| WO | WO 00/54785 A2 | 9/2000 |
| WO | WO 03/091193 A1 | 11/2003 |
| WO | WO 03/091194 A1 | 11/2003 |

OTHER PUBLICATIONS

Verotta et al (2000): STN International HCAPLUS database, (Columbus, Ohio), Accession No. 2000:96293.*
Verotta et al (2007): STN International HCAPLUS database, (Columbus, Ohio), Accession No. 2007:228771.*
Bombardelli et al (2003): STN International HCAPLUS database, (Columbus, Ohio), Accession No. 2003:875233.*
International Preliminary Report on Patentability, mailed Dec. 19, 2013, for Application No. PCT/US2012/040379.
International Search Report and Written Opinion, mailed Feb. 27, 2013, for Application No. PCT/US2012/040379.
Invitation to Pay Additional Fees and, Where Applicable, Protest Fee, mailed Dec. 28, 2012, for Application No. PCT/US/2012/040379.
Abe et al., New construction of the bicycle[3.3.1]nonane system via Lewis acid promoted regioselective ring-opening reaction of the tricycle[4.4.0.0$^{5,7}$] dec-2-ene derivative. Tetrahedron Lett. Sep. 4, 2006;47(36):6347-51.
Barabé et al., Gold-catalyzed synthesis of carbon-bridged medium-sized rings. Org Lett. Sep. 17, 2009;11(18):4236-8.
Beerhues, Hyperforin. Phytochemistry. Oct. 2006;67(20):2201-7.
Bystrov et al., The structure of hyperforin. Tetrahedron Lett. 1975;16(32);2791-2794.
Chatterjee et al., Hyperforin as a possible antidepressant component of hypericum extracts. Life Sci. 1998;63(6):499-510.
Couladouros et al., A short biomimetic approach to the fully functionalized bicyclic framework of type A acylphloroglucinols. Org Lett. Oct. 2009;11(19):4430-3.
Dell'aica et al., Hyperforin blocks neutrophil activation of matrix metalloproteinase-9, motility and recruitment, and restrains inflammation-triggered angiogenesis and lung fibrosis. J Pharmacol Exp Ther. May 2007;321(2):492-500.
Du et al., Inhibition of TRPC6 degradation suppresses ischemic brain damage in rats. J Clin Invest. Oct. 2010;120(10):3480-92.
Gartner et al., Aristoforin, a novel stable derivative of hyperforin, is a potent anticancer agent. Chembiochem. Jan. 2005;6(1):171-7.
Gash et al., Free radical cyclisation of unsaturated epoxides. Tetrahedron. 1989;45(17):5531-5538.
Kraus et al., Synthesis of the core bicyclic system of hyperforin and nemorosone. Tetrahedron Lett. Jan. 20, 2003; 44(4):659-61.
Leuner et al., Hyperforin—a key constituent of St. John's wort specifically activates TRPC6 channels. FASEB J. Dec. 2007;21(14):4101-11.
Leuner et al., Reduced TRPC channel expression in psoriatic keratinocytes is associated with impaired differentiation and enhanced proliferation. PLoS One. Feb. 22, 2011;6(2):e14716.
Mehta et al., A concise approach towards the bicycle[3.3.1]nonan-9-one core present in the phloroglucin natural product hyperforin. Tetrahedron Lett. Feb. 18, 2008;49(8):1417-20.
Menegazzi et al., Protective effects of St. John's wort extract and its component hyperforin against cytokine-induced cytotoxicity in a pancreatic beta-cell line. Int J Biochem Cell Biol 2008;40(8):1509-21.
Moore et al., St. John's wort induces hepatic drug metabolism through activation of the pregnane X receptor. Proc Natl Acad Sci U S A. Jun. 20, 2000;97(13):7500-2.
Müller et al., Specific TRPC6 channel activation, a novel approach to stimulate keratinocyte differentiation. J Biol Chem. Dec. 5, 2008;283(49):33942-54.
Nicolaou et al., Construction of highly functionalized medium-sized rings: synthesis of hyperforin and perforatumone model systems. Angew Chem Int Ed Engl. Jun. 20, 2005;44(25):3895-9.

Nuhant et al., Alpha,alpha'-annulation of 2,6-prenyl-substituted cyclohexanone derivatives with malonyl chloride: application to a short synthesis of (+/−)-clusianone. Formation and rearrangement of a biogenetic-like intermediate. Org Lett. Jan. 18, 2007;9(2):287-9.
Piers et al., Alkylation of 1,5-dimethoxy-1,4-cyclohexadiene. A convenient synthesis of 2-alkyl- and 2-alkenyl-1,3-cyclohexanediones. J Org Chem. Apr. 28, 1977;42(23):3755-57.
Qi et al., Rapid access to polyprenylated phloroglucinols via alkylative dearomatization-annulation: total synthesis of (+/−)-clusianone(1). J Am Chem Soc. Oct. 24, 2007;129(42):12682-3.
Ramsey et al., An introduction to TRP channels. Annu Rev Physiol. 2006;68:619-47.
Rodeschini et al., Synthesis of (+/−)-clusianone:high-yielding bridgehead and diketone substitutions by regioselective lithiation of enol ether derivatives of bicyclo[3.3.1]nonane-2,4,9-triones. Org Lett. Nov. 9, 2006;8(23):5283-5.
Shan et al., Three new hyperforin analogues from Hypericum perforatum. J Nat Prod. Jan. 2001;64(1):127-30.
Shimizu et al., Catalytic asymmetric total synthesis of ent-hyperforin. Angew Chem Int Ed Engl. Feb. 1, 2010;49(6):1103-6.
Shimizu et al., The first catalytic asymmetric total synthesis of ent-hyperforin. Tetrahedron. Aug. 14, 2010;66(33):6569-84.
Siegel et al., Total synthesis of garsubellin A. J Am Chem Soc. Feb. 1, 2006;128(4):1048-9.
Spessard et al., Progress toward the Synthesis of garsubellin A and related phloroglucins: the direct diastereoselective synthesis of the bicyclo[3.3.1]nonane core. Org Lett. May 30, 2002;4(11):1943-6.
Verotta et al., Furohyperforin, a prenylated phloroglucinol from St. John's wort (*Hypericumperforatum*). J Nat Prod. May 1999;62(5):770-2.
Verotta et al., Hyperforin analogues from St. John's wort (*Hypericum perforatum*). J Nat Prod. Mar. 2000;63(3):412-5.
Verotta et al., Synthesis and biological evaluation of hyperforin analogues. Part I. Modification of the enolized cyclohexanedione moiety. J Nat Prod. Apr. 2002;65(4):433-8.
Verotta et al., Oxidative Fragmentation of the Bridged β-Triketone Core of Hyperform. Eur J Org Chem. Jan. 20, 2004;2004(6):1193-1197.
Winn et al., A mutation in the TRPC6 cation channel causes familial focal segmental glomerulosclerosis. Science. Jun. 17, 2005;308(5729):1801-4.
Sears et al., The Structure of catechinic acid. A base rearrangement product of catechin. J Org Chem. 1974;39(22):3244-3247.
Sparling et al., Enantioselective total synthesis of hyperforin. J Am Chem Soc. Jan. 16, 2013;135(2):644-7. doi: 10.1021/ja312150d. Epub Dec. 31, 2012.
Partial Supplementary European Search Report, mailed Apr. 24, 2015, in connection with Application No. EP 12794102.9.
Ahmad et al., Synthetic studies towards garsubellin A: synthesis of model systems and potential mimics by regioselective lithiation of bicyclo[3.3.1]nonane-2,4,9-trione derivatives from catechinic acid. Org Biomol Chem. Jun. 21, 2007;5(12):1924-34. Epub May 15, 2007.
Aredova et al., Bicyclo[3.3.1]nonane-2,9-dione derivatives. Izvestiya Akadeinii Nauk SSSR, Seriya Khimicheskaya. 1976:25(6)1408-1410.
Gravel et al., new access to noradamantanes via generation of selectively protected bicyclic β-diketones. Can J Chem. 1975;53(17):2671-2673. doi: 10.1139/v75-378.
Hashida et al., Base-catalyzed reactions of procyanidin B3: formation of a novel catachinic acid-catechin dimer. J Wood Chem Tech. 2006;26(2):125-140. doi: 10.1080/02773810600701687.
Hashida et al., Base-catalyzed reactions of (—)-epicatechin: formation of enantiomers of base-catalyzed reaction products from (+)-catechin. J Wood Chem Tech. 2003;23(3-4):227-232. doi: 10.1081/WCT-120026930.
Hashida et al., Formation of a novel catechinic acid stereoisomer from base-catalyzed reactions of (+)-catechin. J Wood Chem Tech. 2002;22(1):11-23. doi: 10.1081/WCT-120004431.
Inouye et al., Preparation of bicyclo[3.3.1]nonane-2,4-dione derivatives. Bull Chem Soc of Japan. 1987;60(12):4369-4375.

Jensen et al., The oxidative transformations of (+)catechin and (—)epicatechin as studied by ESR: Formation of hydroxycatechinic acids. Tetrahedron. 1983;39(9):1609-1615. doi: doi:10.1016/S0040-4020(01)88570-7.
Kiatgrajai et al., Kinetics of epimerization of (+)-catechin and its rearrangement to catechinic acid. J Org Chem. 1982;47(15):2910-2912. doi: 10.1021/jo00136a021.
Laks et al., Condensed tannins. Base-catalysed reactions of polymeric procyanidins with phloroglucinol: intramolecular rearrangements. J Chem Soc Perkins Trans 1. 1987:1875-1881. doi: 10.1039/P19870001875.
Ma et al., Prenylated C6-C3 compounds with molecular diversity from the roots of Illicium oligandrum. Phytochemistry. Jan. 2011;72(1):115-25. doi: 10.1016/j.phytochem.2010.10.021. Epub Nov. 25, 2010.
McGraw et al., Condensed tannins: desulfonation of hydroxybenzylsulfonic acids related to proanthocyanidin derivatives. J Wood Chem Tech. 1988;8(1):91-109. doi: 10.1080/02773818808070672.
Moon et al., Versatile intermediates for heteroatom-substituted adamantane derivatives. J Org Chem. 1976;41(11):1899-1903. doi: 10.1021/jo00873a003.
Ohara et al., Condensed tannins: the formation of a diarylpropanol-catechinic acid dimer from base-catalyzed reactions of (+)-catechin. J Wood Chem Tech. 1991;11(2):195-208. doi: 10.1080/02773819108050270.
Singh et al., Physicochemical studies of catechins and epicatechins. J Indian Chem Soc. 1984;61:1044-7.
Tang et al., Rearranged prenylated C6-C3 compounds and a highly oxygenated seco prezizaanetype sesquiterpene from the stem bark of Illicium oligandrum. J Nat Prod. Jun. 2009;72(6):1017-21. doi: 10.1021/np9001702.
Yazaki et al., Effect of sodium hydroxide on stiansny values of extractives from pinus-radiata bark. Holzforschung. 1989;43:281-2.
Chemical Abstracts Service Accession No. 2007:608672 (Ahmad et al., Synthetic studies towards garsubellin A: synthesis of model systems and potential mimics by regioselective lithiation of bicyclo[3.3.1]nonane-2,4,9-trione derivatives from catechinic acid. Org Biomol Chem. Jun. 21, 2007;5(12):1924-34. Epub May 15, 2007).
Chemical Abstracts Service Accession No. 1976: 493925 (Aredova et al., Bicyclo[3.3.1]nonane-2,9-dione derivatives. Izvestiya Akadeinii Nauk SSSR, Seriya Khimicheskaya. 1976:25(6)1408-1410).
Chemical Abstracts Service Accession No. 1975: 592656 (Gravel et al., new access to noradamantanes via generation of selectively protected bicyclic β-diketones. Can J Chem. 1975;53(17):2671-2673. doi: 10.1139/v75-378).
Chemical Abstracts Service Accession No. 2006: 467928 (Hashida et al., Base-catalyzed reactions of procyanidin B3: formation of a novel catachinic acid-catechin dimer. J Wood Chem Tech. 2006;26(2):125-140. doi: 10.1080/02773810600701687).
Chemical Abstracts Service Accession No. 2003: 924314 (Hashida et al., Base-catalyzed reactions of (—)-epicatechin: formation of enantiomers of base-catalyzed reaction products from (+)-catechin. J Wood Chem Tech. 2003;23(3-4):227-232. doi: 10.1081/WCT-120026930.
Chemical Abstracts Service Accession No. 2002: 484376 (Hashida et al., Formation of a novel catechinic acid stereoisomer from base-catalyzed reactions of (+)-catechin. J Wood Chem Tech. 2002;22(1):11-23. doi: 10.1081/WCT-120004431).
Chemical Abstracts Service Accession No. 1988: 528424 (Inouye et al., Preparation of bicyclo[3.3.1]nonane-2,4-dione derivatives. Bull Chem Soc of Japan. 1987;60(12):4369-4375).
Chemical Abstracts Service Accession No. 1983: 469955 (Jensen et al., The oxidative transformations of (+)catechin and (—)epicatechin as studied by ESR: Formation of hydroxycatechinic acids. Tetrahedron. 1983;39(9):1609-1615. doi: doi:10.1016/S0040-4020(01)88570-7).
Chemical Abstracts Service Accession No. 1982: 438206 (Kiatgrajai et al., Kinetics of epimerization of (+)-catechin and its rearrangement to catechinic acid. J Org Chem. 1982;47(15):2910-2912. doi: 10.1021/jo00136a021).

Chemical Abstracts Service Accession No. 1988: 150083 (Laks et al., Condensed tannins. Base-catalysed reactions of polymeric procyanidins with phloroglucinol: intramolecular rearrangements. J Chem Soc Perkins Trans 1. 1987:1875-1881. doi: 10.1039/P19870001875).

Chemical Abstracts Service Accession No. 2010: 1620471 (Ma et al., Prenylated C6-C3 compounds with molecular diversity from the roots of Illicium oligandrum. Phytochemistry. Jan. 2011;72(1):115-25. doi: 10.1016/j.phytochem.2010.10.021. Epub Nov. 25, 2010).

Chemical Abstracts Service Accession No. 1988: 408263 (McGraw et al., Condensed tannins: desulfonation of hydroxybenzylsulfonic acids related to proanthocyanidin derivatives. J Wood Chem Tech. 1988;8(1):91-109. doi: 10.1080/02773818808070672).

Chemical Abstracts Service Accession No. 1988: 408263 (Moon et al., Versatile intermediates for heteroatom-substituted adamantane derivatives. J Org Chem. 1976;41(11):1899-1903. doi: 10.1021/jo00873a003).

Chemical Abstracts Service Accession No. 1991: 607740 (Ohara et al., Condensed tannins: the formation of a diarylpropanol-catechinic acid dimer from base-catalyzed reactions of (+)-catechin. J Wood Chem Tech. 1991;11(2):195-208. doi: 10.1080/02773819108050270).

Chemical Abstracts Service Accession No. 1974: 569237 (Sears et al., Structure of catechinic acid. Base rearrangement product of catechin. J Org Chem. 1974;39(22):3244-7).

Chemical Abstracts Service Accession No. 1986: 5242 (Singh et al., Physicochemical studies of catechins and epicatechins. J Indian Chem Soc. 1984;61:1044-7).

Chemical Abstracts Service Accession No. 2009: 683664 (Tang et al., Rearranged prenylated C6-C3 compounds and a highly oxygenated seco prezizaane-type sesquiterpene from the stem bark of Illicium oligandrum. J Nat Prod. Jun. 2009;72(6):1017-21. doi:.10.1021/np9001702).

Chemical Abstracts Service Accession No. 1989: 556141 (Yazaki et al., Effect of sodium hydroxide on stiansny values of extractives from pinus-radiata bark. Holzforschung. 1989;43:281-2).

Simpkins et al., Synthesis of nemorosone via a difficult bridgehead substitution reaction. Synlett. 2010;4:639-643.

* cited by examiner

*Primary Examiner* — Golam M M Shameem

(74) *Attorney, Agent, or Firm* — Wolf, Greenfield & Sacks, P.C.

(57) ABSTRACT

The present invention provides a novel 11-step enantioselective approach to the natural product hyperforin, which enables access to a wide variety of hyperforin analogs. The present invention also provides pharmaceutical compositions comprising inventive hyperforin analogs. Hyperforin analogs synthesized using the present synthetic method are envisioned useful in the treatment of various conditions, including, but not limited to, depression and conditions characterized by depression, inflammatory skin conditions, diabetes, asthma, chronic obstructive pulmonary disease (COPD), kidney disorders, and ischemic brain damage.

33 Claims, 21 Drawing Sheets

Reagents and conditions: (a) BrBMe₂, NEt₃, DCM, −78 °C; NEt₃, 79%; (b) PPTS, Me₂CO/H₂O, reflux, 90%; (c) Tf₂O, pyr, DCM, −45 to 5 °C, 80%; LDA, TMSCl, THF, −78 °C to rt, 56%; (e) (prenyl)Cu(CN)Li·LiI, TMSCl, THF, −78 to 0 °C, 50%.

Reagents and conditions: (a) MOMCl, DIPEA, DME, 60 °C, 97%; (b) LITMP, TMSCl, THF, −78 to 0 °C, 95%; (c) LiOH, H₂O, diox, 80 °C, 98%; (d) LiOH, H₂O, diox, 80 °C, 99%; (e) LDA, THF, −78 °C; prenyl bromide, −78 °C, 51%; (f) Pd/C, H₂, MeOH, 92%; (g) LiTMP, THF, −78 to 0 °C; iPrC(O)Cl, −78 °C; TBAF, THF, 0 °C, 53%.

HYPERFORIN ANALOGS, METHODS OF SYNTHESIS, AND USES THEREOF

RELATED APPLICATIONS

The present application is a U.S. national stage filing under 35 U.S.C. §371 of international PCT application, PCT/US2012/040379, filed Jun. 1, 2012, which claims priority under 35 U.S.C. §119(e) to U.S. provisional patent application, U.S. Ser. No. 61/493,250, filed Jun. 3, 2011, each of which is incorporated herein by reference.

BACKGROUND OF THE INVENTION

Hyperforin is considered to be the constituent of St. John's Wort responsible for its antidepressant activity (see, e.g., Chatterjee et al., *Life Sci.* (1998) 63:499-510). Hyperforin is the only known selective agonist of TRPC6 (canonical transient receptor potential) ion channel leading to influx of $Ca^{+2}$ and $Na^+$ ions into neurons and neuronal axonal sprouting (see, e.g., Leuner et al., *FASEB J.* (2007) 21:4101-4111). Unlike synthetic SSRI antidepressants, hyperforin causes an increase in synaptic serotonin and norepinephrine levels, possibly by antagonizing TRPC6. Therefore, TRPC6 may be a novel antidepressant target. Since there are few small molecules that are known to selectively activate TRPC channel proteins, and these proteins are being recognized as critical players in various aspects of human physiology, hyperforin is an important lead for discovery of new TRPC channel modulators and possibly new therapeutics (see, e.g., Ramsey et al., *Annu. Rev. Physiol.* (2006) 68:619-647). However, major drawbacks of hyperforin as a therapeutic lead are that it has poor water solubility and it is a potent activator of PXR (pregnane X receptor), which causes upregulation of CYPs (CYP3As and CYP2Cs) and the resultant metabolism of other drugs (see, e.g., Moore et al., *Proc. Natl. Acad. Sci. USA* (2000) 97:7500-7502). Hyperforin has also been reported to have beneficial effects in atopic dermatitis and psoriasis models (see, Leuner et al., *J. Biol. Chem.* (2008) 283:33942-33954, and Leuner et al., *PLoS ONE* (2011) 6:e14716). In addition, it protects pancreatic beta-cells from cytokine-induced apoptosis and therefore may be a treatment for Type I and Type II diabetes (see, Masiello et al., *Int. J. Biochem. Cell Biol.* (2008) 40:1509-1521). Agonists of TRPC6 may also be useful for treatment of asthma and chronic obstructive pulmonary disease (COPD) (see, e.g., Garbisa et al., *J. Pharmacol. Exp. Ther.* (2007) 321:492-500), kidney disorders (e.g., focal and segmented glomerulosclerosis: see, e.g., Winn et al., *Science* (2005) 308:1801-1804); and ischemic brain damage (see, e.g., Du et al., *J. Clin. Invest.* (2010) 120:3480-3492).

Hyperforin is a bicyclic polyprenylated acylphloroglucinol derivative and exists as a mixture of tautomers. The broad shape of most of hyperforins' $^1$H-NMR signals and the poor resolution of the $^{13}$C-NMR is characteristic of the tautomeric equilibrium (see, e.g., Beerhues, *Phytochemistry* (2006) 67:2201-2207). As a result of its important biological and medicinal properties and its unique complex structure, hyperforin has generated intense interest from the synthetic organic and scientific community (see, e.g., Barabé et al., *Org. Lett.* (2009) 11:4236-4238; Couladourous et al., *Org. Lett.* (2009) 11:4430-4433; Kraus et al., *Tetrahedron Lett.* (2003) 44:659-661; Mehta et al., *Tetrahedron Lett.* (2008) 49:1417-1420; Abe et al., *Tetrahedron Lett.* (2006) 47:6347-6351; Nicolaou et al., *Angew. Chem. Int. Ed.* (2005) 44:3895-3899; Spessard et al., *Org. Lett.* (2002) 4:1943-1946). To date only a single total synthesis has been accomplished by Shibasaki and co-workers, in 51 steps and 0.05% overall yield (see, e.g., Shimizu et al., *Angew. Chem. Int. Ed.* (2010) 49:1103-1106; Shimizu et al., *Tetrahedron* (2010) 66:6569-6584). Several syntheses of less complex bicyclic polyprenylated acylphloroglucinols have been achieved, but as yet none of those approaches have been applied to the more complex hyperforin (see, e.g., Nuhant et al., *Org. Lett.* (2007) 9:287-289; Qi et al., *J. Am. Chem. Soc.* (2007) 129: 12682-12683; Rodeschini et al., *Org. Lett.* (2006) 8:5283-5285; Siegel and Danishefsky, *J. Am. Chem. Soc.* (2006) 128:1048-1049). The enantioselective synthesis of hyperforin by Shibasaki is a landmark achievement, but it is not easily amenable to the synthesis of hyperforin analogs. Thus, there remains a need for a practical synthesis of hyperforin that will provide access to a wide variety of hyperforin analogs for biological evaluation.

SUMMARY OF THE INVENTION

The present invention provides a novel approach to the synthesis of hyperforin and hyperforin analogs. The synthesis is particularly amenable to preparing hyperforin analogs as described herein. Pharmaceutical compositions and method of using the hyperforin analogs are also provided.

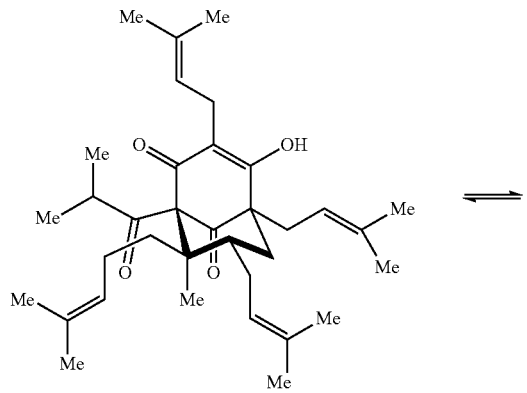 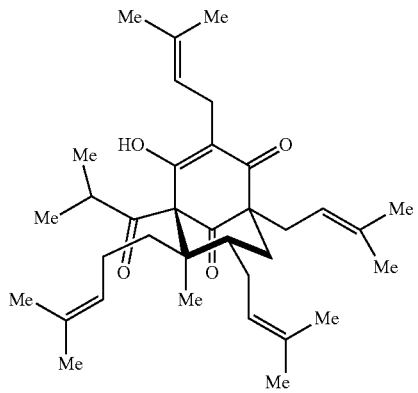

Hyperforin

In one aspect, provided is a compound of Formula (I) or (II):

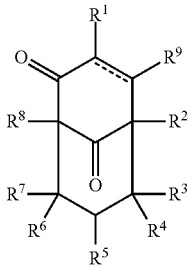
(I)

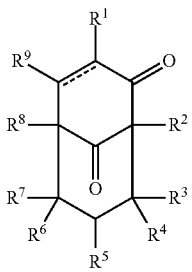
(II)

or a salt, isomer, or tautomer thereof, or mixture thereof; wherein $R^1$, $R^2$, $R^3$, $R^4$, $R^5$, $R^6$, $R^7$, $R^8$, and $R^9$ are as defined herein, and ≡≡≡ represents a single or double bond.

In certain embodiments, wherein ≡≡≡ represents a double bond, the compound of Formula (I) is selected from any one of the two stereoisomers:

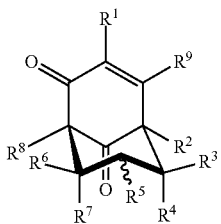
(III)

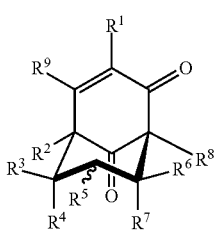
(III-ent)

or a salt, isomer, or tautomer thereof, or mixture thereof, wherein $R^5$ is in the axial or equatorial position.

In certain embodiments, wherein ≡≡≡ represents a double bond, the compound of Formula (II) is selected from any one of the two stereoisomers:

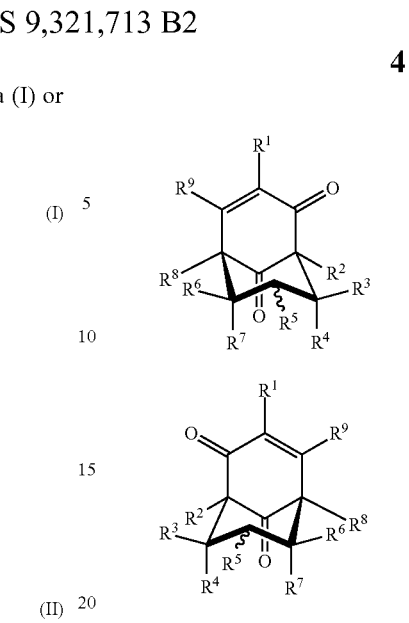
(IV)

(IV-ent)

or a salt, isomer, or tautomer thereof, or mixture thereof, wherein $R^5$ is in the axial or equatorial position.

In another aspect, the invention provides the synthesis of hyperforin and hyperforin analogs. FIGS. 1-18 depict exemplary syntheses of compounds of the present invention, i.e., compounds of Formulae (I), (II), (III), (III-ent), (IV), and (IV-ent), and salts, isomers, and tautomers thereof, and mixtures thereof. Thus, in yet another aspect, the present invention provides synthetic intermediates useful in the present inventive method.

In still yet another aspect, provided are pharmaceutical compositions comprising a compound of the present invention and a pharmaceutically acceptable excipient. In certain embodiments, the pharmaceutical composition comprises an effective amount of a compound of the present invention. In certain embodiments, the effective amount is a therapeutically effective amount. In certain embodiments, the effective amount is a prophylactically effective amount.

In yet another aspect, provided is a method of treating depression in a subject in need thereof, the method comprising administering an effective amount of a compound of the present invention or pharmaceutical composition thereof, to the subject to treat depression. In yet another aspect, provided is a method of treating depression in a subject in need thereof, the method comprising instructing the subject to administer an effective amount of a compound of the present invention or pharmaceutical composition thereof, to treat depression. In still yet another aspect, provided is a compound of the present invention or pharmaceutical composition thereof for use in treating depression. Depression encompasses any condition characterized by a depressed mood, which is optionally and additionally characterized by irritability, instability of mood, and/or changes in mood. Thus, depression encompasses Major Depressive Disorder (MDD), dysthymic disorder (i.e., low mood), melancholic depression, atypical depression, catatonic depression, postpartum depression, and seasonal affective disorder (SAD), as well as conditions which may be characterized by a depressed mood, such as depression associated with insomnia, stress, hormonal mood swings (e.g., during pregnancy, Premenstrual Dysphoric Disorder, puberty, and menopause), mild cognitive impairment, substance-induced mood disorders (e.g., alcoholism), dementia, Alzheimer's disease, Parkinson's disease, Huntington's disease, and psychotic disorders (e.g., Schizoaffective Disorder, Schizophrenia, Delusional Disorder, and Psychotic Disorder Not Otherwise Specified).

Other conditions envisioned treatable using compounds of the present invention include TRPC6-mediated conditions such as asthma and chronic obstructive pulmonary disease (COPD); inflammatory skin conditions (e.g., atopic dermatitis, psoriasis); diabetes (e.g., Type I and Type II diabetes); kidney disorders (e.g., glomerulosclerosis); and ischemic brain damage.

The details of one or more embodiments of the invention are set forth herein. Other features, objects, and advantages of the invention will be apparent from the description, the figures, the examples, and the claims.

DEFINITIONS

Chemical Definitions

Figure 1:
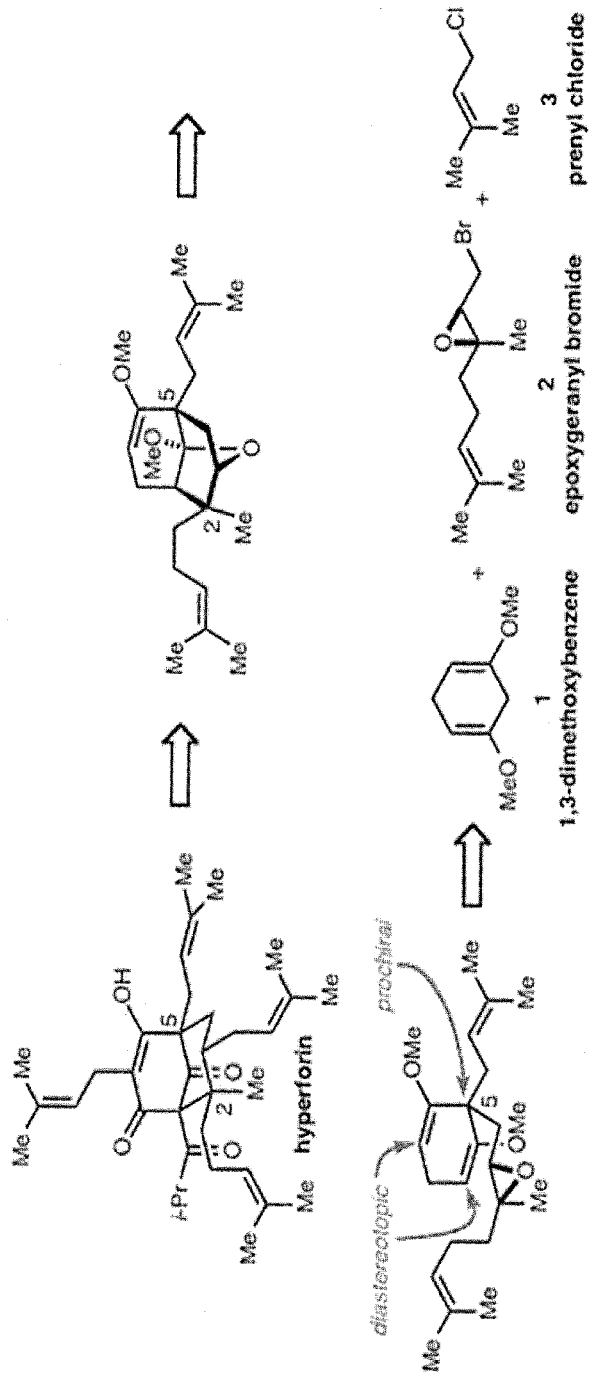
FIG. 1 depicts a retrosynthetic analysis of hyperforin from the simple building blocks 1,3-dimethoxybenzene (1), epoxygeranyl bromide (2), and prenyl bromide (3).

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_1$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is unsubstituted $C_{1-10}$ alkyl (e.g., —$CH_3$). In certain embodiments, the alkyl group is substituted $C_{1-10}$ alkyl.

"Perhaloalkyl" is a substituted alkyl group as defined herein wherein all of the hydrogen atoms are independently replaced by a halogen, e.g., fluoro, bromo, chloro, or iodo. In some embodiments, the alkyl moiety has 1 to 8 carbon atoms ("$C_{1-8}$ perhaloalkyl"). In some embodiments, the alkyl moiety has 1 to 6 carbon atoms ("$C_{1-6}$ perhaloalkyl"). In some embodiments, the alkyl moiety has 1 to 4 carbon atoms ("$C_{1-4}$ perhaloalkyl"). In some embodiments, the alkyl moiety has 1 to 3 carbon atoms ("$C_{1-3}$ perhaloalkyl"). In some embodiments, the alkyl moiety has 1 to 2 carbon atoms ("$C_{1-2}$ perhaloalkyl"). In some embodiments, all of the hydrogen atoms are replaced with fluoro. In some embodiments, all of the hydrogen atoms are replaced with chloro. Examples of perhaloalkyl groups include —CF$_3$, —CF$_2$CF$_3$, —CF$_2$CF$_2$CF$_3$, —CCl$_3$, —CFCl$_2$, —CF$_2$Cl, and the like.

"Alkenyl" refers to a radical of a straight-chain or branched hydrocarbon group having from 2 to 20 carbon atoms, one or more carbon-carbon double bonds, and no triple bonds ("C$_{2-20}$ alkenyl"). In some embodiments, an alkenyl group has 2 to 10 carbon atoms ("C$_{2-10}$ alkenyl"). In some embodiments, an alkenyl group has 2 to 9 carbon atoms ("C$_{2-9}$ alkenyl"). In some embodiments, an alkenyl group has 2 to 8 carbon atoms ("C$_{2-8}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is unsubstituted C$_{2-10}$ alkenyl. In certain embodiments, the alkenyl group is substituted C$_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("C$_{2-20}$ alkynyl"). In some embodiments, an alkynyl group has 2 to 10 carbon atoms ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is unsubstituted C$_{2-10}$ alkynyl. In certain embodiments, the alkynyl group is substituted C$_{2-10}$ alkynyl.

"Carbocyclyl" or "carbocyclic" refers to a radical of a non-aromatic cyclic hydrocarbon group having from 3 to 10 ring carbon atoms ("C$_{3-10}$ carbocyclyl") and zero heteroatoms in the non-aromatic ring system. In some embodiments, a carbocyclyl group has 3 to 8 ring carbon atoms ("C$_{3-8}$ carbocyclyl"). In some embodiments, a carbocyclyl group has 3 to 6 ring carbon atoms ("C$_{3-6}$ carbocyclyl"). In some embodiments, a carbocyclyl group has 3 to 6 ring carbon atoms ("C$_{3-6}$ carbocyclyl"). In some embodiments, a carbocyclyl group has 5 to 10 ring carbon atoms ("C$_{5-10}$ carbocyclyl"). Exemplary C$_{3-4}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is unsubstituted C$_{3-10}$ carbocyclyl. In certain embodiments, the carbocyclyl group is a substituted C$_{3-10}$ carbocyclyl.

In some embodiments, "carbocyclyl" is a monocyclic, saturated carbocyclyl group having from 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-4}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted C$_{3-10}$ cycloalkyl. In certain embodiments, the cycloalkyl group is substituted C$_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, and sulfur ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl and disulfuranyl. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, and the like.

"Aryl" refers to a radical of a monocyclic or polycyclic (e.g., bicyclic or tricyclic) 4n+2 aromatic ring system (e.g., having 6, 10, or 14 it electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of "alkyl" and refers to an alkyl group, as defined herein, substituted by an aryl group, as defined herein, wherein the point of attachment is on the alkyl moiety.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of "alkyl" and refers to an alkyl group, as defined herein, substituted by a heteroaryl group, as defined herein, wherein the point of attachment is on the alkyl moiety.

"Partially unsaturated" refers to a group that includes at least one double or triple bond. The term "partially unsaturated" is intended to encompass rings having multiple sites of unsaturation, but is not intended to include aromatic groups (e.g., aryl or heteroaryl moieties) as herein defined. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; or two geminal hydrogens on a carbon atom are replaced with the group =O, =S, =NN(R$^{bb}$)$_2$, =NNR$^{bb}$C(=O)R$^{aa}$, =NNR$^{bb}$C(=O) OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$) OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3{}^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, 5 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3{}^+$X$^-$, —NH(C$_{1-6}$ alkyl)$_2{}^+$X$^-$, —NH$_2$(C$_{1-6}$ alkyl)$^+$X$^-$, —NH$_3{}^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3{}^-$, ClO$_4{}^-$, OH$^-$, H$_2$PO$_4{}^-$, HSO$_4{}^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

"Halo" or "halogen" refers to fluorine (fluoro, —F), chlorine (chloro, —Cl), bromine (bromo, —Br), or iodine (iodo, —I).

A "leaving group" is an art-understood term referring to a molecular fragment that departs with a pair of electrons in heterolytic bond cleavage, wherein the molecular fragment is an anion or neutral molecule. See, for example, Smith, *March's Advanced Organic Chemistry* 6th ed. (501-502). Exemplary leaving groups include, but are not limited to, halo (e.g., chloro, bromo, iodo) and activated substituted hydroxyl groups (e.g., —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$ wherein R$^{aa}$, R$^{bb}$, and R$^{cc}$ are as defined herein).

A "Lewis acid" refers to a chemical species that is an electron pair acceptor and therefore able to react with a Lewis base to form a Lewis adduct by sharing the electron pair furnished by the Lewis base. A Lewis acid is any species that accepts lone pair electrons. Exemplary Lewis acids include but are not limited to boron (e.g., BF$_3$, BBr$_3$, BCl$_3$), aluminum (e.g., AlCl$_3$, Et$_2$AlCl), tin, titanium (e.g., TiCl$_4$, titanium isopropoxide), nickel, scandium, magnesium, and lanthanum Lewis acids. Other Lewis acids are described herein. Triflates and triflate salts are also used as Lewis acids because of their stability (e.g., for example, silyl triflates such as TMS-OTf, silver triflates, barium triflates, lanthanide triflates, and scandium triflates). Chiral Lewis acids are also contemplated (e.g., for example, acyloxyborane (CAB), methoxyaluminum dichloride). See e.g., Yamamoto, Ed., *Lewis Acid Reagents. A Practical Approach*, Oxford University Press, New York, 1999, incorporated herein by reference.

Nitrogen atoms can be substituted or unsubstituted as valency permits, and include primary, secondary, tertiary, and quaternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein R$^{aa}$, R$^{bb}$, R$^{cc}$ and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3$, $-P(=O)_2R^{aa}$, $-P(=O)(R^{aa})_2$, $-P(=O)(OR^{cc})_2$, $-P(=O)_2N(R^{bb})_2$, and $-P(=O)(NR^{bb})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Exemplary oxygen protecting groups include, but are not limited to, methyl, methoxymethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is an sulfur protecting group (also referred to as a thiol protecting group). Sulfur protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3$, $-P(=O)_2R^{aa}$, $-P(=O)(R^{aa})_2$, $-P(=O)(OR^{cc})_2$, $-P(=O)_2N(R^{bb})_2$, and $-P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3rd edition, John Wiley & Sons, 1999, incorporated herein by reference.

These and other exemplary substituents are described in more detail in the Detailed Description, Examples, and claims. The invention is not intended to be limited in any manner by the above exemplary listing of substituents.

Other Definitions

"Salt" or "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, quaternary salts.

An "isomer" includes any and all geometric isomers and stereoisomers. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of the invention.

"Tautomer" includes two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may be catalyzed by acid or base. Exemplary tautomerizations include keto-to-enol; amide-to-imide; lactam-to-lactim; enamine-to-imine; and enamine-to-(a different) enamine tautomerizations.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or other non-human animals, for example mammals (e.g., primates (e.g., cynomolgus monkeys, rhesus monkeys); commercially relevant mammals such as cattle, pigs, horses, sheep, goats, cats, and/or dogs), birds (e.g., commercially relevant birds such as chickens, ducks, geese, and/or turkeys), reptiles, amphibians, and fish. In certain embodiments, the non-human animal is a mammal. The non-human animal may be a male or female and at any stage of development. A non-human animal may be a transgenic animal.

"Treat," "treating" and "treatment" contemplate an action that occurs while a subject is suffering from a condition which reduces the severity of the condition or retards or slows the progression of the condition ("therapeutic treatment"), and also contemplates an action that occurs before a subject begins to suffer from the condition and which inhibits or reduces the severity of the condition ("prophylactic treatment").

An "effective amount" of a compound refers to an amount sufficient to elicit the desired biological response, i.e., treating the condition. As will be appreciated by those of ordinary skill in this art, the effective amount of a compound of the invention may vary depending on such factors as the desired biological endpoint, the pharmacokinetics of the compound, the condition being treated, the mode of administration, and the age and health of the subject. An effective amount encompasses therapeutic and prophylactic treatment.

A "therapeutically effective amount" of a compound is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a compound is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

DETAILED DESCRIPTION OF CERTAIN EMBODIMENTS OF THE INVENTION

The present invention provides a novel 11-step enantioselective approach to the natural product hyperforin, which enables access to a wide variety of hyperforin analogs. The present invention also provides pharmaceutical compositions comprising inventive hyperforin analogs. Hyperforin analogs synthesized using the present synthetic method are envisioned useful in the treatment of various conditions, including, but not limited to, depression and conditions characterized by depression; inflammatory skin conditions such as dermatitis and psoriasis; diabetes; asthma; chronic obstructive pulmonary disease (COPD); kidney disorders such as glomerulosclerosis; and ischemic brain damage.

Compounds of the Present Invention

In one aspect, provided is a compound of Formula (I):

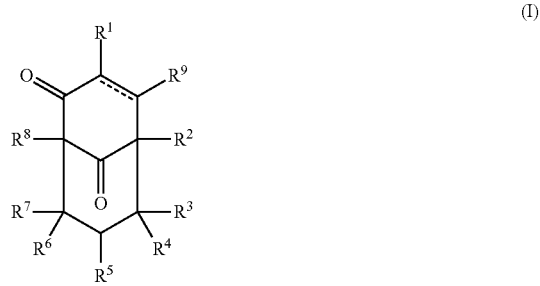

or a salt, isomer, or tautomer thereof, or mixture thereof; wherein:

$R^1$ is hydrogen, halogen, —OH, —OR$^{41}$, —N$_3$, —NH$_2$, —NH(R$^{41}$), —N(R$^{41}$)$_2$, —NH—NH—R$^{41}$, —NR$^{41}$—NHR$^{41}$, —N=NR$^{41}$, —N$_3$, —SH, —SR$^{41}$, —SO$_2$R$^{41}$, —SO$_3$H, —SO$_2$OR$^{41}$, —Si(R$^{41}$)$_3$, —CO$_2$H, —CO$_2$R$^{41}$, —C(=O)R$^{41}$, —C(=O)NH$_2$, —C(=O)NH(R$^{41}$), —C(=O)N(R$^{41}$)$_2$, —C(=O)SH, —C(=O)SR$^{41}$, optionally substituted C$_{1-20}$alkyl, optionally substituted C$_{2-20}$alkenyl, optionally substituted C$_{2-20}$alkynyl, optionally substituted C$_{3-10}$carbocyclyl, optionally substituted 3-10 membered heterocyclyl, optionally substituted C$_{6-14}$aryl, or optionally substituted 5-10 membered heteroaryl, wherein each instance of R$^{41}$ is independently optionally substituted C$_{1-20}$alkyl, optionally substituted C$_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen, sulfur, or nitrogen protecting group, or two $R^{41}$ groups are joined to form an optionally substituted 3-10 membered heterocyclyl or optionally substituted 5-10 membered heteroaryl ring;

$R^2$ is hydrogen, $-Si(R^{42})_3$, $-SO_2R^{42}$, $-SO_3H$, $-SO_2OR^{42}$, $-CO_2H$, $-CO_2R^{42}$, $-C(=O)R^{42}$, $-C(=O)NH_2$, $-C(=O)NH(R^{42})$, $-C(=O)N(R^{42})_2$, $-C(=O)SH$, $-C(=O)SR^{42}$, optionally substituted $C_{1-20}$alkyl, optionally substituted $C_{2-20}$alkenyl, optionally substituted $C_{2-20}$alkynyl, optionally substituted $C_{6-14}$aryl, or optionally substituted 5-10 membered heteroaryl, wherein each instance of $R^{42}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, or optionally substituted 5-10 membered heteroaryl, or an oxygen, sulfur, or nitrogen protecting group, or two $R^{42}$ groups are joined to form an optionally substituted 3-10 membered heterocyclyl or optionally substituted 5-10 membered heteroaryl ring;

$R^3$ is hydrogen, optionally substituted $C_{1-20}$alkyl, optionally substituted $C_{2-20}$alkenyl, or optionally substituted $C_{2-20}$alkynyl;

$R^4$ is hydrogen, optionally substituted $C_{1-20}$alkyl, optionally substituted $C_{2-20}$alkenyl, or optionally substituted $C_{2-20}$alkynyl;

$R^5$ is hydrogen, halogen, $-OH$, $-OR^{45}$, $-NH_2$, $-NHR^{45}$, $-N(R^{45})_2$, $-NH(R^{45})$, $-N(R^{45})_2$, $-NH-NH-R^{45}$, $-NR^{45}-NHR^{45}$, $-N=NR^{45}$, $-N_3$, $-SH$, $-SR^{45}$, $-SO_2R^{45}$, $-SO_3H$, $-SO_2OR^{45}$, $-Si(R^{45})_3$, $-CO_2H$, $-CO_2R^{45}$, $-C(=O)R^{45}$, $-C(=O)NH_2$, $-C(=O)NH(R^{45})$, $-C(=O)N(R^{45})_2$, $-C(=O)SH$, $-C(=O)SR^{45}$, optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, or optionally substituted 5-10 membered heteroaryl, wherein each instance of $R^{45}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, or optionally substituted 5-10 membered heteroaryl, or an oxygen, sulfur, or nitrogen protecting group, or two $R^{45}$ groups are joined to form an optionally substituted 3-10 membered heterocyclyl or optionally substituted 5-10 membered heteroaryl ring;

$R^6$ is hydrogen, $-OH$, $-OR^{46}$, $-NH_2$, $-NHR^{46}$, $-N(R^{46})_2$, $-NH-NH-R^{46}$, $-NR^{46}-NHR^{46}$, $-N=NR^{46}$, $-N_3$, $-SH$, $-SR^{46}$, $-SO_2R^{46}$, $-SO_3H$, $-SO_2OR^{46}$, $-Si(R^{46})_3$, $-CO_2H$, $-CO_2R^{46}$, $-C(=O)R^{46}$, $-C(=O)NH_2$, $-C(=O)NH(R^{46})$, $-C(=O)N(R^{46})_2$, $-C(=O)SH$, $-C(=O)SR^{46}$, optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, or optionally substituted 5-10 membered heteroaryl, wherein each instance of $R^{46}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen, sulfur, or nitrogen protecting group, or two $R^{46}$ groups are joined to form an optionally substituted 3-10 membered heterocyclyl or optionally substituted 5-10 membered heteroaryl ring;

$R^7$ is hydrogen, $-OH$, $-OR^{47}$, $-NH_2$, $-NHR^{47}$, $-N(R^{47})_2$, $-NH-NH-R^{47}$, $-NR^{47}-NHR^{47}$, $N=NR^{47}$, $-N_3$, $-SH$, $-SR^{47}$, $-SO_2R^{47}$, $-SO_3H$, $-SO_2OR^{47}$, $-Si(R^{47})_3$, $-CO_2H$, $-CO_2R^{47}$, $-C(=O)R^{47}$, $-C(=O)NH_2$, $-C(=O)NH(R^{47})$, $-C(=O)N(R^{47})_2$, $-C(=O)SH$, $-C(=O)SR^{47}$, optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, or optionally substituted 5-10 membered heteroaryl, wherein each instance of $R^{47}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen, sulfur, or nitrogen protecting group, or two $R^{47}$ groups are joined to form an optionally substituted 3-10 membered heterocyclyl or optionally substituted 5-10 membered heteroaryl ring;

$R^8$ is hydrogen, halogen, $-OH$, $-OR^{48}$, $-NH_2$, $-NHR^{48}$, $-N(R^{48})_2$, $-NH-NH-R^{48}$, $-NR^{48}-NHR^{48}$, $-N=NR^{48}$, $-N_3$, $-SH$, $-SR^{48}$, $-Si(R^{48})_3$, $-SO_2R^{48}$, $-SO_3H$, $-SO_2OR^{48}$, $-CO_2H$, $-CO_2R^{48}$, $-C(=O)R^{48}$, $-C(=O)NH_2$, $-C(=O)NH(R^{48})$, $-C(=O)N(R^{48})_2$, $-C(=O)SR^{48}$, $-C(OH)(OR^{48})R^{48}$, $-C(OH)_2R^{48}$, $-C(OR^{48})_2R^{48}$, optionally substituted $C_{1-20}$alkyl, optionally substituted $C_{2-20}$alkenyl, optionally substituted $C_{2-20}$alkynyl, optionally substituted $C_{3-10}$ carbocyclyl, optionally substituted 3-10 membered heterocyclyl, $C_{6-14}$ optionally substituted aryl, or optionally substituted 5-10 membered heteroaryl, wherein each instance of $R^{48}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen, sulfur, or nitrogen protecting group, or two $R^{48}$ groups are joined to form an optionally substituted 3-10 membered heterocyclyl or optionally substituted 5-10 membered heteroaryl ring;

$R^9$ is hydrogen, halogen, $-OH$, $-OR^{49}$, $-NH_2$, $-NHR^{49}$, $-N(R^{49})_2$, $-NH-NH-R^{49}$, $-NR^{49}-NHR^{49}$, $-N=NR^{49}$, $-N_3$, $-SH$, $-SR^{49}$, $-Si(R^{49})_3$, $-SO_2R^{49}$, $-SO_3H$, $-SO_2OR^{49}$, $-CO_2H$, $-CO_2R^{49}$, $-C(=O)R^{49}$, $-C(=O)NH_2$, $-C(=O)NH(R^{49})$, $-C(=O)N(R^{49})_2$, $-C(=O)SR^{49}$, $-P(=O)(OH)_2$, $-P(=O)(OH)(OR^{49})$, $-P(=O)(OR^{49})_2$, optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, $C_{6-14}$ optionally substituted aryl, or optionally substituted 5-10 membered heteroaryl, wherein each instance of $R^{49}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen, sulfur, or nitrogen protecting group, or two $R^{49}$ groups are joined to form an optionally substituted 3-10 membered heterocyclyl or optionally substituted 5-10 membered heteroaryl ring; and ===== represents a single or double bond.

In another aspect, provided is a compound of Formula (II):

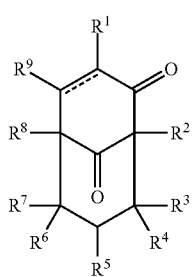

(II)

or a salt, isomer, or tautomer thereof, or mixture thereof; wherein:

$R^1$ is hydrogen, halogen, —OH, —OR$^{41}$, —N$_3$, —NH$_2$, —NH(R$^{41}$), —N(R$^{41}$)$_2$, —NH—NH—R$^{41}$, —NR$^{41}$—NHR$^{41}$, —N=NR$^{41}$, —N$_3$, —SH, —SR$^{41}$, —SO$_2$R$^{41}$, —SO$_3$H, —SO$_2$OR$^{41}$, —Si(R$^{41}$)$_3$, —CO$_2$H, —CO$_2$R$^{41}$, —C(=O)R$^{41}$, —C(=O)NH$_2$, —C(=O)NH(R$^{41}$), —C(=O)N(R$^{41}$)$_2$, —C(=O)SH, —C(=O)SR$^{41}$, optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, or optionally substituted 5-10 membered heteroaryl, wherein each instance of $R^{41}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen, sulfur, or nitrogen protecting group, or two $R^{41}$ groups are joined to form an optionally substituted 3-10 membered heterocyclyl or optionally substituted 5-10 membered heteroaryl ring;

$R^2$ is hydrogen, —Si(R$^{42}$)$_3$, —SO$_2$R$^{42}$, —SO$_3$H, —SO$_2$OR$^{42}$, —CO$_2$H, —CO$_2$R$^{42}$, —C(=O)R$^{42}$, —C(=O)NH$_2$, —C(=O)NH(R$^{42}$), —C(=O)N(R$^{42}$)$_2$, —C(=O)SH, —C(=O)SR$^{42}$, optionally substituted $C_{1-20}$alkyl, optionally substituted $C_{2-20}$alkenyl, optionally substituted $C_{2-20}$alkynyl, optionally substituted $C_{6-14}$aryl, or optionally substituted 5-10 membered heteroaryl, wherein each instance of $R^{42}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, or optionally substituted 5-10 membered heteroaryl, or an oxygen, sulfur, or nitrogen protecting group, or two $R^{42}$ groups are joined to form an optionally substituted 3-10 membered heterocyclyl or optionally substituted 5-10 membered heteroaryl ring;

$R^3$ is hydrogen, optionally substituted $C_{1-20}$alkyl, optionally substituted $C_{2-20}$alkenyl, or optionally substituted $C_{2-20}$alkynyl;

$R^4$ is hydrogen, optionally substituted $C_{1-20}$alkyl, optionally substituted $C_{2-20}$alkenyl, or optionally substituted $C_{2-20}$alkynyl;

$R^5$ is hydrogen, halogen, —OH, —OR$^{45}$, —NH$_2$, —NHR$^{45}$, —N(R$^{45}$)$_2$, —NH(R$^{45}$), —N(R$^{45}$)$_2$, —NH—NH—R$^{45}$, —NR$^{45}$—NHR$^{45}$, —N=NR$^{45}$, —N$_3$, —SH, —SR$^{45}$, —SO$_2$R$^{45}$, —SO$_3$H, —SO$_2$OR$^{45}$, —Si(R$^{45}$)$_3$, —CO$_2$H, —CO$_2$R$^{45}$, —C(=O)R$^{45}$, —C(=O)NH$_2$, —C(=O)NH(R$^{45}$), —C(=O)N(R$^{45}$)$_2$, —C(=O)SH, —C(=O)SR$^{45}$, optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, or optionally substituted 5-10 membered heteroaryl, wherein each instance of $R^{45}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen, sulfur, or nitrogen protecting group, or two $R^{45}$ groups are joined to form an optionally substituted 3-10 membered heterocyclyl or optionally substituted 5-10 membered heteroaryl ring;

$R^6$ is hydrogen, —OH, —OR$^{46}$, —NH$_2$, —NHR$^{46}$, —N(R$^{46}$)$_2$, —NH—NH—R$^{46}$, —NR$^{46}$—NHR$^{46}$, —N=NR$^{46}$, —N$_3$, —SH, —SR$^{46}$, —SO$_2$R$^{46}$, —SO$_3$H, —SO$_2$OR$^{46}$, —Si(R$^{46}$)$_3$, —CO$_2$H, —CO$_2$R$^{46}$, —C(=O)R$^{46}$, —C(=O)NH$_2$, —C(=O)NH(R$^{46}$), —C(=O)N(R$^{46}$)$_2$, —C(=O)SH, —C(=O)SR$^{46}$, optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, or optionally substituted 5-10 membered heteroaryl, wherein each instance of $R^{46}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen, sulfur, or nitrogen protecting group, or two $R^{46}$ groups are joined to form an optionally substituted 3-10 membered heterocyclyl or optionally substituted 5-10 membered heteroaryl ring;

$R^7$ is hydrogen, —OH, —OR$^{47}$, —NH$_2$, —NHR$^{47}$, —N(R$^{47}$)$_2$, —NH—NH—R$^{47}$, —NR$^{47}$—NHR$^{47}$, —N=NR$^{47}$, —N$_3$, —SH, —SR$^{47}$, —SO$_2$R$^{47}$, —SO$_3$H, —SO$_2$OR$^{47}$, —Si(R$^{47}$)$_3$, —CO$_2$H, —CO$_2$R$^{47}$, —C(=O)R$^{47}$, —C(=O)NH$_2$, —C(=O)NH(R$^{47}$), —C(=O)N(R$^{47}$)$_2$, —C(=O)SH, —C(=O)SR$^{47}$, optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, or optionally substituted 5-10 membered heteroaryl, wherein each instance of $R^{47}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen, sulfur, or nitrogen protecting group, or two $R^{47}$ groups are joined to form an optionally substituted 3-10 membered heterocyclyl or optionally substituted 5-10 membered heteroaryl ring;

$R^8$ is hydrogen, halogen, —OH, —OR$^{48}$, —NH$_2$, —NHR$^{48}$, —N(R$^{48}$)$_2$, —NH—NH—R$^{48}$, —NR$^{48}$—NHR$^{48}$, —N=NR$^{48}$, —N$_3$, —SH, —SR$^{48}$, —Si(R$^{48}$)$_3$, —SO$_2$R$^{48}$, —SO$_3$H, —SO$_2$OR$^{48}$, —CO$_2$H, —CO$_2$R$^{48}$, —C(=O)R$^{48}$, —C(=O)NH$_2$, —C(=O)NH(R$^{48}$), —C(=O)N(R$^{48}$)$_2$, —C(=O)SR$^{48}$, —C(OH)(OR$^{48}$)R$^{48}$, —C(OH)$_2$R$^{48}$, —C(OR$^{48}$)$_2$R$^{48}$, optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, $C_{6-14}$ optionally substituted aryl, or optionally substituted 5-10 membered heteroaryl, wherein each instance of $R^{48}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen, sulfur, or nitrogen protecting group, or two $R^{A8}$ groups are joined to form an optionally substituted 3-10 membered heterocyclyl or optionally substituted 5-10 membered heteroaryl ring;

$R^9$ is hydrogen, halogen, —OH, —$OR^{A9}$, —$NH_2$, —$NHR^{A9}$, —$N(R^{A9})_2$, —NH—NH—$R^{A9}$, —$NR^{A9}$—$NHR^{A9}$, —N=$NR^{A9}$, —$N_3$, —SH, —$SR^{A9}$, —$Si(R^{A9})_3$, —$SO_2R^{A9}$, —$SO_3H$, —$SO_2R^{A9}$, —$CO_2H$, —$CO_2R^{A9}$, —$C(=O)R^{A9}$, —$C(=O)NH_2$, —$C(=O)NH(R^{A9})$, —$C(=O)N(R^{A9})_2$, —$C(=O)SR^{A9}$, —$P(=O)(OH)_2$, —$P(=O)(OH)(OR^{A9})$, —$P(=O)(OR^{A9})_2$, optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, $C_{6-14}$ optionally substituted aryl, or optionally substituted 5-10 membered heteroaryl, wherein each instance of $R^{A9}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen, sulfur, or nitrogen protecting group, or two $R^{A9}$ groups are joined to form an optionally substituted 3-10 membered heterocyclyl or optionally substituted 5-10 membered heteroaryl ring; and ═══ represents a single or double bond.

In any of the above embodiments, ═══ represents a single bond. In any of the above embodiments, ═══ represents a double bond.

For example, in certain embodiments wherein ═══ represents a double bond, the compound of Formulae (I) and (II) are of Formulae (I-y) and (II-y), respectively:

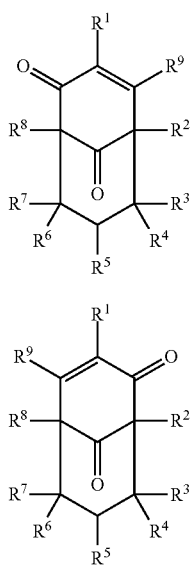

(I-y)

(II-y)

or a salt, isomer, or tautomer thereof, or mixture thereof.

In certain embodiments wherein ═══ represents a single bond, the compound of Formulae (I) and (II) are of Formulae (I-z) and (II-z), respectively:

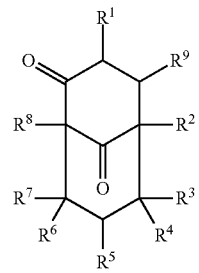

(I-z)

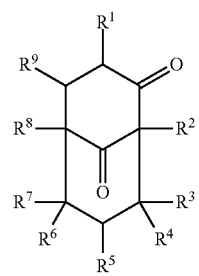

(II-z)

or a salt, isomer, or tautomer thereof, or mixture thereof. It is understood from Formulae (I-z) and (II-z) that cis and trans isomers at the carbons attached to $R^1$ and $R^9$ are contemplated.

In certain embodiments, wherein $R^9$ is —$OR^{A9}$ and ═══ represents a double bond, the compound of Formulae (I) and (II) are of Formulae (I-a) and (II-a), respectively:

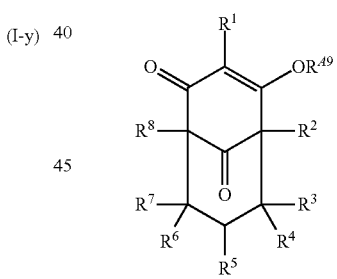

(I-a)

(II-a)

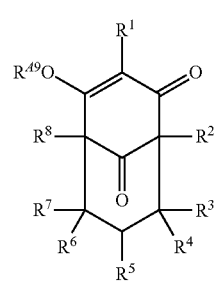

or a salt, isomer, or tautomer thereof, or mixture thereof.

In certain embodiments, wherein $R^9$ is —OH and ═══ represents a double bond, the compounds of Formulae (I) and (II) are tautomers, e.g., Formulae (I-b) and (II-b), respectively:

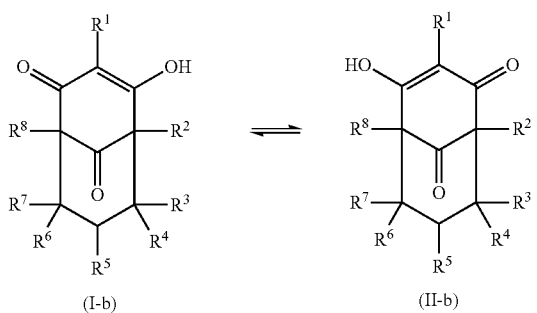

(I-b)          (II-b)

or a salt, isomer, or tautomer thereof, or mixture thereof.

In certain embodiments, wherein ==== represents a double bond, the compound of Formula (I) is selected from any one of two stereoisomers, i.e., of Formula (III) or (III-ent):

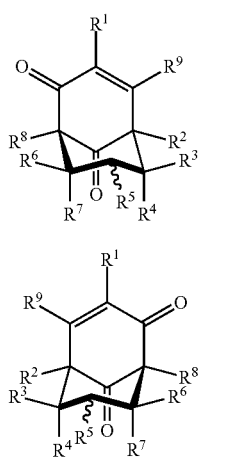

(III)

(III-ent)

or a salt, isomer, or tautomer thereof, or mixture thereof, wherein $R^5$ is in the axial or equatorial position. In certain embodiments, $R^5$ is in the equatorial position. In other embodiments, $R^5$ is in the axial position.

In certain embodiments, wherein $R^9$ is —$OR^{49}$ and ==== represents a double bond, the compound of Formulae (III) and (III-ent) are of Formulae (III-a) and (III-a-ent), respectively:

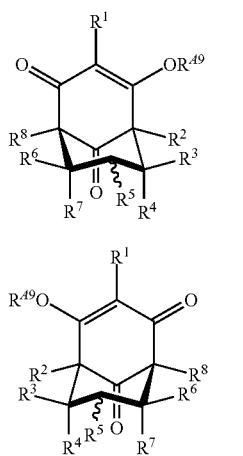

(III-a)

(III-a-ent)

or a salt, isomer, or tautomer thereof, or mixture thereof, wherein $R^5$ is in the axial or equatorial position. In certain embodiments, $R^5$ is in the equatorial position. In other embodiments, $R^5$ is in the axial position.

In certain embodiments, wherein $R^9$ is —OH and ==== represents a double bond, the compound of Formulae (III) and (III-ent) are of Formulae (III-b) and (III-b-ent), respectively:

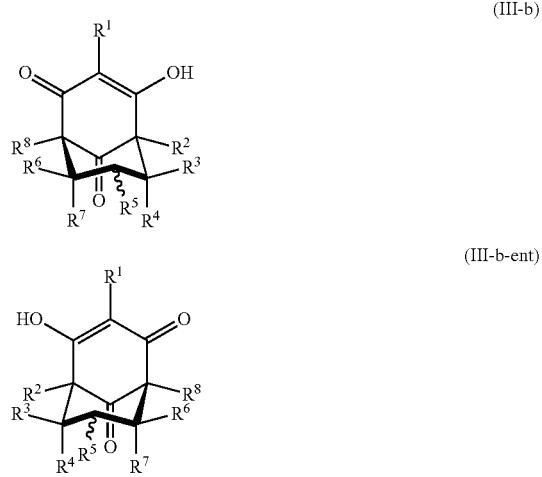

(III-b)

(III-b-ent)

or a salt, isomer, or tautomer thereof, or mixture thereof, wherein $R^5$ is in the axial or equatorial position. In certain embodiments, $R^5$ is in the equatorial position. In other embodiments, $R^5$ is in the axial position.

In certain embodiments, wherein ==== represents a double bond, the compound of Formula (II) is selected from any one of two stereoisomers, i.e., Formula (IV) or (IV-ent):

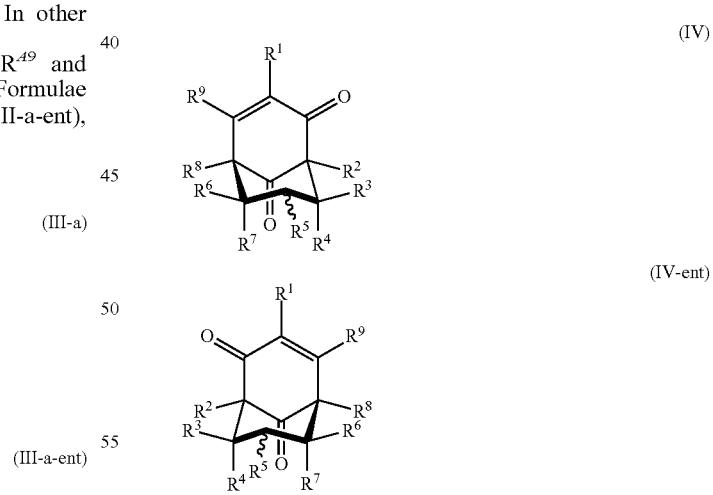

(IV)

(IV-ent)

or a salt, isomer, or tautomer thereof, or mixture thereof, wherein $R^5$ is in the axial or equatorial position. In certain embodiments, $R^5$ is in the equatorial position. In other embodiments, $R^5$ is in the axial position.

In certain embodiments, wherein $R^9$ is —$OR^{49}$ and ==== represents a double bond, the compound of Formulae (IV) and (IV-ent) are of Formulae (IV-a) and (IV-a-ent), respectively:

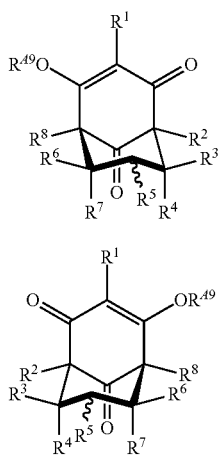

(IV-a)

(IV-a-ent)

or a salt, isomer, or tautomer thereof, or mixture thereof, wherein $R^5$ is in the axial or equatorial position. In certain embodiments, $R^5$ is in the equatorial position. In other embodiments, $R^5$ is in the axial position.

In certain embodiments, wherein $R^9$ is —OH and ==== represents a double bond, the compound of Formulae (IV) and (IV-ent) are of Formulae (IV-b) and (IV-b-ent), respectively:

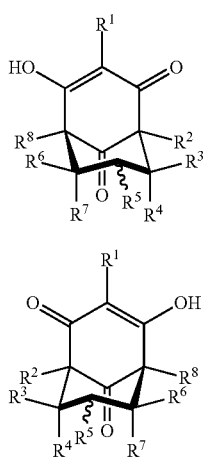

(IV-b)

(IV-b-ent)

or a salt, isomer, or tautomer thereof, or mixture thereof, wherein $R^5$ is in the axial or equatorial position. In certain embodiments, $R^5$ is in the equatorial position. In other embodiments, $R^5$ is in the axial position.

Compounds of Formulae (III-b) and (IV-b) are tautomers:

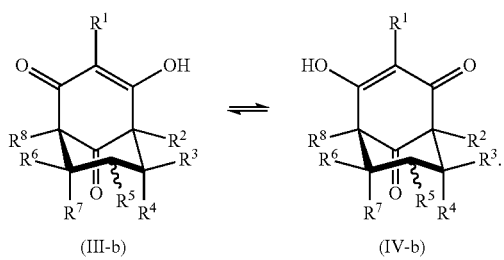

(III-b) (IV-b)

Likewise, compounds of Formulae (III-ent) and (IV-ent) are tautomers:

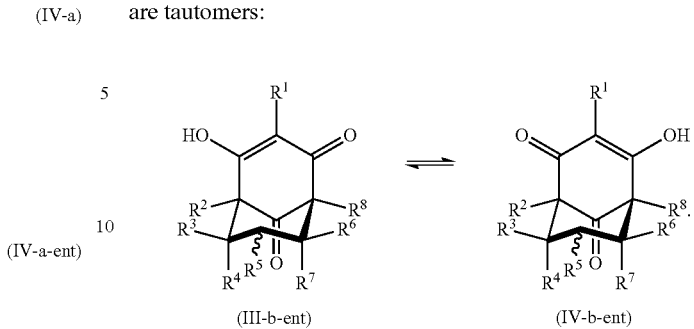

(III-b-ent) (IV-b-ent)

As generally defined above, $R^1$ is hydrogen, halogen, —OH, —$OR^{41}$, —$NH_2$, —$NH(R^{41})$, —$N(R^{41})_2$, —NH—NH—$R^{41}$, —$NR^{41}$—$NHR^{41}$, —N=$NR^{41}$, —$N_3$, —SH, —$SR^{41}$—$SO_2R^{41}$, —$SO_3H$, —$SO_2OR^{41}$, —$Si(R^{41})_3$, —$CO_2H$, —$CO_2R^{41}$, —C(=O)$R^{41}$, —C(=O)$NH_2$, —C(=O)$NH(R^{41})$, —C(=O)$N(R^{41})_2$, —C(=O)SH, —C(=O)$SR^{41}$, optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, or optionally substituted 5-10 membered heteroaryl, wherein each instance of $R^{41}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, or optionally substituted 5-10 membered heteroaryl, or an oxygen, sulfur, or nitrogen protecting group, or two $R^{41}$ groups are joined to form an optionally substituted 3-10 membered heterocyclyl or optionally substituted 5-10 membered heteroaryl ring.

In certain embodiments, $R^1$ is hydrogen.

In certain embodiments, $R^1$ is halogen, i.e., in certain embodiments, $R^1$ is —Br, —Cl, —I, or —F. In certain embodiments, $R^1$ is —Br. In certain embodiments, $R^1$ is —Cl. In certain embodiments, $R^1$ is —I. In certain embodiments, $R^1$ is —F.

In certain embodiments, $R^1$ is —OH or —$OR^{41}$, and $R^{41}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen protecting group.

In certain embodiments, $R^1$ is —$NH_2$, —$NH(R^{41})$, —$N(R^{41})_2$, —NH—NH—$R^{41}$, —$NR^{41}$—$NHR^{41}$, —N=$NR^{41}$, —$N_3$, and each instance of $R^{41}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, or optionally substituted 5-10 membered heteroaryl, or a nitrogen protecting group, or two $R^{41}$ groups are joined to form an optionally substituted 3-10 membered heterocyclyl or optionally substituted 5-10 membered heteroaryl ring.

In certain embodiments, $R^1$ is —SH or —$SR^{41}$, and $R^{41}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or a sulfur protecting group.

In certain embodiments, $R^1$ is —$SO_2R^{A1}$, —$SO_3H$, or —$SO_2OR^{A1}$, and $R^{A1}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen protecting group.

In certain embodiments, $R^1$ is —$CO_2H$, —$CO_2R^{A1}$, —$C(=O)R^{A1}$, —$C(=O)NH_2$, —$C(=O)NH(R^{A1})$, —$C(=O)N(R^{A1})_2$, —$C(=O)SH$, or —$C(=O)SR^{A1}$, and each instance of $R^{A1}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen, sulfur, or nitrogen protecting group, or two $R^{A1}$ groups are joined to form an optionally substituted 3-10 membered heterocyclyl or optionally substituted 5-10 membered heteroaryl ring.

In certain embodiments, $R^1$ is —$CO_2H$.

In certain embodiments, $R^1$ is —$CO_2R^{A1}$, and each instance of $R^{A1}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen protecting group.

In certain embodiments, $R^1$ is —$C(=O)R^{A1}$, and each instance of $R^{A1}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, or optionally substituted 5-10 membered heteroaryl.

In certain embodiments, $R^1$ is —$C(=O)NH_2$, —$C(=O)NH(R^{A1})$, or —$C(=O)N(R^{A1})_2$, and each instance of $R^{A1}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or a nitrogen protecting group, or two $R^{A1}$ groups are joined to form an optionally substituted 3-10 membered heterocyclyl or optionally substituted 5-10 membered heteroaryl ring In certain embodiments, $R^1$ is —$C(=O)SH$ or —$C(=O)SR^{A1}$, and each instance of $R^{A1}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or a sulfur protecting group.

In certain embodiments $R^1$ is —$Si(R^{A1})_3$, and each instance of $R^{A1}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, or optionally substituted 5-10 membered heteroaryl.

In certain embodiments, $R^1$ is optionally substituted $C_{1-20}$alkyl. In certain embodiments, $R^1$ is optionally substituted $C_{1-10}$alkyl. In certain embodiments, $R^1$ is optionally substituted $C_{1-8}$alkyl. In certain embodiments, $R^1$ is optionally substituted $C_{1-6}$alkyl. In certain embodiments, $R^1$ is optionally substituted $C_{1-4}$alkyl. In certain embodiments, $R^1$ is optionally substituted $C_{1-3}$alkyl. In any of the above instances, in certain embodiments, $R^1$ is substituted alkyl; however, in other embodiments, $R^1$ is unsubstituted alkyl. In certain embodiments, $R^1$ is —$CH_3$, —$CH_2CH_3$, —$(CH_2)_2CH_3$, —$(CH_2)_3CH_3$, —$(CH_2)_4CH_3$, —$(CH_2)_5CH_3$, —$(CH_2)_6CH_3$, —$(CH_2)_7CH_3$, —$(CH_2)_8CH_3$, or —$(CH_2)_9CH_3$. In certain embodiments, $R^1$ is —$CH_3$, —$CH_2CH_3$, or —$(CH_2)_2CH_3$. In certain embodiments, $R^1$ is —$CH_2CH_2OR^{B1}$, wherein $R^{B1}$ is hydrogen or an oxygen protecting group. In certain embodiments, $R^1$ is —$CH_2CH_2OH$.

In certain embodiments, $R^1$ is optionally substituted $C_{2-20}$alkenyl. In certain embodiments, $R^1$ is optionally substituted $C_{2-10}$alkenyl. In certain embodiments, $R^1$ is optionally substituted $C_{2-8}$alkenyl. In certain embodiments, $R^1$ is optionally substituted $C_{2-6}$alkenyl. In certain embodiments, $R^1$ is optionally substituted $C_{4-6}$alkenyl. In certain embodiments, $R^1$ is optionally substituted $C_{2-3}$alkenyl. In certain embodiments, $R^1$ is optionally substituted $C_{5-20}$alkenyl. In any of the above instances, in certain embodiments, $R^1$ is substituted alkenyl; however, in other embodiments, $R^1$ is unsubstituted alkenyl. For example, in certain embodiments, $R^1$ is the substituted $C_4$ alkenyl group:

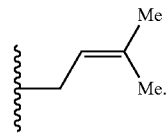

However, in certain embodiments, $R^1$ is not optionally substituted $C_{2-20}$alkenyl. In certain embodiments, $R^1$ is not optionally substituted $C_{2-10}$alkenyl. In certain embodiments, $R^1$ is not optionally substituted $C_{2-8}$alkenyl. In certain embodiments, $R^1$ is not optionally substituted $C_{4-8}$alkenyl. In certain embodiments, $R^1$ is not optionally substituted $C_{4-6}$alkenyl. In certain embodiments, $R^1$ is not optionally substituted $C_4$alkenyl, e.g., for example, in certain embodiments, $R^1$ is not the substituted $C_4$alkenyl group:

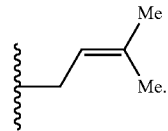

In certain embodiments, $R^1$ is optionally substituted $C_{2-20}$alkynyl. In certain embodiments, $R^1$ is optionally substituted $C_{2-10}$alkynyl. In certain embodiments, $R^1$ is optionally substituted $C_{2-8}$alkynyl. In certain embodiments, $R^1$ is optionally substituted $C_{2-6}$alkynyl. In certain embodiments, $R^1$ is optionally substituted $C_{4-6}$alkynyl. In certain embodiments, $R^1$ is optionally substituted $C_{2-3}$alkynyl. In certain embodiments, $R^1$ is optionally substituted $C_{5-20}$alkynyl. In any of the above instances, in certain embodiments, $R^1$ is substituted alkynyl; however, in other embodiments, $R^1$ is unsubstituted alkynyl.

In certain embodiments, $R^1$ is optionally substituted $C_{3-10}$carbocyclyl. In certain embodiments, $R^1$ is optionally substituted $C_{3-8}$carbocyclyl. In certain embodiments, $R^1$ is optionally substituted $C_{3-6}$carbocyclyl. In certain embodiments, $R^1$ is optionally substituted $C_{4-6}$carbocyclyl. In certain embodiments, $R^1$ is optionally substituted $C_{5-6}$carbocyclyl. In any of the above instances, in certain embodiments, $R^1$ is substituted carbocyclyl; however, in other embodiments, $R^1$ is unsubstituted carbocyclyl.

In certain embodiments, $R^1$ is optionally substituted 3-10 membered heterocyclyl. In certain embodiments, $R^1$ is optionally substituted 3-8 membered heterocyclyl. In certain embodiments, $R^1$ is optionally substituted 3-6 membered heterocyclyl. In certain embodiments, $R^1$ is optionally substituted 4-6 membered heterocyclyl. In certain embodiments, $R^1$ is optionally substituted 5-6 membered heterocyclyl. In any of the above instances, in certain embodiments, $R^1$ is substituted heterocyclyl; however, in other embodiments, $R^1$ is unsubstituted heterocyclyl.

In certain embodiments, $R^1$ is optionally substituted $C_{6-14}$aryl. In certain embodiments, $R^1$ is optionally substituted $C_6$ aryl (i.e., phenyl). In certain embodiments, $R^1$ is optionally substituted $C_{10}$ aryl (i.e., napthyl). In certain embodiments, $R^1$ is optionally substituted $C_{14}$ aryl (i.e., anthracyl). In any of the above instances, in certain embodiments, $R^1$ is substituted aryl; however, in other embodiments, $R^1$ is unsubstituted aryl.

In certain embodiments, $R^1$ is optionally substituted 5-10 membered heteroaryl. In certain embodiments, $R^1$ is optionally substituted 5-8 membered heteroaryl. In certain embodiments, $R^1$ is optionally substituted 5-6 membered heteroaryl. In any of the above instances, in certain embodiments, $R^1$ is substituted heteroaryl; however, in other embodiments, $R^1$ is unsubstituted heteroaryl.

As generally defined above, $R^2$ is hydrogen, —Si($R^{A2}$)$_3$, —SO$_2$R$^{A2}$, —SO$_3$H, —SO$_2$OR$^{A2}$, —CO$_2$H, —CO$_2$R$^{A2}$, —C(=O)R$^{A2}$, —C(=O)NH$_2$, —C(=O)NH(R$^{A2}$), —C(=O)N(R$^{A2}$)$_2$, —C(=O)SH, —C(=O)SR$^{A2}$, optionally substituted $C_{1-20}$alkyl, optionally substituted $C_{2-20}$alkenyl, optionally substituted $C_{2-20}$alkynyl, optionally substituted $C_{6-14}$aryl, or optionally substituted 5-10 membered heteroaryl, wherein each instance of $R^{A2}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen, sulfur, or nitrogen protecting group, or two $R^{A2}$ groups are joined to form an optionally substituted 3-10 membered heterocyclyl or optionally substituted 5-10 membered heteroaryl ring.

In certain embodiments, $R^2$ is hydrogen.

In certain embodiments $R^2$ is —Si($R^{A2}$)$_3$, and each instance of $R^{A2}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, or optionally substituted 5-10 membered heteroaryl.

In certain embodiments, $R^2$ is —SO$_2$R$^{A2}$, —SO$_3$H, or —SO$_2$OR$^{A2}$, and $R^{A2}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen protecting group.

In certain embodiments $R^2$ is —CO$_2$H, —CO$_2$R$^{A2}$, —C(=O)R$^{A2}$, —C(=O)NH$_2$, —C(=O)NH(R$^{A2}$), —C(=O)N(R$^{A2}$)$_2$, —C(=O)SH, or —C(=O)SR$^{A2}$, and each instance of $R^{A2}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen, sulfur, or nitrogen protecting group, or two $R^{A2}$ groups are joined to form an optionally substituted 3-10 membered heterocyclyl or optionally substituted 5-10 membered heteroaryl ring.

In certain embodiments, $R^2$ is —CO$_2$H.

In certain embodiments, $R^2$ is —CO$_2$R$^{A2}$, and each instance of $R^{A2}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen protecting group.

In certain embodiments, $R^2$ is —C(=O)R$^{A2}$, and each instance of $R^{A2}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, or optionally substituted 5-10 membered heteroaryl.

In certain embodiments, $R^2$ is —C(=O)NH$_2$, —C(=O)NH($R^{A2}$), or —C(=O)N($R^{A2}$)$_2$, and each instance of $R^{A2}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or a nitrogen protecting group, or two $R^{A2}$ groups are joined to form an optionally substituted 3-10 membered heterocyclyl or optionally substituted 5-10 membered heteroaryl ring In certain embodiments, $R^2$ is —C(=O)SH or —C(=O)SR$^{A2}$, and each instance of $R^{A2}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or a sulfur protecting group.

In certain embodiments, $R^2$ is optionally substituted $C_{1-20}$alkyl. In certain embodiments, $R^2$ is optionally substituted $C_{1-10}$alkyl. In certain embodiments, $R^2$ is optionally substituted $C_{1-8}$alkyl. In certain embodiments, $R^2$ is optionally substituted $C_{1-6}$alkyl. In certain embodiments, $R^2$ is optionally substituted $C_{1-4}$alkyl. In certain embodiments, $R^2$ is optionally substituted $C_{1-3}$alkyl. In any of the above instances, in certain embodiments, $R^2$ is substituted alkyl; however, in other embodiments, $R^2$ is unsubstituted alkyl. In certain embodiments, $R^2$ is —CH$_3$, —CH$_2$CH$_3$, —(CH$_2$)$_2$CH$_3$, —(CH$_2$)$_3$CH$_3$, —(CH$_2$)$_4$CH$_3$, —(CH$_2$)$_5$CH$_3$, —(CH$_2$)$_6$CH$_3$, —(CH$_2$)$_7$CH$_3$, —(CH$_2$)$_8$CH$_3$, or —(CH$_2$)$_9$CH$_3$. In certain embodiments, $R^2$ is —CH$_3$, —CH$_2$CH$_3$, or —(CH$_2$)$_2$CH$_3$.

In certain embodiments, $R^2$ is optionally substituted $C_{2-20}$alkenyl. In certain embodiments, $R^2$ is optionally substituted $C_{2-10}$alkenyl. In certain embodiments, $R^2$ is optionally substituted $C_{2-8}$alkenyl. In certain embodiments, $R^2$ is optionally substituted $C_{2-6}$alkenyl. In certain embodiments, $R^2$ is optionally substituted $C_{4-6}$alkenyl. In certain embodiments, $R^2$ is optionally substituted $C_{2-3}$alkenyl. In certain embodiments, $R^2$ is optionally substituted $C_{5-20}$alkenyl. In any of the above instances, in certain embodiments, $R^2$ is substituted alkenyl; however, in other embodiments, $R^2$ is unsubstituted alkenyl. For example, in certain embodiments, $R^2$ is the substituted $C_4$alkenyl group:

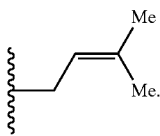

However, in certain embodiments, $R^2$ is not optionally substituted $C_{2-20}$alkenyl. In certain embodiments, $R^2$ is not optionally substituted $C_{2-10}$alkenyl. In certain embodiments, $R^2$ is not optionally substituted $C_{2-8}$alkenyl. In certain embodiments, $R^2$ is not optionally substituted $C_{4-8}$alkenyl. In certain embodiments, $R^2$ is not optionally substituted $C_{4-6}$alkenyl. In certain embodiments, $R^2$ is not optionally substituted $C_4$alkenyl, e.g., for example, in certain embodiments, $R^2$ is not the substituted $C_4$alkenyl group:

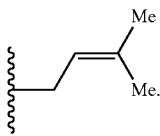 [SMILES: *CC=C(C)C]

In certain embodiments, $R^2$ is optionally substituted $C_{2-20}$alkynyl. In certain embodiments, $R^2$ is optionally substituted $C_{2-10}$alkynyl. In certain embodiments, $R^2$ is optionally substituted $C_{2-8}$alkynyl. In certain embodiments, $R^2$ is optionally substituted $C_{2-6}$alkynyl. In certain embodiments, $R^2$ is optionally substituted $C_{4-6}$alkynyl. In certain embodiments, $R^2$ is optionally substituted $C_{2-3}$alkynyl. In certain embodiments, $R^2$ is optionally substituted $C_{5-20}$alkynyl. In any of the above instances, in certain embodiments, $R^2$ is substituted alkynyl; however, in other embodiments, $R^2$ is unsubstituted alkynyl.

In certain embodiments, $R^2$ is optionally substituted $C_{6-14}$aryl. In certain embodiments, $R^2$ is optionally substituted $C_6$ aryl (i.e., phenyl). In certain embodiments, $R^2$ is optionally substituted $C_{10}$ aryl (i.e., napthyl). In certain embodiments, $R^2$ is optionally substituted $C_{14}$ aryl (i.e., anthracyl). In any of the above instances, in certain embodiments, $R^2$ is substituted aryl; however, in other embodiments, $R^2$ is unsubstituted aryl.

In certain embodiments, $R^2$ is optionally substituted 5-10 membered heteroaryl. In certain embodiments, $R^2$ is optionally substituted 5-8 membered heteroaryl. In certain embodiments, $R^2$ is optionally substituted 5-6 membered heteroaryl. In any of the above instances, in certain embodiments, $R^2$ is substituted heteroaryl; however, in other embodiments, $R^2$ is unsubstituted heteroaryl.

As generally defined above, in certain embodiments, $R^3$ is hydrogen, optionally substituted $C_{1-20}$alkyl, optionally substituted $C_{2-20}$alkenyl, or optionally substituted $C_{2-20}$alkynyl; and $R^4$ is hydrogen, optionally substituted $C_{1-20}$alkyl, optionally substituted $C_{2-20}$alkenyl, or optionally substituted $C_{2-20}$alkynyl.

In certain embodiments, $R^3$ is hydrogen. In certain embodiments, $R^4$ is hydrogen. In certain embodiments, both $R^3$ and $R^4$ are hydrogen.

However, in certain embodiments, $R^3$ is optionally substituted $C_{1-20}$alkyl, optionally substituted $C_{2-20}$alkenyl, or optionally substituted $C_{2-20}$alkynyl, and $R^4$ is hydrogen. In certain embodiments, $R^3$ is optionally substituted $C_{1-20}$alkyl, and $R^4$ is hydrogen. In certain embodiments, $R^3$ is optionally substituted $C_{2-20}$alkenyl, and $R^4$ is hydrogen. In certain embodiments, $R^3$ is optionally substituted $C_{2-20}$alkynyl, and $R^4$ is hydrogen.

In other embodiments, $R^4$ is optionally substituted $C_{1-20}$alkyl, optionally substituted $C_{2-20}$alkenyl, or optionally substituted $C_{2-20}$alkynyl, and $R^3$ is hydrogen. In certain embodiments, $R^4$ is optionally substituted $C_{1-20}$alkyl, and $R^3$ is hydrogen. In certain embodiments, $R^4$ is optionally substituted $C_{2-20}$alkenyl, and $R^3$ is hydrogen. In certain embodiments, $R^4$ is optionally substituted $C_{2-20}$alkynyl, and $R^3$ is hydrogen.

In yet other embodiments, $R^3$ is optionally substituted $C_{1-20}$alkyl, optionally substituted $C_{2-20}$alkenyl, or optionally substituted $C_{2-20}$alkynyl, and $R^4$ is optionally substituted $C_{1-20}$alkyl, optionally substituted $C_{2-20}$alkenyl, or optionally substituted $C_{2-20}$alkynyl.

As generally defined above, $R^5$ is hydrogen, halogen, —OH, —OR$^{A5}$, —NH$_2$, —NHR$^{A5}$, —N(R$^{A5}$)$_2$, —NH—NH—R$^{A5}$, —NR$^{A5}$—NHR$^{A5}$, —N=NR$^{A5}$, —N$_3$, —SH, —SR$^{A5}$, —SO$_2$R$^{A5}$, —SO$_3$H, —SO$_2$OR$^{A5}$, —Si(R$^{A5}$)$_3$, —CO$_2$H, —CO$_2$R$^{A5}$, —C(=O)R$^{A5}$, —C(=O)NH$_2$, —C(=O)NH(R$^{A5}$), —C(=O)N(R$^{A5}$)$_2$, —C(=O)SH, —C(=O)SR$^{A5}$, optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, or optionally substituted 5-10 membered heteroaryl, wherein each instance of $R^A$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen, sulfur, or nitrogen protecting group, or two $R^{A5}$ groups are joined to form an optionally substituted 3-10 membered heterocyclyl or optionally substituted 5-10 membered heteroaryl ring.

In certain embodiments, $R^5$ is in the axial position. In certain embodiments, $R^5$ is in the equatorial position.

In certain embodiments, $R^5$ is hydrogen.

In certain embodiments, $R^5$ is halogen, i.e., in certain embodiments, $R^5$ is —Br, —Cl, —I, or —F. In certain embodiments, $R^5$ is —Br. In certain embodiments, $R^5$ is —Cl. In certain embodiments, $R^5$ is —I. In certain embodiments, $R^5$ is —F. In certain embodiments, $R^5$ is a halogen in the equatorial position. In certain embodiments, $R^5$ is a halogen in the axial position.

In certain embodiments, $R^5$ is —OH or —OR$^{A5}$, and $R^{A5}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen protecting group. In certain embodiments, $R^5$ is —OH. In certain embodiments, $R^5$ is —OR$^{A5}$. In certain embodiments, $R^{A5}$ is an optionally substituted $C_{1-20}$alkyl, e.g., —CH$_3$. For example, in certain embodiments wherein $R^{A5}$ is optionally substituted $C_{1-20}$alkyl, $R^5$ is —OCH$_3$. In certain embodiments, $R^5$ is —OH or —OR$^{A5}$ in the equatorial position. In certain embodiments, $R^5$ is —OH or —OR$^{A5}$ in the axial position.

In certain embodiments, $R^5$ is —NH$_2$, —NHR$^{A5}$, —N(R$^{A5}$)$_2$, —NH—NH—R$^{A5}$, —NR$^{A5}$—NHR$^{A5}$, —N=NR$^{A5}$, or —N$_3$, and each instance of $R^{A5}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or a nitrogen protecting group, or two $R^{A5}$ groups are joined to form an optionally substituted 3-10 membered heterocyclyl or optionally substituted 5-10 membered heteroaryl ring. In certain embodiments, $R^5$ is —NH$_2$, —NHR$^{A5}$, —N(R$^{A5}$)$_2$, —NH—NH—R$^{A5}$, —NR$^{A5}$—NHR$^{A5}$, —N=NR$^{A5}$, or —N$_3$, in the equatorial position. In certain embodiments, $R^5$ is —NH$_2$, —NHR$^{A5}$, —N(R$^{A5}$)$_2$, —NH—NH—R$^{A5}$, —NR$^{A5}$—NHR$^{A5}$, —N=NR$^{A5}$, or —N$_3$, in the axial position.

In certain embodiments, $R^5$ is —SH or —SR$^{A5}$, $R^{A5}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or a sulfur protecting group. In certain embodiments, $R^5$ is —SH or —SR$^{A5}$ in the equatorial position. In certain embodiments, $R^5$ is —SH or —SR$^{A5}$ in the axial position.

In certain embodiments, $R^5$ is —SO$_2$R$^{A5}$, —SO$_3$H, or —SO$_2$OR$^{A5}$, and $R^{A5}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen protecting group. In certain embodiments, $R^5$ is —SO$_2$R$^{A5}$ in the equatorial position. In certain embodiments, $R^5$ is —SO$_2$R$^{A5}$ in the axial position.

In certain embodiments, $R^5$ is —CO$_2$H, —CO$_2$R$^{A5}$, —C(=O)R$^{A5}$, —C(=O)NH$_2$, —C(=O)NH(R$^{A5}$), —C(=O)N(R$^{A5}$)$_2$, —C(=O)SH, or —C(=O)SR$^{A5}$, and each instance of $R^{A5}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen, sulfur, or nitrogen protecting group, or two $R^{A5}$ groups are joined to form an optionally substituted 3-10 membered heterocyclyl or optionally substituted 5-10 membered heteroaryl ring. In certain embodiments, $R^5$ is —CO$_2$H, —CO$_2$R$^{A5}$, —C(=O)R$^{A5}$, —C(=O)NH$_2$, —C(=O)NH(R$^{A5}$), —C(=O)N(R$^{A5}$)$_2$, —C(=O)SH, or —C(=O)SR$^{A5}$ in the equatorial position. In certain embodiments, $R^5$ is —CO$_2$H, —CO$_2$R$^{A5}$, —C(=O)R$^{A5}$, —C(=O)NH$_2$, —C(=O)NH(R$^{A5}$), —C(=O)N(R$^{A5}$)$_2$, —C(=O)SH, or —C(=O)SR$^{A5}$ in the axial position.

In certain embodiments, $R^5$ is —CO$_2$H.

In certain embodiments, $R^5$ is —CO$_2$R$^{A5}$, and each instance of $R^{A5}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen protecting group.

In certain embodiments, $R^5$ is —C(=O)R$^{A5}$, and each instance of $R^{A5}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, or optionally substituted 5-10 membered heteroaryl.

In certain embodiments, $R^5$ is —C(=O)NH$_2$, —C(=O)NH(R$^{A5}$), or —C(=O)N(R$^{A5}$)$_2$, and each instance of $R^{A5}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or a nitrogen protecting group, or two $R^{A5}$ groups are joined to form an optionally substituted 3-10 membered heterocyclyl or optionally substituted 5-10 membered heteroaryl ring In certain embodiments, $R^5$ is —C(=O)SH or —C(=O) SR$^{A5}$, and each instance of $R^{A5}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or a sulfur protecting group.

In certain embodiments $R^5$ is —Si(R$^{A5}$)$_3$, and each instance of $R^{A5}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, or optionally substituted 5-10 membered heteroaryl. In certain embodiments, $R^5$ is —Si(R$^{A5}$)$_3$ in the equatorial position. In certain embodiments, $R^5$ is —Si(R$^{A5}$)$_3$ in the axial position.

In certain embodiments, $R^5$ is optionally substituted $C_{1-20}$alkyl. In certain embodiments, $R^5$ is optionally substituted $C_{1-10}$alkyl. In certain embodiments, $R^5$ is optionally substituted $C_{1-8}$alkyl. In certain embodiments, $R^5$ is optionally substituted $C_{1-6}$alkyl. In certain embodiments, $R^5$ is optionally substituted $C_{1-4}$alkyl. In certain embodiments, $R^5$ is optionally substituted $C_{1-3}$alkyl. In any of the above instances, in certain embodiments, $R^5$ is substituted alkyl; however, in other embodiments, $R^5$ is unsubstituted alkyl. In certain embodiments, $R^5$ is —CH$_3$, —CH$_2$CH$_3$, —(CH$_2$)$_2$CH$_3$, —(CH$_2$)$_3$CH$_3$, —(CH$_2$)$_4$CH$_3$, —(CH$_2$)$_5$CH$_3$, —(CH$_2$)$_6$CH$_3$, —(CH$_2$)$_7$CH$_3$, —(CH$_2$)$_8$CH$_3$, or —(CH$_2$)$_9$CH$_3$. In certain embodiments, $R^1$ is —CH$_3$, —CH$_2$CH$_3$, or —(CH$_2$)$_2$CH$_3$. In certain embodiments, $R^5$ is alkyl in the equatorial position. In certain embodiments, $R^5$ is alkyl in the axial position.

In certain embodiments, $R^5$ is optionally substituted $C_{2-20}$alkenyl. In certain embodiments, $R^5$ is optionally substituted $C_{2-10}$alkenyl. In certain embodiments, $R^5$ is optionally substituted $C_{2-8}$alkenyl. In certain embodiments, $R^5$ is optionally substituted $C_{2-6}$alkenyl. In certain embodiments, $R^5$ is optionally substituted $C_{4-6}$alkenyl. In certain embodiments, $R^5$ is optionally substituted $C_{2-3}$alkenyl. In certain embodiments, $R^5$ is optionally substituted $C_{5-20}$alkenyl. In any of the above instances, in certain embodiments, $R^5$ is substituted alkenyl; however, in other embodiments, $R^5$ is unsubstituted alkenyl. For example, in certain embodiments, $R^5$ is the substituted $C_4$alkenyl group:

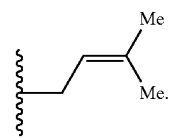

In certain embodiments, $R^5$ is alkenyl in the equatorial position. In certain embodiments, $R^5$ is alkenyl in the axial position.

However, in certain embodiments, $R^5$ is not optionally substituted $C_{2-20}$alkenyl. In certain embodiments, $R^5$ is not optionally substituted $C_{2-10}$alkenyl. In certain embodiments, $R^5$ is not optionally substituted $C_{2-8}$alkenyl. In certain embodiments, $R^5$ is not optionally substituted $C_{4-8}$alkenyl. In certain embodiments, $R^5$ is not optionally substituted $C_{4-6}$alkenyl. In certain embodiments, $R^5$ is not optionally substituted $C_4$alkenyl, e.g., for example, in certain embodiments, $R^5$ is not the substituted $C_4$alkenyl group:

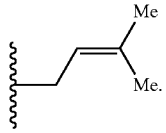 [SMILES: *CC=C(C)C]

In certain embodiments, $R^5$ is optionally substituted $C_{2-20}$alkynyl. In certain embodiments, $R^5$ is optionally substituted $C_{2-10}$alkynyl. In certain embodiments, $R^5$ is optionally substituted $C_{2-8}$alkynyl. In certain embodiments, $R^5$ is optionally substituted $C_{2-6}$alkynyl. In certain embodiments, $R^5$ is optionally substituted $C_{4-6}$alkynyl. In certain embodiments, $R^5$ is optionally substituted $C_{2-3}$alkynyl. In certain embodiments, $R^5$ is optionally substituted $C_{5-20}$alkynyl. In any of the above instances, in certain embodiments, $R^5$ is substituted alkynyl; however, in other embodiments, $R^5$ is unsubstituted alkynyl. In certain embodiments, $R^5$ is alkynyl in the equatorial position. In certain embodiments, $R^5$ is alkynyl in the axial position.

In certain embodiments, $R^5$ is optionally substituted $C_{3-10}$carbocyclyl. In certain embodiments, $R^5$ is optionally substituted $C_{3-8}$carbocyclyl. In certain embodiments, $R^5$ is optionally substituted $C_{3-6}$carbocyclyl. In certain embodiments, $R^5$ is optionally substituted $C_{4-6}$carbocyclyl. In certain embodiments, $R^5$ is optionally substituted $C_{5-6}$carbocyclyl. In any of the above instances, in certain embodiments, $R^5$ is substituted carbocyclyl; however, in other embodiments, $R^5$ is unsubstituted carbocyclyl. In certain embodiments, $R^5$ is carbocyclyl in the equatorial position. In certain embodiments, $R^5$ is carbocyclyl in the axial position.

In certain embodiments, $R^5$ is optionally substituted 3-10 membered heterocyclyl. In certain embodiments, $R^5$ is optionally substituted 3-8 membered heterocyclyl. In certain embodiments, $R^5$ is optionally substituted 3-6 membered heterocyclyl. In certain embodiments, $R^5$ is optionally substituted 4-6 membered heterocyclyl. In certain embodiments, $R^5$ is optionally substituted 5-6 membered heterocyclyl. In any of the above instances, in certain embodiments, $R^5$ is substituted heterocyclyl; however, in other embodiments, $R^5$ is unsubstituted heterocyclyl. In certain embodiments, $R^5$ is heterocyclyl in the equatorial position. In certain embodiments, $R^5$ is heterocyclyl in the axial position.

In certain embodiments, $R^5$ is optionally substituted $C_{6-14}$aryl. In certain embodiments, $R^5$ is optionally substituted $C_6$ aryl (i.e., phenyl). In certain embodiments, $R^5$ is optionally substituted $C_{10}$ aryl (i.e., napthyl). In certain embodiments, $R^5$ is optionally substituted $C_{14}$ aryl (i.e., anthracyl). In any of the above instances, in certain embodiments, $R^5$ is substituted aryl; however, in other embodiments, $R^5$ is unsubstituted aryl. In certain embodiments, $R^5$ is aryl in the equatorial position. In certain embodiments, $R^5$ is aryl in the axial position.

In certain embodiments, $R^5$ is optionally substituted 5-10 membered heteroaryl. In certain embodiments, $R^5$ is optionally substituted 5-8 membered heteroaryl. In certain embodiments, $R^5$ is optionally substituted 5-6 membered heteroaryl. In any of the above instances, in certain embodiments, $R^5$ is substituted heteroaryl; however, in other embodiments, $R^5$ is unsubstituted heteroaryl. In certain embodiments, $R^5$ is heteroaryl in the equatorial position. In certain embodiments, $R^5$ is heteroaryl in the axial position.

As generally defined above, $R^6$ is hydrogen, —OH, —OR$^{A6}$, —NH$_2$, —NHR$^{A6}$, —N(R$^{A6}$)$_2$, —NH—NH—R$^{A6}$, —NR$^{A6}$—NHR$^{A6}$, —N=NR$^{A6}$, —N$_3$, —SH, —SR$^{A6}$, —SO$_2$R$^{A6}$, —SO$_3$H, —SO$_2$OR$^{A6}$, —Si(R$^{A6}$)$_3$, —CO$_2$H, —CO$_2$R$^{A6}$, —C(=O)R$^{A6}$, —C(=O)NH$_2$, —C(=O)NH(R$^{A6}$), —C(=O)N(R$^{A6}$)$_2$, —C(=O)SH, —C(=O)SR$^{A6}$, optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, or optionally substituted 5-10 membered heteroaryl, wherein each instance of R$^{A6}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen, sulfur, or nitrogen protecting group, or two R$^{A6}$ groups are joined to form an optionally substituted 3-10 membered heterocyclyl or optionally substituted 5-10 membered heteroaryl ring.

In certain embodiments, $R^6$ is hydrogen.

In certain embodiments, $R^6$ is —OH or —OR$^{A6}$, and R$^{A6}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen protecting group.

In certain embodiments, $R^6$ is —NH$_2$, —NHR$^{A6}$, or —N(R$^{A6}$)$_2$, and each instance of R$^{A6}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, or optionally substituted 5-10 membered heteroaryl, or a nitrogen protecting group, or two R$^{A6}$ groups are joined to form an optionally substituted 3-10 membered heterocyclyl or optionally substituted 5-10 membered heteroaryl ring.

In certain embodiments, $R^6$ is —SH or —SR$^{A6}$, and R$^{A6}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or a sulfur protecting group.

In certain embodiments, $R^6$ is —SO$_2$R$^{A6}$, —SO$_3$H, or —SO$_2$OR$^{A6}$, and R$^{A6}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen protecting group.

In certain embodiments, $R^6$ is —Si(R$^{A6}$)$_3$, and each instance of R$^{A6}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, or optionally substituted 5-10 membered heteroaryl.

In certain embodiments, $R^6$ is —CO$_2$H, —CO$_2$R$^{A6}$, —C(=O)R$^{A6}$, —C(=O)NH$_2$, —C(=O)NH(R$^{A6}$), —C(=O)N(R$^{A6}$)$_2$, —C(=O)SH, or —C(=O)SR$^{A6}$, and each instance of R$^{A6}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen, sulfur, or nitrogen protecting group, or two $R^{A6}$ groups are joined to form an optionally substituted 3-10 membered heterocyclyl or optionally substituted 5-10 membered heteroaryl ring.

In certain embodiments, $R^6$ is —$CO_2H$.

In certain embodiments, $R^6$ is —$CO_2R^{A6}$, and each instance of $R^{A6}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen protecting group.

In certain embodiments, $R^5$ is —C(=O)$R^{A6}$, and each instance of $R^{A6}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, or optionally substituted 5-10 membered heteroaryl.

In certain embodiments, $R^6$ is —C(=O)$NH_2$, —C(=O)NH($R^{A6}$), or —C(=O)N($R^{A6}$)$_2$, and each instance of $R^{A6}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or a nitrogen protecting group, or two $R^{A6}$ groups are joined to form an optionally substituted 3-10 membered heterocyclyl or optionally substituted 5-10 membered heteroaryl ring In certain embodiments, $R^6$ is —C(=O)SH or —C(=O)$SR^{A6}$, and each instance of $R^{A6}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or a sulfur protecting group.

In certain embodiments, $R^6$ is optionally substituted $C_{1-20}$alkyl. In certain embodiments, $R^6$ is optionally substituted $C_{1-10}$alkyl. In certain embodiments, $R^6$ is optionally substituted $C_{1-8}$alkyl. In certain embodiments, $R^6$ is optionally substituted $C_{1-6}$alkyl. In certain embodiments, $R^6$ is optionally substituted $C_{1-4}$alkyl. In certain embodiments, $R^6$ is optionally substituted $C_{1-3}$alkyl. In any of the above instances, in certain embodiments, $R^6$ is substituted alkyl; however, in other embodiments, $R^6$ is unsubstituted alkyl. In certain embodiments, $R^6$ is —$CH_3$, —$CH_2CH_3$, —$(CH_2)_2CH_3$, —$(CH_2)_3CH_3$, —$(CH_2)_4CH_3$, —$(CH_2)_5CH_3$, —$(CH_2)_6CH_3$, —$(CH_2)_7CH_3$, —$(CH_2)_8CH_3$, or —$(CH_2)_9CH_3$. In certain embodiments, $R^6$ is —$CH_3$, —$CH_2CH_3$, or —$(CH_2)_2CH_3$.

In certain embodiments, $R^6$ is optionally substituted $C_{2-20}$alkenyl. In certain embodiments, $R^6$ is optionally substituted $C_{2-10}$alkenyl. In certain embodiments, $R^6$ is optionally substituted $C_{2-8}$alkenyl. In certain embodiments, $R^6$ is optionally substituted $C_{2-6}$alkenyl. In certain embodiments, $R^6$ is optionally substituted $C_{4-6}$alkenyl. In certain embodiments, $R^6$ is optionally substituted $C_{2-3}$alkenyl. In certain embodiments, $R^6$ is optionally substituted $C_{5-20}$alkenyl. In any of the above instances, in certain embodiments, $R^6$ is substituted alkenyl; however, in other embodiments, $R^6$ is unsubstituted alkenyl. For example, in certain embodiments, $R^6$ is the substituted $C_5$alkenyl group:

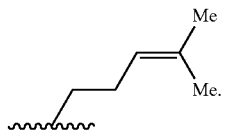 [SMILES: *CCC=C(C)C]

However, in certain embodiments, $R^6$ is not optionally substituted $C_{2-20}$alkenyl. In certain embodiments, $R^6$ is not optionally substituted $C_{2-10}$alkenyl. In certain embodiments, $R^6$ is not optionally substituted $C_{2-8}$alkenyl. In certain embodiments, $R^6$ is not optionally substituted $C_{4-8}$alkenyl. In certain embodiments, $R^6$ is not optionally substituted $C_{4-6}$alkenyl. In certain embodiments, $R^6$ is not optionally substituted $C_5$alkenyl, e.g., for example, in certain embodiments, $R^6$ is not the substituted $C_5$alkenyl group:

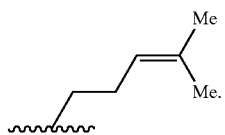

In certain embodiments, $R^6$ is optionally substituted $C_{2-20}$alkynyl. In certain embodiments, $R^6$ is optionally substituted $C_{2-10}$alkynyl. In certain embodiments, $R^6$ is optionally substituted $C_{2-8}$alkynyl. In certain embodiments, $R^6$ is optionally substituted $C_{2-6}$alkynyl. In certain embodiments, $R^6$ is optionally substituted $C_{4-6}$alkynyl. In certain embodiments, $R^6$ is optionally substituted $C_{2-3}$alkynyl. In certain embodiments, $R^6$ is optionally substituted $C_{5-20}$alkynyl. In any of the above instances, in certain embodiments, $R^6$ is substituted alkynyl; however, in other embodiments, $R^6$ is unsubstituted alkynyl.

In certain embodiments, $R^6$ is optionally substituted $C_{3-10}$carbocyclyl. In certain embodiments, $R^6$ is optionally substituted $C_{3-8}$carbocyclyl. In certain embodiments, $R^6$ is optionally substituted $C_{3-6}$carbocyclyl. In certain embodiments, $R^6$ is optionally substituted $C_{4-6}$carbocyclyl. In certain embodiments, $R^6$ is optionally substituted $C_{5-6}$carbocyclyl. In any of the above instances, in certain embodiments, $R^6$ is substituted carbocyclyl; however, in other embodiments, $R^6$ is unsubstituted carbocyclyl.

In certain embodiments, $R^6$ is optionally substituted 3-10 membered heterocyclyl. In certain embodiments, $R^6$ is optionally substituted 3-8 membered heterocyclyl. In certain embodiments, $R^6$ is optionally substituted 3-6 membered heterocyclyl. In certain embodiments, $R^6$ is optionally substituted 4-6 membered heterocyclyl. In certain embodiments, $R^6$ is optionally substituted 5-6 membered heterocyclyl. In any of the above instances, in certain embodiments, $R^6$ is substituted heterocyclyl; however, in other embodiments, $R^6$ is unsubstituted heterocyclyl.

In certain embodiments, $R^6$ is optionally substituted $C_{6-14}$aryl. In certain embodiments, $R^6$ is optionally substituted $C_6$ aryl (i.e., phenyl). In certain embodiments, $R^6$ is optionally substituted $C_{10}$ aryl (i.e., napthyl). In certain embodiments, $R^6$ is optionally substituted $C_{14}$ aryl (i.e., anthracyl). In any of the above instances, in certain embodiments, $R^6$ is substituted aryl; however, in other embodiments, $R^6$ is unsubstituted aryl.

In certain embodiments, $R^6$ is optionally substituted 5-10 membered heteroaryl. In certain embodiments, $R^6$ is optionally substituted 5-8 membered heteroaryl. In certain embodiments, $R^6$ is optionally substituted 5-6 membered heteroaryl.

In any of the above instances, in certain embodiments, $R^6$ is substituted heteroaryl; however, in other embodiments, $R^6$ is unsubstituted heteroaryl.

As generally defined above, $R^7$ is hydrogen, —OH, —OR$^{A7}$, —NH$_2$, —NHR$^{A7}$, —N(R$^{A7}$)$_2$, —NH—NH—R$^{A7}$, —NR$^{A7}$—NHR$^{A7}$, —N=NR$^{A7}$, —N$_3$, —SH, —SR$^{A7}$, —SO$_2$R$^{A7}$, —SO$_3$H, —SO$_2$OR$^{A7}$, —Si(R$^{A7}$)$_3$, —CO$_2$H, —CO$_2$R$^{A7}$, —C(=O)R$^{A7}$, —C(=O)NH$_2$, —C(=O)NH (R$^{A7}$), —C(=O)N(R$^{A7}$)$_2$, —C(=O)SH, —C(=O)SR$^{A7}$, optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, or optionally substituted 5-10 membered heteroaryl, wherein each instance of R$^{A7}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen, sulfur, or nitrogen protecting group, or two R$^{A7}$ groups are joined to form an optionally substituted 3-10 membered heterocyclyl or optionally substituted 5-10 membered heteroaryl ring.

In certain embodiments, $R^7$ is hydrogen.

In certain embodiments, $R^7$ is —OH or —OR$^{A7}$, and R$^{A7}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen protecting group.

In certain embodiments, $R^7$ is —NH$_2$, —NHR$^{A7}$, —N(R$^{A7}$)$_2$, —NH—NH—R$^{A7}$, —NR$^{A7}$—NHR$^{A7}$, —N=NR$^{A7}$, or —N$_3$, and each instance of R$^{A7}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or a nitrogen protecting group, or two R$^{A7}$ groups are joined to form an optionally substituted 3-10 membered heterocyclyl or optionally substituted 5-10 membered heteroaryl ring.

In certain embodiments, $R^7$ is —SH or —SR$^{A7}$, and R$^{A7}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or a sulfur protecting group.

In certain embodiments, $R^7$ is —SO$_2$R$^{A7}$, —SO$_3$H, or —SO$_2$OR$^{A7}$, and R$^{A7}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen protecting group.

In certain embodiments, $R^7$ is —Si(R$^{A7}$)$_3$, and each instance of R$^{A7}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, or optionally substituted 5-10 membered heteroaryl.

In certain embodiments, $R^7$ is —CO$_2$H, —CO$_2$R$^{A7}$, —C(=O)R$^{A7}$, —C(=O)NH$_2$, —C(=O)NH(R$^{A7}$), —C(=O)N(R$^{A7}$)$_2$, —C(=O)SH, or —C(=O)SR$^{A7}$, and each instance of R$^{A7}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen, sulfur, or nitrogen protecting group, or two R$^{A7}$ groups are joined to form an optionally substituted 3-10 membered heterocyclyl or optionally substituted 5-10 membered heteroaryl ring.

In certain embodiments, $R^7$ is —CO$_2$H.

In certain embodiments, $R^5$ is —CO$_2$R$^{A7}$, and each instance of R$^{A7}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen protecting group.

In certain embodiments, $R^7$ is —C(=O)R$^{A7}$, and each instance of R$^{A7}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, or optionally substituted 5-10 membered heteroaryl.

In certain embodiments, $R^7$ is —C(=O)NH$_2$, —C(=O)NH(R$^{A7}$), or —C(=O)N(R$^{A7}$)$_2$, and each instance of R$^{A7}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or a nitrogen protecting group, or two R$^{A7}$ groups are joined to form an optionally substituted 3-10 membered heterocyclyl or optionally substituted 5-10 membered heteroaryl ring In certain embodiments, $R^7$ is —C(=O)SH or —C(=O)SR$^{A7}$, and each instance of R$^{A7}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or a sulfur protecting group.

In certain embodiments, $R^7$ is optionally substituted $C_{1-20}$alkyl. In certain embodiments, $R^7$ is optionally substituted $C_{1-10}$alkyl. In certain embodiments, $R^7$ is optionally substituted $C_{1-8}$alkyl. In certain embodiments, $R^7$ is optionally substituted $C_{1-6}$alkyl. In certain embodiments, $R^7$ is optionally substituted $C_{1-4}$alkyl. In certain embodiments, $R^7$ is optionally substituted $C_{1-3}$alkyl. In any of the above instances, in certain embodiments, $R^7$ is substituted alkyl; however, in other embodiments, $R^7$ is unsubstituted alkyl. In certain embodiments, $R^7$ is —CH$_3$, —CH$_2$CH$_3$, —(CH$_2$)$_2$CH$_3$, —(CH$_2$)$_3$CH$_3$, —(CH$_2$)$_4$CH$_3$, —(CH$_2$)$_5$CH$_3$, —(CH$_2$)$_6$CH$_3$, —(CH$_2$)$_7$CH$_3$, —(CH$_2$)$_8$CH$_3$, or —(CH$_2$)$_9$CH$_3$. In certain embodiments, $R^7$ is —CH$_3$, —CH$_2$CH$_3$, or —(CH$_2$)$_2$CH$_3$. In certain embodiments, $R^7$ is —CH$_3$. However, in certain embodiments, $R^7$ is not —CH$_3$.

In certain embodiments, $R^7$ is optionally substituted $C_{2-20}$alkenyl. In certain embodiments, $R^7$ is optionally substituted $C_{2-10}$alkenyl. In certain embodiments, $R^7$ is optionally substituted $C_{2-8}$alkenyl. In certain embodiments, $R^7$ is optionally substituted $C_{2-6}$alkenyl. In certain embodiments, $R^7$ is optionally substituted $C_{4-6}$alkenyl. In certain embodiments, $R^1$ is optionally substituted $C_{2-3}$alkenyl. In certain embodiments, $R^7$ is optionally substituted $C_{5-20}$alkenyl. In any of the above instances, in certain embodiments, $R^7$ is substituted alkenyl; however, in other embodiments, $R^7$ is unsubstituted alkenyl.

In certain embodiments, $R^7$ is optionally substituted $C_{2-20}$alkynyl. In certain embodiments, $R^7$ is optionally substituted $C_{2-10}$alkynyl. In certain embodiments, $R^7$ is optionally substituted $C_{2-8}$alkynyl. In certain embodiments, $R^7$ is optionally substituted $C_{2-6}$alkynyl. In certain embodiments, $R^7$ is optionally substituted $C_{4-6}$alkynyl. In certain embodiments, $R^7$ is optionally substituted $C_{2-3}$alkynyl. In certain embodiments, $R^7$ is optionally substituted $C_{5-20}$alkynyl. In any of the above instances, in certain embodiments, $R^7$ is substituted alkynyl; however, in other embodiments, $R^7$ is unsubstituted alkynyl.

In certain embodiments, $R^7$ is optionally substituted $C_{3-10}$carbocyclyl. In certain embodiments, $R^7$ is optionally substituted $C_{3-8}$carbocyclyl. In certain embodiments, $R^7$ is optionally substituted $C_{3-6}$carbocyclyl. In certain embodiments, $R^7$ is optionally substituted $C_{4-6}$carbocyclyl. In certain embodiments, $R^7$ is optionally substituted $C_{5-6}$carbocyclyl. In any of the above instances, in certain embodiments, $R^7$ is substituted carbocyclyl; however, in other embodiments, $R^7$ is unsubstituted carbocyclyl.

In certain embodiments, $R^7$ is optionally substituted 3-10 membered heterocyclyl. In certain embodiments, $R^7$ is optionally substituted 3-8 membered heterocyclyl. In certain embodiments, $R^7$ is optionally substituted 3-6 membered heterocyclyl. In certain embodiments, $R^7$ is optionally substituted 4-6 membered heterocyclyl. In certain embodiments, $R^7$ is optionally substituted 5-6 membered heterocyclyl. In any of the above instances, in certain embodiments, $R^7$ is substituted heterocyclyl; however, in other embodiments, $R^7$ is unsubstituted heterocyclyl.

In certain embodiments, $R^7$ is optionally substituted $C_{6-14}$aryl. In certain embodiments, $R^7$ is optionally substituted $C_6$ aryl (i.e., phenyl). In certain embodiments, $R^7$ is optionally substituted $C_{10}$ aryl (i.e., napthyl). In certain embodiments, $R^7$ is optionally substituted $C_{14}$ aryl (i.e., anthracyl). In any of the above instances, in certain embodiments, $R^7$ is substituted aryl; however, in other embodiments, $R^7$ is unsubstituted aryl.

In certain embodiments, $R^7$ is optionally substituted 5-10 membered heteroaryl. In certain embodiments, $R^7$ is optionally substituted 5-8 membered heteroaryl. In certain embodiments, $R^7$ is optionally substituted 5-6 membered heteroaryl. In any of the above instances, in certain embodiments, $R^7$ is substituted heteroaryl; however, in other embodiments, $R^7$ is unsubstituted heteroaryl.

As generally defined above, $R^8$ is hydrogen, halogen, —OH, —OR$^{A8}$, —NH$_2$, —NHR$^{A8}$, —N(R$^{A8}$)$_2$, —NH—NH—R$^{A8}$, —NR$^{A8}$—NHR$^{A8}$, —N=NR$^{A8}$, —N$_3$, —SH, —SR$^{A8}$, —Si(R$^{A82}$)$_3$, —SO$_2$R$^{A8}$, —SO$_3$H, —SO$_2$OR$^{A8}$, —CO$_2$H, —CO$_2$R$^{A8}$, —C(=O)R$^{A8}$, —C(=O)NH$_2$, —C(=O)NH(R$^{A8}$), —C(=O)N(R$^{A8}$)$_2$, —C(=O)SR$^{A8}$, —C(OH)(OR$^{A8}$)R$^{A8}$, —C(OH)$_2$R$^{A8}$, —C(OR$^{A8}$)$_2$R$^{A8}$, optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, $C_{6-14}$ optionally substituted aryl, or optionally substituted 5-10 membered heteroaryl, wherein each instance of R$^{A8}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen, sulfur, or nitrogen protecting group, or two R$^{A8}$ groups are joined to form an optionally substituted 3-10 membered heterocyclyl or optionally substituted 5-10 membered heteroaryl ring.

In certain embodiments, $R^8$ is hydrogen.

In certain embodiments, $R^8$ is halogen, i.e., in certain embodiments, $R^8$ is —Br, —Cl, —I, or —F. In certain embodiments, $R^8$ is —Br. In certain embodiments, $R^8$ is —Cl. In certain embodiments, $R^8$ is —I. In certain embodiments, $R^8$ is —F.

In certain embodiments, $R^8$ is —OH or —OR$^{A8}$, and R$^{A8}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen protecting group.

In certain embodiments, $R^8$ is —NH$_2$, —NHR$^{A8}$, —N(R$^{A8}$)$_2$, —NH—NH—R$^{A8}$, —NR$^{A8}$—NHR$^{A8}$, —N=NR$^{A8}$, —N$_3$, and each instance of R$^{A8}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or a nitrogen protecting group, or two R$^{A8}$ groups are joined to form an optionally substituted 3-10 membered heterocyclyl or optionally substituted 5-10 membered heteroaryl ring.

In certain embodiments, $R^8$ is —SH or —SR$^{A8}$, and R$^{A8}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or a sulfur protecting group.

In certain embodiments, $R^8$ is —Si(R$^{A8}$)$_3$, and each instance of R$^{A8}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, or optionally substituted 5-10 membered heteroaryl.

In certain embodiments, $R^8$ is —SO$_2$R$^{A8}$, —SO$_3$H, or —SO$_2$OR$^{A8}$, and R$^{A8}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen protecting group.

In certain embodiments, $R^8$ is —CO$_2$H, —CO$_2$R$^{A8}$, —C(=O)R$^{A8}$, —C(=O)NH$_2$, —C(=O)NH(R$^{A8}$), —C(=O)N(R$^{A8}$)$_2$, —C(=O)SR$^{A8}$, —C(OH)(OR$^{A8}$)R$^{A8}$, —C(OH)$_2$R$^{A8}$, or —C(OR$^{A8}$)$_2$R$^{A8}$, and each instance of R$^{A8}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen, sulfur, or nitrogen protecting group, or two R$^{A8}$ groups are joined to form an optionally substituted 3-10 membered heterocyclyl or optionally substituted 5-10 membered heteroaryl ring.

In certain embodiments, $R^8$ is —CO$_2$H.

In certain embodiments, $R^8$ is —CO$_2$R$^{A8}$, and each instance of R$^{A8}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen protecting group.

In certain embodiments, $R^8$ is —C(=O)$R^{A8}$, wherein $R^{A8}$ is independently optionally substituted $C_{1-20}$alkyl, e.g., optionally substituted $C_{1-10}$alkyl, optionally substituted $C_{1-8}$alkyl, optionally substituted $C_{1-6}$alkyl, optionally substituted $C_{1-4}$alkyl, optionally substituted $C_{1-3}$alkyl, or optionally substituted $C_{1-2}$alkyl. However, in certain embodiments, $R^8$ is not —C(=O)$R^{A8}$. In certain embodiments, $R^8$ is not —C(=O)$R^{A8}$ wherein $R^{A8}$ is independently optionally substituted $C_{1-20}$alkyl, e.g., optionally substituted $C_{1-10}$alkyl, optionally substituted $C_{1-8}$alkyl, optionally substituted $C_{1-6}$alkyl, optionally substituted $C_{1-4}$alkyl, optionally substituted $C_{1-3}$alkyl, or optionally substituted $C_{1-2}$alkyl. In certain embodiments, $R^8$ is not —C(=O)$R^{A8}$ wherein $R^{A8}$ is optionally substituted $C_3$alkyl, e.g., n-propyl (—$(CH_2)_2CH_3$) or isopropyl (—$CH(CH_3)_2$). In certain embodiments, $R^8$ is not —C(=O)CH(CH_3)_2$.

In certain embodiments, $R^8$ is —C(=O)$NH_2$, —C(=O)NH($R^{A8}$), or —C(=O)N($R^{A8}$)$_2$, and each instance of $R^{A8}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or a nitrogen protecting group, or two $R^{A8}$ groups are joined to form an optionally substituted 3-10 membered heterocyclyl or optionally substituted 5-10 membered heteroaryl ring.

In certain embodiments, $R^8$ is —C(=O)SH or —C(=O)S$R^{A8}$, and each instance of $R^{A8}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or a sulfur protecting group.

In certain embodiments, $R^8$ is —C(OH)(OR$^{A8}$)$R^{A8}$, —C(OH)$_2R^{A8}$, or —C(OR$^{A8}$)$_2R^{A8}$, and each instance of $R^{A8}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, an oxygen protecting group, or two $R^{A8}$ groups are joined to form an optionally substituted 3-10 membered heterocyclyl or optionally substituted 5-10 membered heteroaryl ring.

In certain embodiments, $R^8$ is optionally substituted $C_{1-20}$alkyl. In certain embodiments, $R^1$ is optionally substituted $C_{1-10}$alkyl. In certain embodiments, $R^8$ is optionally substituted $C_{1-8}$alkyl. In certain embodiments, $R^8$ is optionally substituted $C_{1-6}$alkyl. In certain embodiments, $R^1$ is optionally substituted $C_{1-4}$alkyl. In certain embodiments, $R^8$ is optionally substituted $C_{1-3}$alkyl. In any of the above instances, in certain embodiments, $R^8$ is substituted alkyl; however, in other embodiments, $R^8$ is unsubstituted alkyl. In certain embodiments, $R^8$ is —$CH_3$, —$CH_2CH_3$, —$(CH_2)_2CH_3$, —$(CH_2)_3CH_3$, —$(CH_2)_4CH_3$, —$(CH_2)_5CH_3$, —$(CH_2)_6CH_3$, —$(CH_2)_7CH_3$, —$(CH_2)_8CH_3$, or —$(CH_2)_9CH_3$. In certain embodiments, $R^8$ is —$CH_3$, —$CH_2CH_3$, or —$(CH_2)_2CH_3$. In certain embodiments, $R^8$ is —$CH_2CH_2OR^{B8}$, wherein $R^{B8}$ is hydrogen or an oxygen protecting group. In certain embodiments, $R^8$ is —$CH_2CH_2OH$.

In certain embodiments, $R^8$ is optionally substituted $C_{2-20}$alkenyl. In certain embodiments, $R^8$ is optionally substituted $C_{2-10}$alkenyl. In certain embodiments, $R^8$ is optionally substituted $C_{2-8}$alkenyl. In certain embodiments, $R^8$ is optionally substituted $C_{2-6}$alkenyl. In certain embodiments, $R^8$ is optionally substituted $C_{4-6}$alkenyl. In certain embodiments, $R^8$ is optionally substituted $C_{2-3}$alkenyl. In certain embodiments, $R^8$ is optionally substituted $C_{5-20}$alkenyl. In any of the above instances, in certain embodiments, $R^8$ is substituted alkenyl; however, in other embodiments, $R^8$ is unsubstituted alkenyl.

In certain embodiments, $R^8$ is optionally substituted $C_{2-20}$alkynyl. In certain embodiments, $R^8$ is optionally substituted $C_{2-10}$alkynyl. In certain embodiments, $R^8$ is optionally substituted $C_{2-8}$alkynyl. In certain embodiments, $R^8$ is optionally substituted $C_{2-6}$alkynyl. In certain embodiments, $R^8$ is optionally substituted $C_{4-6}$alkynyl. In certain embodiments, $R^8$ is optionally substituted $C_{2-3}$alkynyl. In certain embodiments, $R^8$ is optionally substituted $C_{5-20}$alkynyl. In any of the above instances, in certain embodiments, $R^8$ is substituted alkynyl; however, in other embodiments, $R^8$ is unsubstituted alkynyl.

In certain embodiments, $R^8$ is optionally substituted $C_{3-10}$carbocyclyl. In certain embodiments, $R^8$ is optionally substituted $C_{3-8}$carbocyclyl. In certain embodiments, $R^8$ is optionally substituted $C_{3-6}$carbocyclyl. In certain embodiments, $R^8$ is optionally substituted $C_{4-6}$carbocyclyl. In certain embodiments, $R^8$ is optionally substituted $C_{5-6}$carbocyclyl. In any of the above instances, in certain embodiments, $R^8$ is substituted carbocyclyl; however, in other embodiments, $R^8$ is unsubstituted carbocyclyl.

In certain embodiments, $R^8$ is optionally substituted 3-10 membered heterocyclyl. In certain embodiments, $R^8$ is optionally substituted 3-8 membered heterocyclyl. In certain embodiments, $R^8$ is optionally substituted 3-6 membered heterocyclyl. In certain embodiments, $R^8$ is optionally substituted 4-6 membered heterocyclyl. In certain embodiments, $R^8$ is optionally substituted 5-6 membered heterocyclyl. In any of the above instances, in certain embodiments, $R^8$ is substituted heterocyclyl; however, in other embodiments, $R^8$ is unsubstituted heterocyclyl.

In certain embodiments, $R^8$ is optionally substituted $C_{6-14}$aryl. In certain embodiments, $R^8$ is optionally substituted $C_6$ aryl (i.e., phenyl). In certain embodiments, $R^8$ is optionally substituted $C_{10}$ aryl (i.e., napthyl). In certain embodiments, $R^8$ is optionally substituted $C_{14}$ aryl (i.e., anthracyl). In any of the above instances, in certain embodiments, $R^8$ is substituted aryl; however, in other embodiments, $R^8$ is unsubstituted aryl.

In certain embodiments, $R^8$ is optionally substituted 5-10 membered heteroaryl. In certain embodiments, $R^8$ is optionally substituted 5-8 membered heteroaryl. In certain embodiments, $R^8$ is optionally substituted 5-6 membered heteroaryl. In any of the above instances, in certain embodiments, $R^8$ is substituted heteroaryl; however, in other embodiments, $R^8$ is unsubstituted heteroaryl.

As generally defined above, $R^9$ is hydrogen, halogen, —OH, —OR$^{A9}$, —$NH_2$, —NHR$^{A9}$, —N(R$^{A9}$)$_2$, —NH—NH—R$^{A9}$, —NR$^{A9}$—NHR$^{A9}$, —N=NR$^{A9}$, —$N_3$, —SH, —SR$^{A9}$, —Si(R$^{A9}$)$_3$, —$SO_2R^{A9}$, —$SO_3H$, —$SO_2OR^{A9}$, —$CO_2H$, —$CO_2R^{A9}$, —C(=O)R$^{A9}$, —C(=O)$NH_2$, —C(=O)NH(R$^{A9}$), —C(=O)N(R$^{A9}$)$_2$, —C(=O)SR$^{A9}$, —P(=O)(OH)$_2$, —P(=O)(OH)(OR$^{A9}$), —P(=O)(OR$^{A9}$)$_2$, optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, $C_{6-14}$ optionally substituted aryl, or optionally substituted 5-10 membered heteroaryl, wherein each instance of $R^{A9}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen, sulfur, or nitrogen protecting group, or two $R^{A9}$ groups are joined to form an optionally substituted 3-10 membered heterocyclyl or optionally substituted 5-10 membered heteroaryl ring.

In certain embodiments, $R^9$ is hydrogen.

In certain embodiments, $R^9$ is halogen, i.e., in certain embodiments, $R^9$ is —Br, —Cl, —I, or —F. In certain embodiments, $R^9$ is —Br. In certain embodiments, $R^9$ is —Cl. In certain embodiments, $R^9$ is —I. In certain embodiments, $R^9$ is —F.

In certain embodiments, $R^9$ is —OH or —OR$^{A9}$, and R$^{A9}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen protecting group. In certain embodiments, $R^9$ is —OH. In certain embodiments, $R^9$ is —OR$^{A9}$. However, in certain embodiments, $R^9$ is not —OH. In certain embodiments, $R^9$ is not —OR$^{A9}$.

In certain embodiments, $R^9$ is —NH$_2$, —NHR$^{A9}$, —N(R$^{A9}$)$_2$, —NH—NH—R$^{A9}$, —NR$^{A9}$—NHR$^{A9}$, —N=NR$^{A9}$, or —N$_3$, and each instance of R$^{A9}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or a nitrogen protecting group, or two R$^{A9}$ groups are joined to form an optionally substituted 3-10 membered heterocyclyl or optionally substituted 5-10 membered heteroaryl ring.

In certain embodiments, $R^9$ is —SH or —SR$^{A9}$, and R$^{A9}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or a sulfur protecting group.

In certain embodiments, $R^9$ is —Si(R$^{A9}$)$_3$, and each instance of R$^{A9}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, or optionally substituted 5-10 membered heteroaryl.

In certain embodiments, $R^9$ is —SO$_2$R$^{A9}$, —SO$_3$H, or —SO$_2$OR$^{A9}$, and R$^{A9}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen protecting group.

In certain embodiments, $R^9$ is —CO$_2$H, —CO$_2$R$^{A9}$, —C(=O)R$^{A9}$, —C(=O)NH$_2$, —C(=O)NH(R$^{A9}$), —C(=O)N(R$^{A9}$)$_2$, or —C(=O)SR$^{A9}$, and each instance of R$^{A9}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen, sulfur, or nitrogen protecting group, or two R$^{A9}$ groups are joined to form an optionally substituted 3-10 membered heterocyclyl or optionally substituted 5-10 membered heteroaryl ring.

In certain embodiments, $R^9$ is —CO$_2$H.

In certain embodiments, $R^9$ is —CO$_2$R$^{A9}$, and each instance of R$^{A9}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen protecting group.

In certain embodiments, $R^9$ is —C(=O)R$^{A9}$, and each instance of R$^{A9}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, or optionally substituted 5-10 membered heteroaryl.

In certain embodiments, $R^9$ is —C(=O)NH$_2$, —C(=O)NH(R$^{A9}$), or —C(=O)N(R$^{A9}$)$_2$, and each instance of R$^{A9}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or a nitrogen protecting group, or two R$^{A9}$ groups are joined to form an optionally substituted 3-10 membered heterocyclyl or optionally substituted 5-10 membered heteroaryl ring In certain embodiments, $R^9$ is —C(=O)SH or —C(=O)SR$^{A9}$, and each instance of R$^{A9}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or a sulfur protecting group.

In certain embodiments, $R^9$ is —P(=O)(OH)$_2$, —P(=O)(OH)(OR$^{A9}$), or —P(=O)(OR$^{A9}$)$_2$, and each instance of R$^{A9}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen protecting group.

In certain embodiments, $R^9$ is optionally substituted $C_{1-20}$alkyl. In certain embodiments, $R^9$ is optionally substituted $C_{1-10}$alkyl. In certain embodiments, $R^9$ is optionally substituted $C_{1-8}$alkyl. In certain embodiments, $R^9$ is optionally substituted $C_{1-6}$alkyl. In certain embodiments, $R^9$ is optionally substituted $C_{1-4}$alkyl. In certain embodiments, $R^9$ is optionally substituted $C_{1-3}$alkyl. In any of the above instances, in certain embodiments, $R^9$ is substituted alkyl; however, in other embodiments, $R^9$ is unsubstituted alkyl.

For example, in certain embodiments, $R^9$ is unsubstituted alkyl, e.g., selected from the group consisting of —CH$_3$, —CH$_2$CH$_3$, —(CH$_2$)$_2$CH$_3$, —(CH$_2$)$_3$CH$_3$, —(CH$_2$)$_4$CH$_3$, —(CH$_2$)$_5$CH$_3$, —(CH$_2$)$_6$CH$_3$, —(CH$_2$)$_7$CH$_3$, —(CH$_2$)$_8$CH$_3$, and —(CH$_2$)$_9$CH$_3$.

In certain embodiments, $R^9$ is substituted alkyl group, e.g., a $C_{1-20}$alkyl group substituted with —P(=O)(OH)$_2$, —P(=O)(OH)(OR$^{B9}$), —P(=O)(OR$^{B9}$)$_2$, —CO$_2$H, —CO$_2$R$^{B9}$, —C(=O)R$^{B9}$, —C(=O)NH$_2$, —C(=O)NH(R$^{B9}$), —C(=O)N(R$^{B9}$)$_2$, —C(=O)SR$^{B9}$, —SO$_2$R$^{B9}$, —SO$_3$H, or —SO$_2$OR$^{B9}$, wherein each instance of R$^{B9}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen, sulfur, or nitrogen protecting group. For example, in the above instance, in certain embodiments $R^9$ is —$(CH_2)_nP(=O)(OH)_2$, —$(CH_2)_nP(=O)(OH)(OR^{B9})$, —$(CH_2)_nP(=O)(OR^{B9})_2$, —$(CH_2)_nCO_2H$, —$(CH_2)_nCO_2R^{B9}$, —$(CH_2)_nC(=O)R^{B9}$, —$(CH_2)_nC(=O)NH_2$, —$(CH_2)_nC(=O)NH(R^{B9})$, —$(CH_2)_nC(=O)N(R^{B9})_2$, —$(CH_2)_nC(=O)SR^{B9}$, —$(CH_2)_nSO_2R^{B9}$, —$(CH_2)_nSO_3H$, or —$(CH_2)_nSO_2OR^{B9}$, wherein n is 1, 2, 3, or 4.

In certain embodiments, $R^9$ is optionally substituted $C_{2-20}$alkenyl. In certain embodiments, $R^9$ is optionally substituted $C_{2-10}$alkenyl. In certain embodiments, $R^9$ is optionally substituted $C_{2-8}$alkenyl. In certain embodiments, $R^9$ is optionally substituted $C_{2-6}$alkenyl. In certain embodiments, $R^9$ is optionally substituted $C_{4-6}$alkenyl. In certain embodiments, $R^9$ is optionally substituted $C_{2-3}$alkenyl. In certain embodiments, $R^9$ is optionally substituted $C_{5-20}$alkenyl. In any of the above instances, in certain embodiments, $R^9$ is substituted alkenyl; however, in other embodiments, $R^9$ is unsubstituted alkenyl.

In certain embodiments, $R^9$ is optionally substituted $C_{2-20}$alkynyl. In certain embodiments, $R^9$ is optionally substituted $C_{2-10}$alkynyl. In certain embodiments, $R^9$ is optionally substituted $C_{2-8}$alkynyl. In certain embodiments, $R^9$ is optionally substituted $C_{2-6}$alkynyl. In certain embodiments, $R^1$ is optionally substituted $C_{4-6}$alkynyl. In certain embodiments, $R^9$ is optionally substituted $C_{2-3}$alkynyl. In certain embodiments, $R^9$ is optionally substituted $C_{5-20}$alkynyl. In any of the above instances, in certain embodiments, $R^9$ is substituted alkynyl; however, in other embodiments, $R^9$ is unsubstituted alkynyl.

In certain embodiments, $R^9$ is optionally substituted $C_{3-10}$carbocyclyl. In certain embodiments, $R^9$ is optionally substituted $C_{3-8}$carbocyclyl. In certain embodiments, $R^9$ is optionally substituted $C_{3-6}$carbocyclyl. In certain embodiments, $R^9$ is optionally substituted $C_{4-6}$carbocyclyl. In certain embodiments, $R^9$ is optionally substituted $C_{5-6}$carbocyclyl. In any of the above instances, in certain embodiments, $R^9$ is substituted carbocyclyl; however, in other embodiments, $R^9$ is unsubstituted carbocyclyl.

In certain embodiments, $R^9$ is optionally substituted 3-10 membered heterocyclyl. In certain embodiments, $R^9$ is optionally substituted 3-8 membered heterocyclyl. In certain embodiments, $R^9$ is optionally substituted 3-6 membered heterocyclyl. In certain embodiments, $R^9$ is optionally substituted 4-6 membered heterocyclyl. In certain embodiments, $R^9$ is optionally substituted 5-6 membered heterocyclyl. In any of the above instances, in certain embodiments, $R^9$ is substituted heterocyclyl; however, in other embodiments, $R^9$ is unsubstituted heterocyclyl.

In certain embodiments, $R^9$ is optionally substituted $C_{6-14}$aryl. In certain embodiments, $R^9$ is optionally substituted $C_6$ aryl (i.e., phenyl). In certain embodiments, $R^9$ is optionally substituted $C_{10}$ aryl (i.e., napthyl). In certain embodiments, $R^9$ is optionally substituted $C_{14}$ aryl (i.e., anthracyl). In any of the above instances, in certain embodiments, $R^9$ is substituted aryl; however, in other embodiments, $R^9$ is unsubstituted aryl.

In certain embodiments, $R^9$ is optionally substituted 5-10 membered heteroaryl. In certain embodiments, $R^9$ is optionally substituted 5-8 membered heteroaryl. In certain embodiments, $R^9$ is optionally substituted 5-6 membered heteroaryl. In any of the above instances, in certain embodiments, $R^9$ is substituted heteroaryl; however, in other embodiments, $R^9$ is unsubstituted heteroaryl.

Figure 13:
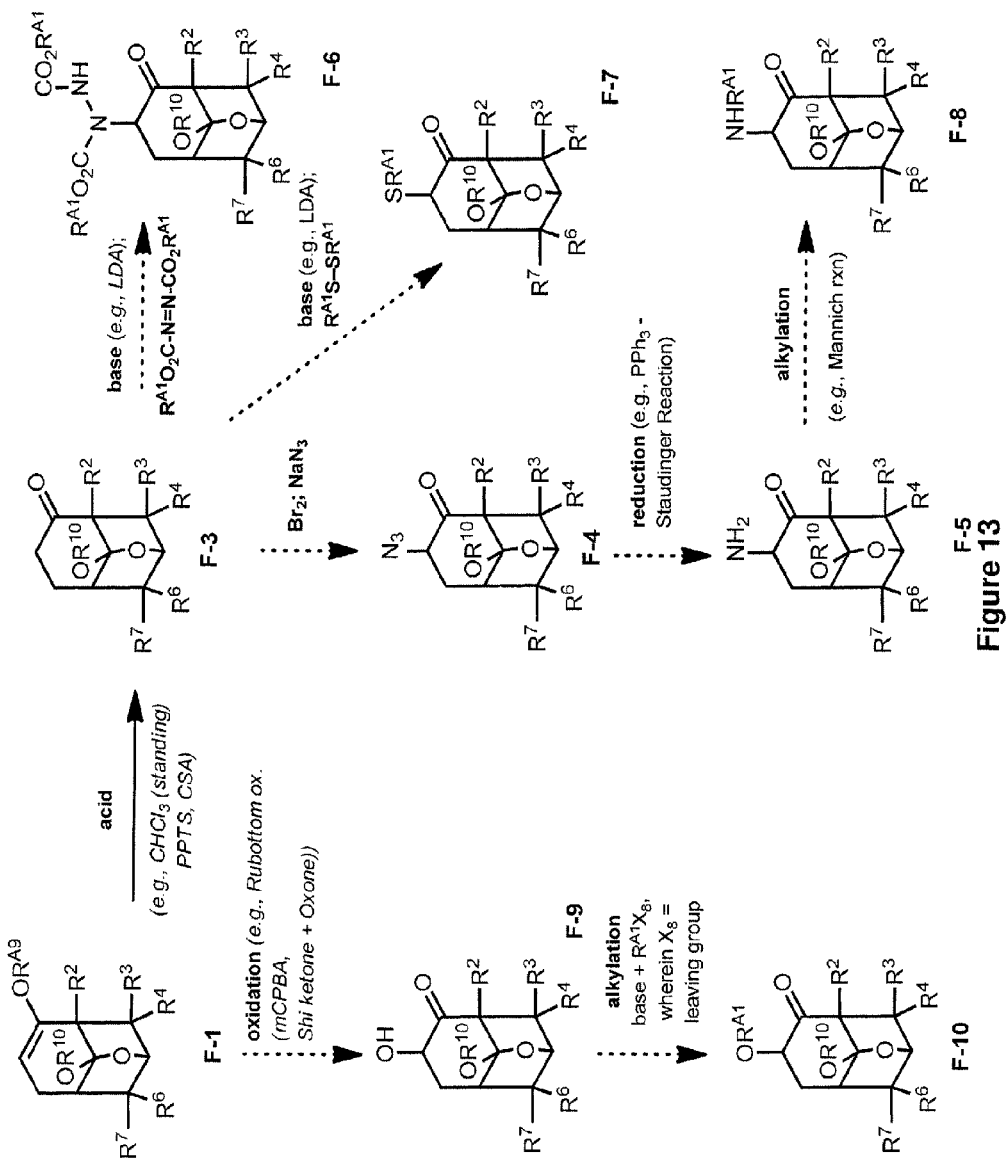
FIG. 13 depicts exemplary and proposed synthetic modification of intermediate F-1.
Figure 14:
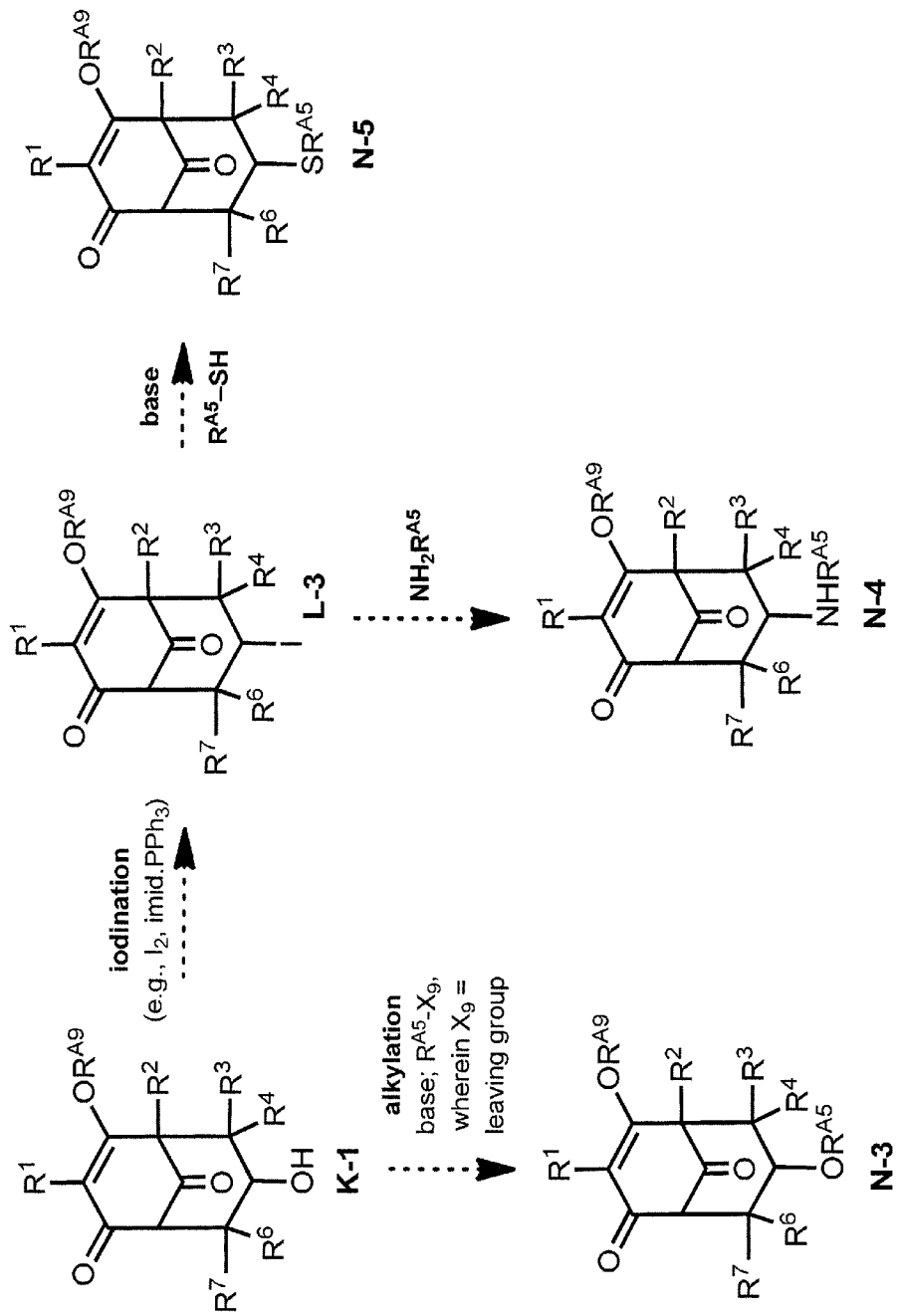
FIG. 14 depicts proposed synthetic modification of intermediate K-1.
Figure 15:
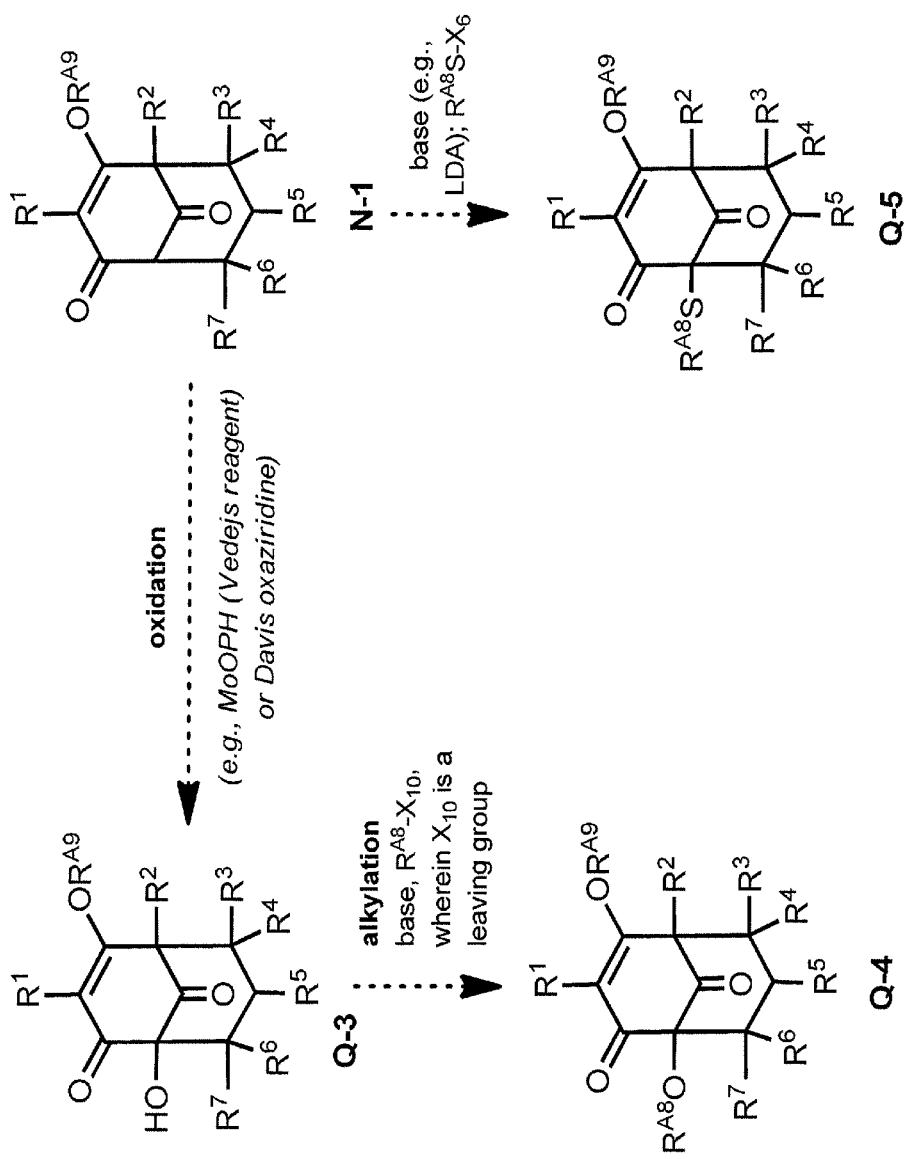
FIG. 15 depicts proposed synthetic modification of intermediate N-1.
Figure 16:
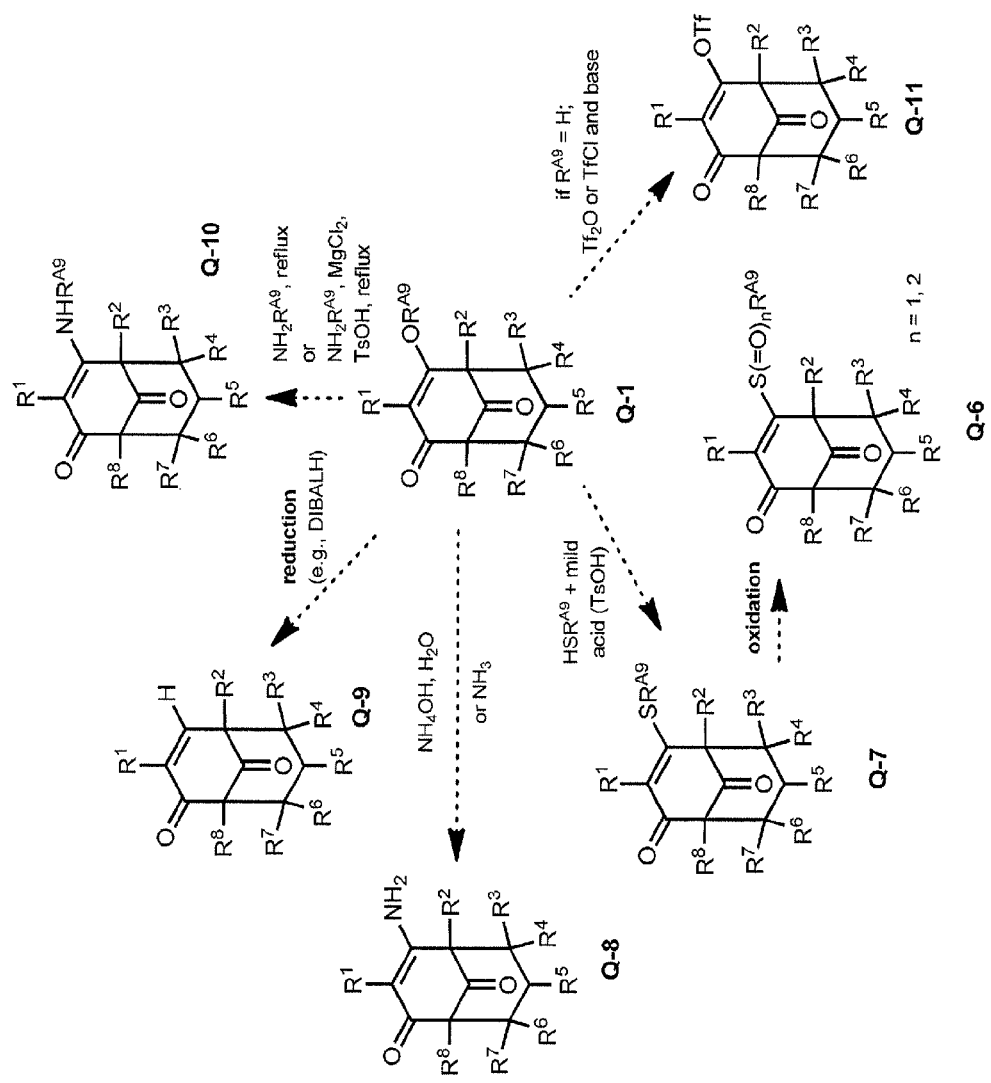
FIG. 16 depicts proposed synthetic modification of intermediate Q-1 and Q-11.
Figure 17:
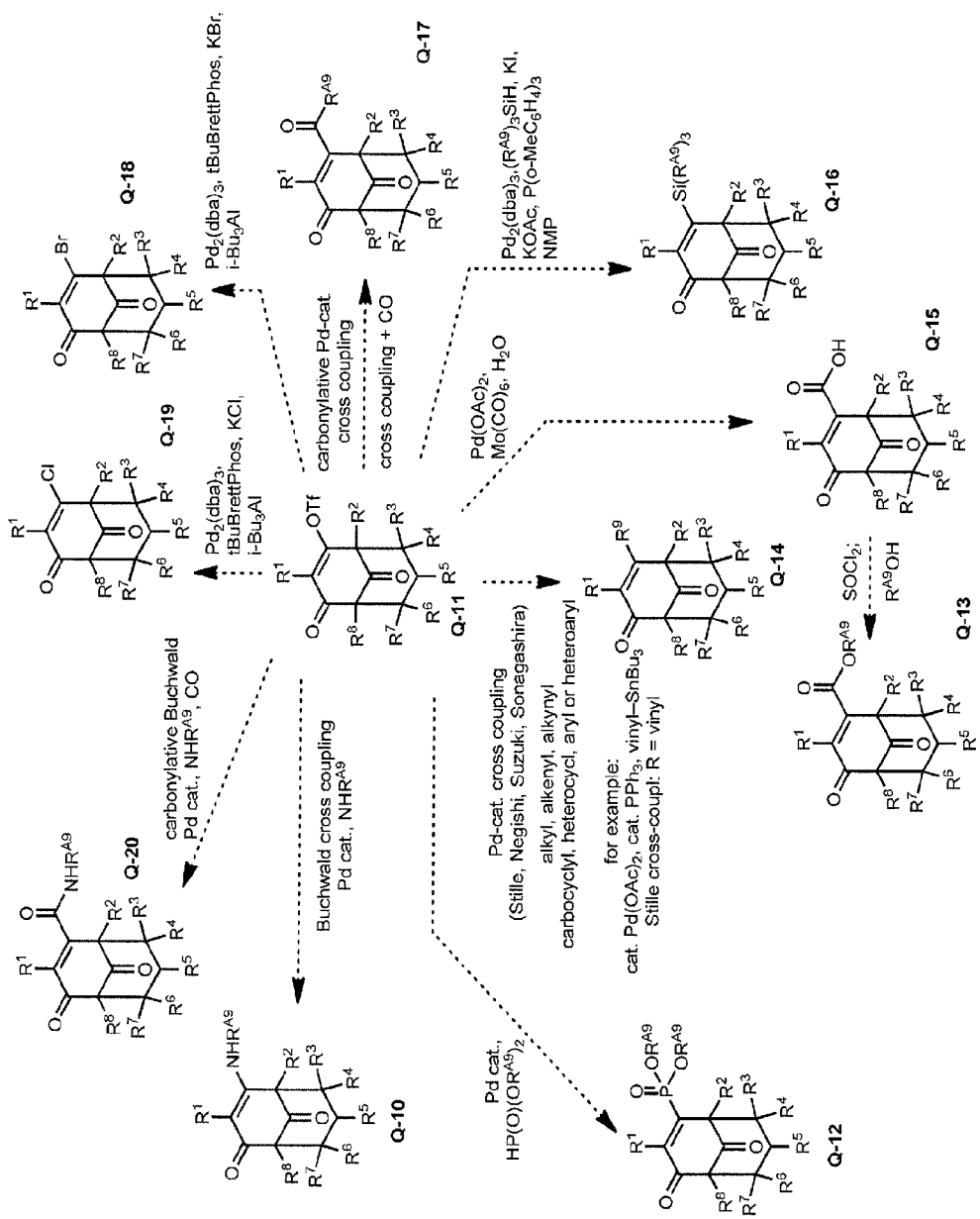
FIG. 17 depicts proposed synthetic modification of intermediate Q-11.
Figure 18A:
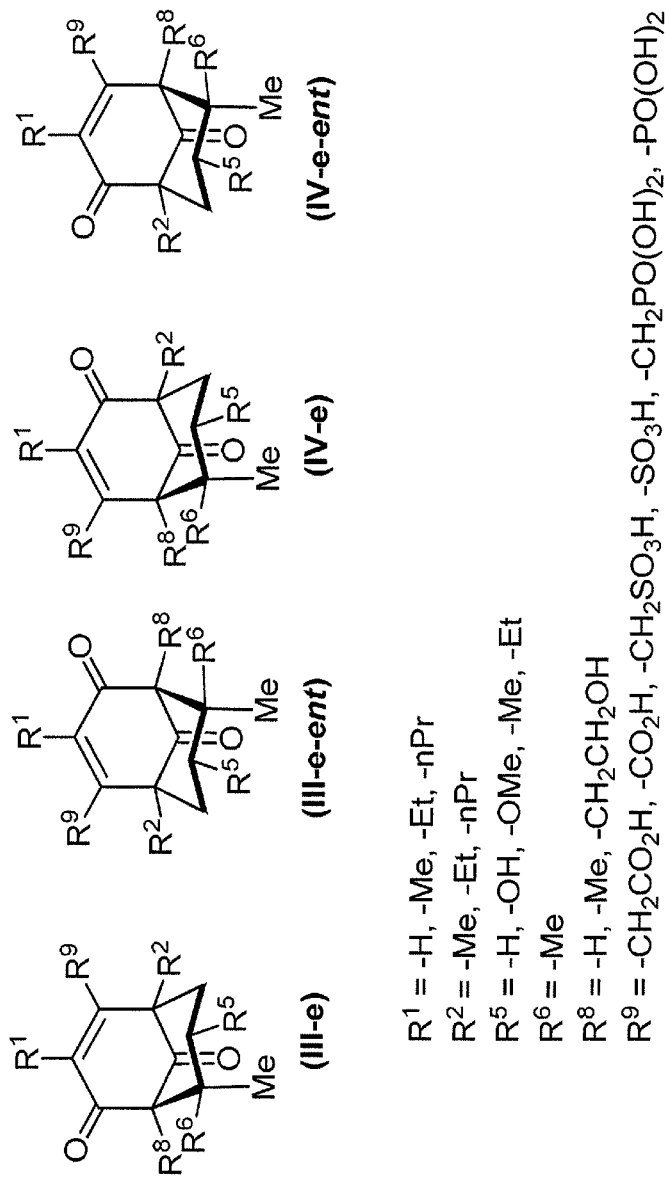
FIGS. 18A and 18B depict exemplary analogs of hyperforin accessible via the inventive synthetic methodology.
Figure 18B:
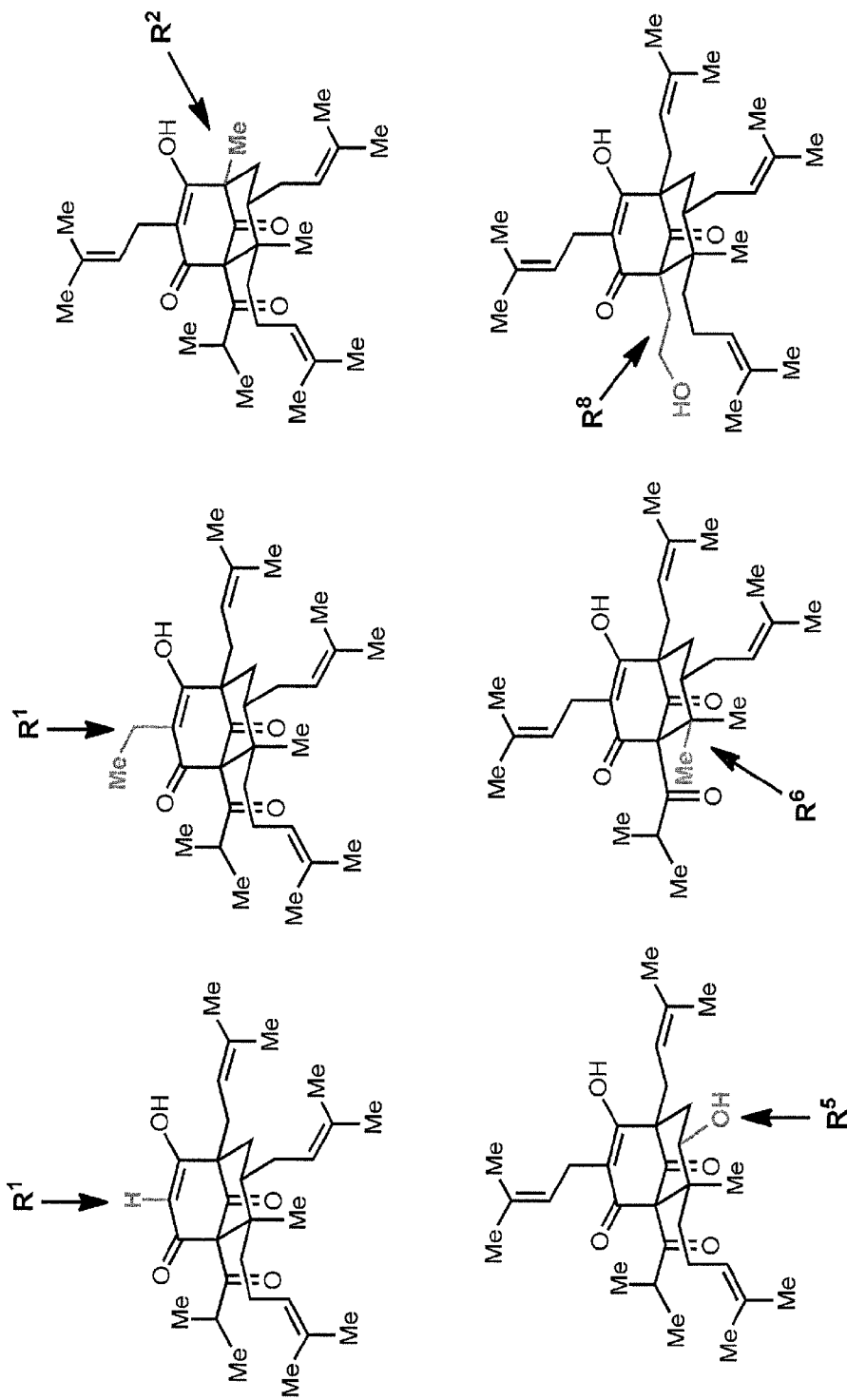

Various combinations of the above embodiments are also contemplated, see, e.g., FIG. 13 depicted herein.

For example, in certain embodiments, wherein $R^5$ is in the equatorial position, provided is a compound of Formula (III-c), (III-c-ent), (IV-c), or (IV-c-ent):

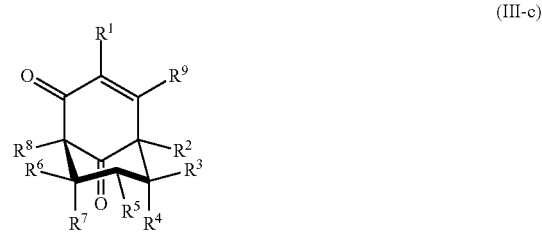
(III-c)

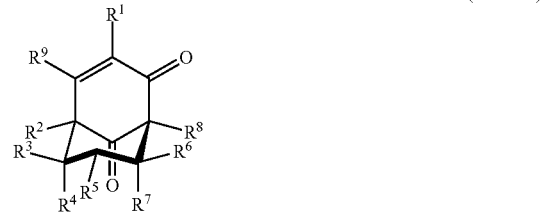
(III-c-ent)

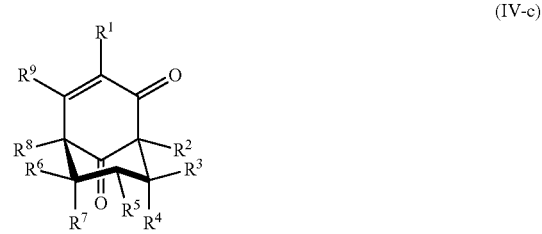
(IV-c)

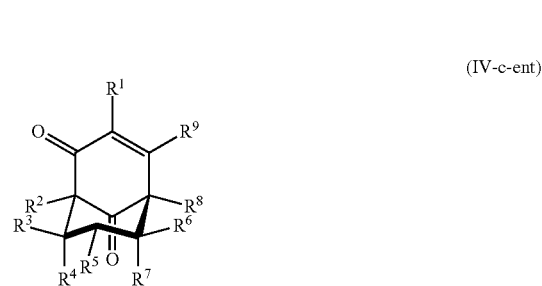
(IV-c-ent)

or a salt, isomer, or tautomer thereof, or mixture thereof. In certain embodiments, $R^1$ is hydrogen. In certain embodiments, $R^1$ is —$CH_3$. In certain embodiments, $R^1$ is —$CH_2CH_3$. In certain embodiments, $R^1$ is —$(CH_2)_2CH_3$. In certain embodiments, $R^2$ is —$CH_3$. In certain embodiments, $R^2$ is —$CH_2CH_3$. In certain embodiments, $R^2$ is —$(CH_2)_2CH_3$. In certain embodiments, $R^5$ is hydrogen. In certain embodiments, $R^5$ is —OH. In certain embodiments, $R^5$ is —$OCH_3$. In certain embodiments, $R^5$ is —$CH_3$. In certain embodiments, $R^5$ is —$CH_2CH_3$. In certain embodiments, $R^6$ is —$CH_3$. In certain embodiments, $R^7$ is —$CH_3$. In certain embodiments, $R^8$ is hydrogen. In certain embodiments, $R^8$ is —$CH_3$. In certain embodiments, $R^8$ is —$CH_2CH_2OH$. In certain embodiments, $R^9$ is —$CH_2CO_2H$. In certain embodiments, $R^9$ is —$CH_2SO_3H$. In certain embodiments, $R^9$ is —$CH_2P(=O)(OH)_2$. In certain embodiments, $R^9$ is —$CO_2H$. In certain embodiments, $R^9$ is —$SO_3H$. In certain embodiments, $R^9$ is —$P(=O)(OH)_2$.

In certain embodiments, wherein $R^5$ is in the equatorial position and $R^3$ and $R^4$ are hydrogen, provided is a compound of Formula (III-d), (III-d-ent), (IV-d), or (IV-d-ent):

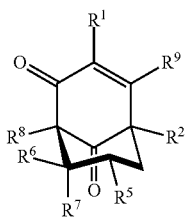 (III-d)

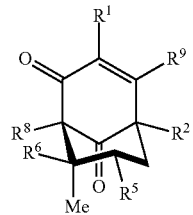 (III-e)

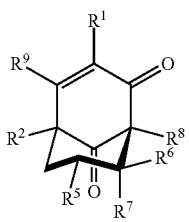 (III-d-ent)

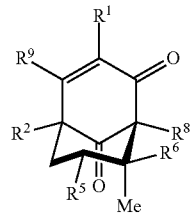 (III-e-ent)

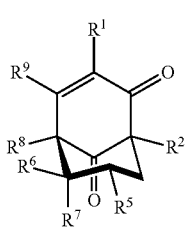 (IV-d)

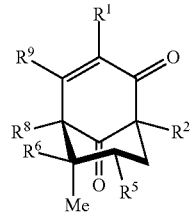 (IV-e)

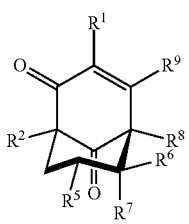 (IV-d-ent)

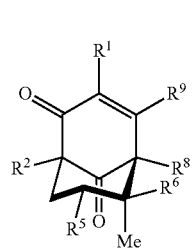 (IV-e-ent)

or a salt, isomer, or tautomer thereof, or mixture thereof. In certain embodiments, $R^1$ is hydrogen. In certain embodiments, $R^1$ is —$CH_3$. In certain embodiments, $R^1$ is —$CH_2CH_3$. In certain embodiments, $R^1$ is —$(CH_2)_2CH_3$. In certain embodiments, $R^2$ is —$CH_3$. In certain embodiments, $R^2$ is —$CH_2CH_3$. In certain embodiments, $R^2$ is —$(CH_2)_2CH_3$. In certain embodiments, $R^5$ is hydrogen. In certain embodiments, $R^5$ is —OH. In certain embodiments, $R^5$ is —$OCH_3$. In certain embodiments, $R^5$ is —$CH_3$. In certain embodiments, $R^5$ is —$CH_2CH_3$. In certain embodiments, $R^6$ is —$CH_3$. In certain embodiments, $R^7$ is —$CH_3$. In certain embodiments, $R^8$ is hydrogen. In certain embodiments, $R^8$ is —$CH_3$. In embodiments, $R^8$ is —$CH_2CH_2OH$. In certain embodiments, $R^9$ is —$CH_2CO_2H$. In certain embodiments, $R^9$ is —$CH_2SO_3H$. In certain embodiments, $R^9$ is —$CH_2P(=O)(OH)_2$. In certain embodiments, $R^9$ is —$CO_2H$. In certain embodiments, $R^9$ is —$SO_3H$. In certain embodiments, $R^9$ is —$P(=O)(OH)_2$.

In certain embodiments, wherein $R^5$ is in the equatorial position, $R^3$ and $R^4$ are hydrogen, and $R^7$ is methyl, provided is a compound of Formula (III-e), (III-e-ent), (IV-e), or (IV-e-ent):

or a salt, isomer, or tautomer thereof, or mixture thereof. In certain embodiments, $R^1$ is hydrogen. In certain embodiments, $R^1$ is —$CH_3$. In certain embodiments, $R^1$ is —$CH_2CH_3$. In certain embodiments, $R^1$ is —$(CH_2)_2CH_3$. In certain embodiments, $R^2$ is —$CH_3$. In certain embodiments, $R^2$ is —$CH_2CH_3$. In certain embodiments, $R^2$ is —$(CH_2)_2CH_3$. In certain embodiments, $R^5$ is hydrogen. In certain embodiments, $R^5$ is —OH. In certain embodiments, $R^5$ is —$OCH_3$. In certain embodiments, $R^5$ is —$CH_3$. In certain embodiments, $R^5$ is —$CH_2CH_3$. In certain embodiments, $R^6$ is —$CH_3$. In certain embodiments, $R^8$ is hydrogen. In certain embodiments, $R^8$ is —$CH_3$. In certain embodiments, $R^8$ is —$CH_2CH_2OH$. In certain embodiments, $R^9$ is —$CH_2CO_2H$. In certain embodiments, $R^9$ is —$CH_2SO_3H$. In certain embodiments, $R^9$ is —$CH_2P(=O)(OH)_2$. In certain embodiments, $R^9$ is —$CO_2H$. In certain embodiments, $R^9$ is —$SO_3H$. In certain embodiments, $R^9$ is —$P(=O)(OH)_2$.

In certain embodiments, wherein $R^5$ is in the equatorial position, $R^3$ and $R^4$ are hydrogen, and $R^6$ and $R^7$ are methyl, provided is a compound of Formula (III-f), (III-f-ent), (IV-f), or (IV-f-ent):

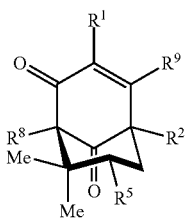
(III-f)

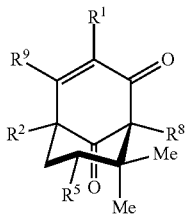
(III-f-ent)

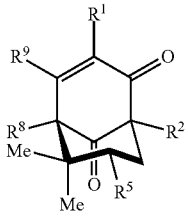
(IV-f)

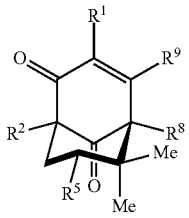
(IV-f-ent)

or a salt, isomer, or tautomer thereof, or mixture thereof. In certain embodiments, $R^1$ is hydrogen. In certain embodiments, $R^1$ is —$CH_3$. In certain embodiments, $R^1$ is —$CH_2CH_3$. In certain embodiments, $R^1$ is —$(CH_2)_2CH_3$. In certain embodiments, $R^2$ is —$CH_3$. In certain embodiments, $R^2$ is —$CH_2CH_3$. In certain embodiments, $R^2$ is —$(CH_2)_2CH_3$. In certain embodiments, $R^5$ is hydrogen. In certain embodiments, $R^5$ is —OH. In certain embodiments, $R^5$ is —$OCH_3$. In certain embodiments, $R^5$ is —$CH_3$. In certain embodiments, $R^5$ is —$CH_2CH_3$. In certain embodiments, $R^8$ is hydrogen. In certain embodiments, $R^8$ is —$CH_3$. In certain embodiments, $R^8$ is —$CH_2CH_2OH$. In certain embodiments, $R^9$ is —$CH_2CO_2H$. In certain embodiments, $R^9$ is —$CH_2SO_3H$. In certain embodiments, $R^9$ is —$CH_2P(=O)(OH)_2$. In certain embodiments, $R^9$ is —$CO_2H$. In certain embodiments, $R^9$ is —$SO_3H$. In certain embodiments, $R^9$ is —$P(=O)(OH)_2$.

In certain embodiments, the compound is a new compound, i.e., not hyperforin or known analog thereof; see, e.g., compounds disclosed in Verotta et al., *J. Nat. Prod.* (2002) 65:433-438; Sleeman et al., *Chem Bio Chem* (2005) 6:171-177; Verotta et al., *Eur. J. Org. Chem.* (2004) 2004:1193-1197; Shan et al., *J. Nat. Prod.* (2001) 64:127-130; Verotta et al., *J. Nat. Prod.* (1999) 62:770-772; Verotta et al., *J. Nat. Prod.* (2000) 63:412-415; PCT Application Publication No. WO 2003/091193; PCT Application Publication No. WO 2003/091194; PCT Application Publication No. WO 1999/064388; and U.S. Application Publication No. 2002/6444662, each of which is incorporated herein by reference.

Methods of Preparation

The present invention further provides methods of preparing compounds of the present invention, i.e., compounds of Formulae (I), (II), (III), (III-ent), (IV), and (IV-ent), and salts, isomers, or tautomers thereof, or mixtures thereof, as described herein. Methods of preparing said compounds is further depicted in FIGS. 1-18.

For example, in one aspect, provided is a method of preparing a compound of Formula (F-1):

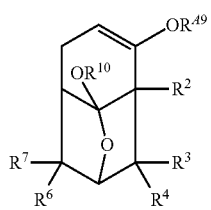
(F-1)

or salt thereof, wherein $R^2$, $R^3$, $R^4$, $R^6$, $R^7$, and $R^{49}$ are as defined herein, and $R^{10}$ is —$SO_2R^{410}$, —$Si(R^{410})_3$, —$CO_2R^{410}$, —$C(=O)R^{410}$, optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen protecting group, wherein each instance of $R^{410}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, or optionally substituted 5-10 membered heteroaryl;

the method comprising cyclizing a compound of Formula (E-1):

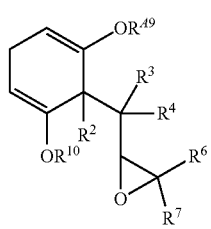
(E-1)

or salt thereof, to provide a compound of Formula (F-1), or salt thereof.

Figure 11:
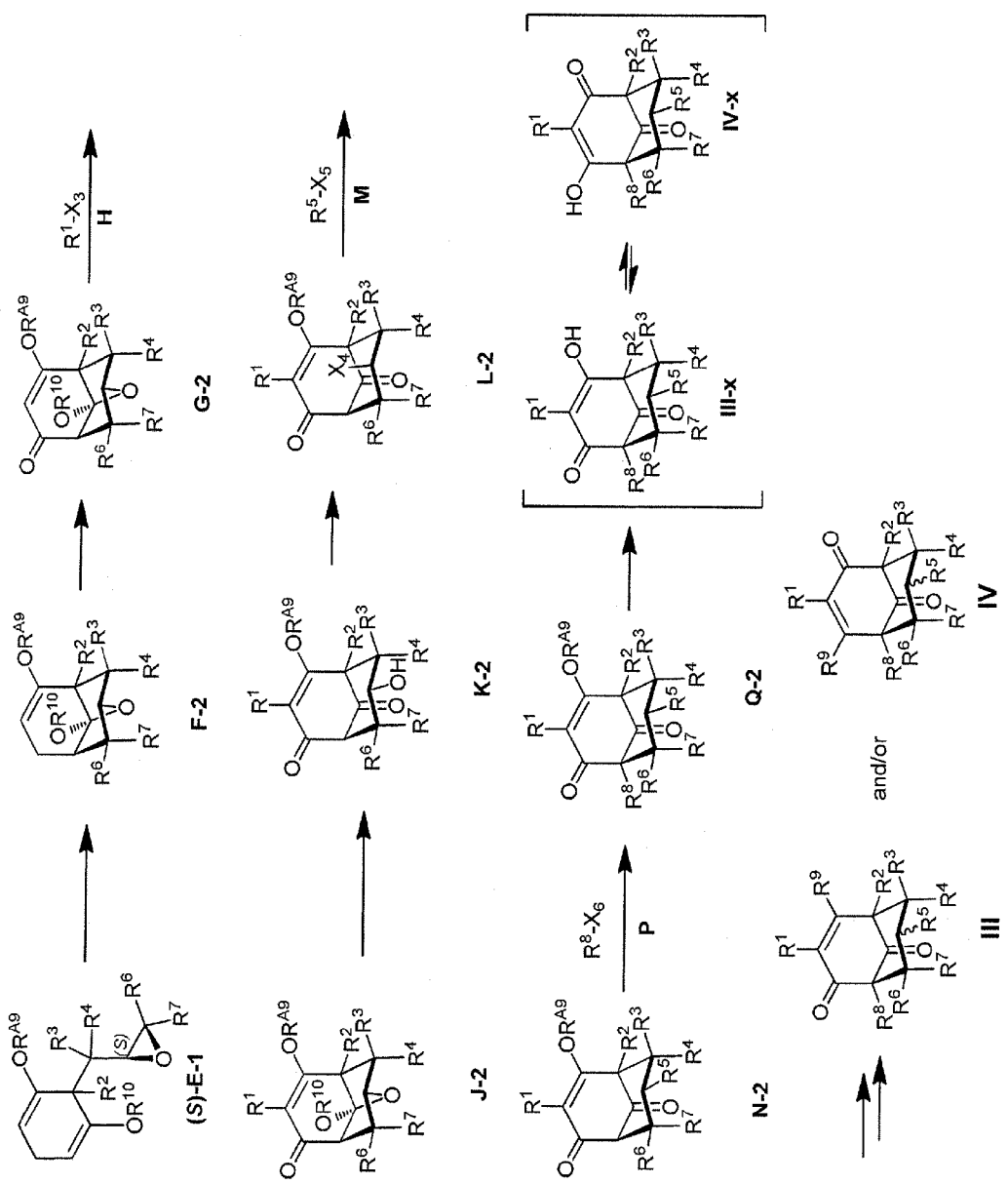
FIGS. 11 and 12 depict the syntheses of the stereoisomers of compounds of Formulae (I) and (II), e.g., compounds of Formulae (III) and (IV) (FIG. 11) and the enantiomers of compounds of Formulae (III) and (IV), i.e., compounds of Formulae (III-ent) and (IV-ent) (FIG. 12).
Figure 12:
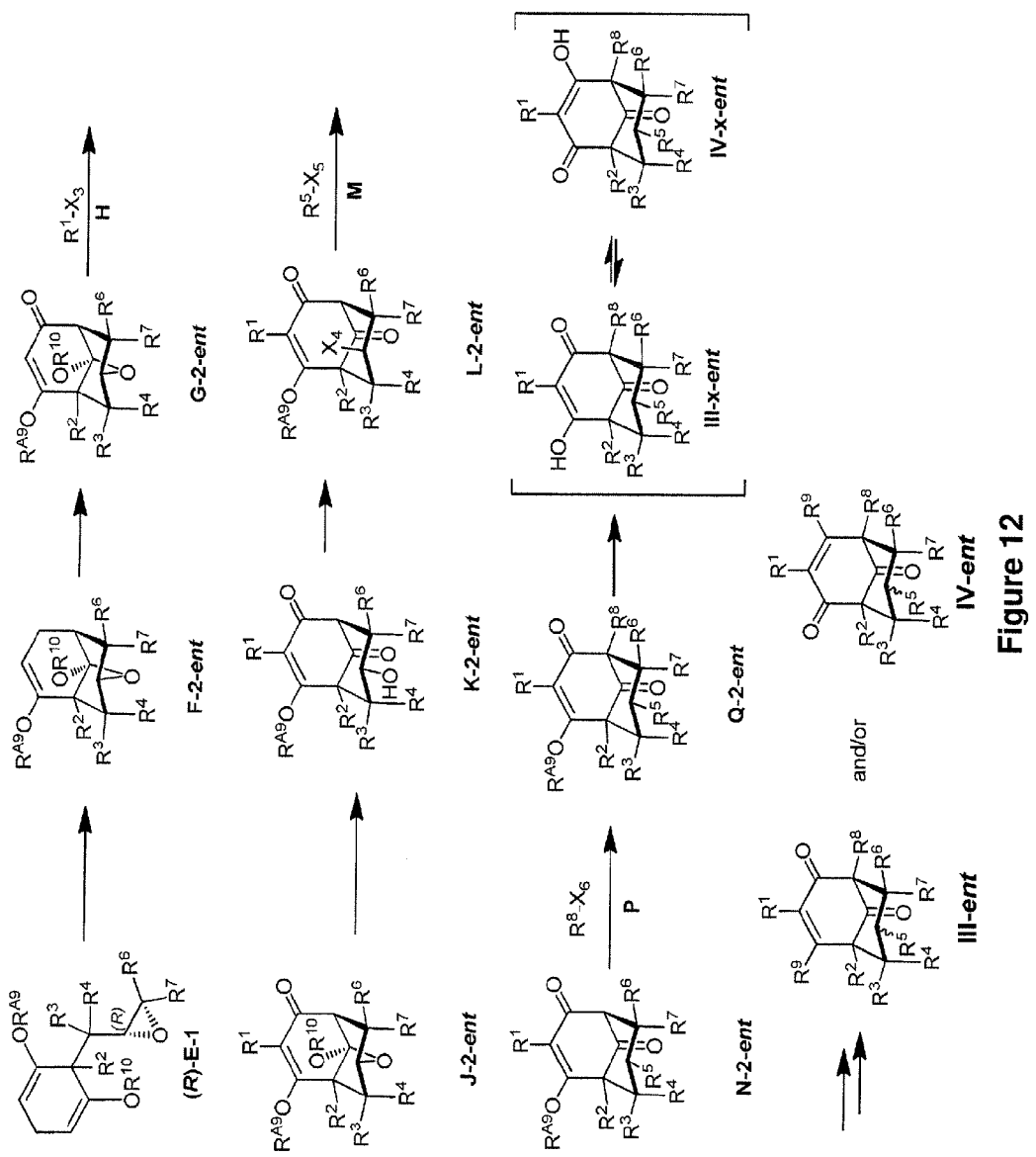

In certain embodiments, the compound of Formula (F-1) is a compound of Formula (F-2) or (F-2-ent), as depicted in FIGS. 11 and 12, respectively. In this instance, in certain embodiments, the stereochemistry of the epoxide group of compound (E-1), i.e., (S)-(E-1) or (R)-(E-1), directs the resulting stereochemistry of the cyclized product.

In certain embodiments, the step of cyclizing comprises contacting a compound of Formula (E-1) with a Lewis acid, as defined herein. In certain embodiments, the Lewis acid is a metal complex (e.g., a zinc complex, tin complex, aluminum complex, magnesium complex, scandium complex, titanium complex) or a metalloid complex (e.g., boron complex). In certain embodiments, the Lewis acid is a halide complex, e.g., a fluoride complex (e.g., $BF_3.OEt_2$), chloride complex (e.g., $SnCl_4$, $TiCl_4$, $Et_2AlCl$, $EtAlCl_2$, $AlCl_3$), or bromide complex (e.g., MgBr$_2$.OEt$_2$). In certain embodiments, the Lewis acid is a triflate, e.g., a silyl triflate (e.g., trimethylsilyl triflate (TMSOTf)), tin triflate (Sn(OTf)$_2$), zinc triflate (Zn(OTf)$_2$), or scandium triflate (Sc(OTf)$_3$).

In certain embodiments, the compound of Formula (E-1), or salt thereof, is provided by contacting a compound of Formula (D):

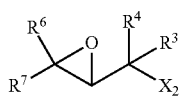
(D)

or salt thereof, wherein X$_2$ is a leaving group, as defined herein;
with a compound of Formula (C-1):

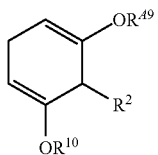
(C-1)

or salt thereof, in the presence of a base to provide the compound of Formula (E-1), or salt thereof;
wherein:

R$^6$ is hydrogen, —Si(R$^{46}$)$_3$, —CO$_2$H, —CO$_2$R$^{46}$, —C(=O)R$^{46}$, —C(=O)NH$_2$, —C(=O)NH(R$^{46}$), —C(=O)N(R$^{46}$)$_2$, —C(=O)SH, —C(=O)SR$^{46}$, optionally substituted C$_{1-20}$alkyl, optionally substituted C$_{2-20}$alkenyl, optionally substituted C$_{2-20}$alkynyl, optionally substituted C$_{3-10}$carbocyclyl, optionally substituted 3-10 membered heterocyclyl, optionally substituted C$_{6-14}$aryl, or optionally substituted 5-10 membered heteroaryl, wherein each instance of R$^{46}$ is independently optionally substituted C$_{1-20}$alkyl, optionally substituted C$_{2-20}$alkenyl, optionally substituted C$_{2-20}$alkynyl, optionally substituted C$_{3-10}$carbocyclyl, optionally substituted 3-10 membered heterocyclyl, optionally substituted C$_{6-14}$aryl, optionally substituted 5-10 membered heteroaryl, or an oxygen, sulfur, or nitrogen protecting group, or two R$^{46}$ groups are joined to form an optionally substituted 3-10 membered heterocyclyl or optionally substituted 5-10 membered heteroaryl ring; and R$^7$ is hydrogen, —Si(R$^{47}$)$_3$, —CO$_2$H, —CO$_2$R$^{47}$, —C(=O)R$^{47}$, —C(=O)NH$_2$, —C(=O)NH(R$^{47}$), —C(=O)N(R$^{47}$)$_2$, —C(=O)SH, —C(=O)SR$^{47}$, optionally substituted C$_{1-20}$alkyl, optionally substituted C$_{2-20}$alkenyl, optionally substituted C$_{2-20}$alkynyl, optionally substituted C$_{3-10}$carbocyclyl, optionally substituted 3-10 membered heterocyclyl, optionally substituted C$_{6-14}$aryl, or optionally substituted 5-10 membered heteroaryl, wherein each instance of R$^{47}$ is independently optionally substituted C$_{1-20}$alkyl, optionally substituted C$_{2-20}$alkenyl, optionally substituted C$_{2-20}$alkynyl, optionally substituted C$_{3-10}$carbocyclyl, optionally substituted 3-10 membered heterocyclyl, optionally substituted C$_{6-14}$aryl, optionally substituted 5-10 membered heteroaryl, or an oxygen, sulfur, or nitrogen protecting group, or two R$^{47}$ groups are joined to form an optionally substituted 3-10 membered heterocyclyl or optionally substituted 5-10 membered heteroaryl ring.

In certain embodiments, X$_2$ is a halogen leaving group, i.e., bromo, chloro, or iodo. In certain embodiments, X$_2$ is bromo.

In certain embodiments, the base is an organolithium reagent (e.g., tBuLi, sBuLi, nBuLi), and the compound of Formula (C-1) is treated with the base prior to contacting it with the compound of Formula (D). In certain embodiments, an additive is added after the compound of Formula (C-1) is treated with base and prior to contacting it with compound of Formula (D). In certain embodiments, the additive is, but is not limited to, BaI$_2$, MgBr$_2$, HMPA, or TMEDA.

Figure 9A:
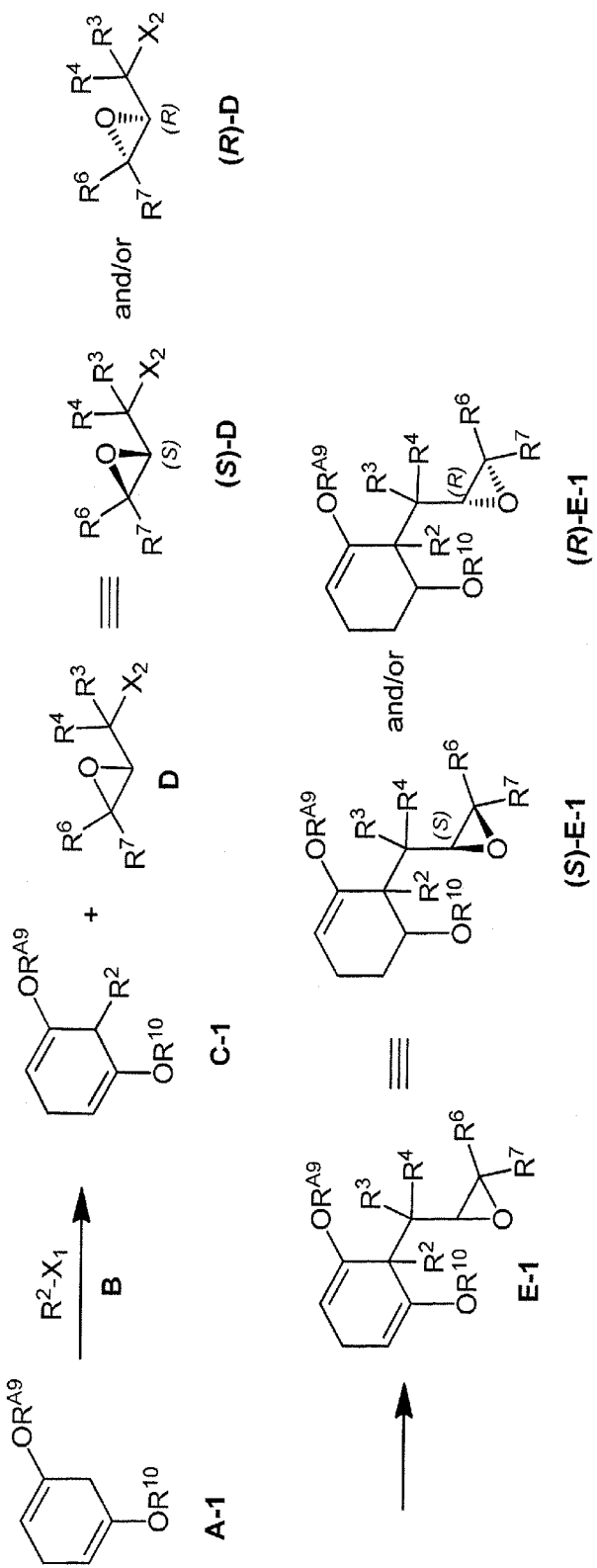
FIGS. 9A and 9B depict two exemplary routes to intermediate E-1.

In certain embodiments, the compound of Formula (D) is a chiral epoxide, i.e., of the Formula (S)-(D) or (R)-(D) as depicted in FIG. 9A. In this instance, in certain embodiments, reaction of (S)-(D) with (C-1) provides the product (S)-(E-1), and reaction of (R)-(D) with (C-1) provide the product (R)-(E-1).

Alternatively, in certain embodiments, the compound of Formula (E-1), or salt thereof, is provided by reducing a compound of Formula (E-2):

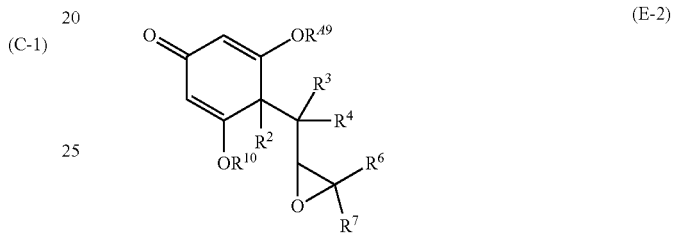
(E-2)

or salt thereof.

In certain embodiments, the step of reducing comprises a hydride reagent. In certain embodiments, the hydride reagent is lithium aluminum hydride (LAH). In certain embodiments, the hydride reagent is diisobutylaluminum hydride (DIBAL-H).

In certain embodiments, the compound of Formula (E-2), or salt thereof, is provided by coupling a compound of Formula (C-3):

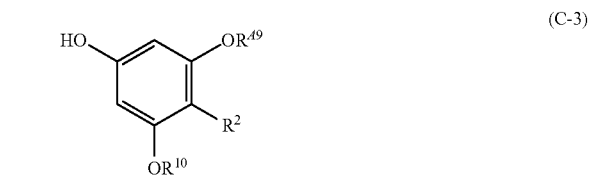
(C-3)

or salt thereof, with a compound of Formula (D):

(D)

or salt thereof, wherein X$_2$ is a leaving group, to provide the compound of Formula (E-2) or salt thereof.

In certain embodiments, X$_2$ is a halogen leaving group, i.e., bromo, chloro, or iodo. In certain embodiments, X$_2$ is bromo.

In certain embodiments, the coupling step is palladium-catalyzed allylation reaction. In certain embodiments, the palladium-catalyzed allylation comprises using a palladium (II) salt (e.g., Pd(OAc)$_2$, PdCl$_2$, Pd(O$_2$CCF$_3$)$_2$, Pd(OAc)$_2$/C), triphenylphosphine, and a titanium Lewis acid (e.g., TiCl$_4$, titanium isopropoxide).

Figure 9B:
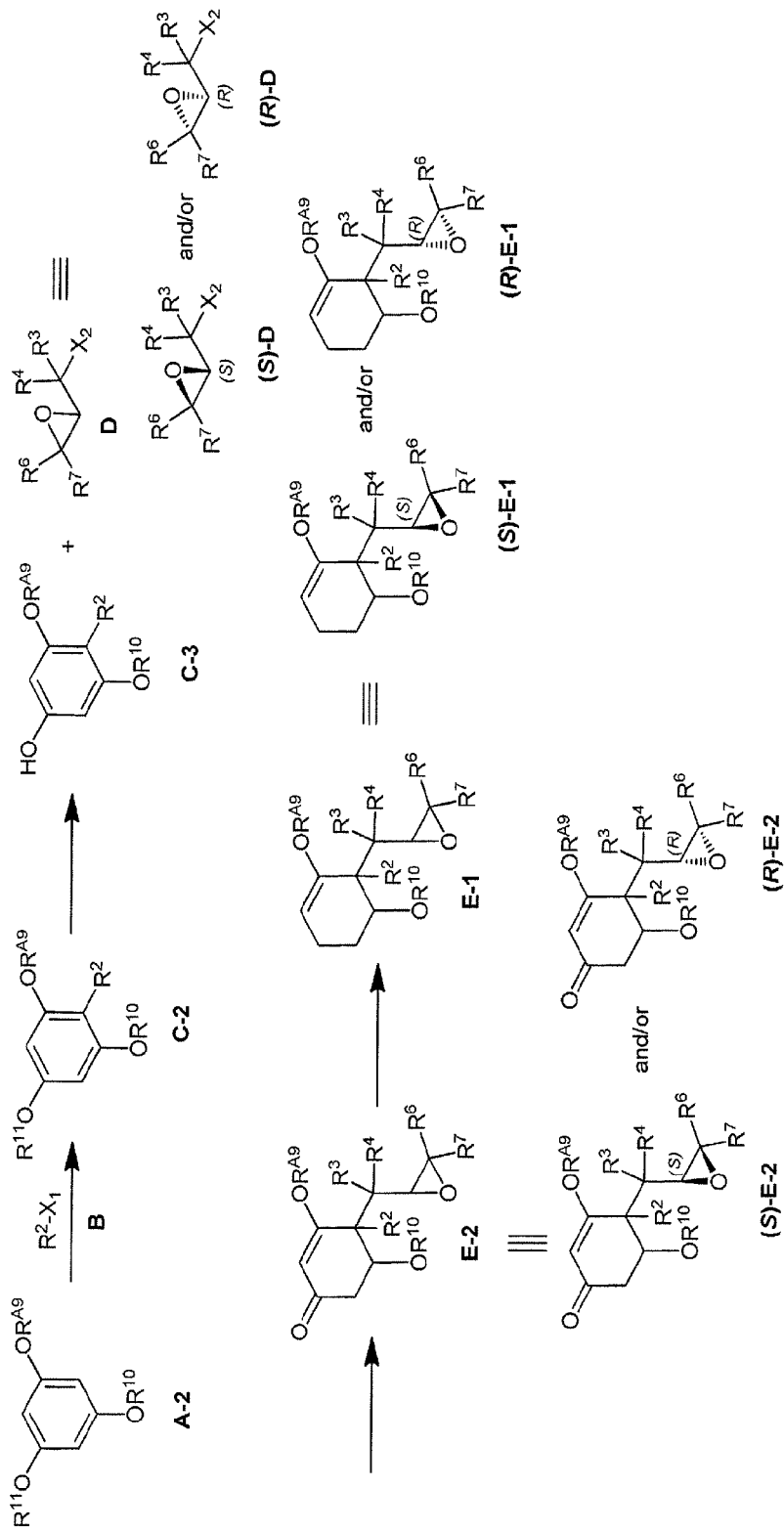
Figure 10:
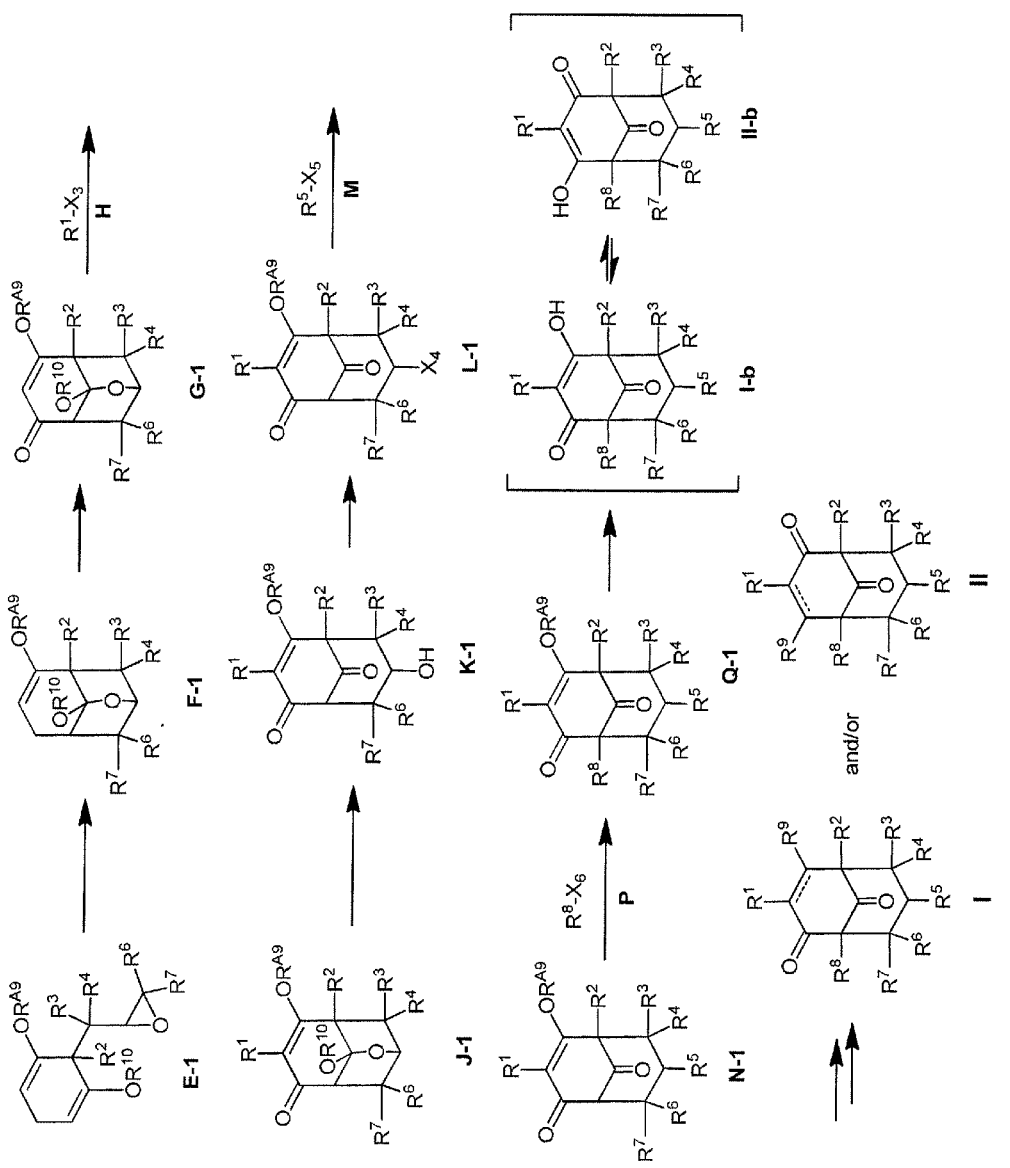
FIG. 10 depicts the synthesis of compounds of Formulae (I) and (II).

In certain embodiments, the compound of Formula (D) is a chiral epoxide, i.e., of the Formula (S)-(D) or (R)-(D) as depicted in FIG. 9B. In this instance, in certain embodiments, reaction of (S)-(D) with (C-3) provides the product (S)-(E-2), and reaction of (R)-(D) with (C-3) provide the product (R)-(E-2).

In certain embodiments, the compound of Formula (C-3), or salt thereof, is provided by deprotecting a compound of Formula (C-2):

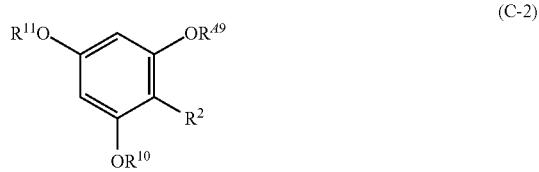

(C-2)

or salt thereof;
wherein $R^{11}$ is —$SO_2R^{411}$, —$Si(R^{411})_3$, —$CO_2R^{411}$, —$C(\!=\!O)R^{411}$, optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, $C_{6-14}$optionally substituted aryl, optionally substituted 5-10 membered heteroaryl, or an oxygen protecting group, wherein each instance of $R^{41}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl.

In certain embodiments, $R^{11}$ is —$Si(R^{411})_3$. In certain embodiments, $R^{11}$ is triisopropylsilyl (TIPS) (—$Si(iPr)_3$). In certain embodiments, the deprotecting step comprises a fluoride reagent, e.g., tetra-n-butylammonium fluoride (TBAF), tris(dimethylamino)sulfonium difluorotrimethylsilicate (TASF), or potassium fluoride.

In any of the above or below instances, in certain embodiments, $R^2$ is hydrogen. However, in certain optional embodiments, $R^2$ is not hydrogen. In these instances, in certain optional embodiments, the compound of Formula (C-2), or salt thereof, is provided by contacting a compound of Formula (A-2):

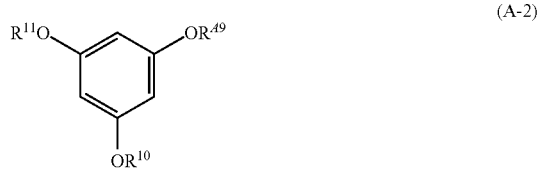

(A-2)

or salt thereof, with a compound of Formula (B):

$R^2$—$X_1$ (B)

or salt thereof, wherein $X_1$ is a leaving group, as defined herein; and
$R^2$ is —$Si(R^{A2})_3$, —$SO_2R^{A2}$, —$SO_2R^{A2}$, —$CO_2R^{A2}$, —$C(\!=\!O)R^{A2}$, —$C(\!=\!O)NH_2$, —$C(\!=\!O)NH(R^{A2})$, —$C(\!=\!O)N(R^{A2})_2$, —$C(\!=\!O)SH$, —$C(\!=\!O)SR^{A2}$, optionally substituted $C_{1-20}$alkyl, optionally substituted $C_{2-20}$alkenyl, optionally substituted $C_{2-20}$alkynyl, optionally substituted $C_{6-14}$aryl, or optionally substituted 5-10 membered heteroaryl, wherein each instance of $R^{A2}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen, sulfur, or nitrogen protecting group, or two $R^{A2}$ groups are joined to form an optionally substituted 3-10 membered heterocyclyl or optionally substituted 5-10 membered heteroaryl ring; in the presence of a base to provide a compound of Formula (C-2), or salt thereof.

In certain embodiments, $X_1$ is a halogen leaving group, i.e., bromo, chloro, or iodo. In certain embodiments, $X_1$ is bromo.

In certain embodiments, the base is an organolithium reagent (e.g., tBuLi, sBuLi, nBuLi), and the compound of Formula (A-2) is treated with the base prior to contacting it with the compound of Formula (B). In certain embodiments, an additive is added after the compound of Formula (A-2) is treated with base and prior to contacting it with compound of Formula (B). In certain embodiments, the additive is, but is not limited to, $BaI_2$, $MgBr_2$, HMPA, or TMEDA.

In certain embodiments, the method further comprises oxidizing the compound of Formula (F-1), or salt thereof, to provide a compound of Formula (G-1):

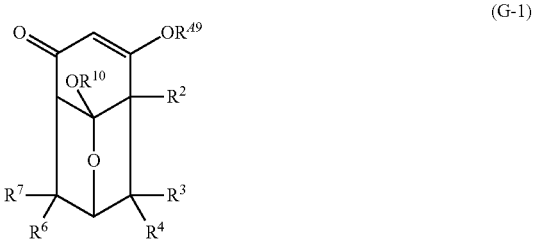

(G-1)

or salt thereof.

In certain embodiments, the step of oxidizing comprises a reagent useful in allylic oxidation; many reagents have been found useful in such a reaction, e.g., for example, chromium-based oxidants ($CrO_3$-pyridine, PCC-pyridine, PDC-pyridine, $CrO_3$-3,5-dimethylpyrazole, PCC-3,5-dimethylpyrazole, PDC-3,5-dimethylpyrazole), ceric ammonium nitrate (CAN), 2,3-dichloro-5,6-dicyano-para-benzoquinone (DDQ), singlet oxygen ($^1O_2$), peroxides (e.g., tert-butyl hydrogen peroxide (TBHP), cumene hydroperoxide (CHP)), a combination of peroxides and various co-oxidants (e.g., CuI-TBHP, [bis(trifluoroacetoxy)iodo]benzene-TBHP, (diacetoxy)iodobenzene-TBHP, Mn(OAc)-3-TBHP, Pd(OAc)-2-TBHP, Pd(OH)$_2$—CHP, Pd(OH)$_2$-TBHP, 2,2'-bipyridyl diselenide-PhIO$_2$, dirhodium tetracaprolactamate-TBHP, RuCl$_3$-TBHP), RuO$_2$, SeO$_2$, and 1-(tert-butylperoxy)-1,2-benziodoxol-3(1H)-one; see, e.g., Larock, *Comprehensive Organic Transformations*, VCH Publishers, Inc., New York, 1989, for other reagents useful for this reaction. In certain embodiments, the step of oxidizing comprises using a peroxide and a metal catalyst. In certain embodiments, the step of oxidizing comprises using a peroxide and a palladium catalyst. In certain embodiments, the step of oxidizing comprises t-butyl hydrogen peroxide (TBHP) and Pd(OH)$_2$. In certain embodiments, the step of oxidizing comprises using a peroxide (e.g., TBHP, CHP) and a hypervalent iodine catalyst (e.g., (diacetoxy)iodobenzene (DIB), (dichloro)iodbenzene (PhICl$_2$), [bis(trifluoroacetoxy)iodo]benzene (PIFA), iodosylbenzene (PhIO), iodoxylbenzene (PhO$_2$)).

In any of the above or below instances, in certain embodiments, $R^1$ is hydrogen. However, in certain optional embodiments, $R^1$ is not hydrogen. In these instances, in certain optional embodiments, the method further comprises installing a non-hydrogen $R^1$ group by contacting the compound of Formula (G-1), or salt thereof, and a compound of Formula (H):

$$R^1\text{—}X_3 \tag{H}$$

or salt thereof, wherein $R^1$ is halogen, —$SO_2R^{41}$, —$SO_2OR^{41}$, —$Si(R^{41})_3$, —$CO_2R^{41}$, —$C(=O)R^{41}$, —$C(=O)NH_2$, —$C(=O)NH(R^{41})$, —$C(=O)N(R^{41})_2$, —$C(=O)SH$, —$C(=O)SR^{41}$, optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, or optionally substituted 5-10 membered heteroaryl, wherein each instance of $R^{41}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, optionally substituted 5-10 membered heteroaryl, or an oxygen, sulfur, or nitrogen protecting group, or two $R^{41}$ groups are joined to form an optionally substituted 3-10 membered heterocyclyl or optionally substituted 5-10 membered heteroaryl ring; and $X_3$ is a leaving group, as defined herein;

in the presence of a base to provide a compound of Formula (J-1):

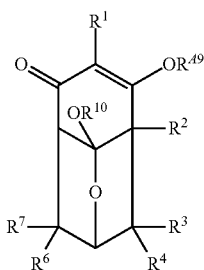

(J-1)

or salt thereof.

In certain embodiments, $X_3$ is a halogen leaving group, i.e., bromo, chloro, or iodo. In certain embodiments, $X_3$ is bromo.

In certain embodiments, the base is lithium tetramethylpiperidide (LiTMP). In certain embodiments, the base is LiTMP, and a cuprate (e.g., lithium 2-thienyl(cyano)copper lithium) is added prior to addition of a compound of formula (H). In certain embodiments, the base is lithium diisopropylamide (LDA). In certain embodiments, the base is an organolithium reagent (e.g., tBuLi, sBuLi, nBuLi). In certain embodiments, the base is lithium hexamethyldisilazine. In certain embodiments, the base is sodium hexamethyldisilazine.

In certain embodiments, the method further comprises deprotecting the compound of Formula (J-1), or salt thereof, to provide a compound of Formula (K-1):

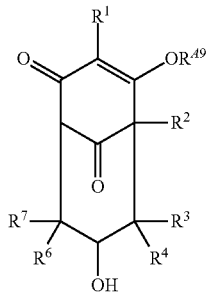

(K-1)

or salt thereof, i.e., wherein $R^5$ is —OH.

In certain embodiments, the step of deprotecting comprises contacting the compound of Formula (J-1) with an acid. In certain embodiments, the oxygen protecting group $R^{10}$ is optionally substituted $C_{1-20}$alkyl, e.g., —$CH_3$. In certain embodiments, the acid is an inorganic acid, e.g., hydrochloric acid, hydrofluoric acid. In certain embodiments, the acid is an organic acid, e.g., oxalic acid, acetic acid, formic acid, para-toluenesulfonic acid, camphorsulfonic acid. In certain embodiments, the acid is a Lewis acid, e.g., boron trifluoride diethyl etherate, scandium triflate.

In certain embodiments, the method further comprises converting the free hydroxyl group of the compound of Formula (K-1), or salt thereof, to $X_4$, wherein $X_4$ is a leaving group as defined herein, to provide a compound of Formula (L-1):

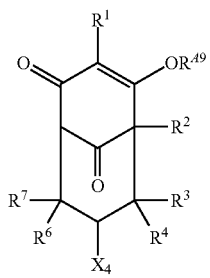

(L-1)

or salt thereof, i.e., wherein $R^5$ is the leaving group $X_4$.

In certain embodiments, $X_4$ is a halogen leaving group, i.e., bromo, chloro, or iodo. In certain embodiments, $X_4$ is iodo. In certain embodiments, $X_4$ is a sulfonated hydroxyl leaving group (e.g., —O-mesylate (—OMs), —O-triflate (—OTf), —O-tosylate (—OTs)).

In certain embodiments, the step of converting comprises contacting the compound of Formula (K-1) under Mitsunobu conditions and $I_2$, e.g., for example, using the $Ph_3P$—$I_2$-imidazole reagent combination, to provide a compound of formula (L-1) wherein $X_4$ is iodo (—I). In certain embodiments, the step of converting comprises converting the compound of Formula (K-1) to the mesylate (e.g., for example, using methanesulfonyl chloride-triethylamine) followed by treatment under Finkelstein conditions, e.g., for example, using sodium iodide in acetone, to provide a compound of formula (L-1) wherein $X_4$ is iodo (—I). In certain embodiments, the step of converting comprises contacting the compound of Formula (K-1) with iodine ($I_2$) to provide a compound of formula (L-1) wherein $X_4$ is iodo (—I). In certain embodiments, the step of converting comprises contacting the compound of Formula (K-1) to N-methyl-N,N'-dicyclohexylcarbodiimidium iodide (DCC-MeI) to provide a compound of formula (L-1) wherein $X_4$ is iodo (—I).

In any of the above or below instances, in certain embodiments, $R^5$ is hydrogen, i.e., for example, in certain embodiments, the group $X_4$ of the compound of Formula (L-1) or the hydroxyl group of the compound of Formula (K-1) is reduced to provide a compound of Formula (N-1) wherein $R^5$ is hydrogen:

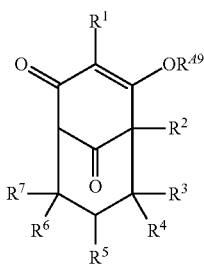

(N-1)

or salt thereof.

Replacement of a hydroxyl group or leaving group with a hydrogen is known in the art. For example, in certain embodiments, the hydroxyl group of the compound of Formula (K-1) is converted to a sulfonated hydroxyl leaving group (e.g., using methanesulfonic anhydride or methanesulfonyl chloride to provide —OMs; using tosyl chloride to provide —OTs) to provide a compound of Formula (L-1) and subsequently treated with a hydride reducing agent (e.g., LiAlH$_4$, (i-Pr)$_2$AlH) to provide a compound of Formula (N-1) wherein $R^5$ is hydrogen. In certain embodiments, a compound of Formula (L-1) or (K-1) is treated with hydrogen gas, zinc, or tributylin hydride in acetic acid to provide a compound of Formula (N-1) wherein $R^5$ is hydrogen. In certain embodiments, a compound of Formula (L-1) or (K-1) is treated with trifluoroacetic acid and triethylsilane to provide a compound of Formula (N-1) wherein $R^5$ is hydrogen. In certain embodiments, a compound of Formula (K-1) is converted to a xanthate (e.g., using NaH—CS$_2$ followed by MeI) and subsequently deoxygenated using Barton deoxygenation conditions (e.g., using n-Bu$_3$SnH-azobisisobutyronitrile (AIBN)) to provide a compound of Formula (N-1) wherein $R^5$ is hydrogen.

Alternatively, in certain embodiments, wherein at least one of $R^3$ and $R^4$ is hydrogen, the group $X_4$ of the compound of Formula (L-1), or the hydroxyl group (—OH) of the compound of Formula (K-1) is eliminated to provide a compound of Formula (O-1) or (O-2):

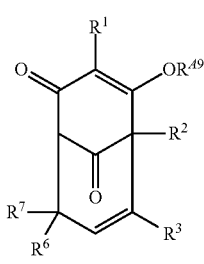

(O-1)

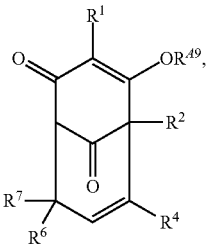

(O-2)

or salt thereof, followed by hydrogenation of the double bond to provide a compound of Formula (N-1), or salt thereof, wherein $R^5$ is hydrogen.

In other embodiments, wherein at least one of $R^6$ and $R^7$ is hydrogen, the group $X_4$ of the compound of Formula (L-1), or the hydroxyl group (—OH) of the compound of Formula (K-1) is eliminated to provide a compound of Formula (O-3) or (O-4):

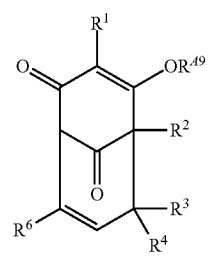

(O-3)

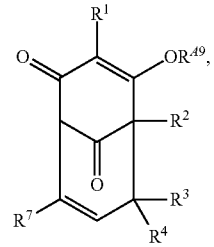

(O-4)

or salt thereof, followed by hydrogenation of the double bond to provide a compound of Formula (N-1), or salt thereof, wherein $R^5$ is hydrogen.

Elimination of the leaving group of Formula (L-1) or the hydroxyl group of (K-1) to provide a double bond, followed by hydrogenation of the double bond is known in the art. For example, in certain embodiments, the hydroxyl group of the compound of Formula (K-1) is converted to a sulfonated hydroxyl leaving group (e.g., using methanesulfonic anhydride or methanesulfonyl chloride to provide —OMs; using tosyl chloride to provide —OTs) to provide a compound of Formula (L-1) and treated with a base (e.g., triethylamine, DBU, pyridine) to provide the eliminated product. Other elimination conditions include treatment of the hydroxyl group of (K-1) with, for example, Martin sulfurane, TsOH, POCl$_3$, or SOCl$_2$, to provide the eliminated product. Synthetic manipulation of the double bond is envisioned as a key entry point for installing desired $R^3$, $R^4$, $R^6$ and/or $R^7$ groups, e.g., for example, installing heteroatom-containing functional groups, such as wherein $R^6$ is —OH, —OR$^{46}$, —NH$_2$, —NHR$^{46}$, —N(R$^{46}$)$_2$, —NH—NH—R$^{46}$, —NR$^{46}$—NHR$^{46}$, —N=NR$^{46}$, —N$_3$, —SH, —SR$^{46}$, —SO$_2$R$^{46}$, —SO$_3$H, or —SO$_2$OR$^{A6}$, or wherein R$^7$ is —OH, —OR$^{A7}$, —NH$_2$, —NHR$^{A7}$, —N(R$^{A7}$)$_2$, —NH—NH—R$^{A7}$, —NR$^{A7}$—NHR$^{A7}$, —N=NR$^{A7}$, —N$_3$, —SH, —SR$^{A7}$, —SO$_2$R$^{A7}$, —SO$_3$H, —SO$_2$OR$^{A7}$. The double bond may be hydrogenated using known conditions, e.g., for example, under hydrogen gas in the presence of a palladium catalyst (e.g., 5-10% Pd/C).

However, in certain optional embodiments, R$^5$ is not hydrogen. In these instances, in certain optional embodiments, the method comprises installing a non-hydrogen R$^5$ group by coupling the compound of Formula (L-1), or salt thereof, with a compound of Formula (M):

$$R^5-X_5 \qquad (M)$$

or salt thereof, to provide a compound of Formula (N-1):

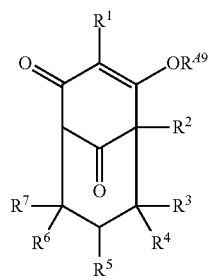

(N-1)

or salt thereof;

wherein R$^5$ is halogen, —SO$_2$R$^{A5}$, —SO$_2$OR$^{A5}$, —Si(R$^{A5}$)$_3$, —CO$_2$R$^{A5}$, —C(=O)R$^{A5}$, —C(=O)NH$_2$, —C(=O)NH (R$^{A5}$), —C(=O)N(R$^{A5}$)$_2$, —C(=O)SH, —C(=O)SR$^{A5}$, optionally substituted C$_{1-20}$alkyl, optionally substituted C$_{2-20}$alkenyl, optionally substituted C$_{2-20}$alkynyl, optionally substituted C$_{3-10}$carbocyclyl, optionally substituted 3-10 membered heterocyclyl, optionally substituted C$_{6-14}$aryl, or optionally substituted 5-10 membered heteroaryl, wherein each instance of R$^{A5}$ is independently optionally substituted C$_{1-20}$alkyl, optionally substituted C$_{2-20}$alkenyl, optionally substituted C$_{2-20}$alkynyl, optionally substituted C$_{3-10}$carbocyclyl, optionally substituted 3-10 membered heterocyclyl, optionally substituted C$_{6-14}$aryl, optionally substituted 5-10 membered heteroaryl, or an oxygen, sulfur, or nitrogen protecting group, or two R$^{A5}$ groups are joined to form an optionally substituted 3-10 membered heterocyclyl or optionally substituted 5-10 membered heteroaryl ring; and X$_5$ is a leaving group, as defined herein, or —Sn(R$^{15}$)$_3$, wherein each instance of R$^{15}$ is optionally substituted C$_{1-10}$alkyl (e.g., methyl, ethyl, n-propyl, n-butyl).

Coupling methods are well known in the art. For example, in certain embodiments, the coupling step comprises an organometallic reagent. In certain embodiments, prior to the contacting step, either the compound of Formula (L-1) wherein X$_4$ is bromo, iodo, or chloro, or the compound of Formula (M) wherein X$_5$ is bromo, iodo, or chloro, is converted to an organometallic reagent such that X$_4$ or X$_5$ and the carbon atom to which X$_4$ or X$_5$ is attached are associated with a metal atom.

For example, in certain embodiments, the compound of Formula (L-1) is converted to an organometallic reagent of the Formula (L-1'):

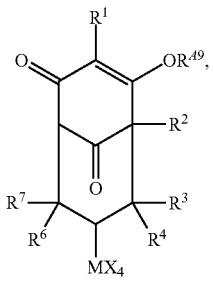

(L-1')

wherein M is a metal atom, e.g., zinc, magnesium, copper, or nickel, and X$_4$ is bromo, iodo, or chloro.

Alternatively, in certain embodiments, the compound of Formula (M) is converted to an organometallic reagent of the Formula (M'):

$$R^5\text{-}M\text{-}X_5 \qquad (M')$$

wherein M is a metal atom, e.g., zinc, magnesium, copper, or nickel, and X$_5$ is bromo, iodo, or chloro.

In any of the above two instances, in certain embodiments, the metal atom is zinc, magnesium, copper, or nickel, and the organometallic reagent is a zinc, magnesium, or nickel organometallic reagent. In certain embodiments, the organometallic reagent is a zinc organometallic reagent. In certain embodiments, the zinc organometallic reagent (L-1') is coupled to the compound of Formula (M) in the presence of a nickel catalyst. In certain embodiments, the zinc organometallic reagent (M') is coupled to the compound of Formula (L-1) in the presence of a nickel catalyst. In certain embodiments, the nickel catalyst is NiCl$_2$(PPh$_3$)$_2$ or NiCl$_2$[1,2-bis (triphenylphosphino)ethane]. In certain embodiments, the zinc organometallic reagent (L-1') is coupled to the compound of Formula (M) in the presence of a copper catalyst. In certain embodiments, the zinc organometallic reagent (M') is coupled to the compound of Formula (L-1) in the presence of a copper catalyst. In certain embodiments, the copper catalyst is CuBr.Me$_2$S.

In other embodiments, the organometallic reagent used for the coupling is the compound of Formula (M), wherein X$_5$ is —Sn(R$^{15}$)$_3$. In these embodiments, the compound of Formula (L-1), wherein X$_4$ is bromo, iodo, or chloro, is treated with the organometallic reagent of Formula (M), wherein X$_5$ is —Sn(R$^{15}$)$_3$, to provide a compound of Formula (N-1). In certain embodiments, the organometallic reagent is the tributyl tin reagent R$_5$—SnBu$_3$. In certain embodiments, the organometallic reagent is used in combination with a radical initiator (e.g., azobisisobutyronitrile (AIBN)). In certain embodiments, R$^5$ is optionally substituted C$_{1-20}$alkyl, optionally substituted C$_{2-20}$alkenyl, optionally substituted C$_{2-20}$alkynyl, optionally substituted C$_{3-10}$carbocyclyl, optionally substituted 3-10 membered heterocyclyl, optionally substituted C$_{6-14}$aryl, or optionally substituted 5-10 membered heteroaryl.

In any of the above or below instances, in certain embodiments, R$^8$ is hydrogen. However, in certain embodiments, R$^8$ is not hydrogen. In this instance, in certain optional embodiments, the method further comprises installing a non-hydrogen R$^8$ group by contacting the compound of Formula (N-1), or salt thereof, with a compound of Formula (P):

$$R^8-X_6 \qquad (P)$$

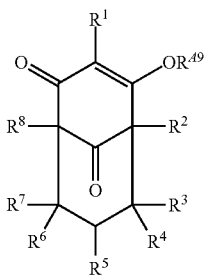

(Q-1)

or salt thereof, in the presence of a base to provide a compound of Formula (Q-1):
or salt thereof,
wherein $R^8$ is halogen, —Si$(R^{48})_3$, —SO$_2R^{48}$, —SO$_2$O$R^{48}$, —CO$_2R^{48}$, —C(=O)$R^{48}$, —C(=O)NH$_2$, —C(=O)NH$(R^{48})$, —C(=O)N$(R^{48})_2$, —C(=O)S$R^{48}$, —C(OH)(O$R^{48}$)$R^{48}$, —C(OH)$_2R^{48}$, —C(O$R^{48})_2R^{48}$, optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, $C_{6-14}$ optionally substituted aryl, or optionally substituted 5-10 membered heteroaryl, wherein each instance of $R^{48}$ is independently optionally substituted $C_{1-20}$alkyl, optionally substituted $C_{2-20}$alkenyl, optionally substituted $C_{2-20}$alkynyl, optionally substituted $C_{3-10}$carbocyclyl, optionally substituted 3-10 membered heterocyclyl, optionally substituted $C_{6-14}$aryl, or optionally substituted 5-10 membered heteroaryl, or an oxygen, sulfur, or nitrogen protecting group, or two $R^{48}$ groups are joined to form an optionally substituted 3-10 membered heterocyclyl or optionally substituted 5-10 membered heteroaryl ring; and
$X_6$ is a leaving group, as defined herein.

In certain embodiments, $X_6$ is a halogen leaving group, i.e., bromo, chloro, or iodo. In certain embodiments, $X_6$ is chloro.

In certain embodiments, the base is an organolithium reagent (e.g., tBuLi, sBuLi, nBuLi, LDA, LiTMP, LiHMDS), and the compound of Formula (N-1) is treated with the base prior to contacting it with the compound of Formula (P). In certain embodiments, the base is an organomagnesium reagent (e.g., iPrMgCl), and the compound of Formula (N-1) is treated with the base prior to contacting it with the compound of Formula (P).

In certain embodiments, the method further comprises deprotecting the compound of Formula (Q-1), or salt thereof, to provide a compound of Formula (I-b) and (II-b) as a tautomeric mixture:

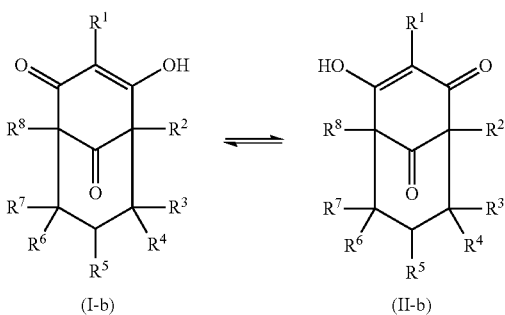

(I-b)  (II-b)

or salt thereof.

In certain embodiments, the deprotection step comprises contacting the compound of Formula (Q-1) with a base. In certain embodiments, the base is a hydroxide, e.g., LiOH, NaOH, or KOH.

Compounds of any of the above Formulae may be further synthetically manipulated before or after any step of the above described synthetic pathway. For example, in certain embodiments, an ester group present on the molecule, e.g., —CO$_2R^{41}$, —CO$_2R^{42}$, —CO$_2R^{45}$, and/or —CO$_2R^{48}$, can be hydrolyzed to the corresponding acid —CO$_2$H. A sulfonic ester group present on the molecule, e.g., —SO$_2$O$R^{41}$, SO$_2$O$R^{42}$, —SO$_2$O$R^{45}$, and/or —SO$_2$O$R^{48}$, can be hydrolyzed to the corresponding sulfonic acid —SO$_3$H. A thiol group —SH present on the molecule can be oxidized to the corresponding sulfonic acid —SO$_3$H. A thiol ether group present on the molecule, e.g., —S$R^{42}$, can be oxidized to the corresponding sulfonyl group, e.g., —SO$_2R^{42}$. Other groups may be synthetically manipulated to provide inventive compounds; see, for example, the synthetic derivatizations of intermediates F-1, K-1, N-1, and Q-1 as depicted in FIGS. 13-18.

Pharmaceutical Compositions and Administration

The present invention provides pharmaceutical compositions comprising a compound of the present invention, e.g., a compound of Formula (I), (II), (III), (III-ent), (IV), or (IV-ent), or a salt, isomer, or tautomer thereof, or mixture thereof, as described herein, and a pharmaceutically acceptable excipient. In certain embodiments, the compound of the present invention or a pharmaceutically acceptable salt thereof is provided in an effective amount in the pharmaceutical composition. In certain embodiments, the effective amount is a therapeutically effective amount. In certain embodiments, the effective amount is a prophylactically effective amount.

Pharmaceutically acceptable excipients include any and all solvents, diluents, or other liquid vehicles, dispersions, suspension aids, surface active agents, isotonic agents, thickening or emulsifying agents, preservatives, solid binders, lubricants and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21st Edition (Lippincott Williams & Wilkins, 2005).

Pharmaceutical compositions described herein can be prepared by any method known in the art of pharmacology. In general, such preparatory methods include the steps of bringing the compound of the present invention (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, and/or mixtures thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered. by rapid inhalation through the nasal passage from a container of the powder held close to the nares.

Formulations for nasal administration may, for example, comprise from about as little as 0.1% (w/w) and as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease, disorder, or condition being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of the invention may be administered orally or parenterally at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional therapeutically active agents. The compounds or compositions can be administered in combination with additional therapeutically active agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The compound or composition can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

Exemplary additional therapeutically active agents include, but are not limited to, anti-depressants, anti-inflammatory agents, immunosuppressant agents, and analgesics. Therapeutically active agents include small organic molecules such as drug compounds (e.g., compounds approved by the US Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins and cells.

Also encompassed by the invention are kits (e.g., pharmaceutical packs). The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the container and the second container are combined to form one unit dosage form.

Uses

The present invention also provides methods of use and treatment of compounds of the present invention, e.g., compounds of Formulae (I), (II), (III), (III-ent), (IV), and (IV-ent), and salts, isomers, and tautomers thereof, and mixtures thereof, as described herein.

For example, in one aspect, provided is a method of treating depression in a subject in need thereof, the method comprising administering an effective amount of compound of the present invention, or a pharmaceutical composition thereof, to the subject to treat depression. Also provided is a method of treating depression in a subject in need thereof, the method comprising instructing the subject to administer an effective amount of compound of the present invention, or a pharmaceutical composition thereof, to treat depression. Further provided is a compound of the present invention, or pharmaceutical composition thereof, for use in treating depression. In certain embodiments, the effective amount is a therapeutically effective amount. In certain embodiments, the effective amount is a prophylactically effective amount.

Depression include any condition characterized by a depressed mood, and may also include irritability, instability of mood, and/or changes in mood. Thus, depression encompasses Major Depressive Disorder (MDD), dysthymic disorder (i.e., low mood), melancholic depression, atypical depression, catatonic depression, postpartum depression, seasonal affective disorder (SAD), but also includes conditions which can be characterized by a depressed mood, such as insomnia, stress, hormonal mood swings (e.g., during pregnancy, Premenstrual Dysphoric Disorder and related conditions, puberty, and menopause), mild cognitive impairment, substance-induced mood disorders (e.g., alcoholism), dementia, Alzheimer's disease, Parkinson's disease, Huntington's disease, and psychotic disorders (e.g., Schizoaffective Disorder, Schizophrenia, Delusional Disorder, and Psychotic Disorder Not Otherwise Specified).

In another aspect, provided is a method of treating TRPC6-mediated condition in a subject in need thereof, the method comprising administering an effective amount of compound of the present invention, or a pharmaceutical composition thereof, to the subject to treat the condition. Also provided is a method of treating a TRPC6-mediated condition in a subject in need thereof, the method comprising instructing the subject to administer an effective amount of compound of the present invention, or a pharmaceutical composition thereof, to treat the condition. Further provided is a compound of the present invention, or pharmaceutical composition thereof, for use in treating a TRPC6-mediated condition. In certain embodiments, the effective amount is a therapeutically effective amount. In certain embodiments, the effective amount is a prophylactically effective amount. As used herein, a "TRPC6-mediated condition" refers to a condition which is ameliorated by activation of TRPC channel proteins. Exemplary conditions include, but are not limited to, asthma and chronic obstructive pulmonary disease (COPD). Other conditions which are envisioned as treatable using the compounds of the present invention include inflammatory skin conditions (e.g., dermatitis, psoriasis), diabetes (e.g., Type I or Type II diabetes), kidney disorders (e.g., focal and segmented glomerulosclerosis) and ischemic brain damage.

Thus, in yet another aspect, provided is a method of treating an inflammatory skin condition in a subject in need thereof, the method comprising administering an effective amount of compound of the present invention, or a pharmaceutical composition thereof, to the subject to treat the condition. Also provided is a method of treating an inflammatory skin condition in a subject in need thereof, the method comprising instructing the subject to administer an effective amount of compound of the present invention, or a pharmaceutical composition thereof, to treat the condition. Further provided is a compound of the present invention, or pharmaceutical composition thereof, for use in treating an inflammatory skin condition. In certain embodiments, the effective amount is a therapeutically effective amount. In certain embodiments, the effective amount is a prophylactically effective amount. In certain embodiments, the inflammatory skin condition is dermatitis. In certain embodiments, the inflammatory skin condition is psoriasis.

In yet another aspect, provided is a method of treating diabetes in a subject at risk of having diabetes or a diabetic subject, the method comprising administering an effective amount of compound of the present invention, or a pharmaceutical composition thereof. Also provided is a method of treating diabetes in a subject at risk of having diabetes or a diabetic subject, the method comprising instructing the subject to administer an effective amount of compound of the present invention, or a pharmaceutical composition thereof. Further provided is a compound of the present invention, or pharmaceutical composition thereof, for use in treating diabetes. In certain embodiments, the effective amount is a therapeutically effective amount. In certain embodiments, the effective amount is a prophylactically effective amount. In certain embodiments, the diabetes is Type I diabetes. In certain embodiments, the diabetes is Type II diabetes. As used herein, a subject who is "at risk of having diabetes" encompasses subjects who have a predisposition (e.g., genetic or otherwise) to develop Type I diabetes, and subjects who exhibit warning signs for Type II diabetes, e.g., diagnosed with "pre-diabetes" or "impaired glucose tolerance" wherein the subject has blood glucose levels higher than normal but not yet high enough to be diagnosed as diabetic.

Examples

In order that the invention described herein may be more fully understood, the following examples are set forth. It should be understood that these examples are for illustrative purposes only and are not to be construed as limiting this invention in any manner.

Synthesis of Hyperforin

The criteria for developing an enantioselective synthesis of hyperforin were that it had to be very concise (approximately 10-15 steps), involve minimal oxidation-state changes, modular, and be derived from starting materials available in bulk quantities. By satisfying these criteria, we would be able to easily access many hyperforin analogs for biological studies. The retrosynthesis of hyperforin is illustrated in FIG. 1. The first simplification was to derive hyperforin from an intermediate where the key C2- and C5 quaternary centers are installed. We envisaged that this intermediate would be derived from a Lewis-acid catalyzed 6-endo-tet cyclization of an enol ether onto a trisubstituted epoxide. We also imagined that the hydroxyl generated by epoxide opening would form a ketal with the transient oxocarbenium ion, thereby protecting the ketone and secondary carbinol. This cyclization starts from a compound where C5 is a quaternary prochiral center. This compound could be derived from the Birch reduction product of 1,3-dimethoxybenzene, epoxygeranyl bromide, and prenyl chloride (see, e.g., Piers et al., *J. Org. Chem.* (1977) 42:3755-3757).

Figure 2:
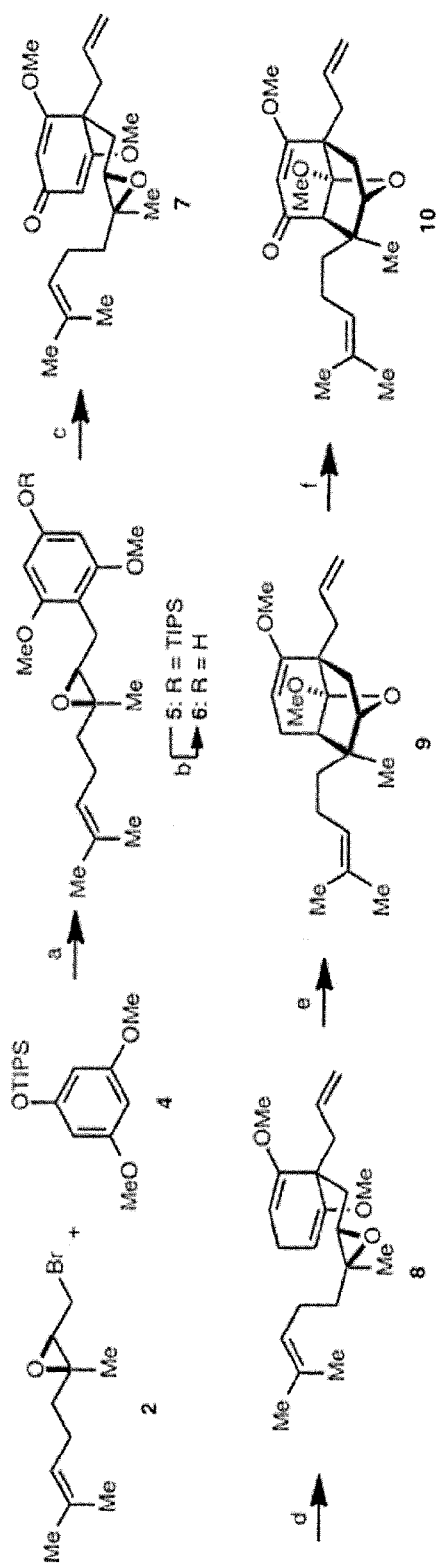
FIG. 2 depicts the synthesis of a model system for the preparation of hyperforin.

To test several of our key proposed steps to make hyperforin, we first followed literature procedures involving Sharpless asymmetric epoxidation and bromination of geraniol to generate 2 in 96% ee (see, Gash et al., *Tetrahedron* (1989) 45:5531-5538) (FIG. 2). Lithiation of known phloroglucinol ether 4 ortho to the two methoxy groups followed by alkylation with 2 afforded 5 in 81% yield. TBAF-mediated TIPS deprotection yielded 84% of phenol 6, which was allylated to form cyclohexadienone 7 in 65% yield. The ketone was reduced to a methylene by treatment with LAH to afford 8 in 44% yield. Exposure of 8 to TMSOTf at −78° C. in the presence of 2,6-di-tert-butyl-4-methylpyridine (DTBMP) afforded 9 in 85% yield as a single diastereomer. Exposing 9 to Pd(OH)$_2$, tert-butyl hydroperoxide, Cs$_2$CO$_3$, and O$_2$ induced allylic oxidation to afford vinylogous ester 10 in an unoptimized 26% yield. Thus, in seven steps (from geraniol) we have assembled much of hyperforin from easily accessible starting materials.

Figure 3:
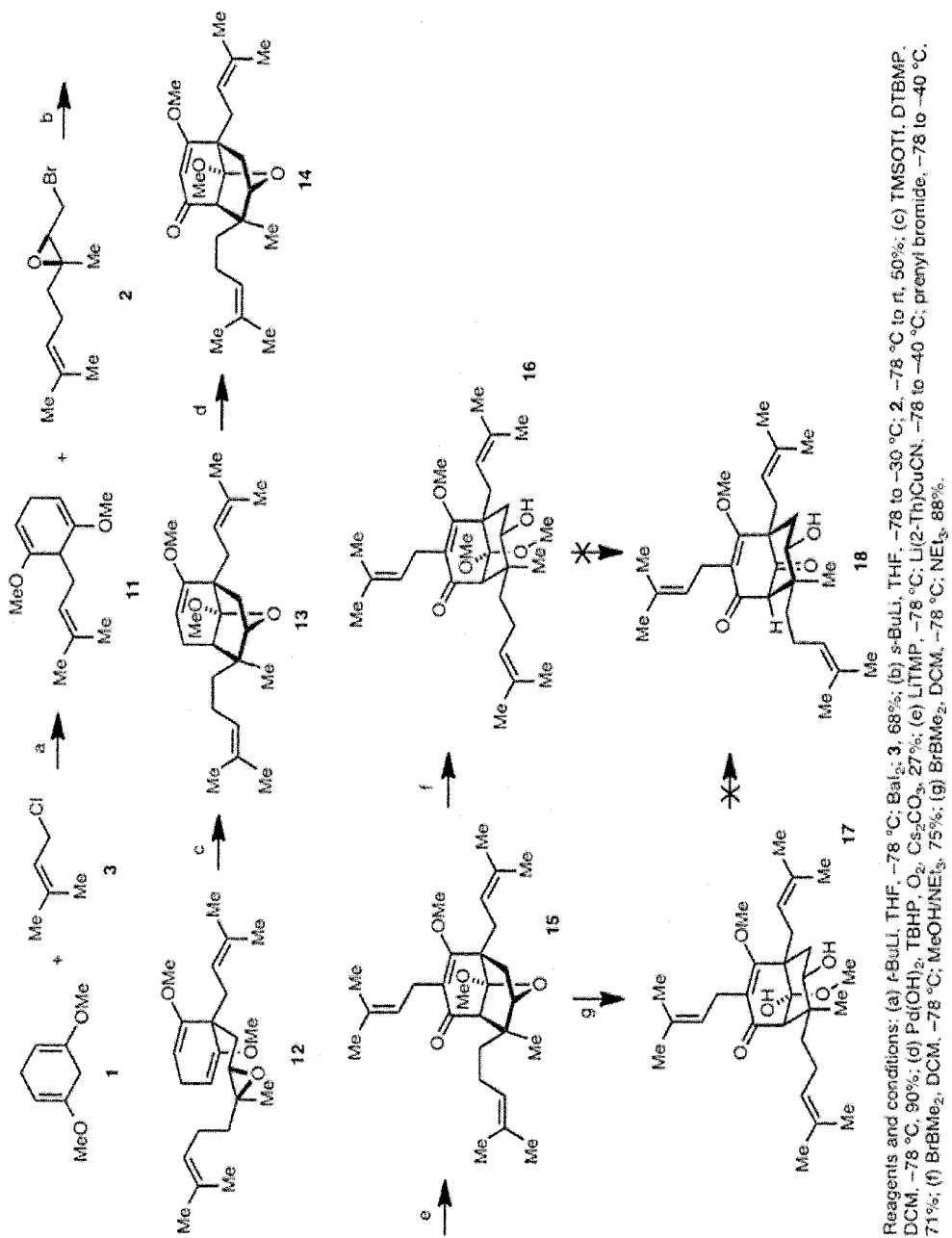
FIG. 3 depicts a proposed synthesis of hyperforin with unsuccessful steps.

The results, described above and depicted in FIG. 2, formed the basis of a proposed 20-step enantioselective synthesis of hyperforin and synthesis of analogs never accessible before. 1,5-Dimethoxy-1,4-cyclohexadiene (1) was lithiated at −78° C. with t-BuLi followed by alkylation with prenyl chloride (3) in the presence of activated BaI$_2$, having 11 in 68% yield (FIG. 3). Exposing 11 to s-BuLi, warming to −30° C. from −78° C., and subsequent alkylation with 1 yielded 12 in 50% yield. Exposure of 12 to TMSOTf at −78° C. in the presence of DTBMP gave intermediate 13 in 90% yield. Pd(OH)$_2$-mediated allylic oxidation of 9 with TBHP and Cs$_2$CO$_3$ afforded vinylogous ester 14 in 27% yield. Sequential treatment of 14 with LiTMP, Li(2-Th)Cu(CN), and prenyl bromide furnished intermediate 15 in 71% yield. The cyclic ketal present in 15 was opened through treatment of 15 with BrBMe$_2$ at −78° C., yielding both dimethyl ketal 16 in 75% yield and hemiketal 17 in 88% yield via quenching with MeOH/NEt$_3$ and NEt$_3$, respectively. Attempts at converting either 16 or 17 into diketone 18 were unsuccessful.

Figure 4A:
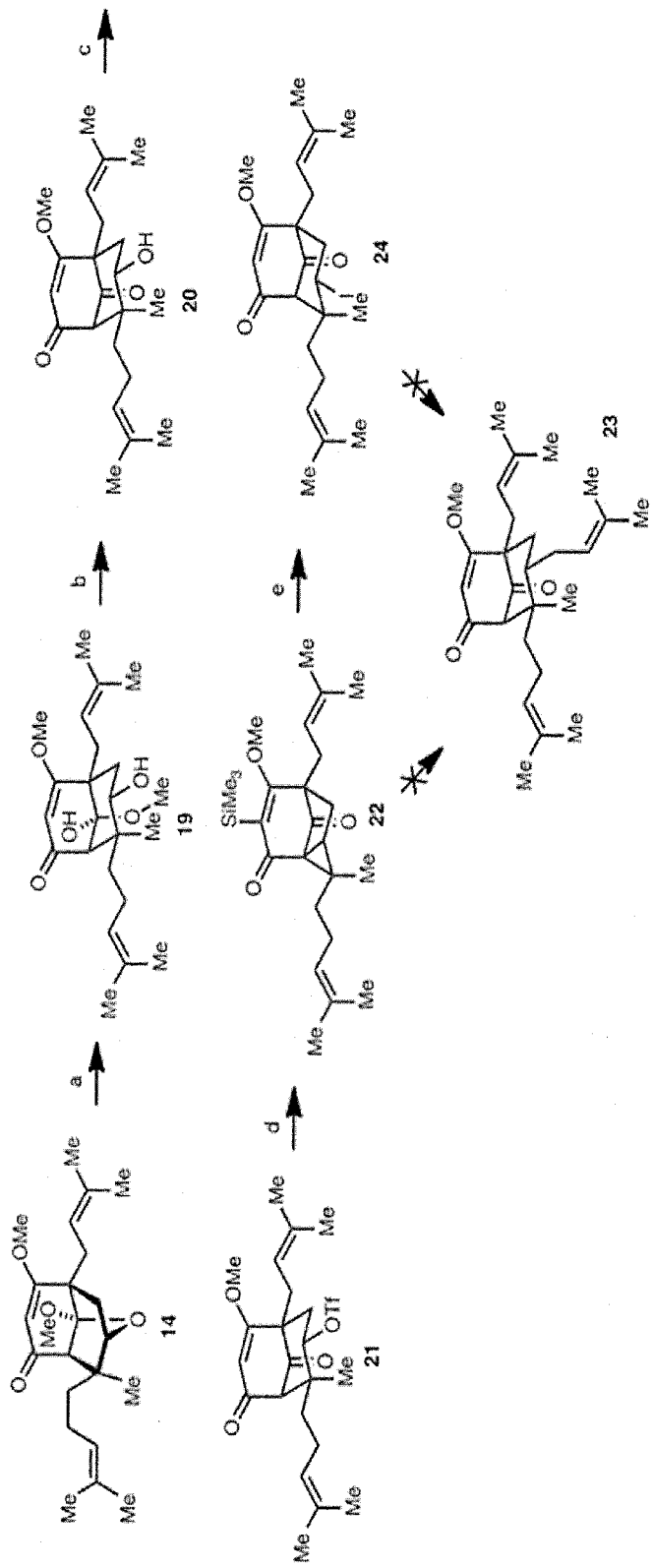
FIGS. 4A and 4B depict a number of proposed synthetic routes to hyperforin with unsuccessful steps.
Figure 4B:
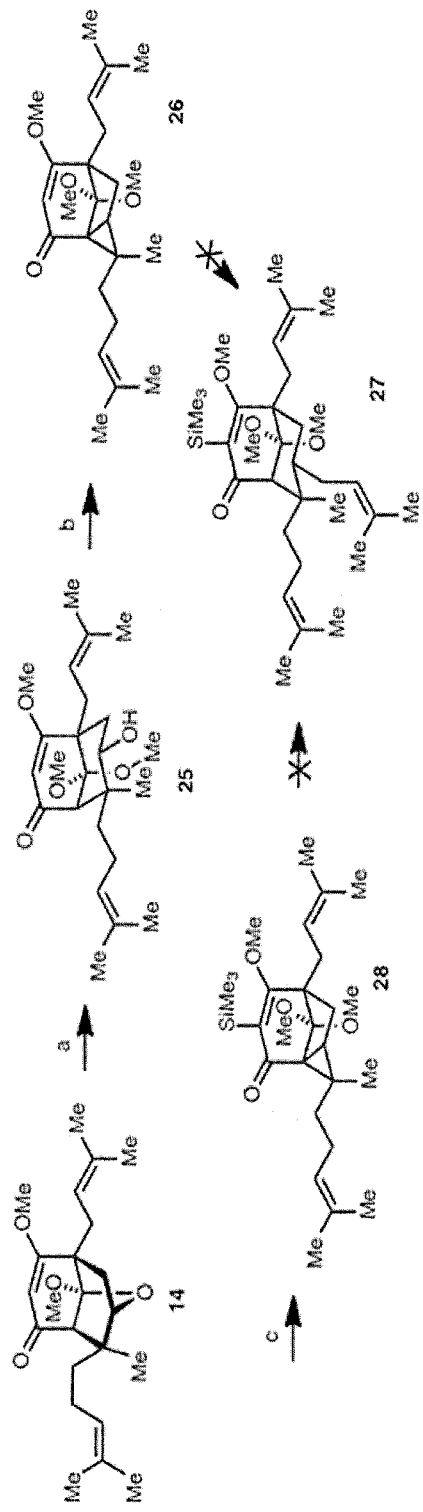

The diketone functionality was installed using an alternative strategy in which treatment of vinylogous ester 14 with BrBMe$_2$ at −78° C. and quenching with NEt$_3$ afforded hemiketal 19 in 79% yield (FIG. 4A). Subsequent treatment of 19 with PPTS in refluxing acetone/H$_2$O afforded diketone 20 in 90% yield. Triflation of 20 with Tf$_2$O in the presence of pyridine gave triflate 21 in 80% yield. Bridgehead lithiation of 21 using LDA in the presence of TMSCl gave cyclopropane 22 in 56% yield. Numerous attempts to utilize the activated cyclopropane found in intermediate 22 to direct the introduction of a prenyl substituent (i.e., formation of intermediate 23) were unsuccessful. One distinct product observed over the course of these studies was iodide 24, which was formed in 50% yield through the treatment of cyclopropane 22 with (prenyl)Cu(CN)Li.LiI in the presence of TMSCl. Various attempts at the conversion of 24 to 23 were also unsuccessful. A problem encountered during these studies was addition of nucleophilic species to the bridging ketone of 22 instead of the activated cyclopropane. In order to circumvent this problem, dimethyl ketal 25 was generated in 61% yield from 14 using NEt$_3$-buffered BrBMe$_2$ (FIG. 4B). Conversion of intermediate 25 to cyclopropane 26 occurred in 35% by first using Tf$_2$O to form an unstable triflate from 25 and subsequent treatment of this triflate with LiNEt$_2$ followed by TMSCl. Attempts at converting intermediate 26 to 27 were unsuccessful, as were attempts from intermediate 28, which was synthesized from 26 using LDA and TMSCl in 57% yield.

Figure 5:
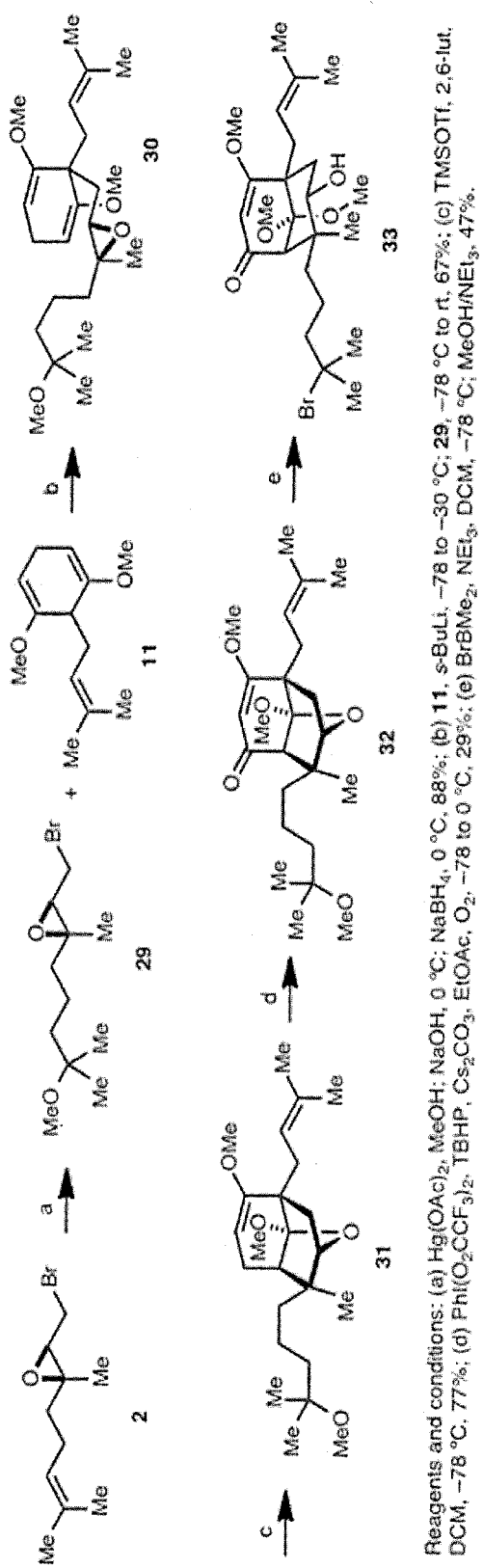
FIGS. 5-6 show exemplary synthetic routes to various intermediates of hyperforin.

In order to install this prenyl substituent, a strategy involving a Keck radical allylation was pursued. This strategy called for the masking the proximal homoprenyl functionality to prevent radical cyclization. Accordingly, solvomercuration-demercuration of epoxide 2 using MeOH solvent gave methyl ether 29 in 88% yield (FIG. 5). As before, deprotonation of diene 11 with s-BuLi with warming from −78 to −30° C. with subsequent treatment with bromide 29 gave cyclization precursor 30 in 67% yield. Cyclization of intermediate 30 using TMSOTf in the presence of 2,6-lutidine gave enol ether 31 in 77% yield. Allylic oxidation of 31 to give vinylogous ester 32 occurred in 29% yield using PhI(O$_2$CCF$_3$)$_2$, TBHP, and O$_2$ in the presence of Cs$_2$CO$_3$ in EtOAc that was warmed from −78 to 0° C. Exposure of 32 to BrBMe$_2$ under NEt$_3$-buffered conditions and quenching with MeOH/NEt$_3$ gave dimethyl ketal 33 (47% yield) in which the tertiary methyl ether was converted to a tertiary bromide. In order to circumvent the formation of a tertiary bromide in this ketal-deprotection step, a more stable protecting group was required.

Figure 6:
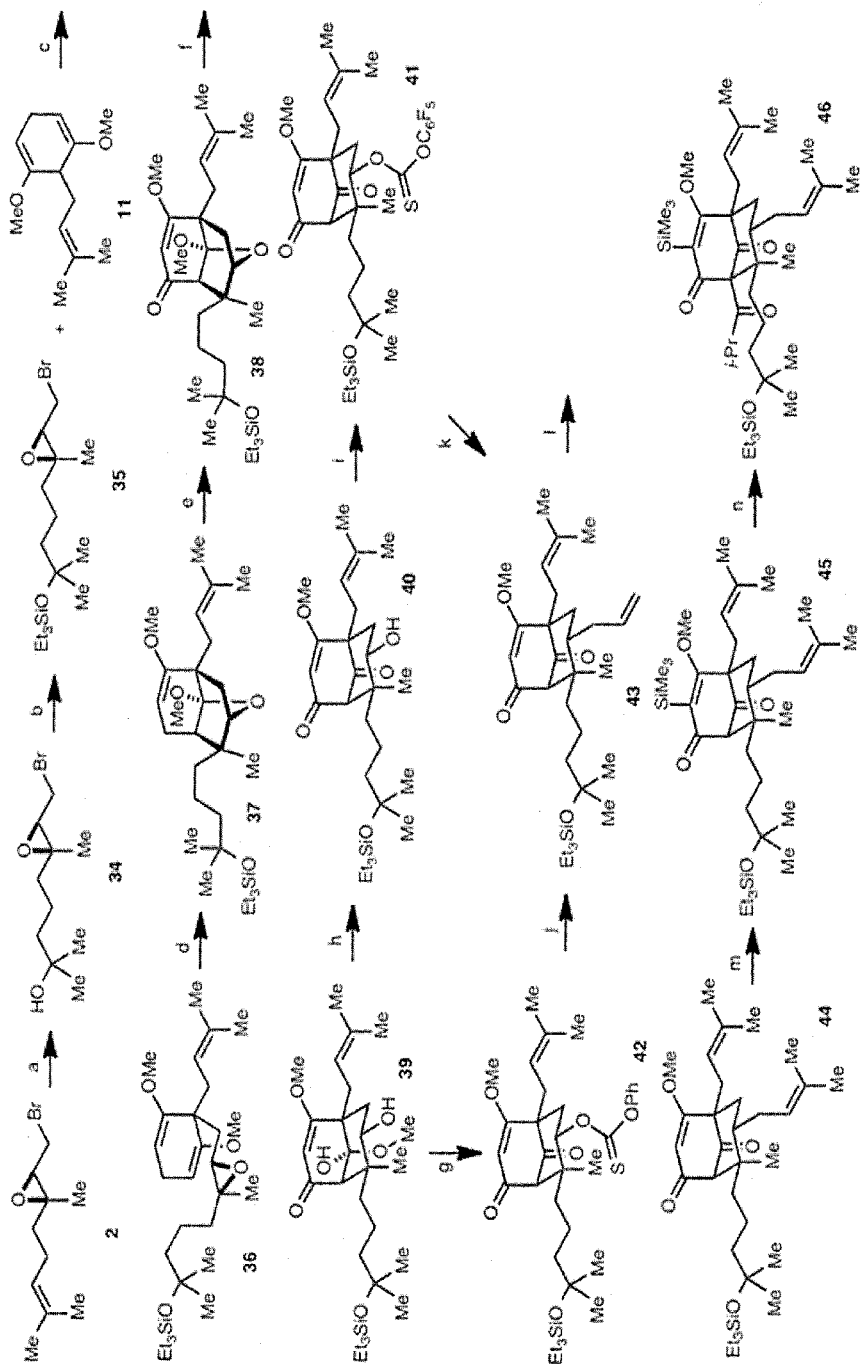
Figure 7:
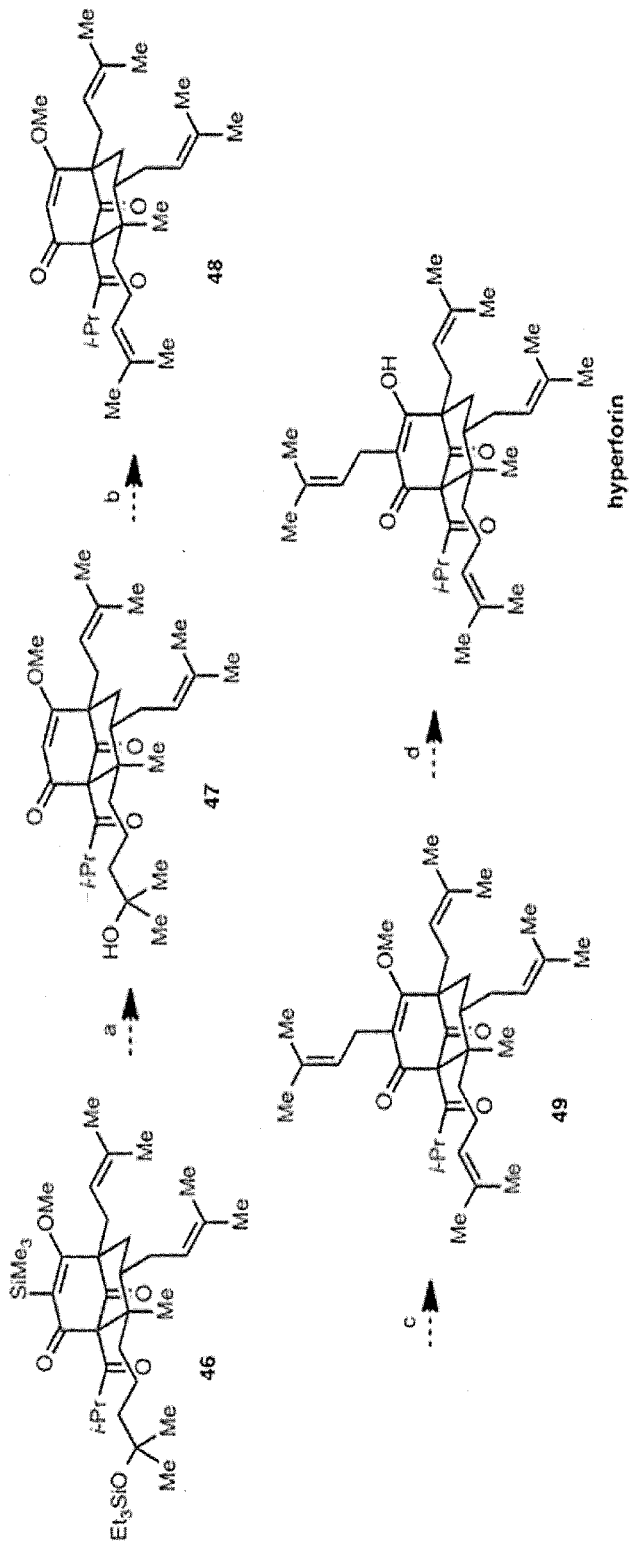
FIG. 7 shows a proposed synthetic route to hyperforin using intermediate 46 illustrated in FIG. 6.

A new strategy was devised in which a tertiary triethylsilyl ether would be used to mask the homoprenyl functional group. Hydromercuration-demercuration of epoxide 2 afforded tertiary alcohol 34 in 97% yield (FIG. 6). Conversion of alcohol 34 to tertiary silyl ether 35 took place in 87% yield using TESCl and imidazole in DMF. Coupling of bromide 35 and diene 11 occurred in the usual manner to afford cyclization precursor 36 in 74% yield. Cyclization of intermediate 36 took place using TMSOTf and 2,6-lutidine to enol ether 37 in 79% yield. Allylic oxidation of 37 using PhI(O$_2$CCF$_3$)$_2$, TBHP, and O$_2$ in the presence of Cs$_2$CO$_3$ in EtOAc that was warmed from −78 to 0° C. gave vinylogous ester 38 in 44% yield. Successful opening of the cyclic ketal present in 38 using NEt$_3$-buffered BrBMe$_2$ at −95° C. gave hemiketal 39 in 57% yield. Conversion of the hemiketal directly to the phenyl thionocarbonate 40 using n-BuLi and PhOC(S)Cl took place in 60% yield. Alternatively, treatment of 39 with LiTMP gave diketone 41 in 79% yield, and subsequent exposure of 41 to C$_6$F$_5$OC(S)Cl in the presence of DMAP and pyridine gave pentafluorothionocarbonate 42 in 55% yield. While both thionocarbonates 40 and 42 were converted to intermediate 43 via a Keck allylation protocol using allyltributylstannane, BEt$_3$, and O$_2$, the latter gave 43 in 73% yield, compared to the former, which gave 43 in 34% yield. Cross metathesis of 43 and 2-methyl-2-butene utilizing Hoveyda-Grubbs catalyst (second generation) gave intermediate 44. Trimethylsilyl protection of the vinylogous ester functionality in 44 took place using LiTMP and TMSCl to yield intermediate 45 in 90% yield. Bridgehead lithiation of 45 using LiTMP and subsequent trapping with isobutyryl chloride gave trione 46 in 24% yield. Shown in FIG. 7 is a proposed synthetic route to hyperforin starting from 46. Deprotection of silyl protecting groups present in 46 using TBAF will give alcohol 47. Dehydration of 47 using TsOH will give intermediate 48. Using previously described conditions, installation of the full carbon skeleton of hyperforin by treating 48 with LiTMP, transmetalation with Li(2-Th)Cu(CN), and trapping with prenyl bromide will give methyl hyperforin 49. Exposure of intermediate 49 to LiOH in hot dioxane will afford hyperforin.

Figure 8:
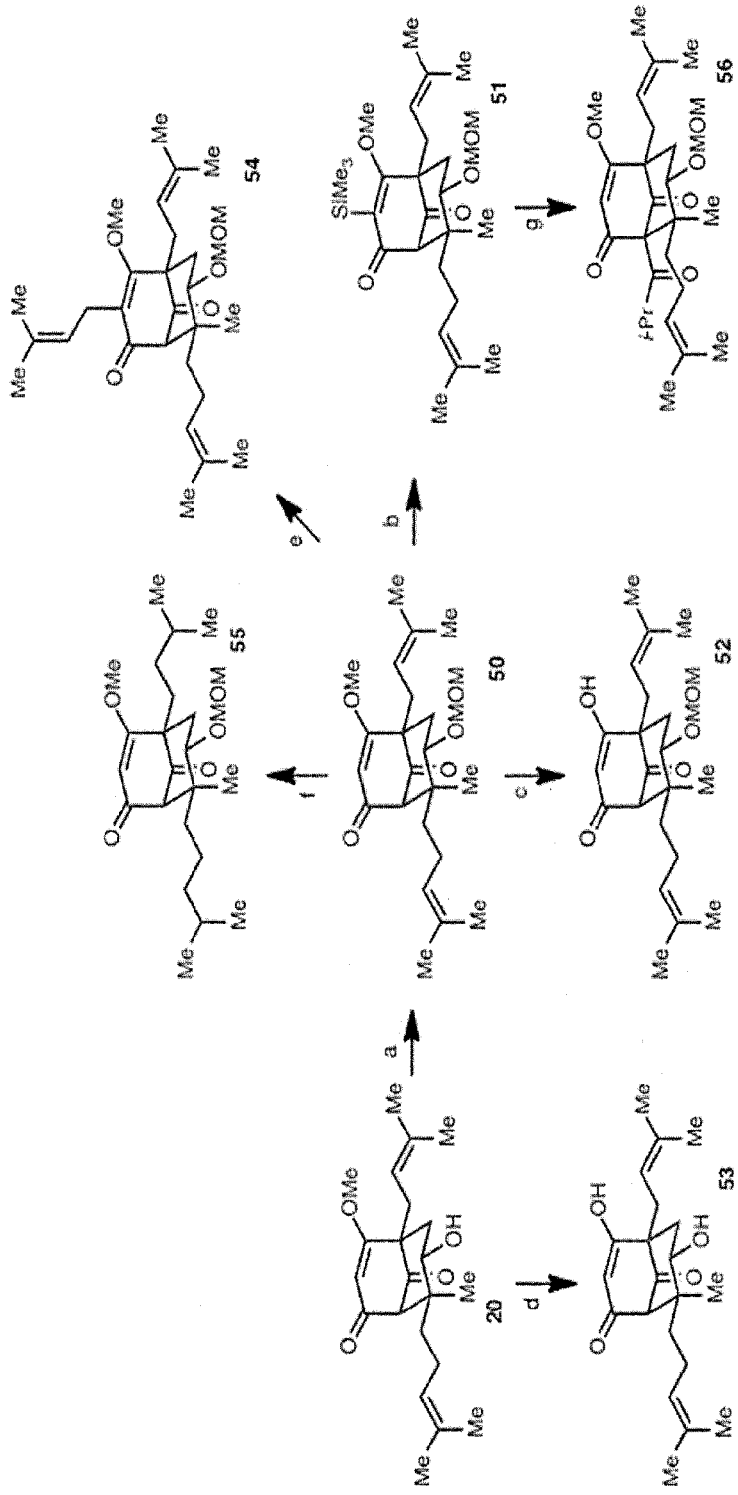
FIG. 8 shows the synthesis of various analogs of hyperforin by the synthetic routes illustrated in FIGS. 3, 4, and 6.

Hyperforin analogs were prepared following the routes depicted in the FIGS. 1-7, especially, in FIGS. 3, 4, and 6, but using different reagents (e.g., other than epoxygeranyl bromide, isobutyryl chloride and/or prenyl chloride; see, e.g., FIGS. 8-18). For example, conversion of alcohol 20 to methoxymethyl ether 50 using MOMCl and DIPEA occurred in 97% yield (FIG. 8). Silylation of the vinylogous ester of 50 using LiTMP and TMSCl gave vinyl silane 51 in 95% yield. Treatment of 50 with wet LiCl in hot dioxane afforded vinylogous acid 52 in 99% yield. Using these conditions, conversion of intermediate 20 to vinylogous acid 53 took place in 98% yield. Prenylation of 50 took place, giving rise to intermediate 54 in 51% yield, by treating 50 sequentially with LDA and prenyl bromide. Hydrogenation of 50 with catalytic Pd/C and an atmosphere of $H_2$ using MeOH as the solvent gave reduced intermediate 55 in 92% yield. Bridgehead lithiation, trapping with isobutyryl chloride, and TBAF-mediated desilylation of 51 afforded trione 56 in 53% yield.

Experimental Data (3,5-Dimethoxy-4-(((2S,3S)-3-methyl-3-(4-methyl-pent-3-en-1-yl)oxiran-2-yl)methyl)phen-oxy)triisopropylsilane (5)

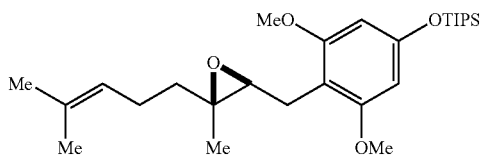

A THF (54 mL) solution of ether 4 (3.169 g, 10.8 mmol, equiv.) was cooled to 0° C. in a 200-mL recovery flask, and butyllithium in hexane (2.60 M, 4.55 mL, 11.8 mmol, 1.1 equiv.) was added dropwise over 5 min. After the addition was complete, the cooling bath was removed, and the resulting yellow solution was stirred a room temperature. After 30 min, the solution was cooled to 0° C. and stirred for an additional 30 min. Bromide 2 (2.76 g, 11.8 mmol, 1.1 equiv.) was then added dropwise over 2 min. The cooling bath was removed, and the resulting clear, colorless solution was stirred for 3 h. The solution was subsequently quenched with saturated aqueous $NH_4Cl$, diluted with $H_2O$, and extracted thrice with EtOAc. The organic extracts were combined, washed with brine, dried over $Na_2SO_4$, and concentrated in vacuo to yield a yellow oil. Flash column chromatography (500 mL $SiO_2$, 95:5 hexane:EtOAc) afforded 4.034 g (8.72 mmol, 81% yield) of 5 as a clear, colorless oil. TLC $R_f$ 0.55 (8:2 hexane:EtOAc). $^1$H NMR (600 MHz; $CDCl_3$): δ 6.10 (s, 2H), 5.29 (s, 1H), 5.00 (t, J=7.1 Hz, 1H), 3.75 (s, 6H), 2.98 (dd, J=13.6, 4.4 Hz, 1H), 2.88 (dd, J=7.6, 4.4 Hz, 1H), 2.68 (dd, J=13.6, 7.6 Hz, 1H), 2.06-2.00 (m, 1H), 1.98-1.92 (m, 1H), 1.64-1.60 (m, 1H), 1.59 (s, 3H), 1.54 (s, 3H), 1.37 (s, 3H), 1.34 (td, J=6.8, 3.2 Hz, 1H), 1.26 (septet, J=7.4 Hz, 3H), 1.12 (d, J=7.4 Hz, 18H). $^{13}$C NMR (125 MHz; $CDCl_3$): δ 159.1, 156.2, 131.7, 124.0, 107.2, 96.4, 63.5, 61.7, 55.7, 39.2, 25.8, 24.1, 22.5, 18.2, 17.7, 16.9, 12.9. IR (NaCl, thin film, $cm^{-1}$) 2961, 2945, 2868, 1606, 1593, 1496, 1463, 1414, 1200, 1158, 1134, 1021, 883, 686. HRMS-ESI (m/z): [M+Na]$^+$ calculated for $C_{27}H_{46}O_4Si$, 485.3058. found, 485.3064.

3,5-Dimethoxy-4-(((2S,3S)-3-methyl-3-(4-methyl-pent-3-en-1-yl)oxiran-2-yl)methyl)phenol (6)

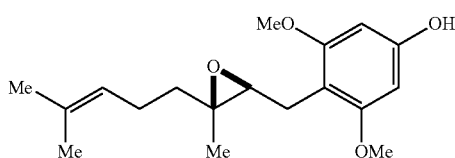

Tetrabutylammonium fluoride in THF (1 M, 9.0 mL, 9.01 mmol, 1.05 equiv.) was added to a THF (30 mL) solution of 5 (3.97 g, 8.58 mmol, 1 equiv.) in a 100-mL pear-shaped flask. After stirring for 30 min, the reaction was quenched with saturated aqueous $NH_4Cl$ and extracted once with hexane and twice with EtOAc. The organic extracts were combined, washed with brine, $Na_2SO_4$, filtered, and concentrated in vacuo to a slight yellow oil. Flash column chromatography (400 mL $SiO_2$, 7:3 to 1:1 hexane:EtOAc) afforded 2.20 g (7.18 mmol, 84% yield) of 6 as a clear, colorless oil. TLC $R_f$ 0.5 (1:1 hexane:EtOAc). $^1$H NMR (500 MHz; $CDCl_3$): δ 6.06 (s, 2H), 5.11 (s, 1H), 4.99 (t, J=7.1 Hz, 1H), 3.76 (s, 6H), 2.97 (dd, J=13.5, 4.6 Hz, 1H), 2.91 (dd, J=7.3, 4.6 Hz, 1H), 2.69 (dd, J=13.5, 7.3 Hz, 1H), 2.07-1.95 (m, 2H), 1.63 (ddd, J=13.9, 9.1, 5.2 Hz, 1H), 1.59 (s, 3H), 1.54 (s, 3H), 1.38 (s, 3H), 1.37-1.33 (m, 1H). $^{13}$C NMR (125 MHz; $CDCl_3$): δ 159.3, 156.4, 131.9, 123.8, 106.1, 92.1, 64.1, 62.6, 55.7, 39.1, 25.8, 24.1, 22.3, 17.7, 16.9. IR (NaCl, thin film, $cm^{-1}$) 3368 (br), 2936, 2840, 1618, 1603, 1475, 1431, 1206, 1134, 999, 816.

4-Allyl-3,5-dimethoxy-4-(((2S,3S)-3-methyl-3-(4-methylpent-3-en-1-yl)oxiran-2-yl)methyl)cyclohexa-2,5-dienone (7)

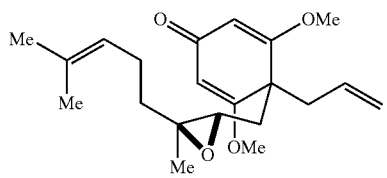

Allyl methyl carbonate (18 μL, 0.16 mmol, 2.5 equiv.) and titanium(IV) isopropoxide (3.7 μL, 12 mmol, 0.2 equiv.) were added in sequence to a peach-colored PhH (0.5 mL) solution of 6 (19 mg, 62 mmol, 1 equiv.), triphenylphosphine (1.3 mg, 5.0 mmol, 0.08 equiv.), and palladium(II) acetate (0.3 mg, 1.2 mmol, 0.02 equiv.) at room temperature in a 10-mL heart-shaped flask, whereupon the solution turned an opaque dark red. After stirring at room temperature for 10 min, the solution was heated to 50° C. After 1 h of heating at this temperature, the solution turned clear dark red. After stirring for a total of 130 min at 50° C., the solution was cooled to room temperature and quenched with saturated aqueous $NH_4Cl$. After diluting with PhH and stirring for 5 min, 1 N HCl was added, and the layers were separated. The aqueous layer was then extracted twice with EtOAc. The organic extracts were combined, washed with brine, dried over $Na_2SO_4$, filtered, and concentrated in vacuo to an inhomogeneous green oil. Flash column chromatography (25 mL $SiO_2$, 4:1 to 7:3 to 1:1 hexane:EtOAc) afforded 14 mg (40 mmol, 65% yield) of 7 as a clear, colorless oil. TLC $R_f$ 0.22 (1:1 hexane:EtOAc). $^1$H NMR (600 MHz; $CDCl_3$): δ 5.59 (d, J=7.7 Hz, 2H), 5.39 (ddt, J=17.1, 10.0, 7.2 Hz, 1H), 5.00-4.92 (m, 3H), 3.73 (s, 3H), 3.70 (s, 3H), 2.61-2.54 (m, 2H), 2.40 (t, J=5.9 Hz, 1H), 2.14 (dd, J=13.9, 5.3 Hz, 1H), 2.04 (dd, J=13.9, 6.6 Hz, 1H), 1.98-1.88 (m, 2H), 1.64 (s, 3H), 1.56 (s, 3H), 1.50 (ddd, J=13.7, 9.7, 6.3 Hz, 1H), 1.27 (ddd, J=13.7, 10.0, 6.5 Hz, 1H), 1.17 (s, 3H). $^{13}$C NMR (125 MHz; $CDCl_3$): δ 188.0, 173.1, 172.6, 132.2, 131.9, 123.6, 118.4, 103.55, 103.45, 60.7, 59.3, 56.2, 56.0, 49.7, 41.7, 38.9, 35.7, 25.8, 23.9, 17.8, 16.7. IR

(2S,3S)-3-((1-Allyl-2,6-dimethoxycyclohexa-2,5-dien-1-yl)methyl)-2-methyl-2-(4-methylpent-3-en-1-yl)oxirane (8)

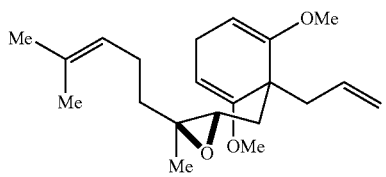

A DCM (0.5 mL) slurry of lithium aluminum hydride (23 mg, 0.61 mmol, 2 equiv.) was cooled to −78° C. in a 10-mL recovery flask, and a DCM (0.5 mL) solution of 7 (106 mg, 0.31 mmol, 1 equiv.) was added via cannula, followed by a DCM (0.5 mL) rinse. The slurry was stirred at −78° C. for 25 min, Et$_2$O (0.5 mL), and the reaction was warmed to 0° C. After stirring for 75 min, the reaction was quenched sequentially with H$_2$O (23 µL), 15 wt % NaOH$_{aq}$ (23 µL), and H$_2$O (63 µL). The reaction was then warmed to room temperature, diluted with H$_2$O, and extracted four times with EtOAc. The organic extracts were combined, washed with H$_2$O and brine, dried over Na$_2$SO$_4$, filtered, and concentrated in vacuo to a brown residue. Flash column chromatography (30 mL SiO$_2$, 19:1 hexane:EtOAc) afforded 45 mg (0.14 mmol, 44% yield) of 8 as a clear, colorless oil. TLC R$_f$ 0.74 (1:1 hexane:EtOAc). $^1$H NMR (600 MHz; CDCl$_3$): δ 5.57 (ddt, J=17.1, 10.1, 7.1 Hz, 1H), 5.05 (t, J=7.2 Hz, 1H), 4.94-4.88 (m, 2H), 4.80 (t, J=3.5 Hz, 1H), 4.76 (t, J=3.5 Hz, 1H), 3.54 (s, 3H), 3.49 (s, 3H), 2.78 (app q, J=3.5 Hz, 2H), 2.64 (dd, J=8.0, 4.0 Hz, 1H), 2.39 (qd, J=12.7, 7.2 Hz, 2H), 2.03 (dd, J=13.7, 4.0 Hz, 1H), 1.97 (q, J=7.9 Hz, 2H), 1.76 (dd, J=13.7, 8.0 Hz, 1H), 1.67 (s, 3H), 1.58 (s, 3H), 1.57-1.54 (m, 1H), 1.29 (dt, J=13.5, 8.4 Hz, 1H), 1.18 (s, 3H). $^{13}$C NMR (125 MHz; CDCl$_3$): δ 153.80, 153.73, 135.3, 131.8, 124.2, 116.1, 93.23, 93.17, 61.25, 61.09, 54.6, 54.2, 46.2, 40.2, 39.4, 34.2, 25.8, 24.2, 24.0, 17.8, 16.8. IR (NaCl, thin film, cm$^{-1}$) 2932, 2831, 1694, 1659, 1451, 1381, 1223, 1206, 1139, 908. HRMS-ESI (m/z): [M+H]$^+$ calculated for C$_{21}$H$_{32}$O$_3$, 333.2424. found, 333.2425.

(3S,3aR,7R,7aS)-7-Allyl-6,7a-dimethoxy-3-methyl-3-(4-methylpent-3-en-1-yl)-2,3,3a,4,7,7a-hexahydro-2,7-methanobenzofuran (9)

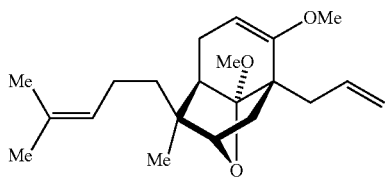

A DCM (6 mL) solution of 8 (100 mg, 0.30 mmol, 1 equiv.) and 2,6-di-tert-butyl-4-methylpyridine (124 mg, 0.60 mmol, 2 equiv.) was cooled to −78° C. in a 20-mL scintillation vial, and trimethylsilyl trifluoromethanesulfonate (65 µL, 0.36 mmol, 1.2 equiv.) was added dropwise. Immediately upon this addition, the solution turned bright yellow. After stirring at −78° C. for 30 min, the reaction was quenched with saturated aqueous NaHCO$_3$ and allowed to warm to room temperature. The mixture was then extracted four times with EtOAc. The organic extracts were combined, washed with brine, dried over Na$_2$SO$_4$, filtered, and concentrated in vacuo to a slight yellow oil. Flash column chromatography (50 mL SiO$_2$, 99:1 hexane:EtOAc) afforded 85 mg (0.26 mmol, 85% yield) of 9 as a clear, colorless oil. TLC R$_f$ 0.53 (9:1 hexane:EtOAc). $^1$H NMR (600 MHz; CDCl$_3$): δ 6.02 (ddt, J=17.2, 10.1, 7.1 Hz, 1H), 5.04 (t, J=7.1 Hz, 1H), 5.01-4.95 (m, 2H), 4.54 (dd, J=5.7, 2.1 Hz, 1H), 3.75 (d, J=5.3 Hz, 1H), 3.48 (s, 3H), 3.47 (s, 3H), 2.42 (dd, J=14.1, 7.3 Hz, 1H), 2.29 (dd, J=14.1, 7.0 Hz, 1H), 2.19 (ddd, J=18.1, 6.7, 2.2 Hz, 1H), 2.07-2.02 (m, 2H), 2.01-1.93 (m, 1H), 1.86 (dd, J=12.4, 5.3 Hz, 1H), 1.81 (d, J=12.4 Hz, 1H), 1.72-1.65 (m, 4H), 1.58 (s, 2H), 1.47-1.42 (m, 1H), 1.25-1.20 (m, 1H), 1.14 (s, 3H). $^{13}$C NMR (125 MHz; CDCl$_3$): δ 158.1, 138.3, 131.7, 124.9, 115.8, 112.5, 90.7, 79.1, 54.6, 51.3, 46.3, 44.4, 42.0, 38.87, 38.72, 33.6, 28.1, 25.9, 22.9, 20.1, 17.8. IR (NaCl, thin film, cm$^{-1}$) 2966, 2930, 1671, 1578, 1460, 1439, 1376, 1304, 1215, 1168, 1136, 1062, 1001, 906. HRMS-ESI (m/z): [M+Na]$^+$ calculated for C$_{21}$H$_{32}$O$_3$, 355.2244. found, 355.2245.

(3S,3aS,7R,7aS)-7-Allyl-6,7a-dimethoxy-3-methyl-3-(4-methylpent-3-en-1-yl)-3,3a,7,7a-tetrahydro-2,7-methanobenzofuran-4(2H)-one (10)

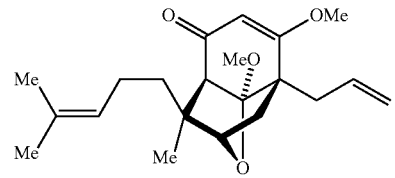

A DCM (0.5 mL) solution of 9 (3.3 mg, 9.9 mmol, 1 equiv.) and cesium carbonate (17.5 mg, 50 mmol, 5 equiv.) was cooled to 0° C. open to the air in a 10-mL heart-shaped flask, and palladium(II) hydroxide on carbon (20 wt % Pd, 0.3 mg, 0.50 mmol, 0.05 equiv.) and tert-butyl hydroperoxide (70 wt % in H$_2$O, 5 µL, 50 µmol, 5 equiv.) were added sequentially. The flask was capped with a rubber septum, an oxygen-filled balloon was attached, and the flask was purged with oxygen. The flask was then placed in a 4° C. refrigerator and stirred vigorously. After 19.5 h, the slurry was diluted with DCM, warmed to room temperature, and filtered through a short plug of SiO$_2$, rinsing with DCM followed by EtOAc. The resulting solution was concentrated in vacuo. Flash column chromatography (2 mL SiO$_2$ in pipette, 9:1 to 4:1 to 1:1 hexane:EtOAc) afforded 0.9 mg (2.6 mmol, 26% yield) of 10 as a colorless residue. TLC R$_f$ 0.56 (1:1 hexane:EtOAc). $^1$H NMR (600 MHz; CDCl$_3$): δ 5.98 (td, J=17.1, 7.9 Hz, 1H), 5.35 (s, 1H), 5.06-5.01 (m, 2H), 4.99 (t, J=7.1 Hz, 1H), 3.91 (d, J=5.5 Hz, 1H), 3.71 (s, 3H), 3.48 (s, 3H), 2.69 (s, 1H), 2.53 (dd, J=14.2, 6.7 Hz, 1H), 2.39 (dd, J=14.2, 7.9 Hz, 1H), 2.06 (d, J=13.1 Hz, 1H), 2.04-1.98 (m, 2H), 1.73-1.67 (m, 1H), 1.64 (s, 3H), 1.55 (s, 3H), 1.43-1.36 (m, 1H), 1.34-1.28 (m, 1H), 1.25 (s, 3H). $^{13}$C NMR (125 MHz; CDCl$_3$): δ 197.8, 180.7, 136.8, 132.1, 124.2, 117.3, 115.2, 100.9, 80.9, 56.8, 56.5, 52.1, 48.3, 48.1, 38.2, 38.0, 34.1, 27.8, 25.8, 22.8, 17.8. HRMS-ESI (m/z): [M+Na]$^+$ calculated for C$_{21}$H$_{30}$O$_4$, 369.2036. found, 369.2034.

1,5-Dimethoxy-6-(3-methylbut-2-en-1-yl)cyclohexa-1,4-diene (11)

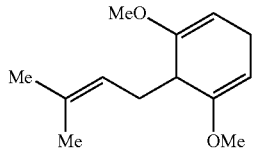

A portion of barium iodide dihydrate was dried over 12 h at 150° C. under 6 mmHg vacuum in a 250-mL round-bottom flask to yield activated barium iodide (8.38 g, 21.4 mmol, 1.1 equiv.), which was taken up in THF (125 mL). Meanwhile, a THF (50 mL) solution of 1 (2.73 g, 19.5 mmol, 1 equiv.) was cooled to −78° C. in a 500-mL round-bottom flask, and a pentane solution of tert-butyllithium (1.63 M, 13.1 mL, 21.4 mmol, 1.1 equiv.) was added over 5 min. After stirring the resulting clear yellow solution at −78° C. for 1 h, the THF slurry of activated barium iodide was transferred via cannula to this solution over 15 min. After stirring the resulting yellow-tan slurry an additional 30 min at −78° C., a THF (2 mL) solution of 3 (2.4 mL, 21.4 mmol, 1.1 equiv.) was added, and the slurry was allowed to warm over 2.25 h. The reaction was then quenched with water and extracted thrice with EtOAc. The organic extracts were combined, washed twice with brine, dried over Na$_2$SO$_4$, filtered, and concentrated in vacuo. The resulting clear oil was slowly loaded onto a SiO$_2$ plug and eluted with 98:2 hexane:EtOAc. The eluent was concentrated in vacuo to afford 2.90 g (13.3 mmol, 68% yield) of 11 as a clear, colorless oil. TLC R$_f$ 0.77 (9:1 hexane:EtOAc). $^1$H NMR (600 MHz; CDCl$_3$): δ 4.99 (t, J=7.4 Hz, 1H), 4.68 (dd, J=4.6, 3.0 Hz, 2H), 3.53 (s, 6H), 2.94-2.91 (m, 1H), 2.78 (ddt, J=20.7, 6.0, 3.0 Hz, 1H), 2.72 (dq, J=20.7, 4.6 Hz, 1H), 2.41 (dd, J=7.4, 4.7 Hz, 2H), 1.64 (s, 3H), 1.55 (s, 3H). $^{13}$C NMR (125 MHz; CDCl$_3$): δ 154.5, 132.8, 120.6, 91.9, 54.4, 41.3, 28.5, 26.1, 24.7, 17.8.

(2S,3S)-3-((2,6-Dimethoxy-1-(3-methylbut-2-en-1-yl)cyclohexa-2,5-dien-1-yl)methyl)-2-methyl-2-(4-methylpent-3-en-1-yl)oxirane (12)

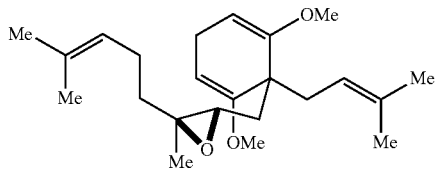

A THF (50 mL) solution of 11 (100 mg, 0.48 mmol, 1 equiv.) was cooled to −78° C. in a 200-mL recovery flask, and a cyclohexane solution of sec-butyllithium (1.63 M, 9.8 mL, 15.9 mmol, 1.5 equiv.) was added slowly over 2 min. The resulting golden yellow solution was allowed to warm to −30° C. over 1 h, whereupon the solution turned deep red. The flask was then cooled to −78° C., and a THF (5 mL) solution of 2 (3.71 g, 15.9 mmol, 1.5 equiv.) was added. The now-bright yellow solution was warmed slowly to −10° C. over 2.25 h, quenched with H$_2$O, and extracted thrice with EtOAc. The organic extracts were combined, washed with brine, dried over Na$_2$SO$_4$, filtered, and concentrated in vacuo to a yellow oil. Flash column chromatography (50 mL SiO$_2$, 99:1 to 49:1 hexane:EtOAc) afforded 1.90 g (5.27 mmol, 50% yield) of 12 as a clear, colorless oil. TLC R$_f$ 0.17 (9:1 hexane:EtOAc). $^1$H NMR (600 MHz; CDCl$_3$): δ 5.05 (t, J=7.1 Hz, 1H), 4.90 (t, J=7.3 Hz, 1H), 4.77 (t, J=3.4 Hz, 1H), 4.73 (t, J=3.5 Hz, 1H), 3.52 (s, 3H), 3.47 (s, 3H), 2.76 (td, J=3.5, 1.3 Hz, 2H), 2.63 (dd, J=8.0, 3.9 Hz, 1H), 2.31 (qd, J=10.7, 7.3 Hz, 2H), 2.04 (dd, J=13.7, 3.9 Hz, 1H), 1.97 (dd, J=7.9, 7.1 Hz, 2H), 1.76 (dd, J=13.7, 8.1 Hz, 1H), 1.69-1.67 (m, 4H), 1.62 (s, 3H), 1.58-1.56 (m, 4H), 1.54 (s, 3H), 1.31-1.25 (m, 2H), 1.18 (s, 3H). $^{13}$C NMR (125 MHz; CDCl$_3$): δ 154.11, 154.05, 132.5, 131.8, 124.2, 120.7, 93.02, 92.92, 61.4, 61.1, 54.5, 54.1, 46.2, 39.5, 34.6, 34.1, 26.1, 25.9, 24.3, 24.1, 17.85, 17.79, 16.8. HRMS-ESI (m/z): [M+Na]$^+$ calculated for C$_{23}$H$_{36}$O$_3$, 383.2557. found, 383.2554.

(3S,3aR,7R,7aS)-6,7a-Dimethoxy-3-methyl-7-(3-methylbut-2-en-1-yl)-3-(4-methylpent-3-en-1-yl)-2,3,3a,4,7,7a-hexahydro-2,7-methanobenzofuran (13)

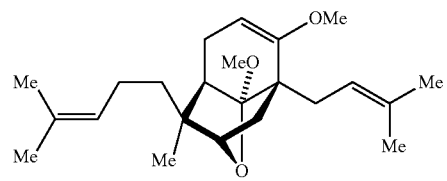

A DCM (100 mL) solution of 12 (1.88 g, 5.21 mmol, 1 equiv.) and 2,6-di-tert-butyl-4-methylpyridine (2.14 g, 10.4 mmol, 2 equiv.) was cooled to −78° C. in a 250-mL round-bottom flask, and trimethylsilyl trifluoromethanesulfonate (1.13 mL, 6.26 mmol, 1.2 equiv.) was slowly added. Immediately upon this addition, the solution turned bright yellow. After stirring at −78° C. for 45 min, the reaction was quenched with saturated aqueous NaHCO$_3$ and allowed to warm to room temperature. The mixture was then extracted thrice with EtOAc. The organic extracts were combined, washed with brine, dried over Na$_2$SO$_4$, filtered, and concentrated in vacuo to a faintly yellow residue. Flash column chromatography (30 mL SiO$_2$, 99:1 to 19:1 hexane:EtOAc) afforded 1.70 g (4.72 mmol, 90% yield) of 13 as a white, crystalline solid. $^1$H NMR (600 MHz; CDCl$_3$): δ 5.34 (t, J=7.1 Hz, 1H), 5.03 (t, J=7.1 Hz, 1H), 4.52 (dd, J=5.5, 2.0 Hz, 1H), 3.74 (d, J=5.1 Hz, 1H), 3.48 (s, 3H), 3.46 (s, 3H), 2.36 (dd, J=14.7, 6.9 Hz, 1H), 2.22-2.17 (m, 2H), 2.03 (td, J=8.6, 6.4 Hz, 2H), 2.01-1.94 (m, 1H), 1.82 (d, J=12.4 Hz, 1H), 1.78 (dd, J=12.4, 5.1 Hz, 1H), 1.69 (s, 3H), 1.67 (s, 3H), 1.61 (s, 3H), 1.58 (s, 3H), 1.45 (td, J=13.0, 4.8 Hz, 1H), 1.22 (td, J=13.0, 4.6 Hz, 1H), 1.14 (s, 3H). $^{13}$C NMR (125 MHz; CDCl$_3$): δ 158.5, 131.6, 131.2, 124.9, 123.6, 112.7, 90.6, 78.9, 54.6, 51.4, 46.5, 44.4, 42.0, 39.4, 33.6, 32.8, 28.2, 26.4, 25.9, 22.9, 20.1, 18.00, 17.85. HRMS-ESI (m/z): [M+H]$^+$ calculated for C$_{23}$H$_{36}$O$_3$, 361.2737. found, 361.2730.

(3S,3aS,7R,7aS)-6,7a-dimethoxy-3-methyl-7-(3-methylbut-2-en-1-yl)-3-(4-methylpent-3-en-1-yl)-3,3a,7,7a-tetrahydro-2,7-methanobenzofuran-4(2H)-one (14)

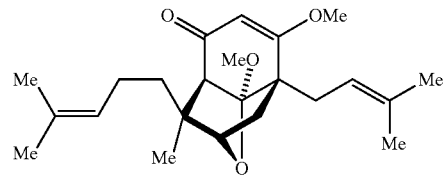

Method A.

A DCM (0.5 mL) solution of 13 (20.0 mg, 55 mmol, 1 equiv.) was cooled to 0° C. in a 2-dram scintillation vial, and cesium carbonate (98 mg, 0.28 mmol, 5 equiv.) and palladium (II) hydroxide on carbon (20 wt % Pd, 30 mg, 55 mmol, 1 equiv.) were added sequentially. A nonane solution of tert-butyl hydroperoxide (5.5 M, 50 μL, 0.28 mmol, 5 equiv.) was then added dropwise over 30 min. After stirring an additional 2.5 h at 0° C., the slurry was diluted with EtOAc and passed through a plug of $SiO_2$, rinsing with EtOAc. The eluent was concentrated in vacuo. Flash column chromatography (30 mL $SiO_2$, 9:1 to 4:1 hexane:EtOAc) afforded 5.5 mg (15 μmol, 27% yield) of 14 as a colorless residue. TLC $R_f$ 0.14 (4:1 hexane:EtOAc). $^1$H NMR (600 MHz; CDCl$_3$): δ 5.35 (s, 1H), 5.30 (t, J=7.1 Hz, 1H), 4.99 (t, J=7.0 Hz, 1H), 3.89 (d, J=5.8 Hz, 1H), 3.71 (s, 3H), 3.47 (s, 3H), 2.68 (s, 1H), 2.43 (dd, J=14.7, 6.3 Hz, 1H), 2.35 (dd, J=14.7, 8.0 Hz, 1H), 2.06 (d, J=13.0 Hz, 1H), 2.03-1.97 (m, 1H), 1.93 (dd, J=13.0, 5.8 Hz, 1H), 1.71 (s, 3H), 1.69-1.66 (m, 1H), 1.64 (s, 3H), 1.63 (s, 3H), 1.55 (s, 3H), 1.39 (td, J=13.0, 4.7 Hz, 1H), 1.34-1.30 (m, 1H), 1.28 (s, 3H). HRMS-ESI (m/z): [M+H]$^+$ calculated for $C_{23}H_{34}O_4$, 375.2530. found, 375.2528.

Method B.

An EtOAc (0.5 mL) slurry of 13 (9.8 mg, 27 μmol, 1 equiv.) and cesium carbonate (38 mg, 0.11 mmol, 4 equiv.) was cooled to −78° C. in a 3-dram scintillation vial, and [bis(trifluoroacetoxy)iodo]benzene (35 mg, 81 μmol, 3 equiv.) was added. A nonane solution of tert-butyl hydroperoxide (5.5 M, 20 μL, 4 equiv.) was added dropwise over 30 min. After stirring an additional 2 h at −78° C., the reaction was quenched at this temperature with the addition of saturated aqueous NaHCO$_3$. The mixture was then extracted thrice with EtOAc. The organic extracts were combined, washed with water and brine, dried over Na$_2$SO$_4$, filtered, and concentrated in vacuo to a faintly yellow oil. Flash column chromatography (30 mL SiO$_2$, 4:1 hexane:EtOAc) afforded 2.2 mg (6.1 μmol, 23% yield) of 14 as a colorless residue.

(3S,3aS,7R,7aS)-6,7a-Dimethoxy-3-methyl-5,7-bis(3-methylbut-2-en-1-yl)-3-(4-methylpent-3-en-1-yl)-3,3a,7,7a-tetrahydro-2,7-methanobenzofuran-4(2H)-one (15)

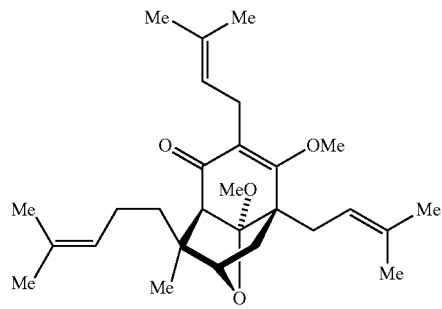

A THF (19 mL) solution of 14 (697 mg, 1.86 mmol, 1 equiv.) was cooled to −78° C. in a 100-mL recovery flask, and a freshly prepared THF solution of lithium tetramethylpiperidide (0.31 M, 6.0 mL, 3.72 mmol, 2 equiv.) was added. The resulting yellow-orange solution was stirred at −78° C. for 20 min. A THF solution of 2-thienyl(cyano)copper lithium (0.22 M, 17 mL, 3.72 mmol, 2 equiv.) was subsequently added over 10 min, and the resulting brown slurry was allowed to warm to −40° C. over 70 min. Once this bath temperature had been attained, the slurry was stirred at −40° C. for 30 min. The slurry was then cooled to −78° C., and prenyl bromide (1.1 mL, 9.3 mmol, 5 equiv.) was added. After warming the slurry to −40° C. over 45 min, the reaction was maintained at this temperature for 15 min and subsequently quenched at −40° C. with saturated aqueous NH$_4$Cl and allowed to warm to room temperature. The mixture was then extracted thrice with EtOAc. The organic extracts were combined, washed with H$_2$O and brine, dried over Na$_2$SO$_4$, filtered, and concentrated in vacuo to give a brown oil. Flash column chromatography (200 mL SiO$_2$, 95:5 hexane:EtOAc) afforded 586 mg (1.32 mmol, 71% yield) of 15 as a colorless oil. TLC $R_f$ 0.66 (7:3 hexane:EtOAc). $^1$H NMR (600 MHz; CDCl$_3$): δ 5.30 (t, J=6.9 Hz, 1H), 4.99 (t, J=6.7 Hz, 1H), 4.96 (t, J=7.2 Hz, 1H), 3.87 (d, J=5.7 Hz, 1H), 3.80 (s, 3H), 3.44 (s, 3H), 3.06-2.99 (m, 2H), 2.72 (s, 1H), 2.46 (dd, J=15.2, 6.7 Hz, 1H), 2.31 (dd, J=15.2, 7.1 Hz, 1H), 2.14 (d, J=12.7 Hz, 1H), 1.99-1.95 (m, 1H), 1.92 (dd, J=12.7, 5.7 Hz, 1H), 1.76-1.71 (m, 1H), 1.71 (s, 3H), 1.67 (s, 3H), 1.64 (s, 3H), 1.63 (s, 6H), 1.55 (s, 3H), 1.35-1.31 (m, 1H), 1.28 (m, 1H), 1.25 (s, 3H). $^{13}$C NMR (126 MHz, CDCl$_3$): δ 198.6, 176.3, 132.2, 131.87, 131.78, 124.2, 122.8, 122.32, 122.26, 114.6, 81.0, 61.0, 56.7, 52.1, 49.2, 48.3, 39.2, 34.3, 32.8, 27.9, 26.3, 25.82, 25.79, 22.74, 22.63, 18.09, 18.03, 17.8. FTIR (thin film) $v_{max}$: 2968, 2925, 1655, 1617, 1449, 1375, 1345, 1331, 1233, 1074, 1009, 941, 829 cm$^{-1}$. HRMS-ESI (m/z): [M+H]$^+$ calculated for $C_{28}H_{42}O_4$, 443.3156. found, 443.3150.

(1S,5R,7S,8S)-7-Hydroxy-4,9,9-trimethoxy-8-methyl-3,5-bis(3-methylbut-2-en-1-yl)-8-(4-methylpent-3-en-1-yl)bicyclo[3.3.1]non-3-en-2-one (16)

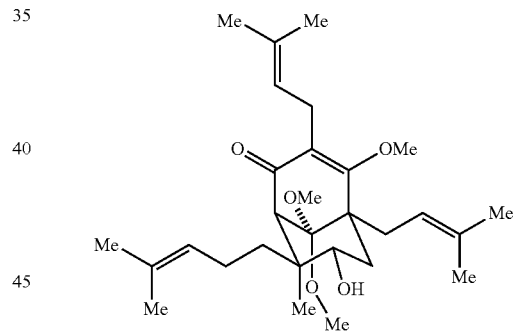

A DCM (5 mL) solution of 15 (55 mg, 0.12 mmol, 1 equiv.) was cooled to −78° C. in a 20-mL recovery flask, and a DCM solution of bromodimethylborane (2.65 M, 430 μL, 1.1 mmol, 9.2 equiv.) was added. After stirring the yellow solution for 25 min at −78° C., it was quenched at −78° C. with 1 mL of a 1:1 mixture of MeOH and NEt$_3$ followed by saturated aqueous NaHCO$_3$. The mixture was warmed to room temperature and extracted thrice with EtOAc. The organic extracts were combined, washed sequentially with H$_2$O, NH$_4$Cl, and brine, dried over Na$_2$SO$_4$, filtered, and concentrated in vacuo to a brown residue. Flash column chromatography (25 mL SiO$_2$, 9:1 hexane:EtOAc) afforded 44 mg (93 μmol, 75% yield) of 16 as a faint yellow syrup. TLC $R_f$ 0.45 (8:2 hexane:EtOAc). $^1$H NMR (600 MHz; CDCl$_3$): δ 5.37 (t, J=7.1 Hz, 1H), 5.04 (t, J=7.2 Hz, 1H), 5.00 (t, J=6.5 Hz, 1H), 3.86 (s, 3H), 3.57 (ddd, J=11.7, 6.6, 5.4 Hz, 1H), 3.33 (s, 3H), 3.20 (s, 3H), 3.12 (dd, J=15.3, 6.4 Hz, 1H), 2.99 (dd, J=15.3, 6.6 Hz, 1H), 2.92 (s, 1H), 2.68 (dd, J=15.4, 7.7 Hz, 1H), 2.35 (dd, J=15.4, 6.9 Hz, 1H), 2.35-2.31 (m, 1H), 1.93-1.87 (m, 1H), 1.87 (dd, J=13.2, 11.9 Hz, 1H), 1.78 (dd, J=13.2, 5.4 Hz, 1H), 1.71 (s, 3H), 1.68 (s, 3H), 1.66 (s, 3H), 1.65 (s, 3H), 1.64 (s, 3H), 1.63 (s, 3H), 1.40 (td, J=12.8, 4.9 Hz, 1H), 1.24-1.21 (m, 1H), 1.10 (s, 3H), 0.98 (td, J=12.8, 4.7 Hz, 1H). $^{13}$C NMR (126 MHz; CDCl$_3$): δ 198.7, 174.5, 132.3, 131.8, 131.4, 125.1, 123.6, 122.50, 122.38, 103.1, 74.0, 62.3, 59.2, 53.7, 51.1, 50.5, 40.5, 39.7, 36.1, 30.7, 26.2, 25.92, 25.85, 23.4, 21.7, 18.2, 17.94, 17.88. FTIR (thin film) $v_{max}$: 3468 (br), 2965, 2925, 2857, 1683, 1613, 1451, 1376, 1336, 1225, 1153, 1100, 1065 cm$^{-1}$. HRMS-ESI (m/z): [M+H]$^+$ calculated for C$_{29}$H$_{46}$O$_5$, 475.3418. found, 475.3406.

(1S,5R,7S,8S,9S)-7,9-Dihydroxy-4,9-dimethoxy-8-methyl-3,5-bis(3-methylbut-2-en-1-yl)-8-(4-methyl-pent-3-en-1-yl)bicyclo[3.3.1]non-3-en-2-one (17)

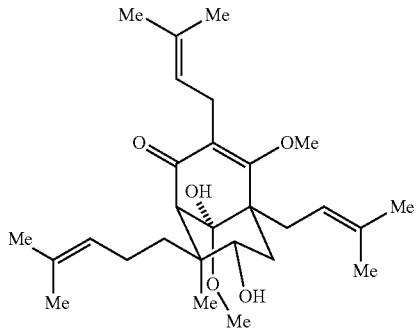 [SMILES: COC1=C(CC=C(C)C)C(=O)C2C(C)(CCC=C(C)C)C(O)CC1(CC=C(C)C)[C@@]2(O)OC]

A DCM (2 mL) solution of 15 (29 mg, 6.6 μmol, 1 equiv.) was cooled to −78° C. in a 10-mL teardrop-shaped flask, and a DCM solution of bromodimethylborane (2.65 M, 0.25 mL, 0.66 mmol, 10 equiv.) was added dropwise. After stirring the bright yellow solution at −78° C. for 10 min, it was quenched sequentially at −78° C. with 1.25 mL NEt$_3$ and saturated aqueous NaHCO$_3$. The mixture was warmed to room temperature and extracted thrice with EtOAc. The organic extracts were combined, washed with brine, dried over Na$_2$SO$_4$, filtered, and concentrated in vacuo to yield a yellow residue. Flash column chromatography (30 mL SiO$_2$, 9:1 hexane:EtOAc) afforded 26.7 mg (58 μmol, 88% yield) of 17 as a yellow oil. TLC R$_f$ 0.38 (7:3 hexane:EtOAc). $^1$H NMR (600 MHz; C$_6$D$_6$): δ 5.55 (dq, J=11.5, 1.3 Hz, 1H), 5.35 (t, J=7.3 Hz, 1H), 5.28 (t, J=6.6 Hz, 1H), 3.71 (s, 1H), 3.67 (dd, J=11.8, 5.3 Hz, 1H), 3.53 (s, 3H), 3.34 (dd, J=15.2, 6.4 Hz, 1H), 3.16 (m, 1H), 3.14 (s, 1H), 3.06 (s, 3H), 2.92 (dd, J=14.1, 11.5 Hz, 1H), 2.86 (tdd, J=12.8, 7.7, 5.0 Hz, 1H), 2.26 (d, J=14.1 Hz, 1H), 2.08 (tt, J=12.5, 6.1 Hz, 1H), 2.00 (dd, J=12.8, 12.0 Hz, 1H), 1.84 (s, 3H), 1.72 (s, 3H), 1.72-1.68 (m, 1H), 1.62 (s, 6H), 1.60-1.58 (m, 1H), 1.56 (s, 3H), 1.42 (s, 3H), 1.27 (td, J=12.7, 4.4 Hz, 1H), 1.12 (s, 3H). $^{13}$C NMR (126 MHz; C$_6$D$_6$): δ 197.3, 171.2, 136.5, 131.8, 131.1, 125.8, 124.5, 123.36, 123.23, 100.2, 73.4, 61.8, 57.5, 52.4, 48.2, 40.9, 39.7, 37.5, 30.8, 26.0, 25.76, 25.72, 23.7, 22.2, 18.01, 17.90, 17.7, 17.3. FTIR (thin film) $v_{max}$: 3464 (br), 2969, 2928, 2859, 1665, 1615, 1450, 1376, 1329, 1235, 1087, 1040, 986, 928, 907, 858, 737 cm-1. HRMS-ESI (m/z): [M+H]+ calculated for C$_{28}$H$_{44}$O$_5$, 461.3262. found, 461.3254.

(1S,5R,7S,8S,9S)-7,9-Dihydroxy-4,9-dimethoxy-8-methyl-5-(3-methylbut-2-en-1-yl)-8-(4-methylpent-3-en-1-yl)bicyclo[3.3.1]non-3-en-2-one (19)

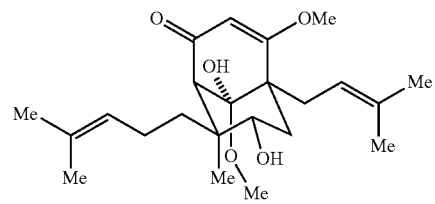 [SMILES: COC1=CC(=O)C2C(C)(CCC=C(C)C)C(O)CC1(CC=C(C)C)[C@@]2(O)OC]

A DCM (3 mL) solution of 14 (98.9 mg, 0.26 mmol, 1 equiv.) and triethylamine (22 μL, 0.16 mmol, 0.6 equiv.) was cooled to −78° C. in a 25-mL recovery flask, and a DCM solution of bromodimethylborane (1.54 M, 1.03 mL, 1.58 mmol, 6 equiv.) was added dropwise. The resulting yellow solution was stirred at −78° C. for 25 min and subsequently quenched sequentially at −78° C. with 1 mL NEt$_3$ and saturated aqueous NaHCO$_3$. After warming the mixture to room temperature, it was extracted thrice with EtOAc. The organic extracts were combined, washed with H$_2$O and brine, dried over Na$_2$SO$_4$, filtered, and concentrated in vacuo to give a yellow-orange oil. Flash column chromatography (30 mL SiO$_2$, 8:2 to 7:3 hexane:EtOAc) afforded 80.8 mg (0.21 mmol, 79% yield) of 19 as a viscous yellow syrup. TLC R$_f$ 0.50 (1:1 hexane:EtOAc). $^1$H NMR (600 MHz; CDCl$_3$): δ 5.48 (s, 1H), 5.26 (d, J=9.0 Hz, 1H), 5.05 (t, J=7.1 Hz, 1H), 3.74 (s, 3H), 3.63-3.59 (m, 1H), 3.57 (s, 1H), 3.26 (s, 3H), 2.87-2.83 (m, 2H), 2.36 (tt, J=12.5, 6.2 Hz, 1H), 2.25 (d, J=14.0 Hz, 1H), 2.01-1.93 (m, 2H), 1.92-1.86 (m, 1H), 1.73 (s, 3H), 1.68 (s, 3H), 1.65 (s, 6H), 1.46 (td, J=13.0, 4.8 Hz, 1H), 1.32 (d, J=5.9 Hz, 1H), 1.11 (s, 3H), 1.05 (td, J=12.9, 4.4 Hz, 1H). $^{13}$C NMR (126 MHz; CDCl$_3$): δ 198.2, 176.1, 137.4, 131.4, 125.0, 122.1, 104.1, 100.6, 73.2, 57.6, 56.6, 51.1, 48.5, 40.5, 39.2, 36.9, 30.0, 26.2, 25.9, 21.9, 18.00, 17.88, 17.0. HRMS-ESI (m/z): [M+H]$^+$ calculated for C$_{23}$H$_{36}$O$_5$, 393.2636. found, 393.2632.

(1S,5R,7S,8S)-7-Hydroxy-4-methoxy-8-methyl-5-(3-methylbut-2-en-1-yl)-8-(4-methylpent-3-en-1-yl)bicyclo[3.3.1]non-3-ene-2,9-dione (20)

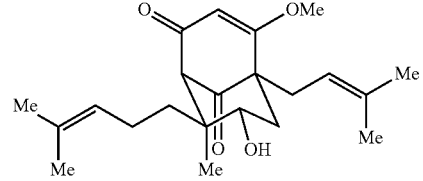 [SMILES: COC1=CC(=O)C2C(=O)C1(CC=C(C)C)CC(O)C2(C)CCC=C(C)C]

A 1:1 acetone:H$_2$O (4 mL) solution of 19 (65 mg, 0.17 mmol, 1 equiv.) and pyridinium para-toluenesulfonate (208 mg, 0.83 mmol, 5 equiv.) was heated to reflux in a 10-mL recovery flask with an affixed reflux condenser. After stirring at reflux for 15.5 h, the solution was cooled, diluted with H$_2$O, and extracted thrice with 1:1 hexane:EtOAc. The organic extracts were combined, washed with H$_2$O and brine, dried over Na$_2$SO$_4$, filtered, and concentrated in vacuo to give a faint yellow oil. Flash column chromatography (20 mL SiO$_2$, 7:3 hexane:EtOAc) afforded 54 mg (0.15 mmol, 90% yield) of 20 as a colorless oil. TLC R$_f$ 0.50 (1:1 hexane:EtOAc). $^1$H NMR (600 MHz; CDCl$_3$): δ 5.67 (s, 1H), 5.08 (t, J=7.1 Hz, 1H), 4.98 (t, J=7.0 Hz, 1H), 3.82-3.80 (m, 1H), 3.75 (s, 3H), 3.19 (s, 1H), 2.49 (dd, J=14.5, 6.3 Hz, 1H), 2.40 (dd, J=14.6, 7.6 Hz, 1H), 2.34 (tt, J=12.6, 6.3 Hz, 1H), 2.11 (dd, J=13.4, 5.4 Hz, 1H), 1.91 (tt, J=12.4, 6.2 Hz, 1H), 1.75 (dd, J=13.3, 11.6 Hz, 1H), 1.67 (s, 2H), 1.66 (s, 3H), 1.65 (s, 3H), 1.64 (s, 3H), 1.61-1.59 (m, 1H), 1.56 (td, J=12.8, 4.8 Hz, 1H), 1.32 (td, J=12.7, 4.8 Hz, 1H), 0.91 (s, 3H). $^{13}$C NMR (126 MHz; CDCl$_3$): δ 205.2, 193.1, 177.5, 134.5, 132.2, 124.3, 119.0, 106.0, 72.1, 69.2, 57.1, 56.0, 45.9, 39.4, 38.1, 29.5, 26.1, 25.9, 21.8, 18.1, 17.9, 15.7. HRMS-ESI (m/z): [M+H]$^+$ calculated for C$_{22}$H$_{32}$O$_4$, 361.2373. found, 361.2357.

(1S,2S,3S,5R)-6-Methoxy-2-methyl-5-(3-methylbut-2-en-1-yl)-2-(4-methylpent-3-en-1-yl)-8,9-dioxobi-cyclo[3.3.1]non-6-en-3-yl trifluoromethanesulfonate (21)

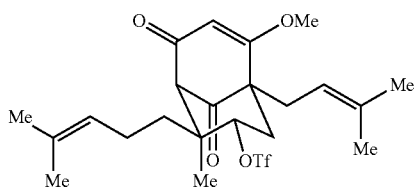

A DCM (20 mL) solution of 20 (253 mg, 0.702 mmol, 1 equiv.) and pyridine (341 µL, 4.21 mmol, 6 equiv.) was cooled to −45° C. in a 50-mL recovery flask, and trifluoromethane-sulfonic anhydride (0.59 mL, 3.5 mmol, 5 equiv.) was added. The resulting viscous yellow slurry was allowed to slowly warm to 5° C. over 2 h, whereupon it was quenched at 5° C. with saturated aqueous NaHCO$_3$. The mixture was extracted thrice with EtOAc. The organic extracts were combined, washed with H$_2$O and brine, dried over Na$_2$SO$_4$, filtered, and concentrated in vacuo to give a yellow oil. This oil was dissolved in 8:2 hexane:EtOAc and passed through a short plug of SiO$_2$, rinsing with 8:2 hexane:EtOAc. The eluent was concentrated in vacuo to give a yellow-orange oil which was used without further purification. This procedure afforded 277 mg (0.56 mmol, 80% yield) of 21 as a yellow oil. TLC R$_f$ 0.54 (8:2 hexane:EtOAc). $^1$H NMR (600 MHz; C$_6$D$_6$): δ 5.32 (s, 1H), 5.19-5.15 (m, 2H), 5.07 (dd, J=11.6, 5.5 Hz, 1H), 3.41 (s, 1H), 2.66 (s, 3H), 2.64-2.57 (m, 1H), 2.45 (dd, J=14.4, 6.6 Hz, 1H), 2.30-2.25 (m, 2H), 1.85 (dd, J=12.9, 11.9 Hz, 1H), 1.81-1.76 (m, 1H), 1.74 (s, 3H), 1.65 (t, J=8.4 Hz, 2H), 1.62 (s, 3H), 1.55 (s, 3H), 1.54 (s, 3H), 0.75 (s, 3H). $^{13}$C NMR (126 MHz; C$_6$D$_6$): δ 201.6, 189.9, 175.4, 134.9, 132.6, 123.6, 118.8, 106.3, 90.6, 68.8, 56.4, 55.3, 45.3, 37.8, 36.6, 29.5, 25.86, 25.80, 21.7, 17.91, 17.82, 16.3. $^{19}$F NMR (470 MHz; C$_6$D$_6$): δ −75.6 (s, 1F). HRMS-ESI (m/z): [M+H]$^+$ calculated for C$_{23}$H$_{31}$F$_3$O$_6$S, 493.1866. found, 493.1865.

6-Methoxy-2-methyl-5-(3-methylbut-2-en-1-yl)-2-(4-methylpent-3-en-1-yl)-7-(trimethylsilyl)tricyclo[3.3.1.0$^{1,3}$]non-6-ene-8,9-dione (22)

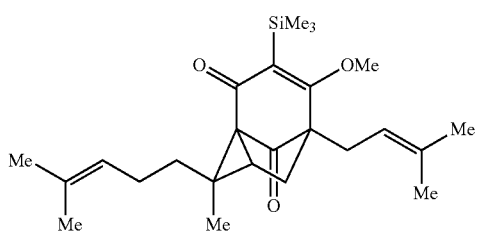 [SMILES: COC1=C([Si](C)(C)C)C(=O)C23C(=O)C1(CC=C(C)C)CC2C3(C)CCC=C(C)C]

A THF (6 mL) solution of 21 (148 mg, 0.300 mmol, 1 equiv.) and chlorotrimethylsilane (1.9 mL, 15 mmol, 50 equiv.) was cooled to −78° C. in a 25-mL recovery flask, and a freshly prepared THF solution of lithium diisopropylamide (0.50 M, 3.0 mL, 1.5 mmol, 5 equiv.) was added slowly. The resulting yellow-orange solution was stirred at −78° C. for 30 min and subsequently quenched at −78° C. with saturated aqueous NaHCO$_3$. After warming to room temperature, the mixture was extracted thrice with EtOAc. The organic extracts were combined, washed with H$_2$O and brine, dried over Na$_2$SO$_4$, filtered, and concentrated in vacuo to give an orange oil. Flash column chromatography (100 mL SiO$_2$, 95:5 hexane:EtOAc) afforded 69.7 mg (0.168 mmol, 56% yield) of 22 as a faint yellow oil. TLC R$_f$ 0.52 (8:2 hexane:EtOAc). $^1$H NMR (600 MHz; C$_6$D$_6$): δ 5.41 (t, J=7.4 Hz, 1H), 5.28 (t, J=7.1 Hz, 1H), 3.22 (s, 3H), 2.59 (dd, J=15.1, 6.4 Hz, 1H), 2.53-2.49 (m, 1H), 2.48 (dd, J=15.1, 8.4 Hz, 1H), 2.18 (m, 1H), 1.86 (ddd, J=13.5, 11.2, 5.2 Hz, 1H), 1.79 (ddd, J=13.5, 11.2, 5.4 Hz, 1H), 1.74 (dd, J=14.0, 5.4 Hz, 1H), 1.68-1.66 (m, 1H), 1.66 (s, 3H), 1.65 (s, 3H), 1.61 (s, 3H), 1.54 (s, 3H), 1.07 (s, 3H), 0.98 (dd, J=7.9, 5.4 Hz, 1H), 0.35 (s, 9H). $^{13}$C NMR (126 MHz; C$_6$D$_6$): δ 200.2, 194.7, 184.3, 134.4, 131.56, 131.55, 124.6, 119.5, 74.1, 61.8, 56.8, 48.0, 38.7, 37.7, 27.7, 26.21, 26.10, 25.8, 17.92, 17.77, 16.3, 0.7. FTIR (thin film) ν$_{max}$: 2968, 2918, 2860, 1762, 1664, 1523, 1451, 1438, 1386, 1233, 1201, 1157, 1042, 962, 845, 761, 691 cm$^{-1}$. HRMS-ESI (m/z): [M+H]$^+$ calculated for C$_{25}$H$_{38}$O$_3$Si, 415.2663. found, 415.2650.

(1S,5R,7S,8S)-7-Iodo-4-methoxy-8-methyl-5-(3-methylbut-2-en-1-yl)-8-(4-methylpent-3-en-1-yl) bicyclo[3.3.1]non-3-ene-2,9-dione (24)

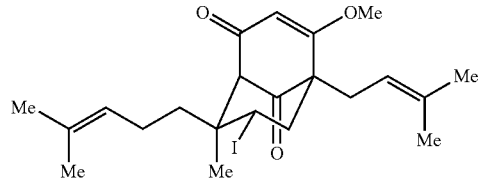 [SMILES: COC1=CC(=O)C2C(=O)C1(CC=C(C)C)CC(I)C2(C)CCC=C(C)C]

A mixture of copper(I) iodide (20 mg, 0.10 mmol, 30.7 equiv.) and lithium chloride (5.3 mg, 0.12 mmol, 36.7 equiv.) in a 10-mL recovery flask was dried under vacuum with a heat gun, cooled under vacuum, and subsequently purged with argon. This procedure was repeated twice more. The residue was then taken up in THF (0.5 mL) and stirred at room temperature for 3 min, whereupon a colorless solution was produced. Meanwhile, a THF (1 mL) solution of tributylpre-nylstannane (37 mg, 0.10 mmol, 30.4 equiv.) was cooled to −78° C. in a 10-mL teardrop-shaped flask, and a hexane solution of n-butyllithium (1.56 M, 63 µL, 0.099 mmol, 29.2 equiv.) was added. The resulting bright yellow solution was stirred at −78° C. for 15 min, and then this solution was transferred via dry-ice cooled cannula to the copper(I) iodide/lithium chloride solution cooled to −78° C. The resulting brown-red solution was stirred at −78° C. for 10 min, and chlorotrimethylsilane (22 µL, 0.17 mmol, 51.0 equiv.) and 22 (1.4 mg, 3.4 µmol, 1 equiv.) in THF (0.25 mL) were added in quick succession, followed by a THF (0.25 mL) rinse of the flask containing 22. The solution was allowed to warm to 0° C. over 40 min and stirred for 3 h at that temperature. After 90 min, a black slurry was observed which turned into a colorless solution by the end of the 3 h period. This solution was then warmed to room temperature, quenched with saturated aqueous NH$_4$Cl, and extracted thrice with EtOAc. The organic extracted were combined, washed with H$_2$O and brine, dried over Na$_2$SO$_4$, filtered, and concentrated in vacuo. Preparatory thin-layer chromatography (8:2 hexane:EtOAc) afforded 0.8 mg (2 µmol, 50% yield) of 24 as a colorless residue. TLC R$_f$ 0.43 (8:2 hexane:EtOAc). $^1$H NMR (600 MHz; CDCl$_3$): δ 5.76 (s, 1H), 5.08 (t, J=7.1 Hz, 1H), 4.97 (t, J=6.3 Hz, 1H), 4.35 (dd, J=12.8, 5.1 Hz, 1H), 3.77 (s, 3H), 3.40 (s, 1H), 2.53-2.46 (m, 2H), 2.45-2.36 (m, 3H), 1.93-1.86 (m, 1H), 1.68 (s, 3H), 1.68 (s, 3H), 1.66 (s, 3H), 1.60 (td, J=13.1, 3.9 Hz, 1H), 1.55 (s, 3H), 1.28 (td, J=13.0, 4.3 Hz, 1H), 1.05 (s, 3H). $^{13}$C NMR (126 MHz; CDCl$_3$): δ 203.7, 192.6, 176.1, 134.8, 132.4, 123.7, 118.7, 106.6, 67.7, 59.4, 57.2, 46.8, 45.1, 41.9, 37.1, 29.2, 26.13, 25.94, 21.8, 21.0, 18.2, 17.9. HRMS-ESI (m/z): [M+H]$^+$ calculated for $C_{22}H_{31}IO_3$, 471.1391. found, 471.1406.

(1S,5R,7S,8S)-7-Hydroxy-4,9,9-trimethoxy-8-methyl-5-(3-methylbut-2-en-1-yl)-8-(4-methylpent-3-en-1-yl)bicyclo[3.3.1]non-3-en-2-one (25)

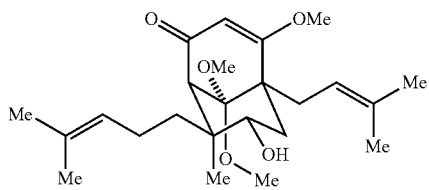

A DCM (6 mL) solution of 14 (456 mg, 1.22 mmol, 1 equiv.) and triethylamine (102 µL, 0.731 mmol, 0.6 equiv.) was cooled to −78° C. in a 20-mL scintillation vial, and a DCM solution of bromodimethylborane (1.26 M, 5.8 mL, 7.3 mmol, 6 equiv.) was added slowly. The orange-red solution was stirred at −78° C. for 45 min and subsequently quenched with a 1:1 mixture of NEt$_3$/MeOH (8 mL) at −78° C., and the slurry was poured onto saturated aqueous NaHCO$_3$. The mixture was extracted thrice with EtOAc. The organic extracts were combined, washed sequentially with 2 N HCl, saturated aqueous NaHCO$_3$, and brine, dried over Na$_2$SO$_4$, filtered, and concentrated in vacuo to give a viscous yellow oil. Flash column chromatography (150 mL SiO$_2$, 8:2 hexane:EtOAc) afforded 303 mg (0.745 mmol, 61% yield) of 25 as a viscous yellow oil. TLC R$_f$ 0.46 (1:1 hexane:EtOAc). $^1$H NMR (600 MHz; CDCl$_3$): δ 5.40 (s, 1H), 5.34 (t, J=7.2 Hz, 1H), 5.04 (t, J=7.2 Hz, 1H), 3.67 (s, 3H), 3.57-3.54 (m, 1H), 3.35 (s, 3H), 3.23 (s, 3H), 2.89 (s, 1H), 2.68 (dd, J=15.3, 8.0 Hz, 1H), 2.39-2.33 (m, 2H), 1.92-1.88 (m, 1H), 1.84 (dd, J=12.9, 12.1 Hz, 1H), 1.72 (dd, J=13.2, 5.2 Hz, 1H), 1.68 (s, 3H), 1.64 (s, 6H), 1.61 (s, 3H), 1.45 (td, J=13.0, 4.8 Hz, 1H), 1.37 (m, 1H), 1.11 (s, 3H), 1.04 (td, J=12.8, 4.5 Hz, 1H). $^{13}$C NMR (126 MHz; CDCl$_3$): δ 198.1, 179.0, 131.9, 131.4, 125.1, 122.1, 103.9, 103.0, 73.5, 59.0, 56.5, 52.4, 51.2, 50.5, 40.6, 39.5, 36.8, 35.9, 30.4, 26.2, 25.9, 21.9, 18.1, 17.9. HRMS-ESI (m/z): [M+H]$^+$ calculated for $C_{24}H_{38}O_5$, 407.2798. found, 407.2805.

6,9,9-Trimethoxy-2-methyl-5-(3-methylbut-2-en-1-yl)-2-(4-methylpent-3-en-1-yl)tricyclo[3.3.1.0$^{1,3}$]non-6-en-8-one (26)

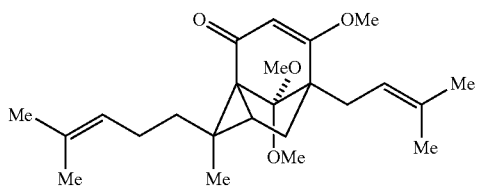

A DCM (2.3 mL) solution of 25 (47.7 mg, 0.12 mmol, 1 equiv.) and pyridine (57 µL, 0.70 mmol, 6 equiv.) was cooled to −40° C. in a 10-mL recovery flask, and trifluoromethanesulfonic anhydride (99 µL, 0.59 mmol, 5 equiv.) was added dropwise. The yellow slurry was allowed to slowly warm to 0° C. over 45 min, whereupon it was quenched at 0° C. with saturated aqueous NaHCO$_3$. The mixture was extracted thrice with EtOAc. The combined organic extracts were washed with H$_2$O and brine, dried over Na$_2$SO$_4$, filtered, and concentrated in vacuo to a brown oil, which was used without further purification due to its propensity to decompose upon standing. A THF (1 mL) solution of this brown oil was cooled to −78° C. in a 10-mL test tube, and a freshly prepared THF solution of lithium diethylamide (0.50 M, 1.2 mL, 0.59 mmol, 5 equiv.) was added. The resulting brown-orange solution was allowed to slowly warm to 0° C. over 40 min and stirred at 0° C. for 10 min. At this time, chlorotrimethylsilane (150 µL, 1.2 mmol, 10 equiv.) was added. The red solution subsequently turned bright orange and was stirred at 0° C. for 15 min. The solution was then quenched at 0° C. with saturated aqueous NaHCO$_3$ and extracted thrice with EtOAc. The organic extracts were combined, washed with H$_2$O and brine, dried over Na$_2$SO$_4$, filtered, and concentrated in vacuo to a brown oil. Flash column chromatography (30 mL SiO$_2$, 9:1 to 8:2 hexane:EtOAc) afforded 16.5 mg (42 µmol, 35% yield over 2 steps) of 26 as a yellow oil. TLC R$_f$ 0.39 (8:2 hexane:EtOAc). TLC R$_f$ 0.39 (8:2 hexane:EtOAc). $^1$H NMR (500 MHz; C$_6$D$_6$): δ 5.58 (t, J=6.9 Hz, 1H), 5.50 (t, J=7.2 Hz, 1H), 5.45 (s, 1H), 3.05 (s, 3H), 3.02 (s, 3H), 3.01 (s, 3H), 2.87-2.79 (m, 2H), 2.37 (m, 2H), 1.99 (dd, J=13.4, 6.6 Hz, 1H), 1.87 (td, J=12.3, 5.2 Hz, 1H), 1.79 (s, 3H), 1.77-1.73 (m, 2H), 1.70 (s, 6H), 1.60 (s, 3H), 1.56 (s, 3H), 0.89 (t, J=7.0 Hz, 1H).

6,9,9-Trimethoxy-2-methyl-5-(3-methylbut-2-en-1-yl)-2-(4-methylpent-3-en-1-yl)-7-(trimethylsilyl)tricyclo[3.3.1.0$^{1,3}$]non-6-en-8-one (28)

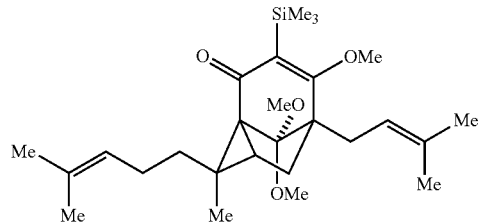

A THF (1 mL) solution of 26 (16 mg, 41 µmol, 1 equiv.) was cooled to −78° C. in a 10-mL recovery flask, and chlorotrimethylsilane (0.21 mL, 1.6 mmol, 40 equiv.) and a freshly prepared THF solution of lithium diisopropylamide (0.50 M, 1.6 mL, 0.82 mmol, 20 equiv.) were added sequentially. The resulting yellow solution was stirred at −78° C. for 45 min and then allowed to warm to room temperature over 3.5 h. The golden yellow solution was then quenched at −20° C. with saturated aqueous NaHCO$_3$ and extracted thrice with EtOAc. The organic extracts were combined, washed with H$_2$O and brine, dried over Na$_2$SO$_4$, filtered, and concentrated in vacuo to a yellow oil. Flash column chromatography (30 mL SiO$_2$, 95:5 to 8:2 hexane:EtOAc) afforded 10.7 mg (23.2 µmol, 57% yield) of 28 as a colorless oil along with 3.9 mg (10 µmol, 24% recovery) of 26. TLC R$_f$ 0.62 (8:2 hexane:EtOAc). $^1$H NMR (600 MHz; C$_6$D$_6$): δ 5.54 (t, J=7.1 Hz, 1H), 5.47 (t, J=7.2 Hz, 1H), 3.37 (s, 3H), 2.99 (s, 3H), 2.97 (s, 3H), 2.77-2.71 (m, 2H), 2.42 (dd, J=15.0, 7.0 Hz, 1H), 2.41-2.34 (m, 1H), 2.06 (dd, J=13.3, 6.6 Hz, 1H), 1.84 (td, J=12.3, 5.2 Hz, 1H), 1.74 (s, 3H), 1.73-1.68 (m, 4H), 1.68 (m, 4H), 1.62 (s, 3H), 1.54 (s, 3H), 0.84 (t, J=7.0 Hz, 1H), 0.48 (s, 9H). $^{13}$C NMR (126 MHz; C$_6$D$_6$): δ 198.9, 184.3, 131.1, 130.9, 129.2, 125.5, 123.1, 110.0, 74.1, 64.0, 53.5, 52.3, 51.0, 50.6, 41.8, 38.0, 31.7, 28.2, 26.6, 25.92, 25.87, 17.82, 17.80, 16.4, 0.9. HRMS-ESI (m/z): [M+H]$^+$ calculated for C$_{27}$H$_{44}$O$_4$Si, 461.3082. found, 461.3094.

(2S,3R)-3-(Bromomethyl)-2-(4-methoxy-4-methyl-pentyl)-2-methyloxirane (29)

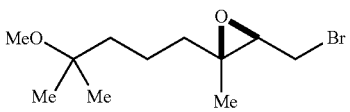

A MeOH (110 mL) solution of mercury(II) acetate (10.3 g, 32.2 mmol, 1.5 equiv.) in a 250-mL round-bottom flask was treated with 2 (5.00 g, 21.4 mmol, 1 equiv.), and the resulting milky white slurry was stirred at room temperature for 15 min. The slurry was then cooled to 0° C., and an aqueous solution of NaOH (3 M, 35 mL) was added. The resulting bright orange slurry was stirred at 0° C. for 2 min, and a basic, aqueous solution of NaBH$_4$ (0.5 M NaBH$_4$ in 3 M NaOH aqueous solution, 35 mL) was added, immediately producing a gray slurry. After stirring an additional 15 min at 0° C., the slurry was diluted with H$_2$O and extracted thrice with 8:2 hexane:EtOAc. The organic extracts were combined, washed thrice with H$_2$O and once with brine, dried over Na$_2$SO$_4$, filtered, and concentrated to a colorless oil. Flash column chromatography (250 mL SiO$_2$, 9:1 to 8:2 hexane:EtOAc) afforded 4.98 g (18.8 mmol, 88% yield) of 29 as a colorless oil along with 187 mg (0.802 mmol, 3.7% recovery) of 2. TLC R$_f$ 0.18 (9:1 hexane:EtOAc). $^1$H NMR (600 MHz; CDCl$_3$): δ 3.53 (dd, J=10.4, 5.9 Hz, 1H), 3.24 (dd, J=10.4, 7.7 Hz, 1H), 3.16 (s, 3H), 3.08 (dd, J=7.7, 5.9 Hz, 1H), 1.65 (t, J=6.2 Hz, 1H), 1.48-1.40 (m, 5H), 1.30 (s, 3H), 1.13 (s, 6H). $^{13}$C NMR (126 MHz; CDCl$_3$): δ 74.5, 63.3, 61.6, 49.3, 39.9, 38.8, 30.0, 25.1, 19.6, 16.2. FTIR (thin film) ν$_{max}$: 2971, 2948, 2915, 2826, 2465, 1382, 1364, 1253, 1221, 1205, 1148, 1083, 891, 652 cm$^{-1}$. HRMS-ESI (m/z): [M+Na]$^+$ calculated for C$_{11}$H$_{21}$BrO$_2$, 287.0617. found, 287.0621.

(2S,3S)-3-((2,6-Dimethoxy-1-(3-methylbut-2-en-1-yl)cyclohexa-2,5-dien-1-yl)methyl)-2-(4-methoxy-4-methylpentyl)-2-methyloxirane (30)

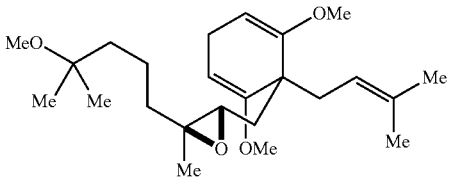

A THF (100 mL) solution of 11 (4.35 g, 20.9 mmol, 1 equiv.) was cooled to −78° C. in a 250-mL round-bottom flask, and a cyclohexane solution of sec-butyllithium (1.21 M, 21.6 mL, 26.1 mmol, 1.25 equiv.) was added slowly over 5 min. The resulting yellow slurry was warmed to −30° C. over 40 min and maintained at that temperature for an additional 15 min. The resulting dark orange-red slurry was cooled to −78° C., and a THF (20 mL) solution of 29 (4.98 g, 18.8 mmol, 0.9 equiv.) was added, followed by two THF (10 mL) rinses of the flask that contained 29. At the end of the initial addition of 29, the slurry became faint yellow, and it was allowed to warm slowly to 0° C. over 3.5 h. The slurry was then quenched with H$_2$O at 0° C., producing a mild effervescence. The mixture was warmed to room temperature and extracted thrice with EtOAc. The organic extracts were combined, washed with H$_2$O and brine, dried over Na$_2$SO$_4$, filtered, and concentrated in vacuo to a yellow oil. Flash column chromatography (400 mL SiO$_2$, 9:1 to 8:2 hexane:EtOAc) afforded 4.95 g (12.6 mmol, 67% yield) of 30 as a colorless oil. TLC R$_f$ 0.38 (8:2 hexane:EtOAc). $^1$H NMR (600 MHz; CDCl$_3$): δ 4.89 (t, J=7.3 Hz, 1H), 4.76 (t, J=3.5 Hz, 1H), 4.72 (t, J=3.5 Hz, 1H), 3.51 (s, 3H), 3.46 (s, 3H), 3.15 (s, 3H), 2.75 (t, J=3.6 Hz, 2H), 2.61 (dd, J=8.0, 3.9 Hz, 1H), 2.34-2.27 (m, 2H), 2.03 (dd, J=13.7, 3.9 Hz, 1H), 1.76 (dd, J=13.7, 8.0 Hz, 1H), 1.62 (s, 3H), 1.54 (s, 3H), 1.51 (m, J=11.0, 5.5, 2.8 Hz, 1H), 1.42-1.37 (m, 2H), 1.35-1.30 (m, 2H), 1.27-1.22 (m, 1H), 1.17 (s, 3H), 1.12 (s, 6H). $^{13}$C NMR (126 MHz; CDCl$_3$): δ 154.07, 154.01, 132.5, 120.7, 93.04, 92.93, 74.6, 61.46, 61.26, 54.5, 54.1, 49.3, 46.2, 40.10, 39.90, 34.6, 34.1, 26.1, 25.22, 25.16, 24.2, 19.8, 17.8, 16.8. FTIR (thin film) ν$_{max}$: 2972, 2912, 2828, 1695, 1659, 1453, 1381, 1364, 1223, 1206, 1151, 1124, 1084, 1033, 973, 952, 849, 779, 689 cm$^{-1}$. HRMS-ESI (m/z): [M+H]$^+$ calculated for C$_{24}$H$_{40}$O$_4$, 393.2999. found, 393.3000.

(3S,3aR,7R,7aS)-6,7-Dimethoxy-3-(4-methoxy-4-methylpentyl)-3-methyl-7-(3-methylbut-2-en-1-yl)-2,3,3a,4,7,7a-hexahydro-2,7-methanobenzofuran (31)

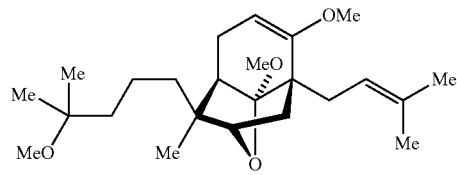

A DCM (63 mL) solution of 30 (4.91 g, 12.5 mmol, 1 equiv.) and 2,6-lutidine (3.0 mL, 37.5 mmol, 3 equiv.) was cooled to −78° C. in a 200-mL round-bottom flask, and trimethylsilyl trifluoromethanesulfonate (4.5 mL, 25.0 mmol, 2 equiv.) was added slowly. The resulting bright yellow solution was stirred at −78° C. for 45 min and subsequently quenched at −78° C. with saturated aqueous NaHCO$_3$. After warming the mixture to room temperature, it was extracted thrice with DCM. The organic extracts were combined, washed successively with 1 N HCl, H$_2$O, and brine, dried over Na$_2$SO$_4$, filtered, and concentrated in vacuo to a faint yellow oil. Flash column chromatography (300 mL SiO$_2$, 95:5 to 9:1 hexane:EtOAc) afforded 3.74 g (9.52 mmol, 77% yield) of 31 as a faint yellow oil. TLC R$_f$ 0.49 (8:2 hexane:EtOAc). $^1$H NMR (600 MHz; CDCl$_3$): δ 5.33 (t, J=7.1 Hz, 1H), 4.51 (dd, J=5.5, 2.1 Hz, 1H), 3.74 (d, J=4.6 Hz, 1H), 3.47 (s, 3H), 3.45 (s, 3H), 3.15 (s, 3H), 2.34 (dd, J=14.7, 6.9 Hz, 1H), 2.21 (dd, J=6.8, 1.8 Hz, 1H), 2.18 (dd, J=6.7, 2.3 Hz, 1H), 2.03 (m, 1H), 2.02-1.99 (m, 1H), 1.77 (dd, J=12.0, 4.6 Hz, 1H), 1.75 (d, J=12.0 Hz, 1H), 1.69 (s, 3H), 1.60 (s, 3H), 1.42-1.28 (m, 4H), 1.18 (td, J=12.6, 3.0 Hz, 1H), 1.12 (s, 3H), 1.11 (s, 3H), 1.11 (s, 3H), 1.03-0.95 (m, 1H). $^{13}$C NMR (126 MHz; CDCl$_3$): δ 158.6, 131.2, 123.5, 112.6, 90.5, 79.0, 74.6, 54.5, 51.4, 49.3, 46.5, 44.5, 41.9, 41.2, 39.3, 34.0, 32.8, 28.2, 26.4, 25.22, 25.14, 20.1, 18.4, 18.0. FTIR (thin film) $v_{max}$: 2968, 2839, 1670, 1451, 1374, 1363, 1208, 1166, 1078, 1006, 843, 805, 785 cm$^{-1}$. HRMS-ESI (m/z): [M+Na]$^+$ calculated for $C_{24}H_{40}O_4$, 415.2819. found, 415.2832.

(3S,3aS,7R,7aS)-6,7a-Dimethoxy-3-(4-methoxy-4-methylpentyl)-3-methyl-7-(3-methylbut-2-en-1-yl)-3,3a,7,7a-tetrahydro-2,7-methanobenzofuran-4(2H)-one (32)

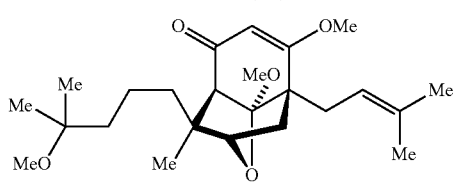

An EtOAc (30 mL, sparged for 30 min with $O_2$ directly prior to the reaction) slurry of cesium carbonate (12.76 g, 36.2 mmol, 4 equiv.), 31 (3.55 g, 9.04 mmol, 1 equiv.), and a nonane solution of tert-butyl hydroperoxide (5.5 M, 6.6 mL, 36 mmol, 4 equiv.) was cooled to −78° C. in a 3-neck 300-mL round-bottom flask with $O_2$ bubbling through the slurry via glass pipette. An EtOAc (25 mL) solution of bis(trifluoroacetoxy)iodobenzene (11.67 g, 27.1 mmol, 3 equiv.) was added dropwise over 30 min, following by an EtOAc (5 mL) rinse of the flask that contained the bis(trifluoroacetoxy)iodobenzene. The slurry was stirred at −78° C. for 2 h and subsequently slowly warmed to 0° C. over 2.25 h. The resulting pink slurry was subsequently quenched at 0° C. with saturated aqueous $Na_2S_2O_3$, $O_2$ bubbling was suspended, and the resulting yellow mixture was stirred vigorously at room temperature for 45 min. The mixture was then extracted thrice with EtOAc. The organic extracts were combined, washed with $H_2O$ and brine, dried over $Na_2SO_4$, filtered, and concentrated in vacuo to a yellow oil. Flash column chromatography (300 mL $SiO_2$, 7:3 hexane:EtOAc) afforded 1.07 g (2.63 mmol, 29% yield) of 32 as a viscous yellow syrup. TLC $R_f$ 0.18 (1:1 hexane:EtOAc). $^1$H NMR (600 MHz; CDCl$_3$): δ 5.33 (s, 1H), 5.29 (t, J=7.2 Hz, 1H), 3.90 (d, J=5.7 Hz, 1H), 3.70 (s, 3H), 3.46 (s, 3H), 3.12 (s, 3H), 2.67 (s, 1H), 2.41 (dd, J=15.0, 6.1 Hz, 1H), 2.34 (dd, J=14.9, 8.0 Hz, 1H), 2.00 (d, J=13.0 Hz, 1H), 1.93 (dd, J=13.1, 5.7 Hz, 1H), 1.69 (s, 3H), 1.62 (s, 3H), 1.39-1.29 (m, 4H), 1.26 (s, 3H), 1.23-1.11 (m, 2H), 1.09 (s, 6H). $^{13}$C NMR (126 MHz; CDCl$_3$): δ 198.0, 181.3, 133.0, 122.1, 115.4, 100.8, 80.7, 74.5, 56.7, 56.4, 52.2, 49.3, 48.6, 48.1, 40.9, 38.8, 34.6, 32.1, 28.0, 26.3, 25.3, 25.0, 18.2, 17.9.

(1S,5R,7S,8S)-8-(4-Bromo-4-methylpentyl)-7-hydroxy-4,9,9-trimethoxy-8-methyl-5-(3-methylbut-2-en-1-yl)bicyclo[3.3.1]non-3-en-2-one (33)

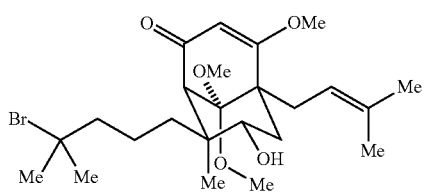

A DCM (3 mL) solution of 32 (160. mg, 0.316 mmol, 1 equiv.) and triethylamine (26.5 μL, 0.189 mmol, 0.6 equiv.) was cooled to −78° C. in a 10-mL recovery flask, and a DCM solution of bromodimethylborane (1.26 M, 1.5 mL, 1.89 mmol, 6 equiv.) was added slowly. After stirring the bright yellow solution at −78° C. for 40 min, a 1:1 mixture of NEt$_3$ and MeOH (3 mL) and saturated aqueous NaHCO$_3$ were added in succession at −78° C. The mixture was then allowed to warm to room temperature and thrice extracted with EtOAc. The organic extracts were combined, washed successively with saturated aqueous NH$_4$Cl, H$_2$O, and brine, dried over Na$_2$SO$_4$, filtered, and concentrated in vacuo to an off-white foam. Flash column chromatography (60 mL SiO$_2$, 7:3 hexane:EtOAc) afforded 73 mg (0.15 mmol, 47% yield) of 33 as a white flocculent solid. TLC $R_f$ 0.17 (7:3 hexane:EtOAc). $^1$H NMR (600 MHz; $C_6D_6$): δ 5.59 (t, J=7.0 Hz, 1H), 5.39 (s, 1H), 3.59 (dd, J=11.8, 5.2 Hz, 1H), 3.07 (s, 1H), 3.03 (s, 3H), 3.02 (s, 3H), 2.98 (s, 3H), 2.76 (dd, J=15.4, 7.6 Hz, 1H), 2.44 (dd, J=15.4, 6.2 Hz, 1H), 2.29-2.22 (m, 1H), 1.91 (t, J=12.4 Hz, 1H), 1.82 (dtd, J=15.4, 10.2, 5.1 Hz, 2H), 1.74-1.71 (m, 13H), 1.60 (s, 3H), 1.21 (s, 3H). $^{13}$C NMR (126 MHz; $C_6D_6$): δ 197.0, 178.3, 130.8, 123.2, 104.2, 103.5, 73.2, 68.5, 58.9, 55.7, 52.5, 50.8, 50.2, 48.7, 40.7, 40.0, 36.4, 35.3, 30.9, 26.1, 20.3, 18.6, 17.7. HRMS-ESI (m/z): [M+H]$^+$ calculated for $C_{24}H_{39}BrO_5$, 487.2054. found, 487.2050.

5-((2S,3R)-3-(Bromomethyl)-2-methyloxiran-2-yl)-2-methylpentan-2-ol (34)

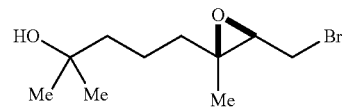

A 1:1 THF/H$_2$O (300 mL) slurry of mercury(II) acetate (41.04 g, 128.7 mmol, 1.5 equiv.) in a 1-L recovery flask was treated with 2 (20.00 g, 85.78 mmol, 1 equiv.), and the resulting yellow solution was stirred at room temperature for 10 min. The solution was then cooled to 0° C., and an aqueous solution of NaOH (3 M, 140 mL) was added. The resulting bright yellow slurry was stirred at 0° C. for 2 min, and a basic, aqueous solution of NaBH$_4$ (0.5 M NaBH$_4$ in 3 M NaOH aqueous solution, 140 mL) was added, immediately producing a gray slurry. After stirring an additional 15 min at 0° C., the slurry was diluted with H$_2$O and extracted thrice with EtOAc. The organic extracts were combined, washed thrice with H$_2$O and once with brine, dried over Na$_2$SO$_4$, filtered, and concentrated in vacuo, which was used without further purification. This procedure afforded 20.81 g (82.86 mmol, 97% yield) of 34 as a faint yellow oil. TLC $R_f$ 0.32 (1:1 hexane:EtOAc). $^1$H NMR (600 MHz; CDCl$_3$): δ 3.53 (dd, J=10.4, 5.9 Hz, 1H), 3.24 (dd, J=10.4, 7.8 Hz, 1H), 3.07 (dd, J=7.7, 6.0 Hz, 1H), 1.67-1.63 (m, 1H), 1.51-1.44 (m, 5H), 1.43-1.39 (m, 1H), 1.31-1.29 (s, 3H), 1.20 (s, 6H). $^{13}$C NMR (126 MHz; CDCl$_3$): δ 71.0, 63.3, 61.5, 43.6, 38.7, 29.9, 29.51, 29.42, 20.0, 16.2.

(5-((2S,3R)-3-(Bromomethyl)-2-methyloxiran-2-yl)-2-methylpentan-2-yl)oxy)triethylsilane (35

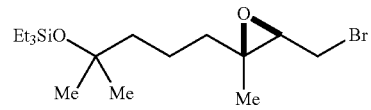

A DMF (210 mL) solution of 34 (20.81 g, 82.86 mmol, 1 equiv.) and imidazole (22.56 g, 331 mmol, 4 equiv.) in a 500-mL recovery flask was treated with chlorotriethylsilane (28 mL, 170 mmol, 2 equiv.). After stirring the resulting yellow solution at room temperature for 2.5 h, it was placed in a room temperature H₂O bath and slowly quenched at room temperature with saturated aqueous NaHCO₃. After vigorously stirring for 5 min, the mixture was extracted thrice with 9:1 hexane:EtOAc. The organic extracts were combined, washed thrice with H₂O and once with brine, dried over Na₂SO₄, filtered, and concentrated in vacuo to a colorless oil. Flash column chromatography (600 mL SiO₂, 98:2 hexane:EtOAc) afforded 26.22 g (71.75 mmol, 87% yield) of 35 as a colorless oil. TLC $R_f$ 0.83 (1:1 hexane:EtOAc). ¹H NMR (600 MHz; CDCl₃): δ 3.55 (dd, J=10.4, 5.9 Hz, 1H), 3.25 (dd, J=10.4, 7.9 Hz, 1H), 3.07 (dd, J=7.8, 5.9 Hz, 1H), 1.66 (ddd, J=13.2, 9.3, 5.3 Hz, 1H), 1.52-1.37 (m, 5H), 1.30 (s, 3H), 1.20 (s, 6H), 0.94 (t, J=7.9 Hz, 9H), 0.56 (q, J=7.9 Hz, 6H). ¹³C NMR (126 MHz; CDCl₃): δ 73.3, 63.4, 61.6, 45.0, 38.9, 30.11, 30.02, 20.2, 16.2, 7.3, 7.0.

(5-((2S,3S)-3-((2,6-Dimethoxy-1-(3-methylbut-2-en-1-yl)cyclohexa-2,5-dien-1-yl)methyl)-2-methyloxiran-2-yl)-2-methylpentan-2-yl)oxy)triethylsilane (36

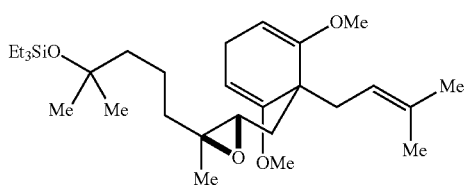

A THF (400 mL) solution of 11 (16.61 g, 79.73 mmol, 1 equiv.) was cooled to −78° C. in a 1-L recovery flask, and a cyclohexane solution of sec-butyllithium (1.43 M, 58 mL, 84 mmol, 1.05 equiv.) was added dropwise over 20 min. The resulting orange solution was allowed to slowly warm to −30° C. over 105 min, and the resulting red-brown solution was stirred at −30° C. for 15 min. The red-brown solution was then cooled to −78° C., and a THF (100 mL) solution of 31 (26.22 g, 71.75 mmol, 0.9 equiv.) was added, followed by two THF (50 mL) rinses of the flask that contained 35. The resulting pale yellow solution was allowed to slowly warm to −35° C. over 2 h and quenched at −35° C. with saturated aqueous NaHCO₃, which produced some effervescence. The mixture was warmed to room temperature and extracted thrice with EtOAc. The organic extracts were combined, washed with H₂O and brine, dried over Na₂SO₄, filtered, and concentrated in vacuo to a yellow oil. Flash column chromatography (800 mL SiO₂, 98:2 hexane:EtOAc) afforded 26.25 g (53.27 mmol, 74% yield) of 36 as a faint yellow oil. TLC $R_f$ 0.11 (95:5 hexane:EtOAc). ¹H NMR (600 MHz; CDCl₃): δ 4.90 (t, J=7.3 Hz, 1H), 4.77 (t, J=3.5 Hz, 1H), 4.72 (t, J=3.6 Hz, 1H), 3.52 (s, 3H), 3.47 (s, 3H), 2.76 (t, J=3.6 Hz, 2H), 2.62 (dd, J=8.0, 4.0 Hz, 1H), 2.31 (qd, J=10.8, 7.6 Hz, 2H), 2.03 (dd, J=13.7, 3.9 Hz, 1H), 1.77 (dd, J=13.7, 7.9 Hz, 1H), 1.63 (s, 3H), 1.55 (s, 3H), 1.53-1.48 (m, 1H), 1.41-1.31 (m, 4H), 1.28-1.21 (m, 1H), 1.18 (s, 3H), 1.17 (s, 6H), 0.94 (t, J=7.9 Hz, 9H), 0.55 (q, J=7.9 Hz, 6H). ¹³C NMR (126 MHz; CDCl₃): δ 154.09, 154.04, 132.5, 120.7, 93.02, 92.90, 73.5, 61.45, 61.32, 54.5, 54.1, 46.2, 45.4, 39.9, 34.6, 34.2, 30.2, 30.0, 26.1, 24.3, 20.2, 17.9, 16.8, 7.3, 7.0.

(5-((3S,3aR,7R,7aS)-6,7a-Dimethoxy-3-methyl-7-(3-methylbut-2-en-1-yl)-2,3,3a,4,7,7a-hexahydro-2,7-methanobenzofuran-3-yl)-2-methylpentan-2-yl)oxy)triethylsilane (37

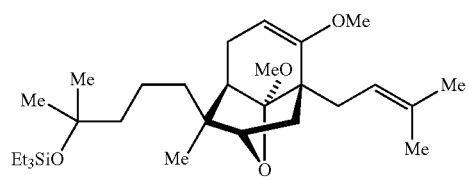

A DCM (30 mL) solution of 36 (2.73 g, 5.54 mmol, 1 equiv.) was cooled to −78° C. in a 100-mL recovery flask, and 2,6-lutidine (1.3 mL, 17 mmol, 3 equiv.) and trimethylsilyl trifluoromethanesulfonate (2.46 g, 11.1 mmol, 2 equiv.) were added sequentially. The resulting yellow solution was stirred at −78° C. for 45 min and subsequently quenched at −78° C. with saturated aqueous NaHCO₃. After warming the mixture to room temperature, it was extracted thrice with EtOAc. The organic extracts were combined, washed sequentially with 2 N HCl, H₂O, saturated aqueous NaHCO₃, and brine, dried over Na₂SO₄, filtered, and concentrated in vacuo to a colorless oil. Flash column chromatography (200 mL SiO₂, 99:1 to 98:2 hexane:EtOAc) afforded 2.15 g (4.35 mmol, 79% yield) of 37 as a faint yellow oil. TLC $R_f$ 0.50 (9:1 hexane:EtOAc). ¹H NMR (600 MHz; CDCl₃): δ 5.33 (t, J=7.1 Hz, 1H), 4.51 (dd, J=5.5, 2.0 Hz, 1H), 3.72 (t, J=2.7 Hz, 1H), 3.47 (s, 3H), 3.45 (s, 3H), 2.34 (dd, J=14.7, 6.8 Hz, 1H), 2.21-2.16 (m, 1H), 2.21-2.16 (m, 1H), 2.04-2.00 (m, 1H), 2.04-2.00 (m, 1H), 1.76 (d, J=2.7 Hz, 1H), 1.69 (s, 3H), 1.61 (s, 3H), 1.37 (m, 1H), 1.35-1.34 (m, 1H), 1.34-1.31 (m, 1H), 1.31-1.29 (m, 1H), 1.19 (m, 1H), 1.16 (s, 3H), 1.16 (s, 3H), 1.12 (s, 3H), 1.08-1.02 (m, 1H), 0.93 (t, J=7.9 Hz, 9H), 0.54 (q, J=7.9 Hz, 6H). ¹³C NMR (126 MHz; CDCl₃): δ 158.6, 131.1, 123.6, 112.6, 90.5, 79.0, 73.4, 54.5, 51.4, 46.49, 46.34, 44.5, 41.9, 39.3, 34.0, 32.7, 30.2, 30.0, 28.2, 26.3, 20.1, 18.9, 17.9, 7.3, 7.0. FTIR (thin film) $v_{max}$: 2960, 2876, 2839, 1669, 1456, 1375, 1240, 1166, 1007, 853, 803, 743, 722 cm⁻¹. HRMS-ESI (m/z): [M+H]⁺ calculated for C₂₉H₅₂O₄Si, 493.3708. found, 493.3716.

(3S,3aS,7R,7aS)-6,7a-Dimethoxy-3-methyl-3-(4-methyl-4-((triethylsilyl)oxy)pentyl)-7-(3-methylbut-2-en-1-yl)-3,3a,7,7a-tetrahydro-2,7-methanobenzofuran-4(2H)-one (38)

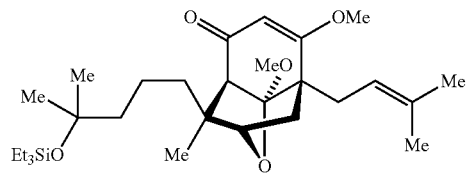

An EtOAc (12 mL, sparged for 30 min with O₂ directly prior to the reaction) slurry of bis(trifluoroacetoxy)iodobenzene (2.63 g, 6.11 mmol, 3 equiv.), cesium carbonate (2.88 g, 8.15 mmol, 4 equiv.), and 37 (1.00 g, 2.04 mmol, 1 equiv.) was cooled to −78° C. in a 2-neck 50-mL round-bottom flask with O₂ bubbling through the slurry via pipette. An EtOAc (2 mL) solution of a nonane solution of tert-butyl hydroperoxide (0.74 mmol, 4.1 mmol, 2 equiv.) was added slowly. The resulting yellow slurry was allowed to slowly warm to 0° C. over 2.25 h and was subsequently quenched at 0° C. with saturated aqueous Na₂S₂O₃. After stirring the mixture vigorously for 45 min, it was extracted thrice with EtOAc. The organic extracts were combined and washed with H₂O and brine. The aqueous extracts were combined and washed with EtOAc. The organic extracts were then combined, dried over Na₂SO₄, filtered, and concentrated in vacuo to a yellow oil. Flash column chromatography (150 mL SiO₂, 9:1 to 8:2 hexane:EtOAc) afforded 453 mg (0.894 mmol, 44% yield) of 38 as a viscous yellow syrup. TLC R$_f$ 0.50 (7:3 hexane:EtOAc). ¹H NMR (500 MHz; CDCl₃): δ 5.28 (s, 1H), 5.24 (t, J=7.1 Hz, 1H), 3.82 (d, J=5.7 Hz, 1H), 3.64 (s, 3H), 3.40 (s, 3H), 2.61 (s, 1H), 2.36 (dd, J=14.8, 6.2 Hz, 1H), 2.28 (dd, J=14.8, 8.1 Hz, 1H), 1.95 (d, J=13.0 Hz, 1H), 1.86 (dd, J=13.0, 5.7 Hz, 1H), 1.63 (s, 3H), 1.56 (s, 3H), 1.26 (m, 1H), 1.24 (m, 1H), 1.21 (m, 1H), 1.20 (m, 1H), 1.19 (s, 3H), 1.09 (s, 6H), 1.04-0.96 (m, 1H), 0.85 (t, J=7.9 Hz, 9H), 0.47 (q, J=7.9 Hz, 6H). ¹³C NMR (126 MHz; CDCl₃): δ 197.8, 181.1, 132.6, 122.0, 115.2, 100.6, 80.6, 73.1, 56.7, 56.2, 52.0, 48.4, 48.0, 45.7, 38.7, 34.5, 32.0, 30.1, 29.7, 27.8, 26.1, 18.5, 17.8, 7.1, 6.8. FTIR (thin film) ν$_{max}$: 2966, 2913, 2875, 1653, 1606, 1457, 1373, 1229, 1172, 1006, 725 cm⁻¹. HRMS-ESI (m/z): [M+Na]⁺ calculated for C₂₉H₅₀O₅Si, 529.3320. found, 529.3304.

(1S,5R,7S,8S,9S)-7,9-Dihydroxy-4,9-dimethoxy-8-methyl-8-(4-methyl-4-((triethylsilyl)oxy)pentyl)-5-(3-methylbut-2-en-1-yl)bicyclo[3.3.1]non-3-en-2-one (39)

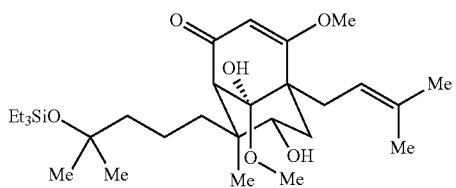

A DCM (20 mL) solution of 38 (794 mg, 1.57 mmol, 1 equiv.) and triethylamine (131 μL, 0.940 mmol, 0.6 equiv.) was cooled to −95° C. in a 100-mL recovery flask, and a DCM solution of bromodimethylborane (1.59 M, 5.9 mL, 9.4 mmol, 6 equiv.) was added slowly over 5 min. The resulting bright yellow solution was stirred at −95° C.±3° C. for 10 min, whereupon it was quenched through the sequential addition of NEt₃ (6 mL) and saturated aqueous NaHCO₃ at −95° C. The mixture was warmed to room temperature and extracted thrice with EtOAc. The organic extracts were combined, washed successively with 2 N HCl, H₂O, saturated aqueous NaHCO₃, and brine, dried over Na₂SO₄, filtered, and concentrated in vacuo to a yellow foam. Flash column chromatography (150 mL SiO₂, 8:2 to 7:3 hexane:EtOAc) afforded 471 mg (0.897 mmol, 57% yield) of 39 as a white flocculent solid. TLC R$_f$ 0.30 (7:3 hexane:EtOAc). ¹H NMR (600 MHz; CDCl₃): δ 5.46 (s, 1H), 5.26 (d, J=10.3 Hz, 1H), 3.74 (s, 3H), 3.61 (dd, J=11.8, 5.3 Hz, 1H), 3.55 (s, 1H), 3.25 (s, 1H), 2.87-2.82 (m, 2H), 2.25 (d, J=14.2 Hz, 1H), 1.95 (t, J=12.4 Hz, 1H), 1.73 (s, 3H), 1.70-1.65 (m, 4H), 1.43 (td, J=13.0, 4.2 Hz, 1H), 1.39-1.35 (m, 1H), 1.32-1.27 (m, 3H), 1.21 (s, 3H), 1.20 (s, 3H), 1.09 (s, 3H), 0.93 (t, J=7.9 Hz, 9H), 0.55 (q, J=7.6 Hz, 6H). ¹³C NMR (126 MHz; CDCl₃): δ 198.2, 176.0, 137.4, 122.1, 104.1, 100.6, 73.8, 73.3, 57.6, 56.5, 51.1, 48.5, 45.9, 40.9, 39.4, 37.0, 30.8, 30.0, 29.4, 26.2, 18.0, 17.0, 7.3, 7.0. HRMS-ESI (m/z): [M+Na]⁺ calculated for C₂₉H₅₂O₆Si, 547.3425. found, 547.3404.

O-((1S,2S,3S,5R)-6-Methoxy-2-methyl-2-(4-methyl-4-((triethylsilyl)oxy)pentyl)-5-(3-methylbut-2-en-1-yl)-8,9-dioxobicyclo[3.3.1]non-6-en-3-yl) O-phenyl carbonothioate (40)

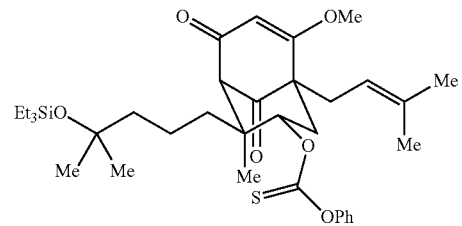

A THF (2 mL) solution of 39 (71 mg, 0.14 mmol, 1 equiv.) was cooled to −78° C. in a 10-mL recovery flask, and a hexane solution of n-butyllithium (2.02 M, 141 μL, 0.28 mmol, 2.1 equiv.) was added dropwise over 5 min. After stirring the solution at −78° C. for 20 min, O-phenyl chlorothionoformate (39 μL, 0.28 mmol, 2.1 equiv.) was added in one portion. The resulting yellow solution was allowed to slowly warm to room temperature over 90 min and was subsequently quenched at room temperature with saturated aqueous NaHCO₃. The mixture was extracted thrice with EtOAc. The organic extracts were combined, washed with H₂O and brine, dried over Na₂SO₄, filtered, and concentrated in vacuo to an orange oil. Flash column chromatography (50 mL SiO₂, 95:5 hexane:EtOAc) afforded 51 mg (81 μmol, 60% yield) of 40 as a colorless oil. TLC R$_f$ 0.58 (7:3 hexane:EtOAc). ¹H NMR (600 MHz; CDCl₃): δ 7.41 (dd, J=8.4, 7.6 Hz, 2H), 7.30 (t, J=7.4 Hz, 1H), 7.08-7.06 (m, 2H), 5.74 (s, 1H), 5.53 (dd, J=11.5, 5.4 Hz, 1H), 4.99 (t, J=7.0 Hz, 1H), 3.80 (s, 3H), 3.25 (s, 1H), 2.56-2.53 (m, 2H), 2.44 (dd, J=14.6, 7.4 Hz, 1H), 1.86 (dd, J=12.9, 11.7 Hz, 1H), 1.69-1.65 (m, 7H), 1.58-1.56 (m, 1H), 1.47-1.41 (m, 2H), 1.37 (m, 2H), 1.23 (s, 3H), 1.23 (s, 3H), 1.03 (s, 3H), 0.95 (t, J=7.9 Hz, 9H), 0.58 (q, J=7.8 Hz, 6H). ¹³C NMR (126 MHz; CDCl₃): δ 204.2, 194.6, 192.2, 177.0, 153.4, 134.9, 129.8, 126.9, 122.0, 118.6, 106.3, 84.6, 73.5, 69.8, 57.3, 55.7, 45.65, 45.58, 38.1, 34.3, 30.5, 29.7, 29.3, 26.1, 18.2, 17.8, 17.5, 7.4, 7.0. HRMS-ESI (m/z): [M+Na]⁺ calculated for C₃₅H₅₂O₆SSi, 651.3152. found, 651.3130.

(1S,5R,7S,8S)-7-Hydroxy-4-methoxy-8-methyl-8-(4-methyl-4-((triethylsilyl)oxy)pentyl)-5-(3-methylbut-2-en-1-yl)bicyclo[3.3.1]non-3-ene-2,9-dione (41)

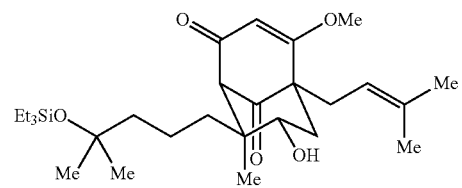

A THF (2 mL) solution of 40 (144 mg, 0.269 mmol, 1 equiv.) was cooled to −78° C. in a 25-mL recovery flask, and a freshly prepared THF solution of lithium tetramethylpiperidide (0.50 M, 2.2 mL, 1.1 mmol, 4 equiv.) was added. The resulting orange solution was stirred at −78° C. for 15 min and then stirred at 0° C. for 40 min. The reaction was then quenched with saturated aqueous NaHCO$_3$ at 0° C. The mixture was warmed to room temperature and extracted thrice with EtOAc. The organic extracts were combined, washed with H$_2$O and brine, dried over Na$_2$SO$_4$, filtered, and concentrated in vacuo to an orange oil. Flash column chromatography (75 mL SiO$_2$, 7:3 hexane:EtOAc) afforded 104.3 mg (0.2117 mmol, 79% yield) of 41 as a faint yellow oil. TLC R$_f$ 0.56 (1:1 hexane:EtOAc). $^1$H NMR (600 MHz; CDCl$_3$): δ 5.63 (s, 1H), 4.95 (t, J=7.0 Hz, 1H), 3.78 (d, J=7.8 Hz, 1H), 3.73 (s, 3H), 3.15 (s, 1H), 2.47 (dd, J=14.5, 6.4 Hz, 1H), 2.37 (dd, J=14.5, 7.6 Hz, 1H), 2.09 (dd, J=13.4, 5.4 Hz, 1H), 1.88 (s, 1H), 1.73 (dd, J=13.3, 11.6 Hz, 1H), 1.65 (m, 7H), 1.52 (td, J=12.6, 3.5 Hz, 1H), 1.39 (td, J=12.5, 4.1 Hz, 1H), 1.34-1.27 (m, 2H), 1.23 (m, 4H), 1.18 (s, 3H), 0.92 (t, J=7.9 Hz, 9H), 0.86 (s, 3H), 0.54 (q, J=7.8 Hz, 6H). $^{13}$C NMR (126 MHz; CDCl$_3$): δ 205.4, 193.1, 177.4, 134.4, 119.0, 105.9, 73.6, 72.0, 69.2, 57.0, 56.0, 46.2, 45.6, 39.4, 38.4, 30.6, 29.50, 29.48, 26.1, 18.1, 17.9, 15.7, 7.3, 6.9. HRMS-ESI (m/z): [M+Na]$^+$ calculated for C$_{28}$H$_{48}$O$_5$Si, 515.3163. found, 515.3170.

O-((1S,2S,3S,5R)-6-Methoxy-2-methyl-2-(4-methyl-4-((triethylsilyl)oxy)pentyl)-5-(3-methylbut-2-en-1-yl)-8,9-dioxobicyclo[3.3.1]non-6-en-3-yl) O-(perfluorophenyl) carbonothioate (42)

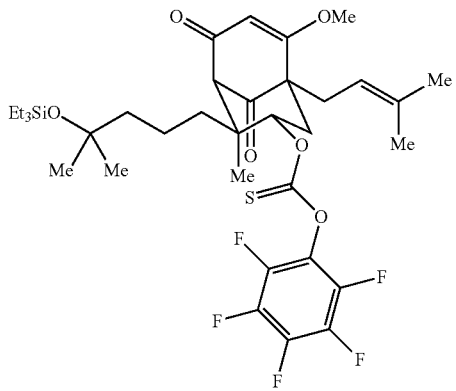

A DCM (2.1 mL) solution of 41 (104.3 mg, 0.2117 mmol, 1 equiv.), 4-(dimethylamino)pyridine (25.9 mg, 0.212 mmol, 1 equiv.), and pyridine (171 μL, 2.12 mmol, 10 equiv.) in a 10-mL recovery flask was treated with O-pentafluorophenyl chlorothionoformate (102 μL, 0.635 mmol, 3 equiv.). The resulting red-orange solution was stirred at room temperature for 1 h, whereupon the solution turned black. The solution was quenched with saturated aqueous NaHCO$_3$ and extracted thrice with EtOAc. The organic extracts were combined, washed with H$_2$O and brine, dried over Na$_2$SO$_4$, filtered, and concentrated in vacuo to a brown-black oil. Flash column chromatography (75 mL SiO$_2$, 95:5 hexane:EtOAc) afforded 84.4 mg (0.117 mmol, 55% yield) of 42 as a yellow oil. TLC R$_f$ 0.69 (7:3 hexane:EtOAc). $^1$H NMR (600 MHz; CDCl$_3$): δ 5.74 (s, 1H), 5.45 (dd, J=11.6, 5.4 Hz, 1H), 4.98 (t, J=6.9 Hz, 1H), 3.80 (s, 3H), 3.27 (s, 1H), 2.55 (dd, J=14.5, 6.3 Hz, 1H), 2.50 (dd, J=13.0, 5.4 Hz, 1H), 2.45 (dd, J=14.5, 7.5 Hz, 1H), 1.92 (t, J=12.3 Hz, 1H), 1.69-1.68 (m, 7H), 1.42-1.29 (m, 5H), 1.21 (s, 6H), 1.07 (s, 3H), 0.94 (t, J=7.9 Hz, 9H), 0.57 (q, J=8.0 Hz, 6H). $^{13}$C NMR (126 MHz; CDCl$_3$): δ 203.7, 191.8, 176.8, 135.1, 118.4, 106.3, 87.2, 73.5, 69.6, 57.4, 55.6, 45.64, 45.45, 38.0, 34.0, 30.4, 29.7, 29.3, 26.1, 18.2, 17.7, 17.4, 7.3, 7.0. $^{19}$F NMR (282 MHz; CDCl$_3$): δ −152.71 (d, J=18.1 Hz, 2F), −156.71 (t, J=21.9 Hz, 1F), −162.21 (t, J=19.8 Hz, 2F). HRMS-ESI (m/z): [M+Na]$^+$ calculated for C$_{34}$H$_{47}$F$_5$O$_6$SSi, 741.2675. found, 741.2667.

(1S,5R,7S,8R)-7-Allyl-4-methoxy-8-methyl-8-(4-methyl-4-((triethylsilyl)oxy)pentyl)-5-(3-methylbut-2-en-1-yl)bicyclo[3.3.1]non-3-ene-2,9-dione (43)

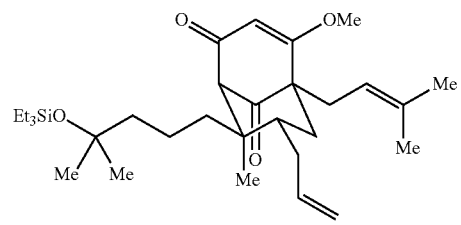

Method A.

A PhH (0.33 mL) and allyltributylstannane (0.66 mL) solution of 40 (24.5 mg, 39.0 μmol, 1 equiv.) in a 10-mL test tube open to air was treated with a hexane solution of triethylborane (1.0 M, 0.12 mL, 117 mmol, 3 equiv.). After stirring the colorless solution at room temperature for 20 min, it was diluted with MeCN, and the excess allyltributylstannane was separated. The MeCN fraction was concentrated in vacuo to a colorless oil. Flash column chromatography (30 mL SiO$_2$, 95:5 to 9:1 hexane:EtOAc) afforded 6.9 mg (13 μmol, 34% yield) of 43 as a colorless residue. TLC R$_f$ 0.23 (9:1 hexane:EtOAc). $^1$H-NMR (600 MHz; CDCl$_3$): δ 5.70 (s, 1H), 5.68-5.61 (m, 1H), 5.01 (d, J=5.5 Hz, 1H), 4.99 (d, J=12.1 Hz, 1H), 4.96 (t, J=7.0 Hz, 1H), 3.73 (s, 3H), 3.13 (s, 1H), 2.46 (dd, J=14.6, 5.6 Hz, 1H), 2.36 (dd, J=14.6, 7.9 Hz, 1H), 2.34-2.31 (m, 1H), 1.97 (dd, J=13.9, 4.6 Hz, 1H), 1.77-1.72 (m, 2H), 1.73-1.70 (m, 1H), 1.64 (s, 3H), 1.64 (m, 1H), 1.63 (s, 3H), 1.46-1.42 (m, 1H), 1.42-1.39 (m, 2H), 1.41-1.38 (m, 1H), 1.34-1.31 (m, 1H), 1.25-1.24 (m, 1H), 1.23 (m, 1H), 1.22 (s, 3H), 1.21 (s, 3H), 0.94 (t, J=7.9 Hz, 9H), 0.81 (s, 3H), 0.57 (q, J=7.9 Hz, 6H). 1C NMR (126 MHz; CDCl$_3$): δ 207.2, 193.9, 177.5, 137.2, 133.9, 119.5, 116.8, 106.5, 73.7, 70.8, 56.97, 56.94, 46.2, 45.7, 39.8, 39.28, 39.15, 33.9, 30.6, 29.8, 29.6, 26.1, 18.11, 18.05, 17.89, 7.4, 7.0. FTIR (thin film) ν$_{max}$: 2961, 2917, 2876, 1733, 1657, 1599, 1460, 1365, 1227, 1171, 1042, 1017, 743, 724 cm$^{-1}$. HRMS-ESI (m/z): [M+Na]$^+$ calculated for C$_{31}$H$_{52}$O$_4$Si, 539.3527. found, 539.3521.

Method B.

A PhH (0.33 mL) and allyltributylstannane (0.66 mL) solution of 42 (15.9 mg, 22.1 μmol, 1 equiv.) in a 10-mL test tube open to air was treated with a hexane solution of triethylborane (1.0 M, 22 μL, 22.1 μmol, 1 equiv.). After stirring the yellow solution at room temperature for 40 min, three additional portions of triethylborane (1.0 M, 22 μL, 22.1 μmol, 1 equiv. each) were added at 40-minute intervals. After the final addition, the solution was stirred at room temperature for an additional 30 min and subsequently purified directed via flash column chromatography (30 mL SiO$_2$, 95:5 to 9:1 hexane:EtOAc) to afford 8.4 mg (16 µmol, 73% yield) of 43 as a colorless residue.

(1S,5R,7S,8R)-4-Methoxy-8-methyl-8-(4-methyl-4-((triethylsilyl)oxy)pentyl)-5,7-bis(3-methylbut-2-en-1-yl)bicyclo[3.3.1]non-3-ene-2,9-dione (44)

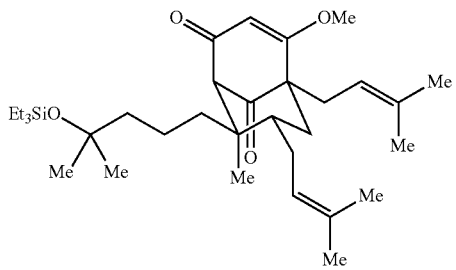

A DCM (0.5 mL) and 2-methyl-2-butene (0.5 mL) solution of 43 (18.4 mg, 35.6 µmol, 1 equiv.) and Hoveyda-Grubbs 2$^{nd}$ generation catalyst (3.3 mg, 5.3 µmol, 0.15 equiv.) in a sealed 10-mL test tube was stirred at 40° C. for 2 h. The olive-black solution was subsequently cooled to room temperature and concentrated in vacuo. Flash column chromatography (50 mL SiO$_2$, 95:5 hexane:EtOAc) afforded 16.7 mg (30.6 µmol, 86% yield) of 44 as a colorless oil. TLC R$_f$ 0.49 (9:1 hexane:EtOAc). $^1$H NMR (600 MHz; CDCl$_3$): δ 5.69 (s, 1H), 4.98-4.94 (m, 2H), 3.73 (s, 3H), 3.12 (s, 1H), 2.45 (dd, J=14.2, 6.0 Hz, 1H), 2.36 (dd, J=14.6, 7.7 Hz, 1H), 2.14-2.11 (m, 1H), 1.93 (dd, J=14.0, 4.1 Hz, 1H), 1.69 (s, 3H), 1.67-1.65 (m, 4H), 1.63 (s, 3H), 1.58-1.54 (m, 4H), 1.50-1.45 (m, 2H), 1.44-1.38 (m, 3H), 1.34-1.30 (m, 2H), 1.22 (s, 3H), 1.21 (s, 3H), 0.94 (t, J=7.9 Hz, 9H), 0.82 (s, 3H), 0.57 (q, J=7.8 Hz, 6H). $^{13}$C NMR (126 MHz; CDCl$_3$): δ 207.4, 194.0, 177.5, 133.8, 133.3, 122.9, 119.7, 106.5, 73.7, 70.9, 57.1, 56.9, 46.4, 45.7, 40.9, 39.5, 39.2, 30.6, 29.9, 29.6, 27.9, 26.10, 26.05, 18.16, 18.13, 18.06, 17.92, 7.4, 7.0. HRMS-ESI (m/z): [M+Na]$^+$ calculated for C$_{33}$H$_{56}$O$_4$Si, 567.3840. found, 567.3831.

(1R,5R,7S,8R)-4-Methoxy-8-methyl-8-(4-methyl-4-((triethylsilyl)oxy)pentyl)-5,7-bis(3-methylbut-2-en-1-yl)-3-(trimethylsilyl)bicyclo[3.3.1]non-3-ene-2,9-dione (45)

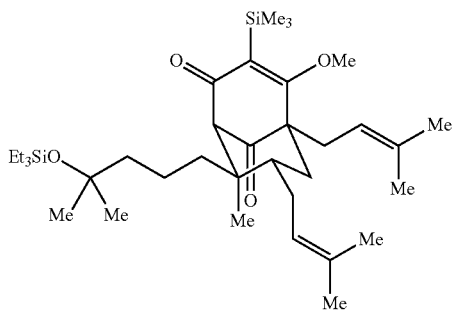

A THF (1 mL) solution of 44 (22.9 mg, 42.0 µmol, 1 equiv.) was cooled to −78° C. in a 10-mL test tube, and chlorotrimethylsilane (53 µL, 0.42 mmol, 10 equiv.) and a freshly prepared THF solution of lithium tetramethylpiperidide (0.50 M, 420 µL, 0.21 mmol, 5 equiv.) were sequentially added. The golden yellow solution was slowly warmed to 0° C. over 1 h and quenched at 0° C. with saturated aqueous NaHCO$_3$. The mixture was warmed to room temperature and extracted thrice with EtOAc. The organic extracts were combined, washed with H$_2$O and brine, dried over Na$_2$SO$_4$, filtered, and concentrated in vacuo to a yellow oil. Flash column chromatography (20 mL SiO$_2$, 98:2 hexane:EtOAc) afforded 23.4 mg (37.9 µmol, 90% yield) of 45 as a colorless oil. TLC R$_f$ 0.40 (95:5 hexane:EtOAc). $^1$H NMR (600 MHz; CDCl$_3$): δ 5.02-4.97 (m, 2H), 3.83 (s, 3H), 3.11 (s, 1H), 2.51 (dd, J=14.4, 6.3 Hz, 1H), 2.37 (dd, J=14.5, 7.5 Hz, 1H), 2.15-2.11 (m, 1H), 1.99 (dd, J=14.0, 3.7 Hz, 1H), 1.69 (s, 3H), 1.68-1.63 (m, 9H), 1.57 (s, 3H), 1.48 (td, J=12.7, 3.9 Hz, 1H), 1.46-1.37 (m, 2H), 1.30 (td, J=12.2, 4.1 Hz, 1H), 1.26-1.24 (m, 1H), 1.21 (s, 3H), 1.21 (s, 3H), 1.14 (td, J=12.6, 4.2 Hz, 1H), 0.94 (t, J=7.9 Hz, 9H), 0.80 (s, 3H), 0.57 (q, J=8.1 Hz, 6H), 0.23 (s, 9H). $^{13}$C NMR (126 MHz; CDCl$_3$): δ 207.9, 198.6, 185.7, 133.70, 133.59, 127.7, 122.8, 120.0, 73.7, 72.6, 64.1, 59.7, 46.7, 45.7, 41.8, 39.29, 39.27, 30.6, 30.0, 29.7, 27.6, 26.02, 25.97, 18.21, 18.14, 17.88, 17.83, 7.4, 7.0, 0.8. HRMS-ESI (m/z): [M+H]$^+$ calculated for C$_{36}$H$_{64}$O$_4$Si$_2$, 617.4416. found, 617.4395.

(1S,5R,7S,8R)-1-Isobutyryl-4-methoxy-8-methyl-8-(4-methyl-4-((triethylsilyl)oxy)pentyl)-5,7-bis(3-methylbut-2-en-1-yl)-3-(trimethylsilyl)bicyclo[3.3.1]non-3-ene-2,9-dione (46)

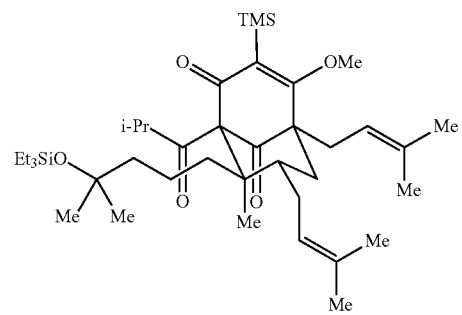

A THF (0.5 mL) solution of 45 (7.0 mg, 11 µmol, 1 equiv.) was cooled to −78° C. in a 10-mL test tube, and a freshly prepared THF solution of lithium tetramethylpiperidide (0.50 M, 113 µL, 57 µmol, 5 equiv.) was added dropwise. The resulting yellow-orange solution was stirred at −78° C. for 10 min and at 0° C. for 10 min. The solution was then cooled to −78° C., and isobutyryl chloride (6.0 µL, 57 µmol, 5 equiv.) was added. The resulting yellow solution was stirred at −78° C. for 50 min, was slowly warmed to 0° C. over 50 min, and subsequently quenched with saturated aqueous NaHCO$_3$. The mixture was warmed to room temperature and extracted thrice with EtOAc. The organic extracts were combined, washed with H$_2$O and brine, dried over Na$_2$SO$_4$, filtered, and concentrated in vacuo to a yellow residue. Preparatory thin-layer chromatography (3×98:2 hexane:EtOAc) afforded 1.8 mg (2.6 µmol, 24% yield) of 46 as a colorless residue along with 1.7 mg (2.8 µmol, 25% recovery) of 45. TLC R$_f$ 0.47 (95:5 hexane:EtOAc). $^1$H-NMR (600 MHz; CDCl$_3$): δ 5.00-4.96 (m, 2H), 3.90 (s, 3H), 2.55 (dd, J=14.6, 6.4 Hz, 1H), 2.41 (dd, J=14.5, 7.7 Hz, 1H), 2.08 (d, J=15.0 Hz, 1H), 1.97 (septet, J=6.5 Hz, 1H), 1.92-1.85 (m, 2H), 1.79-1.72 (m, 1H), 1.68 (s, 3H), 1.66 (s, 3H), 1.57-1.56 (m, 3H), 1.55-1.53 (m, 3H), 1.50-1.42 (m, 2H), 1.39-1.31 (m, 3H), 1.30-1.24 (m, 2H), 1.17 (s, 3H), 1.17 (s, 3H), 1.13 (d, J=6.5 Hz, 3H), 1.02 (d, J=6.5 Hz, 3H), 0.98 (s, 3H), 0.92 (t, J=7.9 Hz, 9H), 0.54 (q, J=7.9 Hz, 6H), 0.26 (s, 9H). HRMS-ESI (m/z): [M+Na]+ calculated for $C_{40}H_{70}O_5Si_2$, 709.4654. found, 709.4626.

(1S,5R,7S,8S)-4-Methoxy-7-(methoxymethoxy)-8-methyl-5-(3-methylbut-2-en-1-yl)-8-(4-methylpent-3-en-1-yl)bicyclo[3.3.1]non-3-ene-2,9-dione (50)

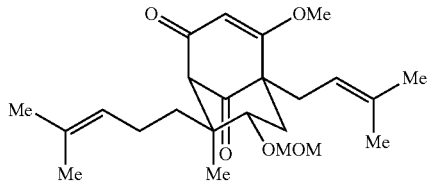

A flame-dried round-bottom flask under argon atmosphere is charged with 458 mg (1.22 mmol, 1 equiv.) of starting material 20, 1.3 mL 1,2-dimethoxyethane, and 953 µL (5.34 mmol, 5.5 equiv.) diisopropylethylamine. With stirring, 376 µL (4.95 mmol, 5.1 equiv.) methoxymethyl chloride is added dropwise. The stirring reaction is heated to 60° C. for four hours before being allowed to cool to room temperature. Once the reaction has cooled, it is transferred to a separatory funnel in 50 mL hexane and the organic layer is washed sequentially with 10% aqueous hydrochloric acid, water, and brine. The organic solution is then dried with $MgSO_4$ and concentrated in vacuo to give a clear to yellow oil. The crude product is purified by silica gel chromatography ($R_f$=0.25 in 4:1 hexane:ethyl acetate) to give 380 mg (97% yield) of 50 as a clear oil. $^1$H NMR (500 MHz, $CDCl_3$) δ ppm 5.67 (s, 1H), 5.07 (tt, J=7.1, 1.4 Hz, 1H), 4.97 (tt, J=6.2, 1.3 Hz, 1H), 4.58 (dd, J=36.8, 7.0 Hz, 2H), 3.75 (s, 3H), 3.60 (dd, J=11.2, 5.5 Hz, 1H), 3.32 (s, 3H), 3.18 (s, 3H), 2.48 (dd, J=14.4, 6.2 Hz, 1H), 2.29-2.42 (m, 2H), 2.21 (dd, J=13.4, 5.4 Hz, 3H), 1.87 (ddt, J=18.3, 12.1, 5.5, 5.5 Hz, 3H), 1.78 (dd, J=13.3, 11.4 Hz, 3H), 1.65 (s, 12H), 1.57 (ddd, J=12.9, 4.6 Hz, 1H), 1.27 (ddd, J=12.9, 4.5 Hz, 1H), 0.92 (s, 3H). $^{13}$C NMR (126 MHz, $CDCl_3$) δ ppm 205.2, 193.0, 177.3, 134.3, 131.8, 124.3, 119.1, 106.0, 97.1, 77.4, 76.9, 69.2, 57.1, 55.9, 55.8, 46.3, 37.6, 37.4, 29.6, 26.0, 25.9, 21.6, 18.1, 17.8, 16.5. HRMS-ESI (m/z): [M+H]+ calculated for $C_{24}H_{36}O_5$, 405.2636. found 405.2637.

(1R,5R,7S,8S)-4-Methoxy-7-(methoxymethoxy)-8-methyl-5-(3-methylbut-2-en-1-yl)-8-(4-methylpent-3-en-1-yl)-3-(trimethylsilyl)bicyclo[3.3.1]non-3-ene-2,9-dione (51)

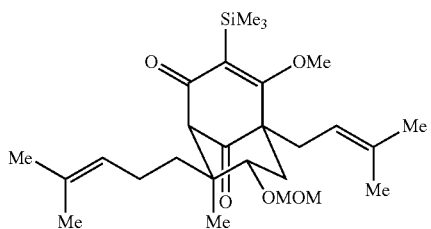

A flame-dried round-bottom flask with magnetic stir bar was charged with 380 mg (0.939 mmol, 1 equiv.) starting material 50 followed by 9.4 mL THF and 596 µL (4.70 mmol, 5 equiv.) of chlorotrimethylsilane with stirring. The solution was cooled in an acetone/dry ice bath for 10 minutes prior to the addition of 9.4 mL of a 0.5M solution of lithium tetramethylpiperidide in THF (4.7 mmol, 5 equiv.). The mixture was stirred at −78° C. for 10 minutes before placing the reaction in a water/ice bath for an additional 10 minutes. The reaction was quenched by the addition of 2 mL of saturated aqueous sodium bicarbonate and transferred to a separatory funnel by the addition of 50 mL hexane. The organic layer was then washed with saturated aqueous sodium bicarbonate, 10% aqueous hydrochloric acid, water, and saturated brine solution. The organic layer was then dried with $MgSO_4$ and concentrated in vacuo to give a yellow oil. Purification by silica gel chromatography ($R_f$=0.25 in 9:1 hexane:ethyl acetate) gave 425 mg (95% yield) of 51 as a clear oil. $^1$H NMR (500 MHz, $CDCl_3$) δ ppm 5.06 (tt, J=7.0, 1.3 Hz, 1H), 4.99 (tt, J=6.9, 1.4 Hz, 1H), 4.59 (dd, J=35.6, 6.8 Hz, 2H), 3.92 (s, 3H), 3.60 (dd, J=11.5, 5.2 Hz, 2H), 3.33 (s, 3H), 3.17 (s, 1H), 2.55 (dd, J=14.5, 6.3 Hz, 1H), 2.38-2.38 (m, 0H), 2.40 (dd, J=14.6, 7.4 Hz, 1H), 2.27-2.34 (m, 1H), 2.24 (dd, J=13.5, 5.2 Hz, 4H), 1.84-1.94 (m, 1H), 1.81 (dd, J=13.4, 11.6 Hz, 2H), 1.63-1.68 (m, 12H), 1.55 (ddd, J=13.0, 4.5 Hz, 1H), 1.17-1.26 (m, 1H), 0.91 (s, 3H), 0.23-0.24 ppm (m, 9H). $^{13}$C NMR (126 MHz, $CDCl_3$) δ ppm 205.9, 197.8, 185.8, 134.2, 131.8, 127.4, 124.4, 119.4, 97.3, 79.2, 70.8, 64.4, 58.4, 55.8, 46.5, 37.7, 37.4, 29.8, 26.0, 25.9, 21.6, 18.1, 17.8, 16.4, 0.7. HRMS-ESI (m/z): [M+H]+ calculated $C_{27}H_{44}O_5Si$, 477.3031. found 477.3031.

(1S,5R,7S,8S)-4-Hydroxy-7-(methoxymethoxy)-8-methyl-5-(3-methylbut-2-en-1-yl)-8-(4-methylpent-3-en-1-yl)bicyclo[3.3.1]non-3-ene-2,9-dione (52)

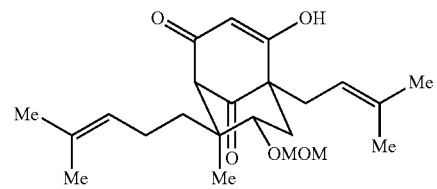

Representative Procedure for Hydrolysis of Vinylogous Ester.

A 1 dram vial equipped with a stir bar is charged with 10.7 mg (0.037 mmol, 1 equiv.) of starting material 50 followed by 575 µL 1,4-dioxan and 575 µL of a solution of lithium hydroxide in water (0.52M, 0.300 mmol, 11.5 equiv.). The reaction was heated with stirring to 80° C. for 16 h. After the reaction was complete, the solution was transferred to a separatory funnel with diethyl ether and the pH was adjusted to 1 with 10% aqueous hydrochloric acid. The organic layer was separated and dried with $MgSO_4$ and concentrated in vacuo to give a clear oil. The crude product was filtered through a small pipet column of silica gel with 20:1 dichloromethane:methanol as eluent to give 10.1 mg (99% yield) of 52 as a clear oil. 1H NMR (500 MHz, $CDCl_3$) δ ppm 5.67 (s, 1H), 5.11-4.99 (m, 2H), 4.63 (dd, J=7.0, 20.9 Hz, 2H), 3.65 (dd, J=5.5, 11.5 Hz, 1H), 3.37 (s, 3H), 3.19 (s, 1H), 2.46 (ddd, J=6.7, 14.1, 35.1 Hz, 2H), 2.34-2.21 (m, 1H), 2.15 (dd, J=5.6, 13.3 Hz, 1H), 1.93 (tt, J=5.9, 12.3 Hz, 1H), 1.84 (dd, J=11.7, 13.2 Hz, 1H), 1.73-1.59 (m, 12H), 1.39-1.28 (m, 2H), 0.96 (s, 3H). HRMS-ESI (m/z): [M+Na]$^+$ calculated for $C_{23}H_{34}O_5$, 413.2298. found 413.2296.

(1S,5R,7S,8S)-4,7-Dihydroxy-8-methyl-5-(3-methylbut-2-en-1-yl)-8-(4-methylpent-3-en-1-yl)bicyclo[3.3.1]non-3-ene-2,9-dione (53)

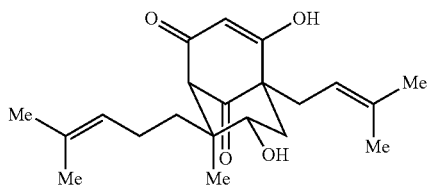 [SMILES: CC(C)=CCCC1(C)C(O)CC2(CC=C(C)C)C(=O)C1C(=O)C=C2O]

Prepared according to representative procedure on a scale of 0.037 mmol of 20 (13.2 mg) and 0.421 mmol of lithium hydroxide (10.1 mg). The crude material was filtered through silica gel using 10:1 dichloromethane:methanol as the eluent to give 53 as a white solid in a 98% yield (12.4 mg). $^1$H NMR (500 MHz, CDCl$_3$) δ ppm 5.68 (s, 1H), 5.07 (t, J=7.0 Hz, 1H), 4.99 (t, J=6.3 Hz, 1H), 3.78 (dd, J=5.3, 11.8 Hz, 1H), 3.19 (s, 1H), 2.44 (ddd, J=7.3, 14.7, 39.0 Hz, 2H), 2.29-2.16 (m, 1H), 2.05-1.92 (m, 2H), 1.81 (t, J=12.5 Hz, 1H), 1.67 (s, 3H), 1.64 (s, 3H), 1.63 (s, 3H), 1.62 (s, 3H), 1.40-1.29 (m, 2H), 0.95 (s, 3H). HRMS-ESI (m/z): [M+Na]$^+$ calculated for $C_{21}H_{30}O_4$, 369.2036. found 369.2034.

(1S,5R,7S,8S)-4-Methoxy-7-(methoxymethoxy)-8-methyl-3,5-bis(3-methylbut-2-en-1-yl)-8-(4-methylpent-3-en-1-yl)bicyclo[3.3.1]non-3-ene-2,9-dione (54)

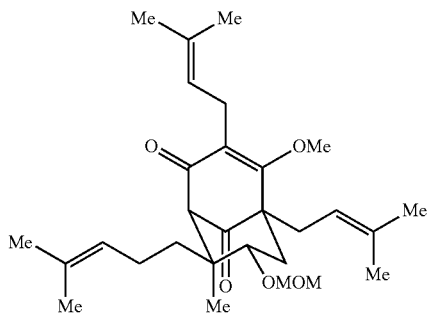

A 1 dram vial equipped with a stir bar is charged with 12.6 mg (0.031 mmol, 1 equiv.) of starting material 50 followed by 660 μL of THF. The solution is cooled to −78° C. prior to the addition of 124 μL of LDA (0.50 M, 0.062 mmol, 2 equiv.). The mixture was then stirred for 20 minutes followed by the addition of 18 μL (0.155 mmol, 5 equiv.) of prenyl bromide. Stirring was continued for an additional 20 minutes at which time the reaction was quenched by the addition of 500 μL of saturated aqueous ammonium chloride. The reaction was transferred to a separatory funnel in diethyl ether, and the organic layer was washed twice with water, dried with MgSO$_4$, and concentrated in vacuo. The crude product was purified by silica gel chromatography (R$_f$=0.25 in 9:1 hexane:ethyl acetate), affording 7.5 mg (51% yield) of 54 as a clear oil. $^1$H NMR (500 MHz, CDCl$_3$) δ ppm 5.07 (t, J=7.0 Hz, 1H), 5.04-4.94 (m, 2H), 4.58 (dd, J=7.0, 47.1 Hz, 2H), 3.95 (s, 3H), 3.60 (dd, J=5.3, 11.4 Hz, 1H), 3.33 (s, 3H), 3.25 (s, 1H), 3.13 (d, J=6.4 Hz, 2H), 2.50 (dd, J=6.2, 14.7 Hz, 1H), 2.42-2.28 (m, 2H), 2.25 (dd, J=5.2, 13.4 Hz, 1H), 1.96-1.84 (m, 1H), 1.77 (dd, J=11.5, 13.3 Hz, 1H), 1.71-1.61 (m, 18H), 1.58-1.51 (m, 2H), 1.30-1.23 (m, 2H), 1.18 (dt, J=4.3, 12.8 Hz, 2H), 0.91 (s, 3H). HRMS-ESI (m/z): [M+H]$^+$ calculated for $C_{29}H_{44}O_5$, 473.3262. found 473.3250.

(1S,5R,7S,8S)-5-Isopentyl-4-methoxy-7-(methoxymethoxy)-8-methyl-8-(4-methylpentyl)bicyclo[3.3.1]non-3-ene-2,9-dione (55)

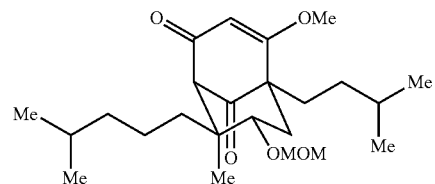

A 1 dram vial equipped with a stir bar is charged with 14.9 mg (0.037 mmol, 1 equiv.) of starting material 50 followed by 370 μL of methanol. The vial was flushed with argon, and 8.5 mg of palladium (5 wt % on activated carbon, 0.004 mmol, 0.10 equiv.) was added. The vial was then flushed with hydrogen, and a balloon contained hydrogen was affixed to the vial through a rubber septum cap. The mixture was stirred for 25 min at which time the mixture was filtered through Celite®. The filter cake was rinsed with copious amounts of methanol, and the collected filtrate was concentrated. The crude product was purified by silica gel chromatography (R$_f$=0.25 in 9:1 hexane:ethyl acetate), affording 14.5 mg (92% yield) of 55 as a clear oil. $^1$H NMR (500 MHz, CDCl$_3$) δ ppm 5.69 (s, 1H), 4.58 (dd, J=6.9, 52.4 Hz, 2H), 3.80 (s, 3H), 3.59 (dd, J=5.4, 11.3 Hz, 1H), 3.33 (s, 3H), 3.15 (s, 1H), 2.20 (dd, J=5.4, 13.4 Hz, 1H), 1.79 (dt, J=4.5, 12.6 Hz, 1H), 1.72 (dd, J=11.3, 13.3 Hz, 1H), 1.66-1.48 (m, 3H), 1.31-1.14 (m, 4H), 1.14-1.05 (m, 1H), 0.90-0.85 (m, 15H). HRMS-ESI (m/z): [M+K]$^+$ calculated for $C_{24}H_{40}O_5$, 447.2507. found 447.2511.

(1R,5R,7S,8S)-1-Isobutyryl-4-methoxy-7-(methoxymethoxy)-8-methyl-5-(3-methylbut-2-en-1-yl)-8-(4-methylpent-3-en-1-yl)bicyclo[3.3.1]non-3-ene-2,9-dione (56)

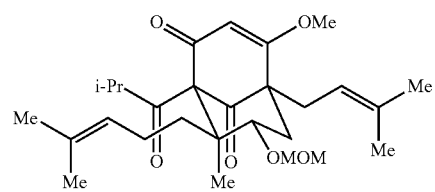

A 1 dram vial equipped with a stir bar is charged with 14.3 mg (0.030 mmol, 1 equiv.) of 51 and 150 μL of THF. The solution was cooled to −78° C. in a dry ice/acetone bath, and 300 μL of a solution of LiTMP (0.5M in THF, 0.150 mmol, 5 equiv.) was added dropwise. The yellow solution was stirred at −78° C. for 10 minutes followed by warming to 0° C. in a water/ice bath for 10 minutes and then recooling to −78° C. prior to addition of 15.7 µL (0.15 mmol, 5 equiv.) of isobutyryl chloride. The reaction was stirred 30 minutes prior to quenching by the addition of 500 µL of saturated aqueous ammonium chloride. The solution was transferred to a separatory funnel with 15 mL of hexane, and the organic layer was washed sequentially saturated aqueous 10% aqueous hydrochloric acid, water, and brine; dried with $MgSO_4$; and concentrated in vacuo. The crude product was found to contain an inseparable mixture of product and 51. The mixture was purified by silica gel chromatography ($R_f$=0.25 in 9:1 hexane:ethyl acetate) and carried forward as a mixture. A 1 dram vial equipped with a stir bar is charged with 9.0 mg (0.016 mmol, 1 equiv.) of the mixture followed by 100 µL of THF. The vial was cooled in a water/ice bath and 18 µL of TBAF (1.0 M in THF, 0.018, 1.1 equiv.) is added. The mixture is stirred for 15 min at which time it is transferred to a separatory funnel, and the organic layer is washed sequentially saturated aqueous sodium bicarbonate, water, and brine. The organic layer is then dried with $MgSO_4$ and concentrated in vacuo to give a yellow oil. The crude product is purified by preparative TLC ($R_f$=0.25 in 3:1 hexane:ethyl acetate) to give 4.1 mg (53% yield) of 56 as a clear oil. $^1$H NMR (500 MHz, $CDCl_3$) δ 5.85 (s, 1H), 5.07-4.96 (m, 2H), 4.61 (dd, J=6.8, 15.5 Hz, 2H), 3.82 (s, 3H), 3.58 (dd, J=5.2, 11.3 Hz, 1H), 3.32 (s, 3H), 2.48 (ddd, J=7.5, 14.5, 34.2 Hz, 2H), 2.18-2.04 (m, J=5.9, 13.2, 17.3 Hz, 4H), 1.96 (s, 1H), 1.77 (dd, J=11.4, 13.4 Hz, 1H), 1.67 (d, J=3.0 Hz, 6H), 1.64 (s, 3H), 1.59 (s, 3H), 1.55 (s, 3H), 1.30-1.21 (m, J=2.6, 2.6 Hz, 1H), 1.14 (s, 3H), 1.12 (d, J=6.5 Hz, 3H), 1.05 (d, J=6.5 Hz, 3H). HRMS-ESI (m/z): [M+H]$^+$ calculated for $C_{28}H_{42}O_6$, 475.3054. found, 475.3045.

Other Embodiments

This application refers to various issued patents, published patent applications, journal articles, books, manuals, and other publications, all of which are incorporated herein by reference.

The foregoing has been a description of certain non-limiting embodiments of the invention. Those of ordinary skill in the art will appreciate that various changes and modifications to this description may be made without departing from the spirit or scope of the present invention, as defined in the following claims.

What is claimed is:

1. A compound of Formula (I) or (II):

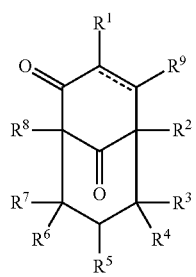

(I)

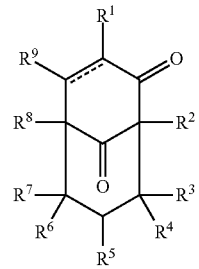

(II)

or a salt, isomer, or tautomer thereof, or mixture thereof; wherein:

$R^1$ is hydrogen, halogen, —OH, —OR$^{41}$, —N$_3$, —NH$_2$, —NH(R$^{41}$), —N(R$^{41}$)$_2$, —NH—NH—R$^{41}$, —NR$^{41}$—NHR$^{41}$, —N=NR$^{41}$, —SH, —SR$^{41}$, —SO$_2$R$^{41}$, —SO$_3$H, —SO$_2$OR$^{41}$, —Si(R$^{41}$)$_3$, —CO$_2$H, —CO$_2$R$^{41}$, —C(=O)R$^{41}$, —C(=O)NH$_2$, —C(=O)NH(R$^{41}$), —C(=O)N(R$^{41}$)$_2$, —C(=O)SH, —C(=O)SR$^{41}$, optionally substituted $C_{1-20}$ alkyl, optionally substituted $C_{2-20}$ alkenyl, optionally substituted $C_{2-20}$ alkynyl, optionally substituted $C_{3-10}$ carbocyclyl, optionally substituted 3-10 membered heterocyclyl, optionally substituted $C_{6-14}$ aryl, or optionally substituted 5-10 membered heteroaryl, wherein each instance of R$^{41}$ is independently optionally substituted $C_{1-20}$ alkyl, optionally substituted $C_{2-20}$ alkenyl, optionally substituted $C_{2-20}$ alkynyl, optionally substituted $C_{3-10}$ carbocyclyl, optionally substituted 3-10 membered heterocyclyl, optionally substituted $C_{6-14}$ aryl, optionally substituted 5-10 membered heteroaryl, or an oxygen, sulfur, or nitrogen protecting group, or two R$^{41}$ groups are joined to form an optionally substituted 3-10 membered heterocyclyl or optionally substituted 5-10 membered heteroaryl ring;

$R^2$ is —Si(R$^{42}$)$_3$, —SO$_2$R$^{42}$, —SO$_3$H, —SO$_2$OR$^{42}$, —CO$_2$H, —CO$_2$R$^{42}$, —C(=O)R$^{42}$, —C(=O)NH$_2$, —C(=O)NH(R$^{42}$), —C(=O)N(R$^{42}$)$_2$, —C(=O)SH, —C(=O)SR$^{42}$, optionally substituted $C_{1-20}$ alkyl, optionally substituted $C_{2-20}$ alkenyl, optionally substituted $C_{2-20}$ alkynyl, optionally substituted $C_{6-14}$ aryl, or optionally substituted 5-10 membered heteroaryl, wherein each instance of R$^{42}$ is independently optionally substituted $C_{1-20}$ alkyl, optionally substituted $C_{2-20}$ alkenyl, optionally substituted $C_{2-20}$ alkynyl, optionally substituted $C_{3-10}$ carbocyclyl, optionally substituted 3-10 membered heterocyclyl, optionally substituted $C_{6-14}$ aryl, or optionally substituted 5-10 membered heteroaryl, or an oxygen, sulfur, or nitrogen protecting group, or two R$^{42}$ groups are joined to form an optionally substituted 3-10 membered heterocyclyl or optionally substituted 5-10 membered heteroaryl ring;

$R^3$ is hydrogen, optionally substituted $C_{1-20}$ alkyl, optionally substituted $C_{2-20}$ alkenyl, or optionally substituted $C_{2-20}$ alkynyl;

$R^4$ is hydrogen, optionally substituted $C_{1-20}$ alkyl, optionally substituted $C_{2-20}$ alkenyl, or optionally substituted $C_{2-20}$ alkynyl;

$R^5$ is hydrogen, —OH, or —OR$^{45}$, wherein R$^{45}$ is optionally substituted $C_{1-20}$ alkyl, optionally substituted $C_{2-20}$ alkenyl, optionally substituted $C_{2-20}$ alkynyl, optionally substituted $C_{3-10}$ carbocyclyl, optionally substituted 3-10 membered heterocyclyl, optionally substituted $C_{6-14}$ aryl, optionally substituted 5-10 membered heteroaryl, or an oxygen protecting group;

$R^6$ is —OH, —$OR^{46}$, —$NH_2$, —$NHR^{46}$, —$N(R^{46})_2$, —NH—NH—$R^{46}$, —NR—$NHR^{46}$, —N=$NR^{46}$, —$N_3$, —SH, —$SR^{46}$, —$SO_2R^{46}$, —$SO_3H$, —$SO_2OR^{46}$, —$Si(R^{46})_3$, —$CO_2H$, —$CO_2R^{46}$, —C(=O)$R^{46}$, —C(=O)$NH_2$, —C(=O)NH($R^{46}$), —C(=O)N($R^{46})_2$, —C(=O)SH, —C(=O)$SR^{46}$, optionally substituted $C_{1-20}$ alkyl, optionally substituted $C_{2-20}$ alkenyl, optionally substituted $C_{2-20}$ alkynyl, optionally substituted $C_{3-10}$ carbocyclyl, or optionally substituted 3-10 membered heterocyclyl, wherein each instance of $R^{46}$ is independently optionally substituted $C_{1-20}$ alkyl, optionally substituted $C_{2-20}$ alkenyl, optionally substituted $C_{2-20}$ alkynyl, optionally substituted $C_{3-10}$ carbocyclyl, optionally substituted 3-10 membered heterocyclyl, optionally substituted $C_{6-14}$ aryl, optionally substituted 5-10 membered heteroaryl, or an oxygen, sulfur, or nitrogen protecting group, or two $R^{46}$ groups are joined to form an optionally substituted 3-10 membered heterocyclyl or optionally substituted 5-10 membered heteroaryl ring;

$R^7$ is hydrogen, —OH, —$OR^{47}$, —$NH_2$, —$NHR^{47}$, —$N(R^{47})_2$, —NH—NH—$R^{47}$, —NR—$NHR^{47}$, —N=$NR^{47}$, —$N_3$, —SH, —$SR^{47}$, —$SO_2R^{47}$, —$SO_3H$, —$SO_2OR^{47}$, —$Si(R^{47})_3$, —$CO_2H$, —$CO_2R^{47}$, —C(=O)$R^{47}$, —C(=O)$NH_2$, —C(=O)NH($R^{47}$), —C(=O)N($R^{47})_2$, —C(=O)SH, —C(=O)$SR^{47}$, optionally substituted $C_{1-20}$ alkyl, optionally substituted $C_{2-20}$ alkenyl, optionally substituted $C_{2-20}$ alkynyl, optionally substituted $C_{3-10}$ carbocyclyl, optionally substituted 3-10 membered heterocyclyl, optionally substituted $C_{6-14}$ aryl, or optionally substituted 5-10 membered heteroaryl, wherein each instance of $R^{47}$ is independently optionally substituted $C_{1-20}$ alkyl, optionally substituted $C_{2-20}$ alkenyl, optionally substituted $C_{2-20}$ alkynyl, optionally substituted $C_{3-10}$ carbocyclyl, optionally substituted 3-10 membered heterocyclyl, optionally substituted $C_{6-14}$ aryl, optionally substituted 5-10 membered heteroaryl, or an oxygen, sulfur, or nitrogen protecting group, or two $R^{47}$ groups are joined to form an optionally substituted 3-10 membered heterocyclyl or optionally substituted 5-10 membered heteroaryl ring;

$R^8$ is hydrogen, halogen, —OH, —$OR^{48}$, —$NH_2$, —$NHR^{48}$, —$N(R^{48})_2$, —NH—NH—$R^{48}$, —$NR^{48}$—$NHR^{48}$, —N=$NR^{48}$, —$N_3$, —SH, —$SR^{48}$, —$Si(R^{48})_3$, —$SO_2R^{48}$, —$SO_3H$, —$SO_2OR^{48}$, —$CO_2H$, —$CO_2R^{48}$, —C(=O)$R^{48}$, —C(=O)$NH_2$, —C(=O)NH($R^{48}$), —C(=O)N($R^{48})_2$, —C(=O)$SR^{48}$, —C(OH)($OR^{48})R^{48}$, —C(OH)$_2R^{48}$, —C($OR^{48})^2R^{48}$, optionally substituted $C_{1-20}$ alkyl, optionally substituted $C_{2-20}$ alkenyl, optionally substituted $C_{2-20}$ alkynyl, optionally substituted $C_{3-10}$ carbocyclyl, optionally substituted 3-10 membered heterocyclyl, $C_{6-14}$ optionally substituted aryl, or optionally substituted 5-10 membered heteroaryl, wherein each instance of $R^{48}$ is independently optionally substituted $C_{1-20}$ alkyl, optionally substituted $C_{2-20}$ alkenyl, optionally substituted $C_{2-20}$ alkynyl, optionally substituted $C_{3-10}$ carbocyclyl, optionally substituted 3-10 membered heterocyclyl, optionally substituted $C_{6-14}$ aryl, optionally substituted 5-10 membered heteroaryl, or an oxygen, sulfur, or nitrogen protecting group, or two $R^{48}$ groups are joined to form an optionally substituted 3-10 membered heterocyclyl or optionally substituted 5-10 membered heteroaryl ring;

$R^9$ is halogen, —OH, —$OR^{49}$, —$NH_2$, —$NHR^{49}$, —$N(R^{49})_2$, —NH—NH—$R^{49}$, —$NR^{49}$—$NHR^{49}$, —N=$NR^{49}$, —$N_3$, —SH, —$SR^{49}$, —$Si(R^{49})_3$, —$SO_2R^{49}$, —$SO_3H$, —$SO_2OR^{49}$, —$CO_2H$, —$CO_2R^{49}$, —C(=O)$R^{49}$, —C(=O)$NH_2$, —C(=O)NH($R^{49}$), —C(=O)N($R^{49})_2$, —C(=O)$SR^{49}$, —P(=O)(OH)$_2$, —P(=O)(OH)($OR^{49}$), —P(=O)($OR^{49})_2$, optionally substituted $C_{1-20}$ alkyl, optionally substituted $C_{2-20}$ alkenyl, optionally substituted $C_{2-20}$ alkynyl, optionally substituted $C_{3-10}$ carbocyclyl, optionally substituted 3-10 membered heterocyclyl, $C_{6-14}$ optionally substituted aryl, or optionally substituted 5-10 membered heteroaryl, wherein each instance of $R^{49}$ is independently optionally substituted $C_{1-20}$ alkyl, optionally substituted $C_{2-20}$ alkenyl, optionally substituted $C_{2-20}$ alkynyl, optionally substituted $C_{3-10}$ carbocyclyl, optionally substituted 3-10 membered heterocyclyl, optionally substituted $C_{6-14}$ aryl, optionally substituted 5-10 membered heteroaryl, or an oxygen, sulfur, or nitrogen protecting group, or two $R^{49}$ groups are joined to form an optionally substituted 3-10 membered heterocyclyl or optionally substituted 5-10 membered heteroaryl ring; and ===== represents a single or double bond.

2. The compound of claim 1, wherein the compound of Formula (I) is selected from any one of two stereoisomers:

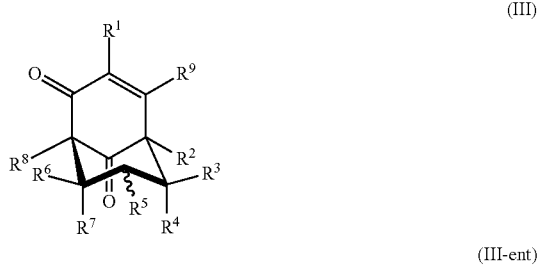

(III)

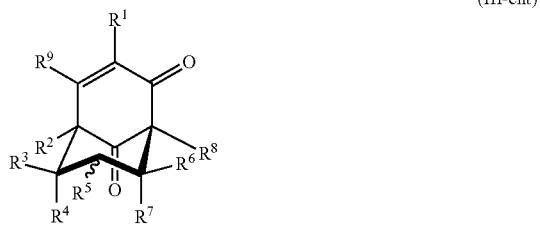

(III-ent)

or a salt, isomer, or tautomer thereof, or mixture thereof, wherein the $R^5$ group is in the axial or equatorial position.

3. The compound of claim 1, wherein the compound of Formula (II) is selected from any one of two stereoisomers:

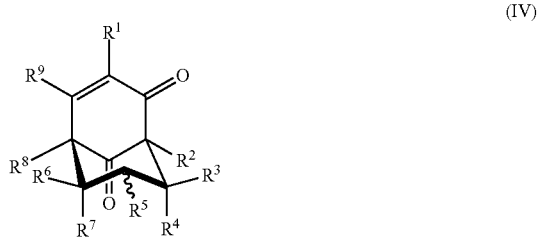

(IV)

-continued (IV-ent)

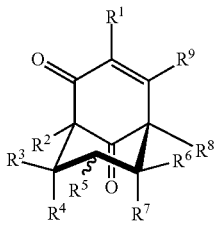

or a salt, isomer, or tautomer thereof, or mixture thereof, wherein the $R^5$ group is in the axial or equatorial position.

4. The compound of claim 1, wherein $R^1$ is hydrogen or optionally substituted $C_{1-20}$ alkyl.

5. The compound of claim 1, wherein $R^2$ is optionally substituted $C_{1-20}$ alkyl.

6. The compound of claim 1, wherein both $R^3$ and $R^4$ are hydrogen.

7. The compound of claim 1, wherein $R^6$ is optionally substituted $C_{1-20}$ alkyl.

8. The compound of claim 1, wherein $R^7$ is hydrogen, —OH, —$OR^{47}$, or optionally substituted $C_{1-20}$ alkyl.

9. The compound of claim 1 wherein $R^8$ is hydrogen or optionally substituted $C_{1-20}$ alkyl.

10. The compound claim 1, wherein $R^9$ is —$SO_2R^{A9}$, —$SO_3H$, —$SO_2OR^{A9}$, —$CO_2H$, —$CO_2R^{A9}$, —$C(=O)R^{A9}$, —$C(=O)NH_2$, —$C(=O)NH(R^{A9})$, —$C(=O)N(R^{A9})_2$, —$C(=O)SR^{A9}$, —$P(=O)(OH)_2$, —$P(=O)(OH)(OR^{A9})$, —$P(=O)(OR^{A9})_2$, or an optionally substituted $C_{1-20}$ alkyl group.

11. The compound of claim 10, wherein the $C_{1-20}$ alkyl group is substituted with —$P(=O)(OH)_2$, —$P(=O)(OH)(OR^{B9})$, —$P(=O)(OR^{B9})_2$, —$CO_2H$, —$CO_2R^{B9}$, —$C(=O)R^{B9}$, —$C(=O)NH_2$, —$C(=O)NH(R^{B9})$, —$C(=O)N(R^{B9})_2$, —$C(=O)SR^{B9}$, —$SO_2R^{B9}$, —$SO_3H$, or —$SO_2OR^{B9}$, wherein each instance of $R^{B9}$ is independently optionally substituted $C_{1-20}$ alkyl, optionally substituted $C_{2-20}$ alkenyl, optionally substituted $C_{2-20}$ alkynyl, optionally substituted $C_{3-10}$ carbocyclyl, optionally substituted 3-10 membered heterocyclyl, optionally substituted $C_{6-14}$ aryl, optionally substituted 5-10 membered heteroaryl.

12. The compound of claim 5, wherein $R^2$ is unsubstituted $C_{1-20}$ alkyl.

13. The compound of claim 12, wherein $R^2$ is —$CH_3$.

14. The compound of claim 1, wherein $R^5$ is —OH.

15. The compound of claim 1, wherein $R^5$ is —$OR^{45}$.

16. The compound of claim 7, wherein $R^6$ is unsubstituted $C_{1-20}$ alkyl.

17. The compound of claim 16, wherein $R^6$ is —$CH_3$.

18. The compound of claim 8, wherein $R^7$ is unsubstituted $C_{1-20}$ alkyl.

19. The compound of claim 18, wherein $R^7$ is —$CH_3$.

20. The compound of claim 1, wherein $R^5$ is —OH, $R^3$ and $R^4$ are hydrogen, and $R^6$ and $R^7$ are methyl.

21. The compound of claim 1, wherein $R^8$ is —$C(=O)R^{A8}$.

22. The compound of claim 1, wherein $R^9$ is —OH or —$OR^{A9}$, and $R^{A9}$ is optionally substituted $C_{1-20}$ alkyl, optionally substituted $C_{2-20}$ alkenyl, optionally substituted $C_{2-20}$ alkynyl, optionally substituted $C_{3-10}$ carbocyclyl, optionally substituted 3-10 membered heterocyclyl, optionally substituted $C_{6-14}$ aryl, optionally substituted 5-10 membered heteroaryl, or an oxygen protecting group.

23. The compound of claim 22, wherein $R^9$ is —OH.

24. The compound of claim 1 wherein the compound of Formula (I) is selected from any one of two stereoisomers:

(III-e)

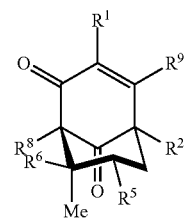

(III-e-ent)

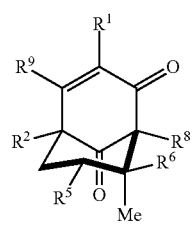

or a salt, isomer, or tautomer thereof, or mixture thereof.

25. The compound of claim 1 wherein the compound of Formula (II) is selected from any one of two stereoisomers:

(IV-e)

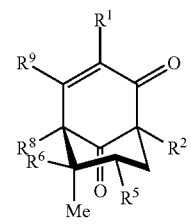

(IV-e-ent)

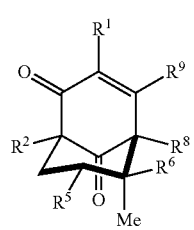

or a salt, isomer, or tautomer thereof, or mixture thereof.

26. The compound of claim 1 selected from the group consisting of:

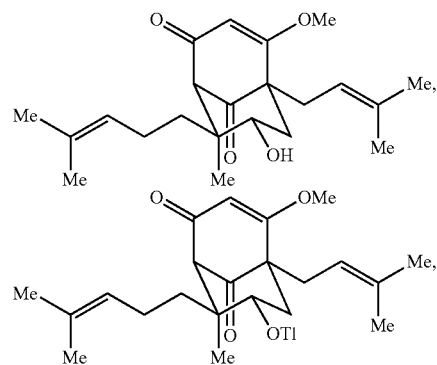

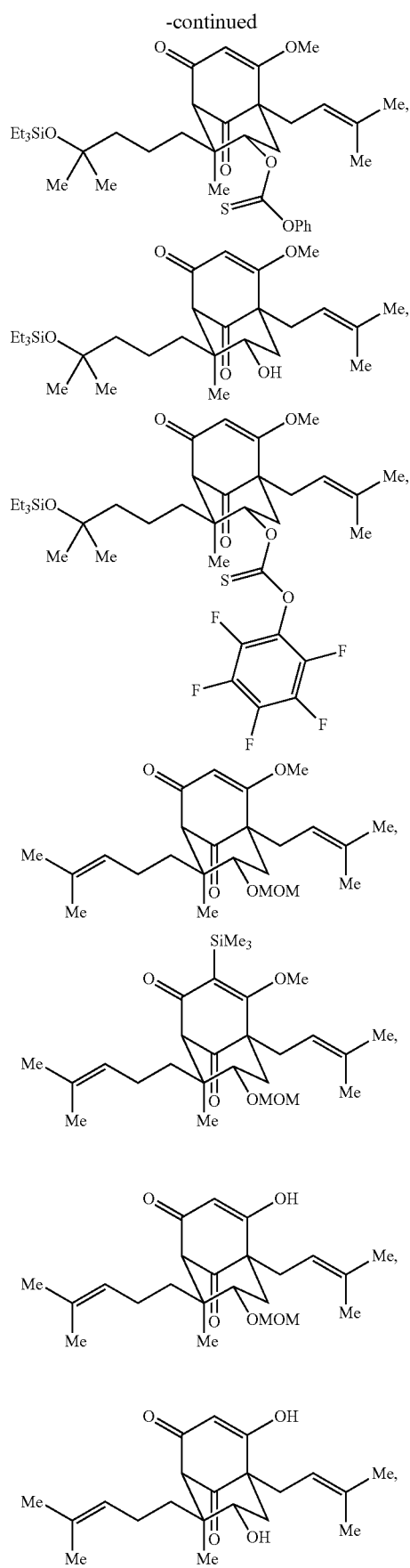

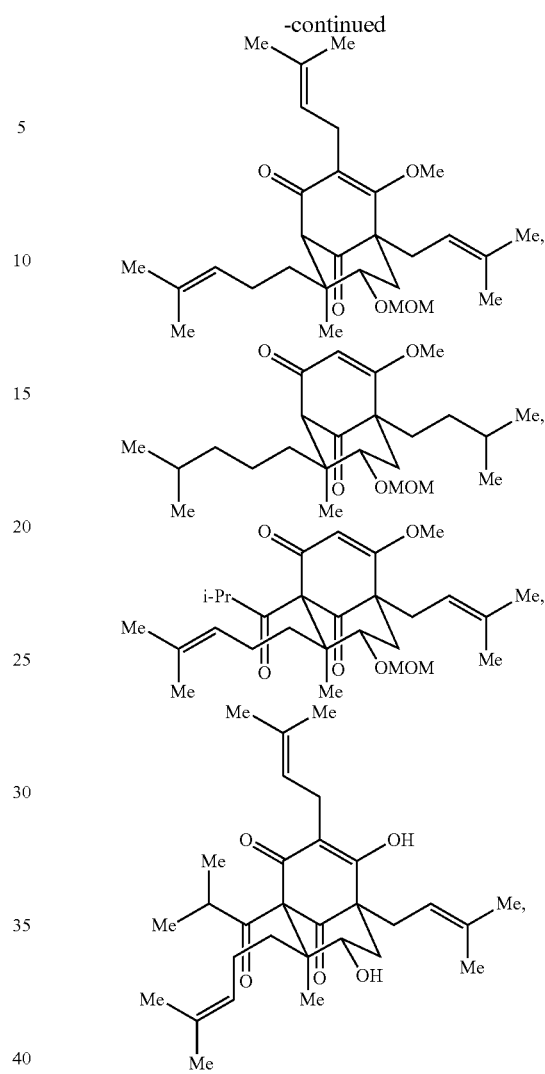

and salts, isomers, and tautomers thereof.

27. The compound of claim 1, wherein $R^9$ is halogen, —OH, —OR$^{A9}$, —NH$_2$, —NHR$^{A9}$, —N(R$^{A9}$)$_2$, —NH—NH—R$^{A9}$, —NR$^{A9}$—NHR$^{A9}$, —N=NR$^{A9}$, —N$_3$, —SH, —SR$^{A9}$, —Si(R$^{A9}$)$_3$, —SO$_2$R$^{A9}$, —SO$_3$H, —SO$_2$OR$^{A9}$, —CO$_2$H, —CO$_2$R$^{A9}$, —C(=O)R$^{A9}$, —C(=O)NH$_2$, —C(=O)NH(R$^{A9}$), —C(=O)N(R$^{A9}$)$_2$, —C(=O)SR$^{A9}$, —P(=O)(OH)$_2$, —P(=O)(OH)(OR$^{A9}$), —P(=O)(OR$^{A9}$)$_2$, optionally substituted $C_{1-20}$ alkyl, optionally substituted $C_{2-20}$ alkenyl, optionally substituted $C_{2-20}$ alkynyl, optionally substituted $C_{3-10}$ carbocyclyl, optionally substituted 3-10 membered heterocyclyl, $C_{6-14}$ optionally substituted aryl, or optionally substituted 5-10 membered heteroaryl, wherein each instance of R$^{A9}$ is independently optionally substituted $C_{1-20}$ alkyl, optionally substituted $C_{2-20}$ alkenyl, optionally substituted $C_{2-20}$ alkynyl, optionally substituted $C_{3-10}$ carbocyclyl, optionally substituted 3-10 membered heterocyclyl, optionally substituted $C_{6-14}$ aryl, optionally substituted 5-10 membered heteroaryl, or an oxygen, sulfur, or nitrogen protecting group, or two R$^{A9}$ groups are joined to form an optionally substituted 3-10 membered heterocyclyl or optionally substituted 5-10 membered heteroaryl ring.

28. The compound of claim 15, wherein R$^{A5}$ is an oxygen protecting group.

29. The compound of claim 15, wherein R$^{A5}$ is an optionally substituted $C_{1-20}$ alkyl.

30. The compound of claim 29, wherein $R^6$ is unsubstituted $C_{1-20}$ alkyl.

31. The compound of claim 30, wherein $R^7$ is unsubstituted $C_{1-20}$ alkyl.

32. The compound of claim 31, wherein $R^3$ and $R^4$ are hydrogen.

33. The compound of claim 1, wherein $R^5$ is hydrogen.

* * * * *